(12) United States Patent
Daugherty et al.

(10) Patent No.: US 12,146,884 B2
(45) Date of Patent: *Nov. 19, 2024

(54) METHODS AND COMPOSITIONS FOR ASSESSING ANTIBODY SPECIFICITIES

(71) Applicant: Serimmune Inc., Goleta, CA (US)

(72) Inventors: Patrick Sean Daugherty, Goleta, CA (US); Kathryn Vinaya Louise Kamath, Santa Barbara, CA (US); Jack Ryan Reifert, Santa Barbara, CA (US)

(73) Assignee: Serimmune Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,566

(22) Filed: Sep. 7, 2023

(65) Prior Publication Data

US 2024/0044911 A1 Feb. 8, 2024

Related U.S. Application Data

(63) Continuation of application No. 18/122,527, filed on Mar. 16, 2023, which is a continuation of application No. 17/096,890, filed on Nov. 12, 2020, now Pat. No. 11,828,762, which is a continuation of application No. 16/544,652, filed on Aug. 19, 2019, now Pat. No. 10,871,494, which is a continuation of application No. 15/991,982, filed on May 29, 2018, now Pat. No. 10,386,373, which is a continuation of application No. 15/775,363, filed as application No. PCT/US2016/061929 on Nov. 14, 2016, now abandoned.

(60) Provisional application No. 62/339,644, filed on May 20, 2016, provisional application No. 62/253,926, filed on Nov. 11, 2015.

(51) Int. Cl.

| | |
|---|---|
| *G01N 33/68* | (2006.01) |
| *C07K 14/195* | (2006.01) |
| *C07K 14/285* | (2006.01) |
| *C07K 14/315* | (2006.01) |
| *C07K 14/435* | (2006.01) |
| *C07K 14/44* | (2006.01) |
| *C07K 14/45* | (2006.01) |
| *C12N 15/10* | (2006.01) |
| *C12Q 1/689* | (2018.01) |
| *G01N 33/53* | (2006.01) |
| *G01N 33/564* | (2006.01) |
| *G01N 33/569* | (2006.01) |

(52) U.S. Cl.
CPC ....... *G01N 33/6854* (2013.01); *C07K 14/195* (2013.01); *C07K 14/285* (2013.01); *C07K 14/315* (2013.01); *C07K 14/43554* (2013.01); *C07K 14/44* (2013.01); *C07K 14/45* (2013.01); *G01N 33/53* (2013.01); *G01N 33/564* (2013.01); *G01N 33/569* (2013.01); *G01N 33/56905* (2013.01); *G01N 33/56911* (2013.01); *G01N 33/56944* (2013.01); *G01N 33/56966* (2013.01); *G01N 33/56983* (2013.01); *G01N 33/56988* (2013.01); *G01N 33/56994* (2013.01); *G01N 33/6842* (2013.01); *G01N 33/6845* (2013.01); *G01N 33/6878* (2013.01); *C12N 15/1037* (2013.01); *C12Q 1/689* (2013.01); *G01N 2333/045* (2013.01); *G01N 2333/05* (2013.01); *G01N 2333/095* (2013.01); *G01N 2333/16* (2013.01); *G01N 2333/18* (2013.01); *G01N 2333/20* (2013.01); *G01N 2333/285* (2013.01); *G01N 2333/29* (2013.01); *G01N 2333/315* (2013.01); *G01N 2333/4353* (2013.01); *G01N 2570/00* (2013.01); *G01N 2800/24* (2013.01); *G01N 2800/26* (2013.01); *Y02A 50/30* (2018.01)

(58) Field of Classification Search
CPC .................................................. C12N 15/1037
See application file for complete search history.

(56) References Cited

U.S. PATENT DOCUMENTS

| | | | |
|---|---|---|---|
| 3,970,518 | A | 7/1976 | Giaever |
| 4,230,685 | A | 10/1980 | Senyei et al. |
| 4,554,088 | A | 11/1985 | Whitehead et al. |
| 5,348,867 | A | 9/1994 | Georgiou et al. |
| 6,274,345 | B1 | 8/2001 | Lee et al. |
| 6,441,140 | B1 | 8/2002 | Comb et al. |
| 6,623,982 | B1 | 9/2003 | Liberti et al. |
| 6,686,164 | B1 | 2/2004 | Olsen et al. |
| 7,129,060 | B1 | 10/2006 | Maurer et al. |
| 7,198,896 | B2 | 4/2007 | Rush et al. |
| 7,256,038 | B2 | 8/2007 | Daugherty et al. |
| 7,587,281 | B2 | 9/2009 | Gershoni et al. |

(Continued)

FOREIGN PATENT DOCUMENTS

| | | |
|---|---|---|
| WO | 2008/021290 A2 | 2/2008 |
| WO | 2016/083874 A1 | 6/2016 |

(Continued)

OTHER PUBLICATIONS

Bowie et al. (Science, 1990, 257:1306-1310) (Year: 1990).*

(Continued)

*Primary Examiner* — Brian Gangle
*Assistant Examiner* — Lakia J Jackson-Tongue
(74) *Attorney, Agent, or Firm* — Goodwin Procter LLP

(57) ABSTRACT

The present invention provides compositions and methods that can be used to determine a peptide signature for an antibody repertoire in a sample comprising multiple antibodies. The method can be used to characterize a phenotype in a sample, such as providing a diagnosis, prognosis or theranosis of a medical condition.

27 Claims, 26 Drawing Sheets

Specification includes a Sequence Listing.

(56) References Cited

U.S. PATENT DOCUMENTS

| | | | |
|---|---|---|---|
| 7,612,019 | B2 | 11/2009 | Daugherty et al. |
| 7,657,378 | B1 | 2/2010 | Brahmachari et al. |
| 7,666,817 | B2 | 2/2010 | Daugherty et al. |
| 7,863,004 | B2 | 1/2011 | Tainsky et al. |
| 8,293,685 | B2 | 10/2012 | Daugherty et al. |
| 8,361,933 | B2 | 1/2013 | Daugherty et al. |
| 8,513,390 | B2 | 8/2013 | Stagliano et al. |
| 8,841,104 | B2 | 9/2014 | Dryga et al. |
| 9,121,828 | B2 | 9/2015 | Daugherty et al. |
| 9,234,847 | B2 | 1/2016 | Daugherty et al. |
| 9,309,510 | B2 | 4/2016 | La Porte et al. |
| 9,428,547 | B2 | 8/2016 | Dryga et al. |
| 9,562,896 | B2 | 2/2017 | Esch et al. |
| 9,632,078 | B2 | 4/2017 | Reidt et al. |
| 9,670,485 | B2 | 6/2017 | Bustamante et al. |
| 9,671,395 | B2 | 6/2017 | Dryga et al. |
| 9,672,324 | B1 | 6/2017 | Kasak et al. |
| 9,770,504 | B2 | 9/2017 | Vitetta |
| 10,386,373 | B2 * | 8/2019 | Daugherty ............. C07K 14/45 |
| 2002/0098503 | A1 | 7/2002 | Kamb |
| 2004/0014028 | A1 | 1/2004 | Lopez et al. |
| 2004/0031072 | A1 * | 2/2004 | La Rosa ................ C07H 21/04 536/23.6 |
| 2004/0048243 | A1 | 3/2004 | Arap et al. |
| 2005/0255464 | A1 | 11/2005 | Hagen et al. |
| 2007/0003954 | A1 | 1/2007 | Kodadek |
| 2007/0207976 | A1 | 9/2007 | Doucette-Stamm et al. |
| 2010/0184620 | A1 | 7/2010 | Rychlewski et al. |
| 2011/0262989 | A1 | 10/2011 | Clarizia et al. |
| 2013/0330335 | A1 | 12/2013 | Bremel et al. |
| 2014/0087963 | A1 | 3/2014 | Johnston et al. |
| 2015/0153354 | A1 | 6/2015 | Trost et al. |
| 2016/0033528 | A1 | 2/2016 | Daugherty et al. |
| 2016/0131662 | A1 | 5/2016 | Kodadek |
| 2016/0349248 | A1 | 12/2016 | Dryga et al. |
| 2016/0370380 | A1 | 12/2016 | Mandecki et al. |
| 2017/0131276 | A1 | 5/2017 | Johnston |
| 2017/0145406 | A1 | 5/2017 | Esch et al. |
| 2017/0153247 | A1 | 6/2017 | Chen |
| 2017/0233832 | A1 | 8/2017 | Jain et al. |
| 2017/0276672 | A1 | 9/2017 | Manuguerra et al. |
| 2019/0264194 | A1 | 8/2019 | Daugherty et al. |
| 2019/0369118 | A1 | 12/2019 | Daugherty et al. |
| 2021/0156873 | A1 | 5/2021 | Daugherty et al. |

FOREIGN PATENT DOCUMENTS

| | | |
|---|---|---|
| WO | 2017/145128 A1 | 8/2017 |
| WO | 2020/033642 A1 | 2/2020 |

OTHER PUBLICATIONS

Ramli et al., "Discovery of *Leptospira* spp. seroreactive peptides using ORFeome phage display." PLoS neglected tropical diseases 13, No. 1 (2019): e0007131. "aminodeoxychorismate synthase, component [Leptospira kirschneri str. H1]," accessed https://www.ncbi.nlm.nih.gov/protein/EKO17404.1, 2 pages.

GenBank: EKO17404.1, "aminodeoxychorismate synthase, component | [Leptospira kirschneri str. H1]," accessed Oct. 2022, https://www.ncbi.nlm.nih.gov/protein/EKO17404.1, 2 pages.

Bowie, J.U. et al., "Deciphering the Message in Protein Sequences: Tolerance to Amino Acid Substitutions," Science, Mar. 16, 1990, vol. 247, No. 4948, pp. 1306-1310.

Amstutz, P., et al., In vitro display technologies: novel developments and applications. Curr Opin Biotechnol, 2001. 12 (4): p. 400-5.

Anderson, K.S., et al., Protein microarray signature of autoantibody biomarkers for the early detection of breast cancer. J Proteome Res, 2011. 10(1): p. 85-96.

Andreatta, M., O. Lund, and M. Nielsen, Simultaneous alignment and clustering of peptide data using a Gibbs sampling approach. Bioinformatics, 2013. 29(1): p. 8-14.

Bailey, T.L. and C. Elkan, Fitting a mixture model by expectation maximization to discover motifs in biopolymers. Proc Int Conf Intell Syst Mol Biol, 1994. 2: p. 28-36.

Bailey, T.L. and C. Elkan, The value of prior knowledge in discovering motifs with MEME. Proc Int Conf Intell Syst Mol Biol, 1995. 3: p. 21-9.

Ballew, J.T., et al., Antibody biomarker discovery through in vitro directed evolution of consensus recognition epitopes. Proc Natl Acad Sci US A, 2013. 110(48): p. 19330-5.

Carmona, S.J., et al., Towards high-throughput immunomics for infectious diseases: use of next-generation peptide microarrays for rapid discovery and mapping of antigenic determinants. Mol Cell Proteomics, 2015, pp. 1871-1884.

Cima-Cabal et al., "Immunodetection of Pneumolysin in Human Urine by ELISA," Journal of Microbiological Methods, Feb. 27, 2003, vol. 54, Iss. 1, pp. 47-55.

Daugherty, P.S., Protein engineering with bacterial display. Curr Opin Struct Biol, 2007. 17(4): p. 474-80.

Fleisher G & Bolognese R (1983) Persistent Epstein-Barr virus infection and pregnancy. J Infect Dis 147(6):982-986.

Georgiou, G., et al., The promise and challenge of high-throughput sequencing of the antibody repertoire. Nat Biotechnol, 2014. 32(2): p. 158-68.

Getz, J.A., T.D. Schoep, and P.S. Daugherty, Peptide discovery using bacterial display and flow cytometry. 2012, Methods Enzymol. 503: p. 75-97.

Griffiths, P. and S. Lumley, Cytomegalovirus. Curr Opin Infect Dis, 2014. 27(6): p. 554-9.

Hadker, N., et al., Financial impact of a novel pre-eclampsia diagnostic test versus standard practice: a decision-analytic modeling analysis from a UK healthcare payer perspective. Dec. 7, 2010, J Med Econ. 13(4): p. 728-37.

Haeri S, Baker AM, & Boggess KA (2010) Prevalence of Epstein-Barr virus reactivation in pregnancy. Am J Perinatol 27(9):715-719.

Halenius, A. and H. Hengel, Human cytomegalovirus and autoimmune disease. Biomed Res Int, 2014. 2014: 15 pages.

Hall SS & Daugherty PS (2009) Quantitative specificity-based display library screening identifies determinants of antibody-epitope binding specificity. Protein Sci 18(9):1926-1934.

Herse, F., et al., Prevalence of agonistic autoantibodies against the angiotensin 11 type 1 receptor and soluble fms-like tyrosine kinase 1 in a gestational age-matched case study. Hypertension, 2009. 53(2): p. 393-8.

Icart J, Didier J, Dalens M, Chabanon G, & Boucays A (1981) Prospective study of Epstein Barr virus (EBV) infection during pregnancy. Biomedicine/ [publiee pour l'A.A.I.C.I.G.] 34(3):160-163.

Kleinrouweler, C.E., et al., Accuracy of circulating placental growth factor, vascular endothelial growth factor, soluble fms-like tyrosine kinase 1 and soluble endoglin in the prediction of pre-eclampsia: a systematic review and meta analysis. BJOG, 2012. 119(7): p. 778-87.

Lain, K.Y. and J.M. Roberts, Contemporary concepts of the pathogenesis and management of preeclampsia. JANIA, 2002. 287(24): p. 3183-6.

Larman, H.B., et al., PhIP-Seq characterization of autoantibodies from patients with multiple sclerosis, type 1 diabetes and rheumatoid arthritis. J Autoimmun, 2013. 43: p. 1-9.

Levine, R.J., et al., Circulating angiogenic factors and the risk of preeclampsia. N Engl J Med, 2004. 350(7): p. 672-83.

MacKay, AP., C.J. Berg, and H.K. Atrash, Pregnancy-related mortality from preeclampsia and eclampsia. Obstet Gynecol, 2001. 97(4): p. 533-8.

Masoura, S., et al., Biomarkers in pre-eclampsia: a novel approach to early detection of the disease. J Obstet Gynaecol, 2012. 32(7): p. 609-16.

Mintz PJ, et al. (2003) Fingerprinting the circulating repertoire of antibodies from cancer patients. Nat Biotechnol 21(1):57-63.

Ohkuchi, A., et al., Evaluation of a new and automated electrochemiluminescence immunoassay for plasma sFlt-1 and PIGF levels in women with preeclampsia. Hypertens Res. 2010. 33(5): p. 422-7.

(56) References Cited

OTHER PUBLICATIONS

Pantazes et al., "Identification of Disease-Specific Motifs in the Antibody Specificity Repertoire via Next-Generation Sequencing," Scientific Reports, Aug. 2, 2016, vol. 6, No. 30312, pp. 1-11.

Parrish, M.R., et al., The effect of immune factors, tumor necrosis factor-alpha, and agonistic autoantibodies to the angiotensin II type I receptor on soluble fma-like tyrosine-I and soluble endoglin production in response to hypertension duringpregnancy. Aug. 2010. Am J Hypertens. 23(8): p. 911-6.

PCT International Search Report and Written Opinion, PCT Application No. PCT/US2016/061929, dated Apr. 6, 2017, 17 pages.

Plebani, Jvi., et al., Recent advances in diagnostic technologies for autoimmune diseases. Autoimmun Rev, 2009. 8(3): p. 238-43.

Rice, J.J. and P.S. Daugherty, Directed evolution of a biterminal bacterial display scaffold enhances the display of diverse peptides. Protein Eng Des Sel, 2008. 21(7): p. 435-42.

Roberts, J.M., Angiotensin-1 receptor autoantibodies: A role in the pathogenesis of preeclampsia? Circulation, 2000. 101(20): p. 2335-7.

Rossitto, G., et al., Elevation of Angiotensin-II Type-I-Receptor Autoantibodies Titer in Primary Aldosteronism as a Result of Aldosterone-Producing Adenoma. Hypertension, 2013. 61(2): p. 526-33.

Samadi, AR., et al., Maternal hypertension and associated pregnancy complications among African-American and other women in the United States. Obstet Gynecol, 1996. 87(4): p. 557-63.

Schiettecatte, J., et al., Multicenter evaluation of the first automated Elecsys sFIt-1 and PlGF assays in normal pregnancies and preeclampsia. Clin Biochem. 2010. 43(9): p. 768-70.

Spatola, B.N., et al., Antibody Repertoire Profiling Using Bacterial Display Identifies Reactivity Signatures of Celiac Disease. Analytical Chemistry, 2012. 85(2): p. 1215-1222.

Wagner, L.K., Diagnosis and management of preeclampsia. Am Fam Physician, 2004. 70(12): p. 2317-24.

Wallis, AB., et al., Secular trends in the rates of preeclampsia, eclampsia, and gestational hypertension, United States, 1987-2004. Am J Hypertens, 2008. 21(5): p. 521-6.

Wallukat, G., et al., Patients with preeclampsia develop agonistic autoantibodies against the angiotensin ATJ receptor. J Clin Invest, 1999. 103(7): p. 945-52.

Wallukat, G., et al., Spontaneously beating neonatal rat heart myocyte culture-a model to characterize angiotensin 11 at(l) receptor autoantibodies in patients with preeclampsia. In Vitro Cell Dev Biol Anim, 2002. 38(7): p. 376-7.

Walther, T., et al., Angiotensin 11 type 1 receptor agonistic antibodies reflect fundamental alterations in the uteroplacental vasculature. Hypertension, 2005. 46(6): p. 1275-9.

Wang, X., et al., Autoantibody signatures in prostate cancer. N Engl J Med, 2005. 353(12): p. 1224-35.

Xu, G.J., et al., Viral immunology. Comprehensive serological profiling of human populations using a synthetic human virome. Science, 2015. 348(6239): p. aaa0698. 23 pages.

Zhang et al., "A Method for De Novo Nucleic Acid Diagnostic Target Discovery," Bioinformatics, Aug. 7, 2014, vol. 30, No. 22, pp. 3174-3180.

Zhou, C.C., et al., Angiotensin receptor agonistic autoantibodies induce pre-eclampsia in pregnant mice. Nat Med, 2008. 14(8): p. 855-62.

Zhou, C.C., et al., Autoantibody from women with preeclampsia induces soluble Fms-like tyrosine kinase-1 production via angiotensin type 1 receptor and calcineurin/nuclear factor of activated T-cells signaling. Hypertension, 2008. 51(4): p. 1010-9.

U.S. Appl. No. 15/991,982, Office Action, Sep. 20, 2018, 14 pages.

Mock et al., "Printed peptide arrays identify prognostic TNC serumantibodies in glioblastoma patients." Oncotarget 6, No. 15 (2015): 13579, 12 pages.

* cited by examiner

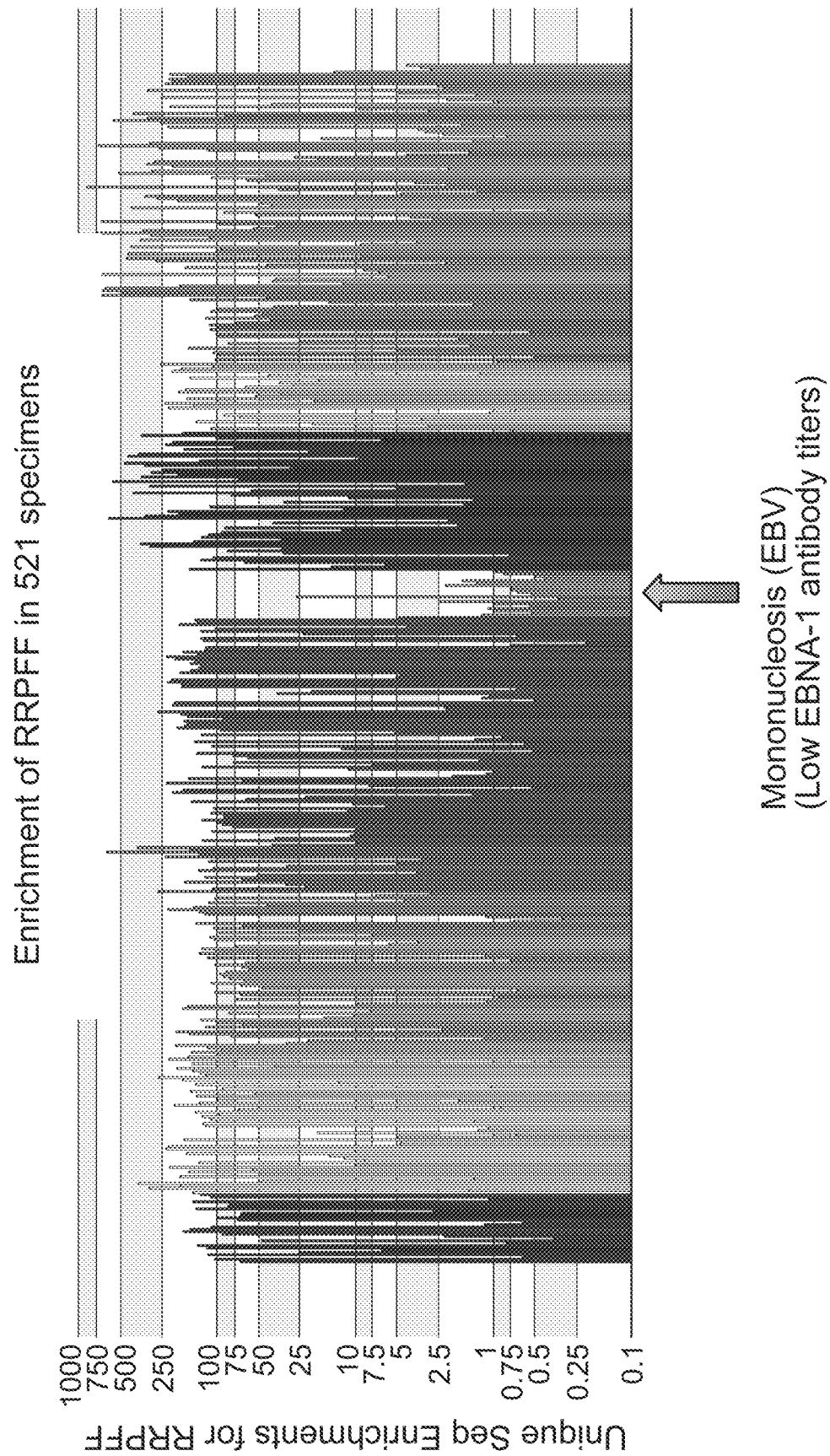

METHODS AND COMPOSITIONS FOR ASSESSING ANTIBODY SPECIFICITIES

CROSS REFERENCE TO RELATED APPLICATIONS

This application is a continuation of U.S. application Ser. No. 18/122,527, filed Mar. 16, 2023, which is a continuation of U.S. application Ser. No. 17/096,890, filed Nov. 12, 2020, which is a continuation of U.S. application Ser. No. 16/544,652, filed Aug. 19, 2019, now U.S. Pat. No. 10,871,494, which is a continuation of U.S. application Ser. No. 15/991,982, filed Mar. 29, 2018, now U.S. Pat. No. 10,386,373, which is a continuation of U.S. Application No. 15/775,363, which is the National Stage of International Application No. PCT/US2016/061929, filed Nov. 14, 2016, which claims the benefit of U.S. Provisional Application Nos. 62/339,644, filed May 20, 2016, and 62/253,926, filed Nov. 11, 2015, each of which is herein incorporated in its entirety by reference.

SEQUENCE LISTING

The instant application contains a Sequence Listing which has been submitted via Patent center and is hereby incorporated by reference in its entirety. Said XML copy, created on Mar. 6, 2024, is named SUI-001C4, and is 1,561,127 bytes in size.

FIELD OF INVENTION

In various embodiments, the invention relates to compositions and methods for diagnosing disease by detecting antibodies in a sample.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art Antibodies present in human specimens serve as the primary analyte and disease biomarker for a large and broad group of infectious, bacterial, viral, allergic, parasitic, and autoimmune diseases. As such, hundreds of distinct antibody detecting tests (collectively referred to as "immunoassays", have been developed to diagnose human disease using tissue samples that include but are not limited to whole blood, serum, plasma, saliva, urine, and tissue aspirates. Immunoassays remain essential to the diagnosis of autoimmune diseases including, but not limited to, Grave's disease, Sjogren's syndrome Celiac disease, Crohn's disease, Rheumatoid arthritis. Immunoassay are also widely used to diagnosis infectious diseases including for example viral infections (e.g. HIV, Hepatitis C, HSV-1, Zika virus, Epstein Barr virus, and others), bacterial infections include for example (*Streptococcus* sp., *Helicobacter pylori, Borrelia burdorferi* (Lyme), and others), fungal infections (e.g. Valley Fever), parasitic infections (e.g., *Trypanosoma cruzi, Toxoplasma gondii, Taenia solium, Toxocara canis*, and others). Furthermore, Immunoassays are often used to identify and monitor allergies (e.g. peanut allergy, milk, pollen, and others. Beyond these areas, immunoassays have demonstrated utility for the diagnosis of neurodegenerative disease, cardiovascular disease, and cancers.

Methods to detect antibodies include radio immunoassay (RIA), enzyme linked immunosorbant assays (ELISA), chemiluminescent assays, and protein and peptide arrays. These assay formats share in common the requirement to develop a molecular chemical reagent that binds to the analyte antibody in a sample in the majority of individuals with disease, to provide sensitivity, but not to any of the many distinct antibodies present in individuals without disease, to provide diagnostic specificity. Such reagents include antibodies, peptides, human proteins, nucleic acid aptamers, and other molecular binding entities [1, 2] [3, 4]. Such reagents are often highly optimized (Ballew J et al., PNAS, 2014) in order to achieve high sensitivity and specificity. Such optimization has been the subject of much research and development. Individual reagents, however, often possess insufficient affinity and specificity for the analytes of interest.

Present method used to develop diagnostic immunoassays limit the overall sensitivity and specificity that can be obtained from the assay, and thus the utility, because they include extraneous antigen matter (i.e., large proteins, peptides, lipids, whole cell lysates) that can result in cross-reactive binding from unrelated antibodies. For example, Lyme disease (infection with *Borrelia burgdorferi*) tests use whole cell lysates that contain a large number of distinct molecular compositions that are not targeted by the immune response *Borrelia*, but capture or detect antibodies generated in response to other infections such as infectious mononucleosis. Thus there is an unmet need for diagnostic technologies that can identify and present only those antigen components that are most specifically recognized by the immune response in individuals with a given phenotype.

Because individual reagents often do not capture or react with a sufficient number of samples from individuals with the disease (i.e. insufficient sensitivity), two or more reagents can be combined into a diagnostic test or used in parallel as an antigen panel. Nevertheless, combining sets of peptides into a single assay to increase the sensitivity of diagnosis is challenging since their non-specific binding, that limits specificity, is generally additive thereby limiting the overall diagnostic specificity of the assay. Experimental identification of the optimal combination of biochemical reagents is difficult given the combinatorial complexity of combining and weighting the antibody reactivities to each antigen in a panel [5, 6].

An important limitation associated with existing immunoassay formats is that they cannot be readily combined or aggregated together. Consequently, performing a large number of tests is additive in terms of cost and labor, thereby decrease the probability of making a correct diagnosis. For example, if an individual is bit by a tick, they may be infected with multiple tick-borne pathogens (there are more than 10 known tick-transmitted infectious agents). In many cases, physicians will only a test for *Borrelia burgdorferi*, even though any of 10s of other organisms may have infected that individual. Thus, there is a need for low cost multiplexed test that can diagnosis any or all of the tick-borne infections. Similarly, if a patient presents with a common symptom (e.g. fever, fatigue, headache), it can be difficult to identify which tests should be ordered to identify potential causes of the presenting symptoms. Thus, there is a need for methods and compositions that can integrate many tests into a single standardized assay, and thus simultaneously test for many different diseases or infections. The present invention provides solution to this problem.

The use of massively parallel DNA sequencing, also known as next-generation sequencing (hereafter referred to as "NGS"), high throughput sequencing, or deep sequencing, has been applied to enable the diagnosis of human diseases [7]. These collective approaches may be referred to generally as "NGS" throughout.

The prospect of analyzing entire human antibody repertoires has been a goal for at least several decades. Reported methods include human proteome arrays, phage display/immunoprecipitation (Ph-IP), peptide and peptoid arrays, and NGS analysis of antibody genes (Ig-Seq) [9][8]. One challenge associated with repertoire characterization is identifying particular peptide sequences to populate arrays limited to ~$10^6$ fields. Hence, prior methods have used small arrays of random peptides, typically having fewer than 300,000 peptides, or peptoids unlikely to closely mimic antigens. Array based approaches are presently limited to small collections of organisms with small proteomes (e.g., viruses) [10]. For peptide arrays, their relatively low peptide sequence diversity limits their ability to find individual sequences and motifs that mimic the bona-fide antigen targeted by an antibody.

A principle advantage of the invention provided herein is that it is unbiased—that is, it does not assume which organisms are antigenic. The method claimed can identify epitopes in any organisms in the rapidly growing protein database, not just pre-specified viruses [10], allowing antigen identification within even the largest proteomes (e.g., wheat genome=17 GB). Thus, the wheat genome alone is 100-1000× larger than the combined genomes of all known human viruses.

SUMMARY

The following embodiments and aspects thereof are described and illustrated in conjunction with systems, compositions and methods which are meant to be exemplary and illustrative, not limiting in scope.

In an aspect, the invention provides a method of identifying a plurality of peptides, comprising: a) providing a biological sample comprising a plurality of antibodies; b) contacting the biological sample with a plurality of peptides; and c) identifying members of the plurality of peptides that form complex members of the plurality of antibodies.

The biological sample may comprise a bodily fluid. Antibodies may be found in any bodily fluid. In some embodiments of the invention, the bodily fluid comprises peripheral blood, plasm, serum lymphatic fluid, sweat, saliva, mucus, or a derivative of any thereof.

In an embodiment, identifying members of the plurality of peptides that form a complex with members of the plurality of antibodies comprises sequencing a nucleic acid that encodes the peptide. Any useful sequencing method may be employed. For example, the sequencing may comprise next generation sequencing (NGS), Sanger sequencing, real-time PCR, or pyrosequencing. However, NGS can provide billions of sequences encoding peptides in a single experiment. The nucleic acid and peptide can be coupled physically, thereby allowing sequencing of the nucleic acid to determine the sequence of the peptide encoded by the nucleic acid. Any useful DNA construct can be used. For example, the nucleic acid molecule may comprise deoxyribonucleic acid (DNA), ribonucleic acid (RNA), or a derivative of any thereof.

In some embodiments, each peptide is directly coupled to its corresponding nucleic acid molecule. For example, the nucleic acid may be bound to a protein complex that comprises the peptide, including without limitation a ribosome display system. In another embodiment, each peptide is indirectly coupled to its corresponding nucleic acid molecule. For example, the corresponding nucleic acid molecule may be contained within a vector that encodes the peptide. As desired, the vector may be configured to express the peptide. The vector can also be comprised in a host cell. In an embodiment, the host cell expresses the peptide. The peptide may be expressed on the surface of the host cell. Appropriate display systems are available in the art or are provided herein. For example, the host cell can be a microbial cell, a bacterial cell, an *E. coli* cell, a eukaryotic cell, a yeast cell, or a mammalian cell.

The method of the invention may further comprise capturing members of the plurality of peptides that form a complex with members of the plurality of antibodies prior to identifying members of the plurality of peptides that form complex members of the plurality of antibodies (step c). In an embodiment, the capturing comprises capturing the peptide-bound members of the plurality of antibodies. The peptide-bound members of the plurality of antibodies may be captured to a substrate. Any useful substrate can be used. For example, the substrate can be a planar surface, e.g., a plate well, or a plurality of microbeads (also referred to as microparticles). The plurality of microbeads may be configured to facilitate capture as desired. For example, the microbeads may be magnetic or carry a label, including without limitation a fluorescent label. The bound members of the plurality of antibodies can be captured using a reagent that binds an antibody constant region. For example, the reagent can be Protein A, Protein G, Protein L and/or an anti-immunoglobulin antibody or aptamer. As desired, the reagent is coupled to the substrate, thereby allowing capture of peptide-bound antibodies to the substrate.

In some embodiments, the method of the invention further comprises filtering the plurality of antibodies prior to contacting the biological sample with a plurality of peptides (step b). The filtering may comprise contacting the plurality of antibodies with at least one reagent configured to deplete antibodies that bind to assay components other than the plurality of peptides. In an embodiment, the at least one reagent comprises a host cell as described herein, e.g., a host cell that is configured to display members of the plurality of peptides. The step allows removal of antibodies that bind to the host cell itself instead of members of the plurality of peptides.

In another embodiment, the method of the invention further comprises filtering the plurality of peptides prior to contacting the biological sample with a plurality of peptides (step b). The filtering of the plurality of peptides may comprise contacting the plurality of peptides with at least one reagent configured to deplete peptides that form a complex with assay components other than the plurality of antibodies. In an embodiment, the at least one reagent configured to deplete peptides comprises Protein A, Protein G, Protein L, and/or an anti-immunoglobulin antibody or aptamer.

As desired, filtering or depletion of both the plurality of antibodies and the plurality of peptides can be performed.

In some embodiments, the methods of the invention further comprise determining at least one peptide motif from the members of the plurality of peptides identified in c) above. The determining may comprise aligning sequences of the members of the plurality of peptides identified in c) above. The aligning may comprise using a computational alignment algorithm. Such algorithms are known in the art or provided herein. For example, the MEME program may be used as described further below.

In an aspect, the invention provides a method of identifying at least one peptide indicative of a phenotype in a biological sample comprising: a) identifying a plurality of peptides in the biological sample according to the method of the invention as described above; b) comparing the presence or level of members of the plurality of peptides identified in (a) to a reference value; and c) identifying a peptide with a presence or level that differs from the reference based on the comparison in b), thereby identifying the at least peptide indicative of the phenotype. The reference value for each member of the plurality of peptides may comprise a presence or level of that member of the plurality of peptides in a control sample.

In another aspect, the invention provides a method of identifying at least one peptide motif indicative of a phenotype in a biological sample comprising: a) identifying at least one peptide motif in the biological sample according to the method of the invention as described above; b) comparing the presence or level of the at least one peptide motif identified in step a) to a reference value; and c) identifying at least one peptide motif with a presence or level that differs from the reference based on the comparison in b), thereby identifying the at least one peptide motif indicative of the phenotype. The reference value may comprise a presence or level of the same peptide motif in a control sample.

In still another aspect, the invention provides a method of characterizing a phenotype in a biological sample comprising: a) identifying a plurality of peptides in the biological sample according to the method of the invention as described above; b) comparing the presence or level of each member of the plurality of peptides identified in a) to a reference value; and c) identifying a peptide with a presence or level that differs from the reference based on the comparison in b), thereby characterizing the phenotype. The reference value for each member of the plurality of peptides may comprise a presence or level of that member of the plurality of peptides in a control sample. In an embodiment, the biological sample is from a subject and the method is used to characterize the phenotype in the subject.

In yet another aspect, the invention provides a method of characterizing a phenotype in a biological sample comprising: a) identifying at least one peptide motif in the biological sample according to the method of the invention as described above; b) comparing the presence or level of the at least one peptide motif identified in step a) to a reference value; and c) identifying at least one peptide motif with a presence or level that differs from the reference based on the comparison in b), thereby identifying the at least one peptide motif indicative of the phenotype. In an embodiment, the reference value comprises a presence or level of the same peptide motif in a control sample. In an embodiment, the biological sample is from a subject and the method is used to characterize the phenotype in the subject.

The control sample in the aspects above may have a different phenotype than the biological sample. One of skill will appreciate that the control sample can be chosen to facilitate identification of peptides indicative of a phenotype or useful for characterizing a phenotype. For example, if the phenotype of interest is a medical condition, the control may be a sample that does not have the same condition. Or if the phenotype of interest is a state of a medical condition, the control may be a sample that has a different state of the condition. As still another example, if the phenotype of interest is exposure to an environmental insult or pathogen, the control may be a sample that has not been exposed to the environmental insult or pathogen.

In some embodiments of the methods of the invention, the phenotype comprises a medical condition, e.g., a disease or disorder. The characterizing may comprise a diagnosis, prognosis or theranosis of the disease or disorder. The characterizing may comprise determining a stage, grade, progression, severity, treatment regimen likely to be beneficial or not, and/or treatment response of the disease or disorder.

The disease or disorder can be any disease or disorder having an immune component. For the example, the disease or disorder may comprise an infectious, autoimmune, parasitic, allergic, oncological, neurological, cardiovascular, pregnancy-related or endocrine disease or disorder. In some embodiments, the disease or disorder comprises an infectious disease or an autoimmune disease. The disease, disorder, or infection can be celiac disease (CD), Sjogren's Syndrome (SS), systemic lupus erythematosus (SLE), Epstein-Barr virus (EBV), rhinovirus, cytomegalovirus (CMV), *Streptococcus* sp., human immunodeficiency virus (HIV), *Haemophilus* influenza, *Borrelia burgdorferi, Babesia microti, Ehrlichia* sp., *Anaplasma* sp., *Trypanosoma cruzi, Leishmania* sp., *Taenia solium, Toxocara canis,* or *Toxoplasma gondii*. The disease or disorder may comprise a microbial infection, viral infection, bacterial infection, protozoan infection, parasitic infection, or fungal infection.

In one embodiment, the disease or disorder comprises celiac disease (CD) and the at least one peptide motif is selected from QXXXPF[PS]E (SEQ ID NO: 6), PFSEM (SEQ ID NO: 7), PFSEX[FW] (SEQ ID NO: 8), QPXXPFX[ED] (SEQ ID NO: 4) or combinations thereof.

In another embodiment, the disease or disorder comprises Chagas disease and the at least one peptide motif is selected from Table. 1

In another embodiment, the disease or disorder comprises Lyme disease and the at least one peptide motif is selected from Table 2.

In another embodiment, the disease or disorder comprises Toxoplasmosis and the at least one peptide motif is selected from Table 3.

In another embodiment, the disease or disorder comprises Cysticercosis and the at least one peptide motif is selected from Table 4.

In another embodiment, the disease or disorder comprises primary Epstein-Barr virus (EBV) infection (mononucleosis) and the at least one peptide motif is selected from Table 5.

In another embodiment, the disease or disorder comprises Zika virus infection and the at least one peptide motif is selected from Table 6 or Table 7.

In another embodiment, the disease or disorder comprises Human Immunodeficiency virus (HIV) infection and the at least one peptide motif is selected from Table 8.

In another embodiment, the disease or disorder comprises latent Epstein-Barr virus (EBV) infection and the at least one peptide motif is selected from Table 9.

In still another embodiment, the disease or disorder comprises rhinovirus and the at least one peptide motif is selected from Table 10.

In yet another embodiment, the disease or disorder comprises cytomegalovirus (CMV) and the at least one peptide motif is selected from Table 11.

In an embodiment, the disease or disorder comprises *Streptococcus* infection and the at least one peptide motif is selected from Table 12.

In an embodiment, the disease or disorder comprises *Leishmania* infection and the at least one peptide motif is selected from Table 13.

In an embodiment, the disease or disorder comprises *Babesia* infection and the at least one peptide motif is selected from Table 14.

In an embodiment, the disease or disorder comprises *Ehrlichia* infection and the at least one peptide motif is selected from Table 15.

In an embodiment, the disease or disorder comprises *Anaplasma* infection and the at least one peptide motif is selected from Table 16.

In an embodiment, the disease or disorder comprises *Toxocara canis* infection and the at least one peptide motif is selected from Table 17.

In another aspect, the invention provides a peptide comprising a sequence in any of Tables 1-18. In a related aspect, the method comprises a composition comprising at least one such peptide.

One of skill will appreciate that the methods of the invention can be used to assess peptides and/or motifs characteristic of multiple phenotypes in a single experiment or assay.

In an aspect, the invention provides the use of at least one reagent to carry out the method of the invention described herein. In a related aspect, the invention provides a kit comprising at least one reagent to carry out the method. The at least one reagent can be any useful reagent that can be used to carry out the subject methods. In some embodiments, the at least one reagent comprises at least one of: at least one peptide provided by the invention; a composition provided by the invention; a peptide library display system; an antibody binding agent; a primer set; or a depletion reagent. The peptide library display system may comprise an *E. coli* display system. In one embodiment, the peptide library display system comprises a naïve or random peptide library. Such a naïve library can be used to screen a sample for peptides, motifs and patterns. See, for example, FIG. 1 and related discussion. In other embodiments, the peptide library display system is configured to characterize a phenotype. See, e.g., FIG. 2A and FIG. 2B and related discussion.

Provided herein are methods for treating a disease in a subject in need thereof. In various embodiments, the methods include identifying a disease comprising identifying at least one peptide, at least one peptide motif or a combination of one or more peptides and peptide motifs indicative of a phenotype (for example, a disuse or disorder) in a biological sample by the methods described herein and treating the disease. In exemplary embodiments, treatments include but are not limited to administration of effective amounts of therapeutic agents, prescribing life style changes (such as dietary changes and/or exercise) or combinations thereof.

In exemplary embodiments, the diseases include but are not limited to an infectious, autoimmune, parasitic, allergic, oncological, neurological, cardiovascular, pregnancy-related or endocrine disease or disorder. In some embodiments, the disease or disorder comprises an infectious disease or an autoimmune disease. The disease, disorder, or infection can be celiac disease (CD), Sjogren's Syndrome (SS), systemic lupus erythematosus (SLE), Epstein-Barr virus (EBV), rhinovirus, cytomegalovirus (CMV), *Streptococcus* sp., human immunodeficiency virus (HIV), *Haemophilus* influenza, *Borrelia burgdorferi*, *Babesia micron*, *Ehrlichia* sp., *Anaplasma* sp., *Trypanosoma cruzi*, *Leishmania* sp., *Taenia solium, Toxocara canis*, or *Toxoplasma gondii*. The disease or disorder may comprise a microbial infection, viral infection, bacterial infection, protozoan infection, parasitic infection, or fungal infection. Treatments for each of the diseases and the effective amounts for the treatments will be apparent to a person of skill in the art.

In one embodiment, the disease is celiac disease and exemplary treatments include but are not limited to recommending gluten-free diet to the subject. Further treatments and effective dosages will be apparent to a person of skill in the art.

In another embodiment, the disease is Chagas disease and treatment include but are not limited to administering an effective amount of benznidazole, nifurtimox or combinations thereof. For heart-related complications of Chagas disease, treatments may include medications, a pacemaker or other devices to regulate your heart rhythm, surgery, or even a heart transplant. For digestive-related complications of Chagas disease, treatments may include diet modification, medications, corticosteroids or, in severe cases, surgery. Further treatments and effective dosages will be apparent to a person of skill in the art.

In a further embodiment the disease is Lyme disease. In some embodiments, the subject diagnosed with Lyme disease is treated with therapeutically effective amounts of appropriate antibiotics (for example, doxycycline, amoxicillin, or cefuroxime axetil). Patients with certain neurological or cardiac forms of Lyme disease may require intravenous treatment with drugs such as ceftriaxone or penicillin. Further treatments and effective dosages will be apparent to a person of skill in the art.

In an embodiment, the disease is *Toxoplasma gondii* infection. In some embodiments, the subjects diagnosed with *Toxoplasma gondii* are treated with pyrimethamine and sulfadiazine, plus folinic acid. Further treatments and effective dosages will be apparent to a person of skill in the art.

In one embodiment, the disease is a *Taenia solium* infection (Cysticercosis). In some embodiments, the subjects diagnosed with Cysticercosis are treated with praziquantel (Biltricide), niclosamide, albendazole (Albenza) or combinations thereof. Further treatments and effective dosages will be apparent to a person of skill in the art.

In another embodiment, the disease is mononucleosis by EBV infection. In some embodiments, treatments for mononucleosis by EBV infection include rest, fluid and anti-viral agents such including acyclovir, ganciclovir and/or foscarnet. Further treatments and effective dosages will be apparent to a person of skill in the art.

In an embodiment, the disease is a Zika virus infection. In exemplary embodiments, treatment for Zika virus infection includes rest and fluids and acetaminophen or paracetamol. Further treatments and effective dosages will be apparent to a person of skill in the art.

In one embodiment, the disease is an HIV infection. In exemplary embodiments, the treatment for HIV includes antiretroviral therapy. Further treatments and effective dosages will be apparent to a person of skill in the art.

In an embodiment, the disease is Sjogren's syndrome. In exemplary embodiments, the treatment for Sjogren's syndrome includes pilocarpine, cevimeline, NSAIDS, Hydroxychloroquine or combinations thereof. Further treatments and effective dosages will be apparent to a person of skill in the art.

In one embodiment, the disease is a Rhinovirus infection. In exemplary embodiments, the treatment for rhinovirus infections include rest, hydration, antihistamines, and nasal decongestants and in case of further bacterial infection, antibacterial agents. Further treatments and effective dosages will be apparent to a person of skill in the art.

In an embodiment, the disease is a Cytomegalovirus infection. In exemplary embodiments, treatments for Cytomegalovirus infections include valganciclovir ganciclovir foscarnet, cidofovir or maribavir. Further treatments and effective dosages will be apparent to a person of skill in the art.

In some embodiments, the disease is a bacterial infections (for example, *Streptococcus* sp. infection, *Borrelia* infection, *Ehrlichia* infection, *Anaplasma* infection, *Haemophilus* influenza infection or *Babesia* infection). In exemplary embodiments, treatment for bacterial infections include antibacterial agents such a antibiotics, cephalosporin antibiotics, macrolide antibiotics, penicillin antibiotics, quinolone antibiotics, sulphonamide antibiotics, tetracycline antibiotics or combinations thereof. Further treatments and effective dosages will be apparent to a person of skill in the art.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Exemplary embodiments are illustrated in referenced figures. It is intended that the embodiments and figures disclosed herein are to be considered illustrative rather than restrictive. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 also discloses SEQ ID NOS 877-894, respectively, in order of appearance.

FIG. 11B illustrates the utility of the absence of motif enrichment in a sample, that is specific for Epstein Barr virus infection. "RRPFF" is disclosed as SEQ ID NO: 937.

DETAILED DESCRIPTION OF THE INVENTION

Figure 1:
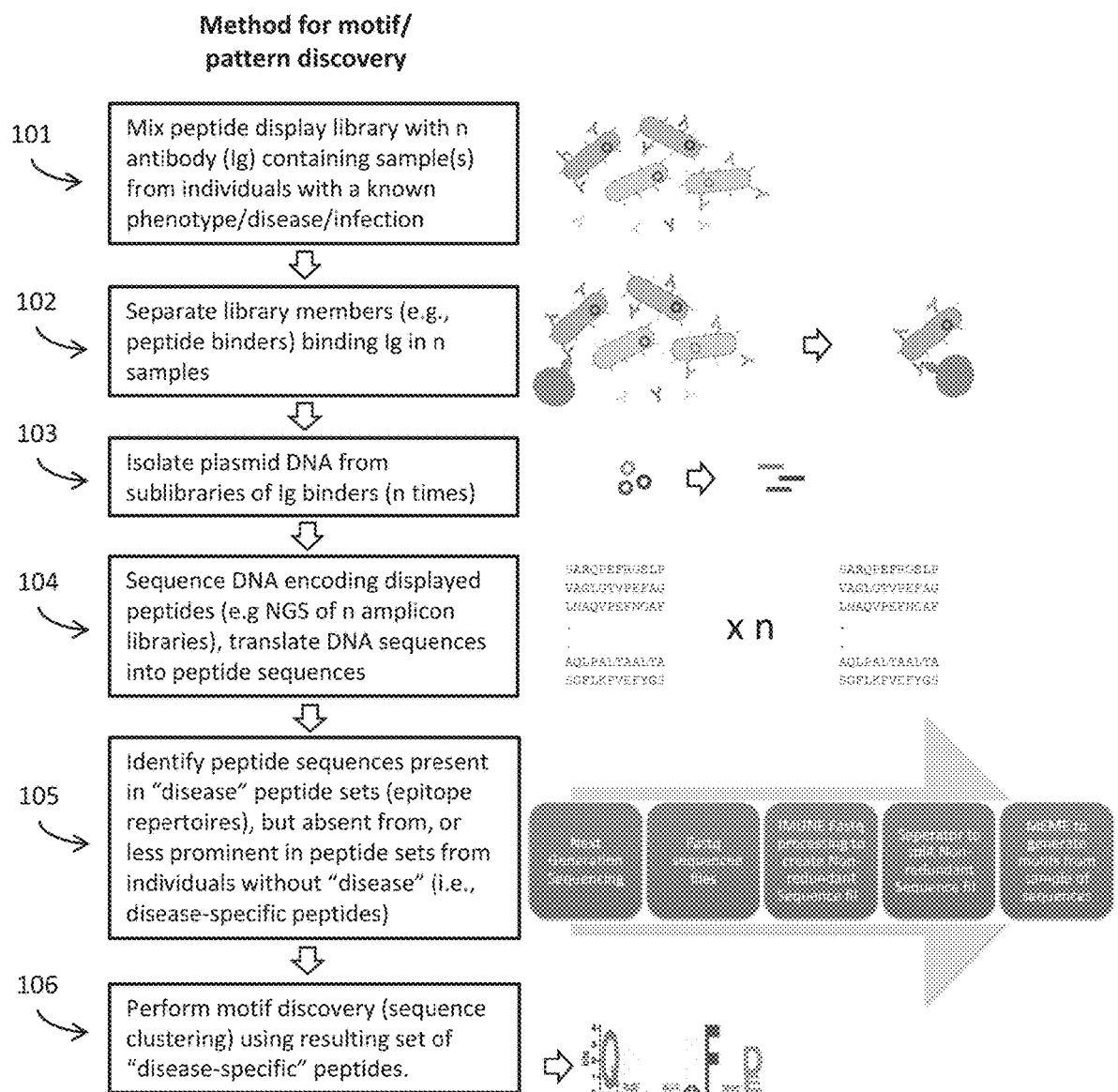
FIG. 1 illustrates an overview of a method of identifying in a sample, which can be used for peptide motif or pattern discovery (SEQ ID NOS 872-876 and 872-876, respectively, in order of columns, and QPXXPFX[ED] (SEQ ID NO: 4)).

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, NY 2006); Smith, March's Advanced Organic Chemistry Reactions, Mechanisms and Structure 7th ed., J. Wiley & Sons (New York, NY 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N Y 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor NY, 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The invention provides compositions and methods that can be used to detect the presence of an antibody specificity in a biological sample containing a mixture of antibodies. The method may comprise measuring the enrichment of specific peptide motifs in a set of thousands or more, e.g., at least $10^5$ peptides, that bind to antibodies present in the sample. The method of the invention may be referred to herein as "Display-seq."

As used herein, "specificity" can refer to an antibody species that binds to particular antigen, or a peptide motif, pattern, or sequence containing an antibody's preferred amino acid contact residues.

The invention further provides a method to discover amino acid sequence motifs ("motifs"), which, when enriched within a sample dataset, can be used to characterize a phenotype. As an example, the phenotype may be a disease or disorder and the characterization can include a diagnosis, prognosis or theranosis for the disease or disorder. In an embodiment, the method is used to detect a disease in an individual by determining motifs present in the individual. The invention enables the facile discovery of synthetic peptide compositions that enable detection of antibodies in a mixture.

The invention further provides amino acid sequence motifs and synthetic peptide compositions useful for detecting antigen-specific antibodies present within a sample. The presence of antigen specific antibodies can be indicative or diagnostic of disease or disorder, e.g., an infection. Thus, in various embodiments, the compositions and methods of the invention are used for diagnosing human disease, for assessing vaccine efficacy and safety, or for monitoring changes in immune status. The invention may overcome limitations of diagnostic methods utilizing isolated biochemical reagents. For example, the invention does not require experimental optimization of a single reagent, it allows for arbitrary combinations of motifs to be used to make diagnostic decisions, and it allows for measurement of a large number of motif enrichments with a single data set, thereby seamlessly integrating many different biological assays into one process.

The compositions and methods of the invention are described further below. Briefly, a random peptide library is co-incubated with a sample that contains a mixture of different antibodies. Peptide library members that capture antibodies are then recovered. The sequences of all peptides in the enriched library of binders are then determined, thereby providing a signature of antibody specificities in the sample. The peptide library may be displayed on the surface of a biological entity that comprises a nucleic acid sequence encoding the peptide. The identity of peptides that were bound by antibodies can be determined by sequencing the nucleic acids. In some embodiments, the sequencing comprises massively parallel DNA sequencing or next generation sequencing (NGS). Analysis of peptide signatures and antibody specificities in a sample can be used to characterize a phenotype, such as providing a diagnosis, prognosis or theranosis of a disease or disorder.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of progression, delay or slowing of progression or invasiveness, and amelioration or palliation of symptoms associated with the brain insulin resistance. Treatment also includes a decrease in mortality or an increase in the lifespan of a subject as compared to one not receiving the treatment.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder described herein. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

As used herein, the term "administering," refers to the placement an agent as disclosed herein into a subject by a method or route which results in at least partial localization of the agents at a desired site.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, -carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A protein refers to any of a class of nitrogenous organic compounds that consist of large molecules composed of one or more long chains of amino acids and are an essential part of all living organisms. A protein may contain various modifications to the amino acid structure such as disulfide bond formation, phosphorylations and glycosylations. A linear chain of amino acid residues may be called a "polypeptide." A protein contains at least one polypeptide. Short polypeptides, e.g., containing less than 20-30 residues, are sometimes referred to as "peptides." The terms protein, polypeptide and peptide may be used interchangeably herein to refer to molecules comprised of amino acid residues.

An antibody (Ab), also known as an immunoglobulin (Ig), is a large, Y-shape protein produced by plasma cells that is used by the immune system to identify and neutralize pathogens such as bacteria and viruses. The antibody recognizes a unique molecule of the agent, called an antigen, via the antibody's so-called variable region[11].

The term "autoantibody" as used herein refers to an antibody produced by the immune system in an organism in response to, and directed against, a constituent of its own tissues. Many autoimmune diseases and disorders, e.g., lupus erythematosus, celiac disease and type 1 diabetes, are caused by such autoantibodies wherein the immune system fails to properly distinguish between "self" and "non-self."

Figure 3:
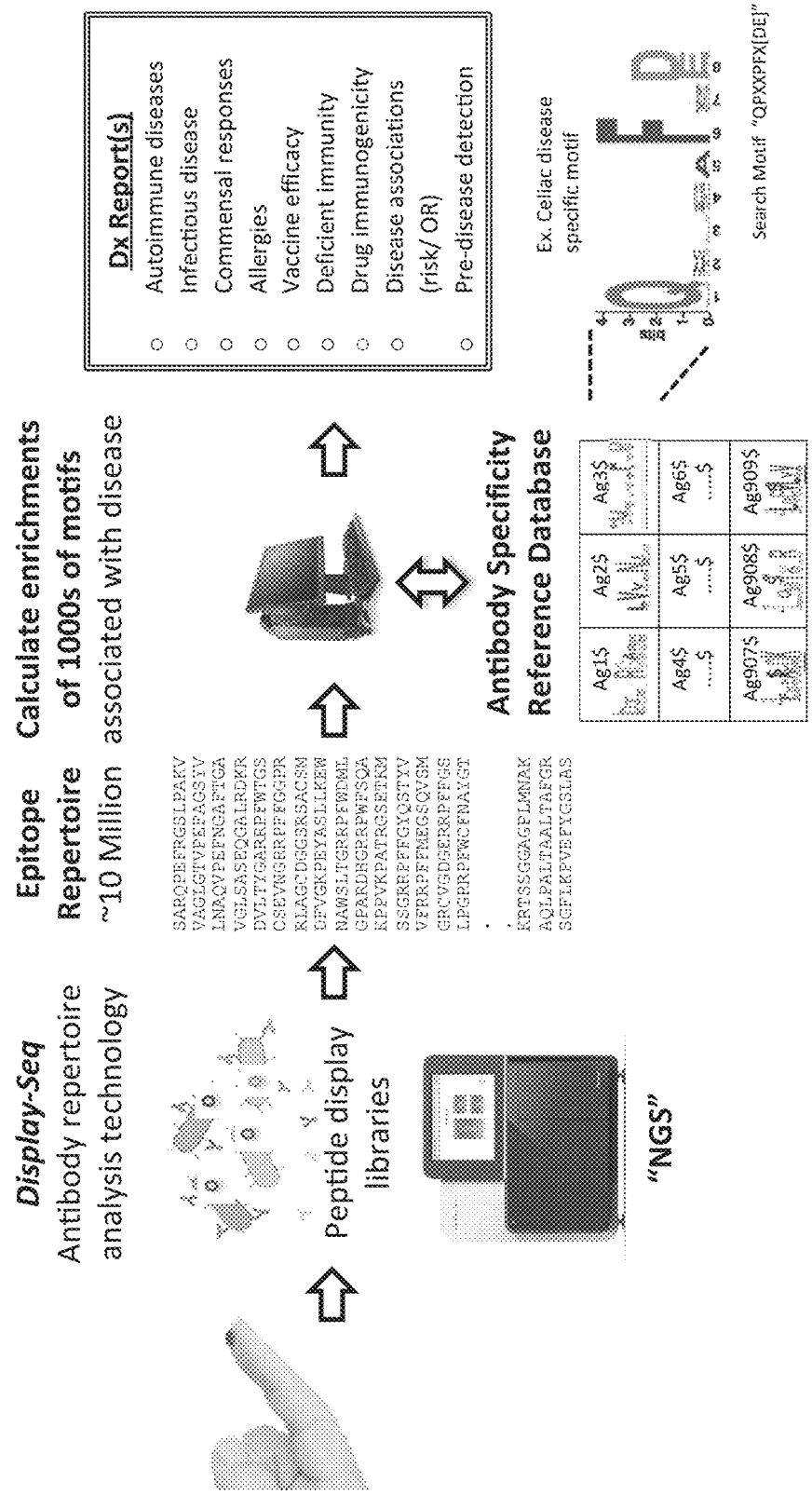
FIG. 3 illustrates a method of diagnosing a subject as having Celiac disease. The method includes i) enriching a collection of antibody binding peptides from a random peptide library of 6-60 amino acids for binding to a biological sample, ii) isolating plasmid DNA from the enriched library, iii) subjecting the amplicon library to sequencing (NGS), iii) counting the enrichment of a motif previously validated to be both sensitive and specific for celiac disease (e.g. QPXXPFX[DE] (SEQ ID NO: 4)), and comparing this enrichment to a reference value or threshold value.
Figure 4A:
FIG. 4A illustrates the method and workflow to develop multiplexed diagnostic motif panels (SEQ ID NOS 895-914, respectively, in order of appearance).
Figure 4B:
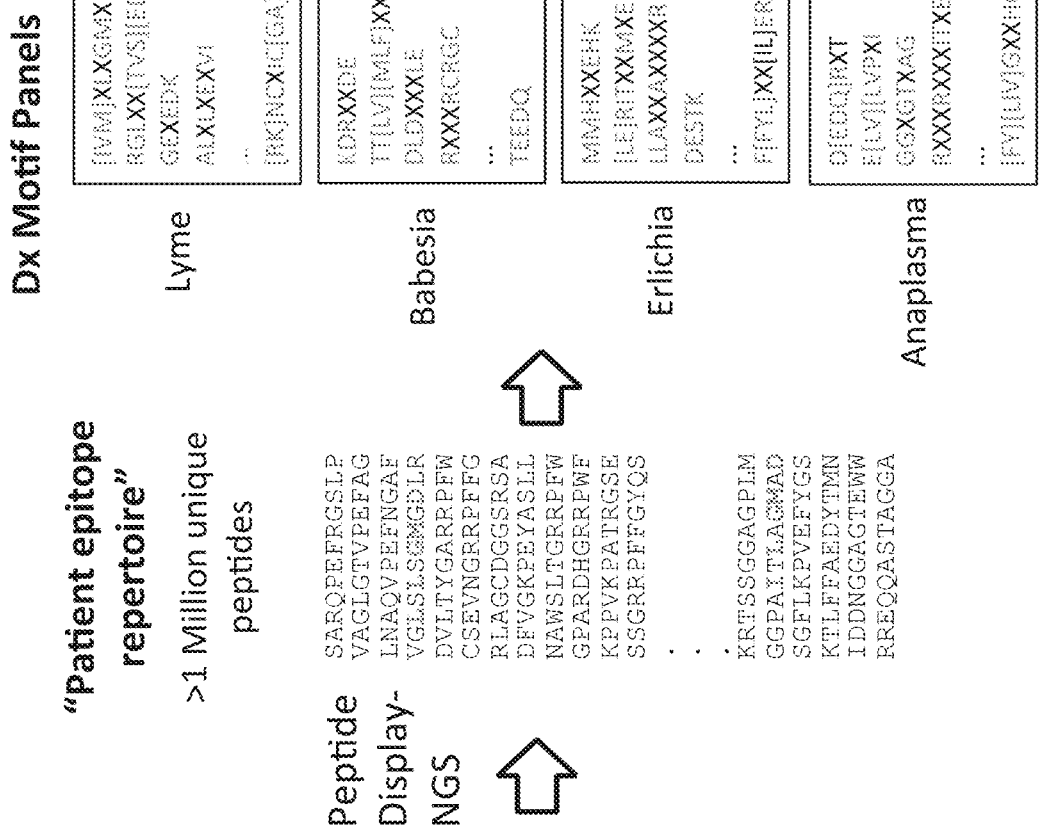
FIG. 4B illustrates the how multiple motif panels can be used to simultaneously diagnose multiple different diseases (SEQ ID NOS 872-874, 915-925, 876, 926-928, and 895-914, respectively, in order of columns).

The term "motif" as used herein comprises an amino acid sequence pattern, which comprises preferred amino acids at each position of a peptide sequence. For example, [DE]TX [FYL]K (SEQ ID NO: 1) where "X" is any amino acid and each letter corresponds to the conventional one-letter amino acid code. The notation [XYZ] within a motif means that the indicated position comprises one amino acid that is selected from "X or Y or Z". Motifs may alternatively be presented graphically as a sequence "logo," wherein the frequencies of occurrence of individual amino acids at each position in a motif are represented by the height of the character (e.g. one letter amino acid code) at that position. A larger letter indicates a higher frequency of occurrence. Examples are shown in FIG. 1 and FIG. 3 herein.

The term "pattern" refers to a sequence of amino acids, wherein the sequence may vary in length and may have intervening random amino acids. For example, DTXFK (SEQ ID NO: 2) and DXTXFXXK (SEQ ID NO: 3) are patterns.

The term "specificity repertoire" as used herein comprises the set of all binding specificities, (e.g. motifs, peptides, or patterns) comprised within an antibody repertoire.

The term "epitope" refers to the part of an antigen molecule/s to which an antibody attaches itself. For example, in the case of a protein antigen, the epitope can be the amino acid sequence or protein structural region to which an antibody binds.

The term "epitope repertoire" as used herein comprises the set of all antigens recognized, or bound by, by antibodies within a sample, or group of samples. For example, the epitope repertoire may refer to the set of all peptides or antigens recognized, or bound by, by antibodies within a sample, or group of samples.

The term "enrichment" as used herein refers to the number of observations of a peptide, pattern, or motif within an epitope repertoire divided by the number expected within a random dataset of equivalent size. For example, in a hypothetical 9-mer peptide library (-XXXXXXXXX-), where X is any amino acid, the pattern QPXXPFX[ED] (SEQ ID NO: 4) is expected to occur once in every 800,000 (($1aa/20aa$)$^4$×($2aa/20aa$)×2) random sequences (aa=amino acid). If 4 million sequences were determined, then one would expect to observe five (5) occurrences (i.e., once in every 800,000 sequences). As an example, if the pattern was actually observed in 50 unique peptides sequences (i.e. 50 observations) in an epitope repertoire, then the pattern would be "enriched" by 10-fold versus random.

The term "threshold" as used herein refers to the magnitude or intensity that must be exceeded for a certain reaction, phenomenon, result, or condition to occur or be considered relevant. For example, the threshold can be a numerical value above which enrichment is considered relevant. The relevance can depend on context, e.g., it may refer to a positive, reactive or statistically significant relevance.

The term "peptide display library" as used herein refers to any one of a family of methods wherein a sequence of amino acids is physically associated with a nucleic acid sequence that encodes that peptide. See [12].

The term "peptide signature" as used herein refers to the antigenic peptide repertoire detected in a sample. A peptide signature may comprise the enrichment of various peptides and/or common motifs observed in the sample The term "ELISA" as used herein refers to an enzyme-linked immunosorbent assay, which is a wet-lab test that uses antibodies and color change to identify a substance. Methods of performing ELISA assays are known to those of skill in the art. Typically, antigens from a sample are attached to a surface, such as the well of an ELISA plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate. The amount of color produced can correlate with the amount of antigen in the sample. The immunoassay format may be modified to use detection systems other than enzyme-mediated color change, e.g., radioactivity or fluorescence. The term "RIA" as used herein refers to a radioimmunoassay, "MIA" as used herein refers to a magneticimmunoassay, and "ECL" as used herein refers to enzymatic chemiluminescence.

The term "depleted sample" as used herein refers to specimen containing a mixture of antibodies wherein certain species of antibodies have been removed from the sample, for example by affinity capture. Depleted samples include those that have been incubated with a subset of the display library (e.g., phage/bacteria/yeast) to remove antibody species that bind to members of the library subset. The library subset could be a single clone that displays the scaffold used to present the peptide on the particle/cell surface or a mixture of two or more cell types that display different peptides that bind to antibodies of known specificity in the sample.

The term "computational depletion" as used herein refers to the removal of peptides from a set of peptides sequences that contain one or more specified motifs. For example, the motif QPXXPFX[DE] (SEQ ID NO: 4), as specified, would remove all instances of peptides in a large set of peptides that contain this motif, thereby computationally depleting the set of peptides carrying an instance of this motif. Many known or abundant motifs can be used to define a set of motifs for depletion. Depletion of common motifs has the effect of enriching rare motifs.

The term "clustering algorithm" as used herein refers to a computational algorithm used to perform "cluster analysis." Cluster analysis or clustering is the task of grouping a set of objects in such a way that objects in the same group (called a cluster) are more similar (in some sense or another) to each other than to those in other groups (clusters). A variety of clustering algorithms are known to those of skill in the art. See, e.g., [13-15].

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, e.g., 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a computational alignment algorithm. Such sequences are then said to be "substantially identical." For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A common example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990).

A "comparison window," as used herein, includes reference to a segment of any one of the number of contiguous positions may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

The term "triplet-phosphoramidite" refers to a synthetic molecule of deoxyribonucleic acid (DNA) composed of three nucleotide bases. See, e.g., (Onto A, 1995), (Kayushin et al., 1996).

The term "surface display" as used herein refers to the presentation of heterologous peptides and proteins on the outer surface of a biological particle such as living cell, virus, or bacteriophage. See [16].

The terms "body fluid" or "bodily fluids" are liquids originating from inside the bodies of organisms. Bodily fluids include amniotic fluid, aqueous humour, vitreous humour, bile, blood (e.g., serum), breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. Immunoglobulin G (IgG), the most abundant antibody subclass, may be found in all body fluids. "Biological sample" also includes a mixture of the above-mentioned body fluids. "Biological samples" may be untreated or pretreated (or pre-processed) biological samples.

The term "disease" refers to an abnormal condition affecting the body of an organism. The term "disorder" refers to a functional abnormality or disturbance. The terms disease or disorder are used interchangeably herein unless otherwise noted or clear given the context in which the term is used. The terms disease and disorder may also be referred to collectively as a "condition."

The term "phenotype" as used herein comprises the composite of an organism's observable characteristics or traits, such as its morphology, development, biochemical or physiological properties, phenology, behavior, and products of behavior.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a disease or disorder, or The term "prognosis," or "px," as used herein refers to predicting the likely outcome of a current standing. For example, a prognosis can include the expected duration and course of a disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

As used here, the terms "massively parallel signature sequencing" (MPSS) or "next generation sequencing" (NGS) and the like are used interchangeably to refer to high throughput nucleic acid sequencing (HTS) approaches. Platforms for NGS that rely on different sequencing technologies are commercially available from a number of vendors such as Pacific Biosciences, Ion Torrent from Thermo Fisher, 454 Life Sciences, Illumina, Inc. (e.g., MiSeq, NextSeq, HiSeq) and Oxford Nanopore. For review of NGS technologies, see, e.g., van Dijk E L et al. Ten years of next-generation sequencing technology. Trends Genet. 2014 September; 30(9):418-26.

General molecular biology terminology and techniques are known to those of skill in the art. See, e.g., Sambrook et al., Molecular Cloning: A Laboratory Manual, Cold Spring Harbor Press, N.Y., (3.sup.rd ed., 2000); and Brent et al., Current Protocols in Molecular Biology, John Wiley & Sons, Inc. (ringbou ed., 2003).

Phenotypes

As described herein, the compositions and methods of the invention may be used to characterize a phenotype in a sample of interest. The phenotype can be any phenotype of interest that may be characterized using the subject compositions and methods. Consider a non-limiting example wherein the phenotype comprises a disease or disorder. In such cases, the characterizing may be providing a diagnosis, prognosis or theranosis for the disease or disorder. In an illustrative embodiment, a sample from a subject is analyzed using the compositions and methods of the invention. The analysis is then used to predict or determine the presence, stage, grade, outcome, or likely therapeutic response of a disease or disorder in the subject. The analysis can also be used to assist in making such prediction or determination.

The repertoire of antibodies present in an organism can be indicative of various antigens that the organism has encountered. Such antigens may be derived from external insults, e.g., viral particles or microorganisms such as bacterial cells or fungi. External insults may also be allergens such as pollen or gluten, or environmental factors such as toxins. An organism may also generate antibodies specific to internal antigens. For example, autoimmune disorders are caused by the formation of antibodies that recognize antigens of the host organism. Autoantibodies to various cancer antigens have been observed. In sum, a host organism can comprise antibodies to numerous external and internal antigens indicative of a multitude of diseases, disorders and other environmental factors. Thus, the compositions and methods of the invention can be used to characterize any number of phenotypes in an organism, including without limitation determining environmental exposures and/or providing a diagnosis, prognosis or theranosis for various medical conditions. These conditions include without limitation infec- Method to Discover Epitopes and Motifs Recognized by a Mixture of Antibodies in a Sample The present invention enables the discovery and identification of amino acid sequence motifs and peptide epitopes that are bound by antibodies within a sample that contains a mixture of antibodies. Thus, the method can provide a peptide signature for the sample. In an embodiment, the sample comprises a bodily fluid as a source of the mixture of antibodies.

An outline of one embodiment of the method is shown in FIG. 1. A peptide library is contacted with a desired number (n) of antibody (Ig) containing sample(s) 101. Each member of the peptide library can be displayed on the surface of a host cell. The sample(s) can be from one or more individual with a known phenotype of interest, including without limitation a disease or infection. This can allow the identification of peptides in the individuals indicative of the phenotype. In a next step 102, library members binding Ig (e.g., peptide binders) in the n samples are separated from non-binders. In this step, the peptides which are bound by antibodies from the sample are identified. The identity of the bound peptides is determined by isolating DNA encoding each peptide from the separated sublibraries of Ig binders (n times) 103. The DNA can be within a vector, e.g., a plasmid, which encodes the peptide. The sequences of the DNAs encoding the displayed peptides (e.g NGS of n amplicon libraries) are translated into the encoded peptide sequences 104. This step thereby provides the peptide signature of the sample. As desired, the peptide sequences present in the peptide sets (epitope repertoires), but absent from, or less prominent in peptide sets from control samples are determined 105. As an example, the individual/s may have a certain disease whereas the control samples are from individuals without the disease. This arrangement may be used to identify disease-specific peptide sets. Further as desired, motif discovery (sequence clustering) is performed using resulting set of the peptides 106. Following the above example, these motifs may comprise disease specific motifs that can be used to characterize (e.g., provide a diagnosis, prognosis or theranosis) of the disease. The Examples herein provide a number of such motifs identified using the methods of the invention for various disease settings.

In an aspect, the invention provides a method of identifying a plurality of peptides, comprising: a) providing a biological sample comprising a plurality of antibodies; b) contacting the biological sample with a plurality of peptides; and c) identifying members of the plurality of peptides that form a complex members of the plurality of antibodies.

The biological sample may comprise a bodily fluid. Antibodies may be found in any bodily fluid. In some embodiments of the invention, the bodily fluid comprises peripheral blood, lymphatic fluid, sweat, saliva, mucus, or a derivative of any thereof.

In an embodiment, identifying members of the plurality of peptides that form a complex with members of the plurality of antibodies comprises sequencing a nucleic acid that encodes the peptide. Any useful sequencing method may be employed. For example, the sequencing may comprise next generation sequencing (NGS), Sanger sequencing, real-time PCR, or pyrosequencing. Next generation sequencing can allow screening a vast number of sequencing in a single experiment. The nucleic acid and peptide can be coupled, thereby allowing sequencing of the nucleic acid to be converted to the sequence of the peptide. Any useful DNA construct can be used. For example, the nucleic acid molecule may comprise deoxyribonucleic acid (DNA), ribonucleic acid (RNA), or a derivative of any thereof.

In some embodiments, each peptide is directly coupled to its corresponding nucleic acid molecule. For example, the nucleic acid may be bound to a protein complex that comprises the peptide, including without limitation a ribosome, mRNA, or DNA display system. In another embodiment, each peptide is indirectly coupled to its corresponding nucleic acid molecule. For example, the corresponding nucleic acid molecule may be contained within a vector that encodes the peptide. As desired, the vector may be configured to express the peptide. The vector can also be comprised in a host cell. In an embodiment, the host cell expresses the peptide. The peptide may be expressed on the surface of the host cell. Appropriate display systems are available in the art or are provided herein. For example, the host cell can be a microbial cell, a bacterial cell, an *E. coli* cell, a eukaryotic cell, a yeast cell, or a mammalian cell.

The method of the invention may further comprise capturing members of the plurality of peptides that form a complex with members of the plurality of antibodies prior to step c). In an embodiment, the capturing comprises capturing the peptide-bound members of the plurality of antibodies. The peptide-bound members of the plurality of antibodies may be captured to a substrate. Any useful substrate can be used. For example, the substrate can be a planar surface, e.g., a plate well, or a plurality of microbeads (also referred to as microparticles). The plurality of microbeads may be configured to facilitate capture as desired. For example, the microbeads may be magnetic or carry a label, including without limitation a fluorescent label. The bound members of the plurality of antibodies can be captured using a reagent that binds an antibody constant region. For example, the reagent can be Protein A, Protein G, Protein L and/or an anti-immunoglobulin antibody or aptamer. As desired, the reagent is coupled to the substrate, thereby allowing capture of peptide-bound antibodies to the substrate.

In some embodiments, the method of the invention further comprises filtering the plurality of antibodies prior to step b). The filtering may comprise contacting the plurality of antibodies with at least one reagent configured to deplete antibodies that bind to assay components other than the plurality of peptides. In an embodiment, the at least one reagent comprises a host cell as described herein, e.g., a host cell that is configured to display members of the plurality of peptides. The step allows removal of antibodies that bind to the host cell itself instead of members of the plurality of peptides.

In another embodiment, the method of the invention further comprises filtering the plurality of peptides prior to step b). The filtering of the plurality of peptides may comprise contacting the plurality of peptides with at least one reagent configured to deplete peptides that form a complex with assay components other than the plurality of antibodies. In an embodiment, the at least one reagent configured to deplete peptides comprises Protein A, Protein G, Protein L, and/or an anti-immunoglobulin antibody or aptamer.

As desired, filtering of both the plurality of antibodies and the plurality of peptides can be performed.

In some embodiments, the methods of the invention further comprise determining at least one peptide motif from the members of the plurality of peptides identified in c). The determining may comprise aligning the sequences of the members of the plurality of peptides identified in c). The aligning may comprise using a computational alignment algorithm. Such algorithms are known in the art or provided herein. For example, the MEME program may be used as described further below.

The following paragraphs provide an exemplary protocol when performing the methods of the invention using peptide libraries displayed on *E. coli* cells to identify antibody specificities in blood (serum) samples. One of skill will appreciate that these methods can use alternate display configurations and/or alternate sample sources. Various useful alternatives are described elsewhere herein. Certain steps would then be altered or perhaps skipped accordingly.

1) Serum depletion step: Antibodies in the starting sample that bind to assay components are first removed to favor recovery of antibodies which bind displayed peptides. For example, antibodies targeting *E. coli* cells can be removed by incubating serum with an *E. coli* strain expressing the library scaffold alone (i.e., no peptides). After the incubation, the bacteria along with any bound antibodies are removed using centrifugation and collection of the supernatant (unbound antibodies).

2) Library clearing step: The peptide display libraries can also be cleared of peptides that may form a complex with particular assay components. For example, peptide libraries can be cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

3) Antibody binding step: The serum and peptide display libraries are contacted to allow antibodies present in the serum sample to bind to peptides displayed on the *E. coli* cells. For example, the depleted serum sample can be incubated with Protein A and G cleared cells expressing the peptide library. Antibodies from serum bound to expressed peptides on the cells are harvested using centrifugation followed by washing to remove non-specific interactions.

4) Library enrichment step: The above step allowed formation of complexes between the antibodies and displayed peptides. These complexes are now recovered. Washed cells are then incubated with magnetic beads coated with protein A and protein G to capture antibodies from the serum, which will also capture the cells expressing peptides that are bound by antibodies. The beads are washed several times while magnetized to remove cells captured non-specifically.

6) Growth step: The final enriched display library (i.e., cells displaying peptides that remain bound to washed beads) is recovered. The cells can be resuspended in growth broth (e.g., LB) and allowed to replicate. Alternatively, one can proceed directly to step 9 or step 10a.

7) Repeat enrichment step: The above steps can be repeated as desired. For example, a second round can further enrich for peptide members of the library that interact with antibodies from serum and reduce non-specific binding cells that may have come through the first round of the screen.

8) Enrichment analysis step: After the one or more rounds of enrichment are completed, the final enriched library is analyzed to confirm and quantify binding of library members to patient serum antibodies (quality control for enrichment). Such analysis can use flow cytometry methodology (FACS).

9) DNA isolation from enriched library step: Each cell contains DNA encoding the peptide that cell displays on its surface. An *E. coli* cell may contain a plasmid vector encoding the peptide. The plasmid is isolated from the enriched library from each serum sample for preparation for sequencing analysis.

NGS technology can be used sequence large numbers of plasmid in a single reaction. Various platforms exist for NGS analysis. Below are alternative methods using the Illumina, Inc. or Life Technologies (Thermo Fisher) platforms. Unless otherwise specified herein, the methods of the invention may employ any appropriate NGS technology.

10a) Amplicon preparation step: (For sequencing using the Illumina platform—MySeq, NextSeq, HiSeq) The "region of interest" (random/peptide region from the library) is amplified using the plasmid as template with forward and reverse primers that flank the random region. The primers contain adaptors specific for use on the Illumina NextSeq. The PCR product is cleaned using magnetic beads that bind DNA and the resulting product is subjected to a second PCR using primers specific to the adaptors from the first PCR. The second PCR primers are provided by an Illumina (Nextra XT) indexing kit. The second PCR primers contain 8 nucleotide indices to provide a unique index combination specific to the amplicon from each sample for tracking of the sample during the sequencing.

10b) Amplicon preparation step: (For sequencing using the Ion platform (Life Technologies)—Personal Genome Machine, Proton) The "region of interest" (random/peptide region from the library) is amplified using the plasmid as template with forward and reverse primers that flank the random region. The primers contain adaptors specific for use on the Ion Proton along with a unique barcode for each sample that will be pooled for sequencing. The PCR product is cleaned using magnetic beads that bind DNA.

11) Amplicon quality control step: After cleaning the second PCR product, the purity is confirmed using gel electrophoresis or a Bioanalyzer 2100 and the quantity of the DNA is determined. Amplicons specific for the enriched libraries from all serum samples screened are normalized and pooled at equal molar concentrations for running on the sequencer.

12a) Sequencing step: The amplicon pool is run on the Illumina NGS instrument per instructions from the manufacturer. Using the NextSeq instrument, a 75 cycle high-output flow cell is used with single read and dual indexing settings. These specifications allow for approximately 400 million total sequences, are sequenced once in the "forward" direction for a length of 75 base pairs (fully covering the 12 amino acid random region in the library), and are also read for both 5 prime and 3 prime indices.

12b) The amplicon pool is run on the Ion Proton instrument per instructions from the manufacturer (Life Technologies).

13) Sequence de-multiplexing step: If required, the resulting sequences are de-multiplexed using the index codes to identify which serum samples the sequences originated from. Indexed sequences are sorted for each sample and subjected to bioinformatics analysis. This analysis may comprise identifying peptide sequences from their respective DNA sequences as determined above. Thus, the peptide signatures or epitope repertoires of the sample/s are determined.

A peptide display library is enriched for library members that bind antibodies within a sample. The library of peptides can be displayed on any useful biological entity, e.g., microbial cells such as bacteria, phage, synthetic beads, yeast cells, or ribosomes. The library may have a high diversity of more than $10^5$ unique library members, e.g., more than $10^6$, $10^7$, $10^8$, $10^9$, $10^{10}$, or more than $10^{11}$ members. Various peptide library compositions can be used including fully random peptide libraries of 3-30 random positions, or using libraries with one or more positions fixed to cysteine to favor the formation of disulfide bonds. Disulfide bonds may increase the affinity of some antibody binding peptide epitopes. Additionally, libraries derived from structural scaffolds can be used including for example, helix-turn-helix (i.e., alpha-alpha), beta-hairpins, alpha-beta, beta-alpha, beta-sheets, zinc fingers, or protein interaction modules including SH2, SH3, and other domains. In some embodiments, the length of random region is chosen to be 10-amino acids, e.g., 10, 11, 12, 13, 14, 15, 16, 17, 18, 19 or 20 amino acids. The random region can have more than 20 amino acids if desired. A peptide library may be configured to i) possess a minimum number of stop codons (that prevent peptide display), and ii) minimizes bias towards certain amino acids that are more abundant in libraries constructed using NNS or NNK codons. One method to accomplish this is prepare synthetic oligonucleotides for PCR reactions, using 20 triplet-phosphoramidites (DNA molecules composed of three bases) that uniquely encode one of the 20 amino acids. Preparation of such libraries is a method known to those skilled in the art of peptide and protein library construction. See, e.g., Directed Evolution Library Creation: Methods and Protocols (Methods in Molecular Biology) Softcover reprint of hardcover 1st ed. 2003 Edition by Frances H. Arnold (Editor), George Georgiou (Editor); ISBN-13: 978-1617374715.

In some embodiments of the invention, the sample to be analyzed is first depleted of antibodies that bind to the biological entity displaying the peptide (e.g., phage, bacteria, yeast, ribosomes, cells), by incubating a mixture of sample containing the antibodies with an excess of the biological entity that does not display a peptide. The entities bound to antibodies are then separated using centrifugation, filtration, sedimentation, or other separation method, and the unbound antibodies are recovered to generate a "depleted sample." The depleted sample is then mixed with, and allowed to contact the library to allow complexes to form between the antibodies and displayed peptides. The mixture can be allowed to incubate for any desired time, e.g., 1, 2, 3, 4, 5, 6, 7, 8, 9, 10 or more than 10 h. Antibodies that are not bound to library peptides are removed from the mixture, e.g., using centrifugation or sedimentation, and recovered antibody-peptide complexes are resuspended into a buffered salt solution. Library members with bound antibodies can be captured using Protein A and/or Protein G to bind to the constant regions of the peptide-bound antibodies, or with anti-human Ig antibodies. The Protein A, Protein G or anti-human antibodies can be bound to a substrate to facilitate capture. For example, the substrate can be a planar surface or bead. In an embodiment, the Protein A, Protein G or anti-human antibodies are coupled to magnetic beads. Labeled cells are then separated using magnetic separation or magnetic activated cell sorting (MACS), and recovered into growth media to amplify the population of selected cells. This process typically results an enrichment of antibody binders in the library from an initial frequency of 0.5-5% to about 50-60% binders. To increase the fraction of binders in the population, and the quality of useable data, the sorting process above can be repeated one or more times to increase the purity of binders within the enriched library, typically to >85%.

Sample preparation for sequencing: As described herein, the amino acid sequence of the bound peptides can be determined by sequencing DNA encoding the peptides. In an embodiment, the peptides are encoded on plasmid DNA comprised in a host cell. The plasmid DNA can be isolated from the cells and the sequence of the DNA encoding the peptides is determined. In some embodiments, the plasmids are used as a template for polymerase chain reaction PCR to create an amplicon library. As desired, each amplicon library enriched against a distinct sample can be given a unique nucleic acid sequence identifier or "bar code" embedded within the amplicon library. This step allows many amplicon libraries to be pooled together and analyzed in a single NGS run.

Sequencing of the samples is then performed. In some embodiments, NGS sequencing is used. The raw DNA sequences are translated into amino acid sequences. If necessary peptide variants arising from sequencing errors are identified as sequences exhibiting identity beyond what is statistically probable. For example, for a 12-mer random peptide library with 12 random amino acid positions, sequences having 10 or 11 identities are unlikely to be unique, since the library contains 10^10 members. The probability of finding two sequences with 10 identities in a library of this size constructed using triplet phorphoramidites is low.

In one embodiment of the invention, a listing of all unique peptides, along with the number of observations (counts) observed in each sample analyzed is generated. From this unique sequence listing, peptides occurring two or more samples obtained from individuals having a given phenotype are enumerated and motifs occurring in those peptides are identified using one or more established motif discovery algorithms, e.g., sequence clustering algorithms such as MEME, available at www.meme-suite.org [13-15]. This step identifies the commonalities between antibody specificities directed towards the same antigens from different individuals. One benefit of finding commonalities in a plurality of samples is that this may more accurately identify a specific motif that can be used to search the epitope repertoires from many different samples. And, the motif will more closely match the corresponding epitope sequence of the antigen that gave rise to the antibody.

The above approach has been applied to serum samples from healthy donors to identify hundreds of motifs. See the Examples herein for details.

For sequence clustering algorithms whose computation time scales as ~N^2, the number of sequences accessed can be reduced to facilitate efficient computations. For example, with current computing power, a size of about 5000 sequences may restrain computation time to a period of less than 12 hrs. However, greater computer power and efficiency and longer computer time can increase the number of sequences used for clustering along with quality and number of motifs generated.

Increasing the number of motifs by computational depletion. In order to identify a larger number of distinct antibody specificities within the epitope repertoire, peptides containing motifs constructed from the largest number of representative sequences (e.g. the motifs with the largest number of "sites" from MEME) are removed from a set of peptides most specific to a sample or set of samples. The set of peptides should be large enough that after performing computational depletion the file is approximately the same size as the file used for the first round of clustering. See, e.g., [13-15]. The resulting depleted file is then used for a new run of sequence clustering for motif discovery. The process can be iterated as desired to identify motifs corresponding to less abundant antibodies within the repertoire whose presence may be important for diagnosis. Computational depletion can identify new motifs, and improve the quality of motifs identified without depletion.

To identify common motifs within the NGS dataset of a single sample, the set of peptides that are present in the sample and also present in one or more other samples selected from a group of samples is determined. This reduced set of peptides can be analyzed using peptide sequence clustering algorithms.

Method to Discover Disease-Specific Epitopes and Motifs

In another embodiment of the invention a listing containing all unique peptides, along with the number of observations (counts) observed in each sample analyzed is generated. The listing is contained in a computer file. From this file, peptides that exhibit the highest specificity and sensitivity for the disease can be identified as those occurring in the largest number of samples from individuals with disease, but the smallest number of samples from individuals without disease. For example, if epitope repertoires are determined for 20 samples from individuals with disease and 20 from age and gender matched controls, then peptides present in more than 10 of 20 disease samples and in none of 20 controls samples (or e.g., <2/20 controls) can be used as input for motif discovery via clustering (e.g., MEME). All peptides present in 1-20 disease samples (e.g., 20/20, 19/20, 18/20/17/20, 16/20, 15/20, 14/20, 13/20, . . . 1/20 etc.) can analyzed by sequence clustering algorithms (e.g., MEME). For peptides present in exactly N samples out of a total of M samples, a threshold number of N can be determined such that the number of peptides within N/M samples can be analyzed using peptide sequence clustering algorithms.

Alternatively, individual peptides that occur in the largest number of disease samples and the fewest (or none) control samples can be aligned. In some embodiments, to identify diagnostic compositions, individual peptides exhibiting the highest disease sample specificity (present in the largest number of disease samples, and fewest control samples) are assayed for reactivity with new samples from individual samples with and without disease to validate their diagnostic utility, and estimate their diagnostic sensitivity and specificity.

To identify those motifs with the most utility for diagnostic use, the enrichment of individual motifs can be calculated in an arbitrary number of samples from healthy controls or other disease controls to identify motifs with the highest specificity. For example, if a motif appears in fewer than 5% of many samples from individuals without CD, or untested controls, but more than 10% of CD cases the significance of enrichment can be calculated using statistical methods to determine a p-value.

Calculating Enrichment

Figure 2A:
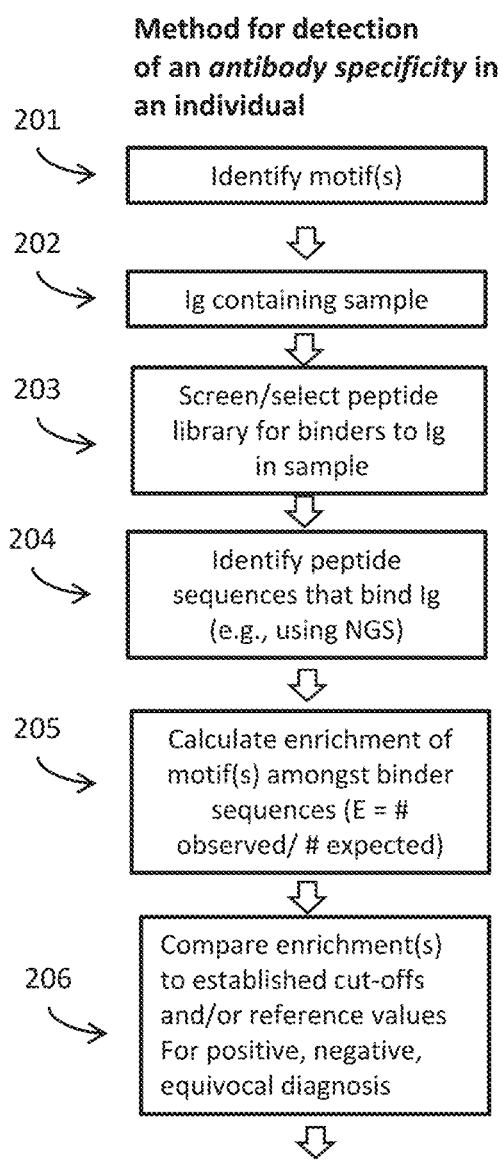
FIG. 2A illustrates an overview of a method of determining an antibody specificity in a subject or individual.

As described herein, the compositions and methods of the invention can be used for determining or measuring an antibody specificity in a sample by determining enrichment of antibodies against various peptide or peptide motifs of interest. An exemplary flow diagram is shown in FIG. 2A. Peptide signatures and/or motif(s) specific to a phenotype of interest are determined as described herein 201. See, e.g., FIG. 1 and related discussion above. A sample comprising antibodies (Ig) is collected from a subject 202. The sample is contacted with a peptide library as described herein and the library is screened for peptide binders to the antibodies in the sample 203. Peptide sequences that are bound by antibodies in the sample are determined as described herein, e.g., using NGS 204. The enrichment of given peptides is calculated amongst the determined peptide sequences 205. This step may also comprise determining peptide motif(s) present in the sample as described herein. The calculated enrichment(s) of the peptides and/or motifs of interest may be used for further analysis as desired, e.g., to compare to established thresholds in order to characterize the sample 216.

In order to detect a given antibody directed towards a predefined amino acid sequence, pattern, or motif, the number of sequence, patterns, or motifs occurring within a sample NGS dataset can be counted, motif enrichment can measured as the number of observations of that sequence/pattern/or motif divided by the number of instances expected by random chance. For example, if one million unique 12-mer peptide sequences from a library constructed using 20 triplet phosphoramidates (i.e., one codon per amino acid) were obtained for a sample, and the distribution of amino acids within the sample was assumed to be approximately random one would expect the pattern QPXXPF (SEQ ID NO: 5) to occur about $[(1/20)^4$ instances/frame$\times$(7 frames)$\times 10^6$=43.74 by random chance.

If the number of instances of this motif/pattern is larger than this number, e.g., 272, one can calculate the enrichment as 272/43.75=6.2-fold and the significance value for the level of enrichment observed can be calculated using an appropriate statistical test (e.g. t-test, z-test, U-test, rank-sum test, etc).

Characterization of Phenotypes

Figure 2B:
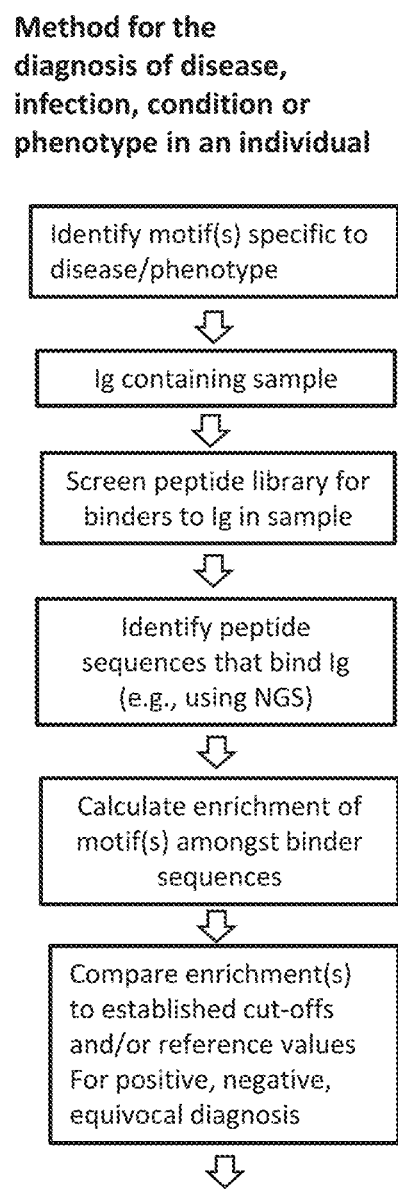
FIG. 2B illustrates an overview of a method of characterizing a phenotype in a subject or individual, e.g., to provide a diagnosis of a condition such as a disease or infection in the individual.

As described herein, the compositions and methods of the invention can be used for characterizing a phenotype of interest, e.g., to provide a diagnosis, prognosis, or theranosis of a condition such as an infection or autoimmune disorder. An exemplary flow diagram is shown in FIG. 2B, FIG. 3. Peptide signatures and/or motif(s) specific to a phenotype of interest are determined as described herein 211. See, e.g., FIG. 1 and related discussion herein. To characterize phenotype in a subject, e.g., a human subject having or suspected of having a medical condition, a sample comprising antibodies (Ig) is collected from the subject 212. The sample is contacted with a peptide library as described herein and the library is screened for binder to the antibodies in the sample 213. Peptide sequences that are bound by antibodies in the sample are determined as described herein, e.g., using NGS 214. The enrichment of given peptides is calculated amongst the determined peptide sequences 215. This step may also comprise determining peptide motif(s) present in the sample as described herein. The calculated enrichment(s) of the peptides and/or motifs of interest is compared to established thresholds 216. This comparison is used to characterize the phenotype, e.g., to provide a positive, negative or equivocal diagnosis of a condition.

The thresholds may be referred to herein as cut-offs, control values, reference values, or the like. One of skill will understand that the manner in which a threshold is calculated can depend on the phenotype and desired characteristics. For example, to determine an exposure to given entity, e.g., a pathogen, the threshold may be the expected random occurrence of the enrichment value (i.e., 1) or close to zero observations. In this setting, an enrichment greater than the threshold can indicate exposure to the entity. In other settings, the threshold may be the enrichment observed in one or more control sample. For example, if the phenotype to be characterized is a disease or disorder, the threshold may be the enrichment observed in a sample without the disease or disorder. In this setting, an enrichment greater than the threshold can indicate the presence of the disease or disorder. In some case, the degree of enrichment may provide further information, including without limitation the severity, stage, grade, or progression of the disease or disorder. One of skill will appreciate how to select an appropriate control given the desired phenotype to be characterized. One of skill will also appreciate that enrichment above or below the threshold may be relevant given a particular setting. A threshold value can be chosen to provide the desired balance between sensitivity and specificity, or according to other relevant statistical measures.

The following paragraphs provide an exemplary protocol when performing the methods of the invention using peptide libraries displayed on the surface of a display host. One of skill will appreciate that these methods can use alternate display configurations and/or alternate sample sources. Various useful alternatives are described elsewhere herein.

In an embodiment, a body fluid sample from an individual is collected. Antibodies that bind to the display library scaffold (bacteria, virus, phage, etc) are first depleted from the sample by contacting the specimen with the display host that does not express a member of the peptide library. Antibodies that do not bind to the host are recovered. In some embodiments of the invention, E. coli display technology is used. In such cases, the display scaffold eCPX can be expressed on the cell surface without an appended peptide sequence. An aliquot of cells is washed once, and resuspended in a pH buffered salt solution. The body fluid sample after these steps may be referred to herein as a "depleted sample."

The depleted sample is then incubated with the peptide display library under conditions that allow binding of antibodies in the sample with displayed peptides. Peptide library members that are bound to antibodies in the sample are separated. In some embodiments, separation is achieved using by capturing the antibody-peptide complexes to a substrate. The substrate can be coupled to one or more binding agent to the constant region of the antibodies in the sample, thereby facilitating capture. In some embodiments, the substrate comprises microparticles (beads) that are functionalized with a binding agent to antibodies, e.g., Protein A, Protein G, Protein L, or an Ig binding antibody. The microparticles may be magnetized to allow for capture using magnetic force. The process may be repeated as desired, e.g., to increase the purity of antibody binding library members.

From the enriched library, an amplicon library of the DNA encoding the members of the peptide library may be prepared for DNA sequencing. The determined DNA sequences are translated into peptide sequences according to typical genetic code, thereby providing a peptide signature for the sample. The number of instances of each unique peptide in the sample may then be counted. Enrichment of peptides and motifs can be calculated as desired. For example, the number of instances of each peptide, pattern, or motif is tabulated, and divided by the number predicted to occur by random chance according to established probability methods.

In some embodiments, the method is used to provide a diagnosis. A predetermined disease-specific peptide, pattern, or motif indicative of the disease can be determined using the methods herein. To diagnose a subject, the peptide signature for the sample from the subject is compared to a predetermined peptide signature of interest. If the enrichment of the appropriate peptide, pattern, or motif is increased beyond an established threshold, then the individual can be diagnosed with disease. An enrichment threshold can be appropriately determined by determination of the enrichments and their standard deviation within a set of samples from individuals that do not have disease and a separate set with disease (i.e. a reference set). A threshold value can be chosen to provide the desired balance between sensitivity and specificity.

The Examples herein provide a number of examples wherein the methods of the invention were used to determine peptide signatures for various disease settings. For instance, Example 1 provides an application of the methods of the invention to Celiac disease (CD). As further described in the Example, a disease specific motif was identified from a set of 16 CD samples and 13 healthy controls. For the motif QPXXPFX[ED] (SEQ ID NO: 4), a threshold enrichment value that maximizes specificity (100%) and sensitivity (95%) is enrichment >11. Accordingly, if a motif is observed in a test sample with an Enrichment value of 11 or more, the individual may be diagnosed with CD. Diagnostic sensitivity and specificity may be further improved by combining multiple motifs. A set or panel of four motifs (QXXXPF[PS]E (SEQ ID NO: 6), PFSEM (SEQ ID NO: 7), PFSEX[FW] (SEQ ID NO: 8), QPXXPFX[ED] (SEQ ID NO: 4) correctly identifies all disease and control samples in both discovery and validation datasets FIG. 5.

The accuracy of detection of an antibody specificity can be improved be increased by combining the enrichment values of two or more sequences, patterns, or motifs in a linear, non-linear, or weighted average.

Combining Diagnostic Assays into One Test

In an aspect, the present invention enables combination or aggregation of multiple assays into one multiplexed assay. The invention may achieve such multiplex analysis without additional labor or cost. Combining assays can be accomplished by performing searches of the peptide signature with two or more disease specific motif sets. For example, one can use the Celiac Disease specific peptides or motifs selected from QXXXPF[PS]E (SEQ ID NO: 6), PFSEM (SEQ ID NO: 7), PFSEX[FW] (SEQ ID NO: 8), QPXXPFX[ED] (SEQ ID NO: 4) alone or in combination with an arbitrary number of motifs or motif panels associated with other diseases. As a further example, the invention can be used to simultaneously assess a sample for infection with *Borrelia burgdorferi, Babesia* sp., *Anaplasma* sp., *Erlichia* sp, *Toxoplasma gondii, Toxocara canis, Taenia solium, Trypansoma cruzi*, HIV, Epstein-Barr virus infection, Zika virus infection and any other condition associated with an antibody response. In such cases, the enrichment of each the disease specific motifs for each disease can be calculated in same manner as for a single disease. An arbitrary number of enrichment calculations can be performed with a given sample. All enrichments that exceed diagnostic thresholds can then be used to make a diagnosis. Accordingly, the compositions and methods of the invention can be used to screen individuals for the presence of various conditions, such as autoimmune diseases and/or infectious agents, in a single assay.

Identification of Peptides, Patterns, and Motifs that Correspond to Known Individual Biomarkers The diagnosis of many individual autoimmune diseases is aided by separate individual tests or panels that detect the presence of common autoantibodies. For example, there are individual tests available for anti-nuclear antibody (ANA), Rheumatoid factor, anti-double stranded DNA antibody (anti-dsDNA), anti-citrullinated peptide (CP), anti-actin antibody, anti-neutrophil cytoplasmic antibody (ANCA) and others. The present invention provides a means to identify peptides, patterns, and motifs that indicate whether one or more of these common autoantibodies is present.

Briefly, one or more samples is analyzed by display-seq as described herein, with and without physical depletion of the target antibody species. For example, to identify motifs that correspond to the known antigen SS-A/Ro, or SS-B/La, a sample demonstrated to containing these antibodies is incubated with cells that display peptides containing putative known antigen motifs (e.g., motif presence is equivalent with SS-A positivity), to affect depletion of antibodies that bind to the known antigen. The original and the depleted samples can be assayed for the presence of antibodies that bind to the known target antigen. Cells displaying motifs that remove, attenuate, or reduce the antigen specific signal (e.g., Absorbance, light emitted, radioactivity, etc) indicate the motif that corresponds to the known antigen.

Identification of Peptides, Patterns, and Motifs that Indicate the Presence of an Autoimmune Disease Autoantibodies have been implicated in a variety of autoimmune diseases and disorders. The type of autoimmune condition and amount of injury to the host organism depend upon the systems and organs targeted by the autoantibodies. In some cases, autoimmune disorders are caused by autoantibodies that primarily affect a single organ and are relatively easier to diagnose and the signs and systems of disease are related to that organ. Examples include targeting of the thyroid in Graves disease or Hashimoto thyroiditis. However, other diseases and disorder may be caused by systemic autoantibodies that effect multiple systems and organs, making such conditions much harder to diagnose. Patients may present with non-specific symptoms such as joint pain, fatigue, fever, rash, cold symptoms, weight loss and muscular weakness. In addition, certain diseases, including Crohn's disease, Lupus, Sjogren's syndrome, and mixed connective tissue disease, are diagnosed using biomarkers that indicate a disease is present but do not identify which disease is present. Examples of such non-specific antibody biomarkers include nuclear antibody (ANA), rheumatoid factor, anti-actin antibody, anti-neutrophil cytoplasmic antibody (ANCA), anti-SS-A, and anti-SS-B. Even though diagnostics to detect these biomarkers may not identify specific disease, they are a useful aid to clinicians, suggesting that further testing and diagnostic work-up should be performed. Even so, some of these tests are cumbersome to perform, and lack quantitative precision, or require a pathologist to determine the staining pattern for example for ANA or ANCA tests.

The present invention provides a means to identify peptides motifs and patterns that indicate an autoimmune disease is present, providing quantitative objective rationale for further testing. The invention therefore provides meaningful benefits over the other above mentioned testing because the invention allows multiple tests to be performed quickly, automatically, and quantitatively for a given sample using the disease specific motifs.

Peptide Signatures and Motifs

The present invention provides compositions and methods to determine signatures of antigenic peptides in a sample comprising a plurality of antibodies. The methods of the invention further comprise determining peptide motifs from a peptide signature. Such peptide signatures and motifs can be used to characterize a phenotype in a sample, such as detecting the presence of a medical condition in order to provide a diagnosis. In some cases, the motifs determined by the subject methods may be correlated with various antigens involved in the disease process. For example, a motif determined by the subject methods may be correlated with a peptide from an allergenic protein or a self-antigen in case of autoimmune conditions.

In an aspect, the invention provides peptides and peptide motifs that are indicative of various conditions. Such peptides motifs are disclosed herein. For example, motifs indicative of various conditions are disclosed in the Examples.

In some embodiments, motifs that are indicative of mononucleosis by Epstein Barr Virus (EBV) infection are any one or more of LFGxx[LM]N(SEQ ID NO: 9); GELxGQ, (SEQ ID NO: 852); EWVxx[YF]D (SEQ ID NO: 10), P[LM]ALxL (SEQ ID NO: 11), KxNExWxV (SEQ ID NO: 12), P[AG]xRTxK (SEQ ID NO: 13), AYTxVN(SEQ ID NO: 14), WN[AS]YxxxN(SEQ ID NO: 15), [RKE]xxWxP[LM]Q (SEQ ID NO: 16), [AS]YxSx[SA][YF](SEQ ID NO: 17), ExYxSPS (SEQ ID NO: 18), MNIxDD (SEQ ID NO: 19), EH[ANK]FW (SEQ ID NO: 20), VHNAY(SEQ ID NO: 21), HG[EA]xLN(SEQ ID NO: 22), [GD]xx[LF]xxP[ML]Q (SEQ ID NO: 23), [LVMI]xNAx[TS][FGI](SEQ ID NO: 24), PxNSYT (SEQ ID NO: 25), RxxPLAxxL (SEQ ID NO: 26), CPKxNxT (SEQ ID NO: 27), Q[PA]H[AM]F (SEQ ID NO: 28), PAxENxxx[GSP] (SEQ ID NO: 29), NID[DE]D (SEQ ID NO: 30), RxQx[VS]D[NA] (SEQ ID NO: 31), Wx[DP]PxHL (SEQ ID NO: 32), TWA[FI][FI] (SEQ ID NO: 33), EDxGHP (SEQ ID NO: 34), [ETA]xxx[YF]xxP[SR]Q (SEQ ID NO: 35), GMxP[RK]Q (SEQ ID NO: 36), Wxx[VI]RxxPxQ (SEQ ID NO: 37), [NE][AG]Y[SAT]xxW (SEQ ID NO: 38), KxI[ST]xYW (SEQ ID NO: 39), YYxY-RxxK (SEQ ID NO: 40), KxHExG[FY] (SEQ ID NO: 41), [MLF]xNPQQ (SEQ ID NO: 853); HHFL[VI] (SEQ ID NO: 42), [LV]CNAY (SEQ ID NO: 43) or combinations thereof.

In some embodiments, peptides indicative of mononucleosis by EBV infection are any one or more of LFGanLN (SEQ ID NO: 44), PGpRTcK (SEQ ID NO: 45), PArRTrK (SEQ ID NO: 46), IaNAgSI (SEQ ID NO: 47), WaqIRhiPyQ (SEQ ID NO: 48) or MrNPQQ (SEQ ID NO: 49) or combinations thereof.

In some embodiments, motifs that are indicative of Rhinovirus infection are any one or more of L[EDQ]EV[LIV][IV][DE]K (SEQ ID NO: 50), E[VI][VIL][IV][DEN]K (SEQ ID NO: 51), E[VI][VI][VI]XK (SEQ ID NO: 52), VXPNI (SEQ ID NO: 53), VVPN (SEQ ID NO: 54), LXEVLVVVP (SEQ ID NO: 55), GPXHTXKV (SEQ ID NO: 56), EXY[VI]DX[VT]LN (SEQ ID NO: 57) or combinations thereof.

In some embodiments, peptides indicative of Rhinovirus infection are any one or more of ELEEV[IV]VDK (SEQ ID NO: 58), LNEVLVVVPNI (SEQ ID NO: 59), GPKHTQKV (SEQ ID NO: 60), EEYVDQVLN (SEQ ID NO: 61) or combinations thereof.

In some embodiments, motifs that are indicative of Cytomegalovirus infection are any one or more of KXDPDXXW[ST] (SEQ ID NO: 62) or KPXLGGK (SEQ ID NO: 63) or combinations thereof.

In some embodiments, peptides indicative of Cytomegalovirus infection include the set of peptides specified by K[[[YH]]]XDPD[[E]]X[[[SFL]]]XWT (SEQ ID NO: 64); (i.e. some positions vary between different strains of CMV), and KPtLGGK (SEQ ID NO: 65) or combinations thereof.

In some embodiments, motifs that are indicative of *Streptococcus* infection are any one or more of [IV]X[PR]QPEKP (SEQ ID NO: 66), KXDDMLN (SEQ ID NO: 67), KXDXMLN (SEQ ID NO: 68), LW]XSAEXEEK (SEQ ID NO: 69), SAEXEXK (SEQ ID NO: or combinations thereof.

In some embodiments, peptides that are indicative of *Streptococcus* infection are any one or more of VKPQPEKP (SEQ ID NO: 71), KTDDMLN (SEQ ID NO: 72), LESAE-KEEK (SEQ ID NO: 73) or combinations thereof.

In some embodiments, motifs that are indicative of *Toxoplasma gondii* infection are any one or more of HExE[FY]Q (SEQ ID NO: 74), LD[MLF]WxE (SEQ ID NO: 75), HCSAC (SEQ ID NO: 76), [FY]xGVVN (SEQ ID NO: 77), KxxxGRGxI (SEQ ID NO: 78), GPH[LA]E (SEQ ID NO: 79), PRREP (SEQ ID NO: 80), CNxxxECY (SEQ ID NO: 81), KxCQPxxC (SEQ ID NO: 82), PxPD[FH][TS] (SEQ ID NO: 83), NxxxExY[AG]xD (SEQ ID NO: 84), P[AG]AxxLD (SEQ ID NO: 85), MPSxSxE (SEQ ID NO: 86), [RK]xYxHR[TS] (SEQ ID NO: 87), K[PA]xFxFxK (SEQ ID NO: 88), DD[CST]xGxR (SEQ ID NO: 89), P[ML]xxHxMY (SEQ ID NO: 90), Kx[ASQ][SAT]xRG (SEQ ID NO: 91), [DG]QPEN (SEQ ID NO: 92), [KHR]N[QN]DG (SEQ ID NO: 93), Nx[EVS]GExY (SEQ ID NO: 94), EP[VI]TG (SEQ ID NO: HGM[PA][KR] (SEQ ID NO: 96), [VIT]PWIF (SEQ ID NO: 97), Kx[STN]VxFQ (SEQ ID NO: 98), [VAI]WSGS (SEQ ID NO: 99), FS[LIAM]xxWG (SEQ ID NO: 100), PTN[PQ]G (SEQ ID NO: 101), [RK]Kxx[YW]xHx[TS] (SEQ ID NO: 102), [HRW]xxHPRF (SEQ ID NO: 103) or combinations thereof.

In some embodiments, motifs that are indicative of *Trypansoma cruzi* infection (Chagas disease) are any one or more of [RK]MRxID (SEQ ID NO: 104), QHxGHP (SEQ ID NO: 105), KxxLPED (SEQ ID NO: 106), [IV]LxxFGY (SEQ ID NO: 107), PLDxxxxIS (SEQ ID NO: 108), ETXIPXE (SEQ ID NO: 109), [VI]Nx[DE][ML]YxP (SEQ ID NO: 110), FLxxIGA (SEQ ID NO: 111), D[VI]x[MI][ILV]x[KR] (SEQ ID NO: 112), RxSPYx[IL]F (SEQ ID NO: 113), VGPRH (SEQ ID NO: 114), PQxQH[ED] (SEQ ID NO: 115), PxxGGFG (SEQ ID NO: 116), KxEGxxMG (SEQ ID NO: 117), KxxGxTxxLS (SEQ ID NO: 118), EMG[FW]Q (SEQ ID NO: 119), [VI]KxGxxDxP (SEQ ID NO: 120), PE[DN]ExYP (SEQ ID NO: 121), HYEWA (SEQ ID NO: 122), [HR]SNMxF (SEQ ID NO: 123), M[TV]GxxYE (SEQ ID NO: 124), Dxx[KH]ExxLL (SEQ ID NO: 125), RxxWx[EDA]x[IV][AR] (SEQ ID NO: 126), PxDxxAx[GPA][TS] (SEQ ID NO: 127), PDxxSxT[ARG] (SEQ ID NO: 128), GRExDG (SEQ ID NO: 129), GVPGxxxK (SEQ ID NO: 130), [LM]xxx[EDQ]VxxIM (SEQ ID NO: 131), SxxxVSGG (SEQ ID NO: 132), A[KR]AG[DN]K (SEQ ID NO: 133), F[RN]xIN[RQ] (SEQ ID NO: 134), YXPVXPXSY (SEQ ID NO: 135), KxTFPD (SEQ ID NO: 136), PFM[FVM]xxR (SEQ ID NO: 137), EFWEP (SEQ ID NO: 138), [FY]GALS (SEQ ID NO: 139), PxGTEN (SEQ ID NO: 140), Gx[KE]PWE (SEQ ID NO: 141), D[IV]Tx[YF][WN] (SEQ ID NO: 142) or combinations thereof.

In some embodiments, peptides are indicative of *Trypansoma cruzi* infection (Chagas disease) are any one or more of QHKGHP (SEQ ID NO: 143), QHIGHP (SEQ ID NO: 144), KaILPED (SEQ ID NO: 145), KkhLPED (SEQ ID NO: 146), KitLPED (SEQ ID NO: 147), KtiLPED (SEQ ID NO: 148), KvILPED (SEQ ID NO: 149), VLkkFGY (SEQ ID NO: 150), VLhlFGY (SEQ ID NO: 151), VLgeFGY (SEQ ID NO: 152), VLepFGY (SEQ ID NO: 153), PLDvekeIS (SEQ ID NO: 154), PLDllkyIS (SEQ ID NO: 155), ETkIPSE (SEQ ID NO: 156), ETeIPsE (SEQ ID NO: 157), ETgIPfE (SEQ ID NO: 158), VNvDLYIP (SEQ ID NO: 159), FLgaIGA (SEQ ID NO: 160), FLlfIGA (SEQ ID NO: 161), FLkaIGA (SEQ ID NO: 162), DIKMIeR (SEQ ID NO: 163), DIiIVsR (SEQ ID NO: 164), DVhMLvR (SEQ ID NO: 165), DVdILeR(SEQ ID NO: 166), RvSPYsIF (SEQ ID NO: 167), VGPRH (SEQ ID NO: 168), PQKQHE (SEQ ID NO: 169), PQgQHD (SEQ ID NO: 170), KsEGefMG (SEQ ID NO: 171), KdEGlaMG (SEQ ID NO: 172), KdnGsTwsLS (SEQ ID NO: 173), KddGsTwaLS (SEQ ID NO: 174), IKqGrlDrP (SEQ ID NO: 175), HYEWA (SEQ ID NO: 176), MVGehYE (SEQ ID NO: 177), MVGkaYE (SEQ ID NO: 178), DqlKEgrlL (SEQ ID NO: 179), DvvKEImLL (SEQ ID NO: 180), DleKEneLL (SEQ ID NO: 181), Dld-KEvsLL (SEQ ID NO: 182), RhqWyAvVA (SEQ ID NO: 183), RhsWfDdVR (SEQ ID NO: 184), RkeWyDvVA (SEQ ID NO: 185), RdrWtEsIA (SEQ ID NO: 186), RatWIDqVR (SEQ ID NO: 187), RyvWnEwVA (SEQ ID NO: 188), PvDstAhGT (SEQ ID NO: 189), PlDcpAlGS (SEQ ID NO: 190), PaDssAhGT (SEQ ID NO: 191), PkDvkAtGS (SEQ ID NO: 192), PpDvsAsGT (SEQ ID NO: 193), PgDlpAkAT (SEQ ID NO: 194), PaDvsAqAT (SEQ ID NO: 195), PpDvpAsGT (SEQ ID NO: 196), PDpaSiTA (SEQ ID NO: 197), PDasSsTA (SEQ ID NO: 198), PDsrSiTA (SEQ ID NO: 199), PDsrSvTA (SEQ ID NO: 200), PDskSpTA (SEQ ID NO: 201), PDseSpTA (SEQ ID NO: 202), GRESDG (SEQ ID NO: 203), GREaDG (SEQ ID NO: 204), GVPGshaK (SEQ ID NO: 205), GVPGcviK (SEQ ID NO: 206), LsprEVytIM (SEQ ID NO: 207), LtntDVtrIM (SEQ ID NO: 208), LedeDVIqIM (SEQ ID NO: 209), MadpEVaaIM (SEQ ID NO: 210), SqadVSGG (SEQ ID NO: 211), SvgsVSGG (SEQ ID NO: 212), SpsgVSGG (SEQ ID NO: 213), SwfdVSGG (SEQ ID NO: 214), FRiINQ (SEQ ID NO: 215), FRaINR (SEQ ID NO: 216), KqTFPD (SEQ ID NO: 217), KaTFPD (SEQ ID NO: 218), PFMVqmR (SEQ ID NO: 219), FGALS (SEQ ID NO: 220), YGALS (SEQ ID NO: 221), PsGTEN (SEQ ID NO: 222), GfKPWE (SEQ ID NO: 223), DITdYN (SEQ ID NO: 224), DVTgFN (SEQ ID NO: 225) or combinations thereof.

In some embodiments, motifs that are indicative of *Taenia solium* (Cysticercosis) infection are any one or more of AxSPN[QEA] (SEQ ID NO: 226), [RP]xAxSxNx[IFMLV] (SEQ ID NO: 227), PDxGVxP (SEQ ID NO: 869); NxxLGL[VT] (SEQ ID NO: 228), [YF]x[DE]IxxFF (SEQ ID NO: 229), IxHFFxG (SEQ ID NO: 230), [ILM][ILM][RK]H[ED]XQ (SEQ ID NO: 231), [ILM][RK]HExQ (SEQ ID NO: 232), KPxx[IL]xLx[KR] (SEQ ID NO: 233), NxDxxYYxx[WF] (SEQ ID NO: 234), GLDGP (SEQ ID NO: 235), RSxHDxxN (SEQ ID NO: 236), FDxFN[IL] (SEQ ID NO: 237), TIFxGK (SEQ ID NO: 238), R[AV]xS[TQ]H (SEQ ID NO: 239), KWHGxY (SEQ ID NO: 240), MPEDK (SEQ ID NO: 241), Exxx[FY]x[AS]D[NT] (SEQ ID NO: 242), NQSxxKx[VI] (SEQ ID NO: 243), KxY[NAS]PY (SEQ ID NO: 244), [PQ][VL]HPRI (SEQ ID NO: 245), EDGMxxW (SEQ ID NO: 246), YASXQE (SEQ ID NO: 247), KQxQ[QK]E (SEQ ID NO: 248), K[AS]VFD[IVM] (SEQ ID NO: 249), PN[QE]x[DN]P (SEQ ID NO: 250), P[QA]XM[DN]I (SEQ ID NO: 251), [WR]x[RKH][ST]xFD (SEQ ID NO: 252), KxEPGxK (SEQ ID NO: 253), DDCLP (SEQ ID NO: 254), NXXXXGXHLE (SEQ ID NO: 255), DxxHLEG (SEQ ID NO: 256), RPxx[TS]HN (SEQ ID NO: 257), KxHS[IV]Y (SEQ ID NO: 258), KxHSx[IV]S (SEQ ID NO: 259), MSGYE (SEQ ID NO: 260), YXIWGP (SEQ ID NO: 261), RxxWxMN[RK] (SEQ ID NO: 262), QPxxT[FY]E (SEQ ID NO: 263), YGYNQ (SEQ ID NO: 264) or combinations thereof.

In some embodiments, peptides that are indicative of *Taenia solium* (Cysticercosis) infection are any one or more of ArSPN (SEQ ID NO: 265), AgSpNri (SEQ ID NO: 266), PDgGVmP (SEQ ID NO: 267), NpkLGLT (SEQ ID NO: 268) or combinations thereof.

In some embodiments, motifs that are indicative of latent Epstein-Barr virus (EBV) are any one or more of GRRPFF (SEQ ID NO: 269), GGGxGAGGG (SEQ ID NO: 270), EG[PA]ST[GA]R (SEQ ID NO: 271), KXXSC[IVL]GC[RK] (SEQ ID NO: 272), SCIGCK (SEQ ID NO: 273), CIGC (SEQ ID NO: 274), VxLPHW (SEQ ID NO: 275), LPHW (SEQ ID NO: 276), PQDT[GA]PR (SEQ ID NO: 277), GPPWWP (SEQ ID NO: 278), QQPTTXGW (SEQ ID NO: 279), [LMIV]FDXDWYP (SEQ ID NO: 280) or combinations thereof.

In some embodiments, peptides that are indicative of latent Epstein-Barr virus (EBV) are any one or more of GRRPFF (SEQ ID NO: 281), GGGAGAGGG (SEQ ID NO: 282), EGPSTGPR (SEQ ID NO: 283), KRPSCIGCK (SEQ ID NO: 284), KEVKLPHWTPT (SEQ ID NO: 285), PQDTAPR (SEQ ID NO: 286), GPPWWP (SEQ ID NO: 287), QQPTTEGH (SEQ ID NO: 288), LFPDDWYP (SEQ ID NO: 289) or combinations thereof.

In some embodiments, motifs that are indicative of HIV infection are any one or more of CxGxLIC(SEQ ID NO: 290), CxxKx[IV]C[IV] (SEQ ID NO: 291), W[GAS]CxGxxxC (SEQ ID NO: 292), [RK]KL[IV]E (SEQ ID NO: 293), KLIMT (SEQ ID NO: 294), [QE]xxPFRY (SEQ ID NO: 295), CxxKx[IV]C[IV] (SEQ ID NO: 296), [LF]xx[LIV][ND]KW (SEQ ID NO: 297), [AP][GC]GFG (SEQ ID NO: 298), LIx[TS]TY (SEQ ID NO: 299), [RK]KLxx[MV]Y (SEQ ID NO: 300), GF[GA][AQ][AYV] (SEQ ID NO: 301), GFG[RQ]x[FNY] (SEQ ID NO: 302), [KR]KxIH[VIM] (SEQ ID NO: 303), R[IV]PFG (SEQ ID NO: 304), KLIxx[TY]T (SEQ ID NO: 305) or combinations thereof.

In some embodiments, peptides that are indicative of HIV infection are any one or more of CSGKLIC (SEQ ID NO: 306), CSGKLICT (SEQ ID NO: 307), WGCSGKLIC (SEQ ID NO: 308), CSGKLICT (SEQ ID NO: 309), LLALDKW (SEQ ID NO: 310), AVGMG (SEQ ID NO: 311), LICTT (SEQ ID NO: 312), GFGAV (SEQ ID NO: 313), RKgIrI (SEQ ID NO: 314), KKgIaI (SEQ ID NO: 315), RKgI11M (SEQ ID NO: 316), RKsIIIM (SEQ ID NO: 317), KLICTT (SEQ ID NO: 318) or combinations thereof.

In some embodiments, IgG motifs that are indicative of a Zika virus infection are any one or more of VRxxYxQH (SEQ ID NO: 319), CEDxxxHxC (SEQ ID NO: 320), DAEQxxR (SEQ ID NO: 321), WPGIF (SEQ ID NO: 322), CCYDXE (SEQ ID NO: 323), LxPDNxT (SEQ ID NO: 324), FxWGQxY (SEQ ID NO: 325), KxEGHxxxxA (SEQ ID NO: 326), CxxGxCQxK (SEQ ID NO: 327), CCxDxx[DE][ED] (SEQ ID NO: 328), RNGxED (SEQ ID NO: 329), [DE]xRxIYxQ (SEQ ID NO: 330), WxRCGL (SEQ ID NO: 331), D[ED]xRxxYxxH (SEQ ID NO: 332), WCxLx[AV]N (SEQ ID NO: 333), LXTPWI (SEQ ID NO: 334), CWxxxGL[CA] (SEQ ID NO: 335), ID[AV]EP (SEQ ID NO: 336), HF[NK][VT]xK (SEQ ID NO: 337), QxNHQxK (SEQ ID NO: 338) or combinations thereof.

In some embodiments, IgM motifs that are indicative of a Zika virus infection are any one or more of FExKEP (SEQ ID NO: 339), [FYW]DA[VI] (SEQ ID NO: 340), DFDKR (SEQ ID NO: 341), WETC (SEQ ID NO: 342), KLDGP (SEQ ID NO: 343), WIYPxK (SEQ ID NO: 344), V[HS]DSK (SEQ ID NO: 345), EQCGT (SEQ ID NO: 346), [KE][MVIT]PYA (SEQ ID NO: 347), [DE]xxML[RP]W (SEQ ID NO: 348), YExLHx[FY] (SEQ ID NO: 349), WY[TSN]xEK (SEQ ID NO: 350), [YF]H[DNS]AV (SEQ ID NO: 351), DxTG[VI]P (SEQ ID NO: 352), FDxxGEH (SEQ ID NO: 353), QC[AK]xx[HE]C (SEQ ID NO: 354), LW[FY]xPxE (SEQ ID NO: 355), C[MI][PA]GxxC (SEQ ID NO: 356), Cxxxx[AVS]ADC(SEQ ID NO: 357), TTESxV (SEQ ID NO: 854), KDV[GA]E (SEQ ID NO: 855), KPxD[FWM]GxK (SEQ ID NO: 856), VxADGT (SEQ ID NO: 857), M[AP][AT]AD (SEQ ID NO: 858), VPxPK[DG](SEQ ID NO: 859), QxKP[TS]D (SEQ ID NO: 860), F[TS]xDGF (SEQ ID NO: 861), Wx[RK]VY[VA] (SEQ ID NO: 862), [CS]T[TS]Exxx[YF](SEQ ID NO: 863), YxETC[TI](SEQ ID NO: 864) or combinations thereof.

In some embodiments, motifs that are indicative of Borellia burdorferi infection (Lyme disease) are any one or more of VQQExxxxxP (SEQ ID NO: 358), QQEGxxxx[YC] (SEQ ID NO: 359), QEG[IV]Q (SEQ ID NO: 360), G[IV]QxEG (SEQ ID NO: 361), [LI]xxA[ILV]xxRG (SEQ ID NO: 362), [ATNSD]xxxxAl[LAM]xR (SEQ ID NO: 363), Ix[LM]xGFxK (SEQ ID NO: 364), LxGM[RQ]K (SEQ ID NO: 365), [HR]xDxTNxF (SEQ ID NO: 366), [DA]DPTN (SEQ ID NO: 367), [KR]x[DE]xTNxF (SEQ ID NO: 368), [ET][ML]HKF (SEQ ID NO: 369), [ML]xxEFHK (SEQ ID NO: 370), Q[TI]EQxxxxxK (SEQ ID NO: 371), DxSP[IL]E (SEQ ID NO: 372), PFx[AP]YxK (SEQ ID NO: 373), VxxYFxx[LV]xK (SEQ ID NO: 374), KxVDxDR (SEQ ID NO: 375), [DN][AS]A[AG]F (SEQ ID NO: 376), Cx[NA]xKFC (SEQ ID NO: 377), Kx[GRST]AE[YF] (SEQ ID NO: 378), HQV[PA]xxx[DHE] (SEQ ID NO: 379), IPxxV[IF]xxR (SEQ ID NO: 380), Cx[ALT]xWEx[CA] (SEQ ID NO: 381), CxxxCA[IL]xxR (SEQ ID NO: 382), I[IV]Ixx[MT]xK (SEQ ID NO: 383), QG[ITL]x[KN][FY] (SEQ ID NO: 384), KxxPPxIN (SEQ ID NO: 385), G[YF][FY]FxxK (SEQ ID NO: 386), DKNVx[IV] (SEQ ID NO: 387), [QE][KR][ND]xSG (SEQ ID NO: 388), K[RK]PGD (SEQ ID NO: 389), EGAxQP (SEQ ID NO: 390), GSPEY (SEQ ID NO: 391) or combinations thereof.

In some embodiments, peptides that are indicative of Borellia burdorferi infection (Lyme disease) are any one or more of VQQEgaqqqP (SEQ ID NO: 392), QEGVQ (SEQ ID NO: 393), GVQqEG (SEQ ID NO: 394), IlkAVveRG (SEQ ID NO: 395), IaaAIvIRG (SEQ ID NO: 396), DqiaaA-IAIR (SEQ ID NO: 397), AkkmrAILvR (SEQ ID NO: 398), AenhkAILfR (SEQ ID NO: 399), IkLpGFkK (SEQ ID NO: 400), IfLeGFIK (SEQ ID NO: 401), LrGMRK (SEQ ID NO: 402), DDPTN (SEQ ID NO: 403), KtDrTNdF (SEQ ID NO: 404), KdDpTNkF (SEQ ID NO: 405), KtDrTNdF (SEQ ID NO: 406), TLHKF (SEQ ID NO: 407), QTEQsststK (SEQ ID NO:408), DISPIE (SEQ ID NO: 409), PFSAYiK (SEQ ID NO: 410), VkdYFdsLaK (SEQ ID NO: 411), DAAAF (SEQ ID NO: 412), KfRAEF (SEQ ID NO: 413), KsSAEF (SEQ ID NO: 414), KgGAEF (SEQ ID NO: 415), IIIidTsK (SEQ ID NO: 416), IIIngMtK (SEQ ID NO: 417), IIItnMeK (SEQ ID NO: 418), QGIiNY (SEQ ID NO: 419), QGIcNY (SEQ ID NO: 420), KetPPaLN (SEQ ID NO: 421), GFYFifK (SEQ ID NO: 422), DKNVKI (SEQ ID NO: 423), EKNsSG (SEQ ID NO: 424), KKPGD (SEQ ID NO: 425), EGAqQP (SEQ ID NO: 426), GSPEY (SEQ ID NO: 427) or combinations thereof.

In some embodiments, peptides that are indicative of Toxoplasma gondii infection are any one or more of HEhEFQ (SEQ ID NO: 428), LDFWrE (SEQ ID NO: 429), LDFWqE (SEQ ID NO: 430), LDMWeE (SEQ ID NO: 431), HCSAC (SEQ ID NO: 432), FsGVVN (SEQ ID NO: 433), YpGVVN (SEQ ID NO: 434), KgshGRGfI (SEQ ID NO: 435), GPHAE (SEQ ID NO: 436), PRREP (SEQ ID NO: 437), PvPDFS (SEQ ID NO: 438), PvPDFT (SEQ ID NO: 439), PlPDFT (SEQ ID NO: 440), PlPDFS (SEQ ID NO: 441), PaPDFS (SEQ ID NO: 442), NaglEvYAeD (SEQ ID NO: 443), NrrrErYGeD (SEQ ID NO: 444), PGAvlLD (SEQ ID NO: 445), PAAskLD (SEQ ID NO: 446), PAAesLD (SEQ ID NO: 447), PGAarLD (SEQ ID NO: 448), PGAldLD (SEQ ID NO: 449), MPSwSnE (SEQ ID NO: 450), MPStSdE (SEQ ID NO: 451), MPSeStE (SEQ ID NO: 452), MPSaSpE (SEQ ID NO: 453), RIYvHRS (SEQ ID NO: 454), RIYrHRT (SEQ ID NO: 455), KgYfHRT (SEQ ID NO: 456), KPpFeFgK (SEQ ID NO: 457), KPgFvFlK (SEQ ID NO: 458), DDSeGaR (SEQ ID NO: 459), DDScGrR (SEQ ID NO: 460), DDSkGdR (SEQ ID NO: 461), DDSsGyR (SEQ ID NO: 462), KeAAgRG (SEQ ID NO: 463), KdASlRG (SEQ ID NO: 464), KgSSgRG (SEQ ID NO: 465), KtSSrRG (SEQ ID NO: 466), KtQTvRG (SEQ ID NO: 467), KrSTlRG (SEQ ID NO: 468), DQPEN (SEQ ID NO: 469), GQPEN (SEQ ID NO:

470), KNNDG (SEQ ID NO: 471), RNNDG (SEQ ID NO: 472), NlVGEeY (SEQ ID NO: 473), NdSGEiY (SEQ ID NO: 474), EPVTG (SEQ ID NO: 475), HGMPK (SEQ ID NO: 476), HGMAK (SEQ ID NO: 477), VPWIF (SEQ ID NO: 478), KsSVpFQ (SEQ ID NO: 479), KeTVnFQ (SEQ ID NO: 480), VWSGS (SEQ ID NO: 481), IWSGS (SEQ ID NO: 482), FSLenWG (SEQ ID NO: 483), FSMgrWG (SEQ ID NO: 484), FSLvlWG (SEQ ID NO: 485), FSLvlWG (SEQ ID NO: 486), FSLtnWG (SEQ ID NO: 487), PTNQG (SEQ ID NO: 488), PTNPG (SEQ ID NO: 489), RKlhWnHrT (SEQ ID NO: 490), KKyrYrHpT (SEQ ID NO: 491), RKavYqHnT (SEQ ID NO: 492), RtlHPRF (SEQ ID NO: 493), HfrHPRF (SEQ ID NO: 494), RvaHPRF (SEQ ID NO: 495), WqaHPRF (SEQ ID NO: 496) or combinations thereof.

In a related aspect, the invention provides peptide display libraries. The peptide library may comprise random peptide libraries that can be used to identity peptide signatures and motifs. See, e.g., FIG. 1. In other embodiments, the peptide library may be configured to detect previously identified peptide signatures and motifs. See, e.g., FIG. 2A and FIG. 2B. Such peptide libraries may comprise one or more of the motifs described in the paragraph above.

Kits

Various compositions and reagents useful for the invention described herein may be provided in kit format. A kit may include, for instance, some or all of the components necessary to carry out the assays described herein. For instance, the kit may comprise buffers, antibody capture reagents (e.g., microbeads coupled to Protein A, Protein G, Protein L, or other anti-Ig antibody or aptamers), enzymes (e.g., for amplification and/or sequencing of nucleic acids), instructions and any other necessary or useful components. The components of the kit may be provided in any suitable form, including frozen, lyophilized, or in a pharmaceutically acceptable buffer such as TBS or PBS. The kit may also include a solid support containing a peptide display library (e.g., microorganisms such as E. coli that express a random peptide library or a peptide library configured for characterizing a phenotype of interest) in any suitable form. The kits may also include other reagents and/or instructions for carrying out assays such as, for example, flow cytometric analysis, ELISA, immunoblotting (e.g., western blot), and sequencing. Kits may also include components such as containers (e.g., tubes) and/or slides pre-formatted to containing control samples and/or reagents with additional space (e.g., tubes, slides and/or space on a slide) for experimental samples. The kit may also comprise one or both of an apparatus for handling and/or storing the sample obtained from the individual and an apparatus for obtaining the sample from the individual (i.e., a needle, lancet, and collection tube or vessel).

EXAMPLES

Below we present examples of the method to identify motifs and peptides useful for the diagnosis of disease. The present method can be applied to any condition wherein an adaptive immune response occurs including infectious, autoimmune, parasitic, allergic, oncological, neurological, cardiovascular, and endocrine diseases and disorders.

Example 1: Celiac Disease—Discovery and Validation of Diagnostic Motifs and Peptides Celiac disease (CD) is characterized by autoimmunity to wheat, barley and rye cereal grain proteins, leading to antibody and T-cell mediated attack of the small intestinal epithelium, and damage to the villi. The resultant damage impairs adsorption of essential nutrients. Two distinct antibody specificities or types are individually diagnostic for the presence of CD. Celiac disease is diagnosed by the presence of IgA autoantibodies towards the human tissue transglutaminase antigen TG2, or alternatively by the presence of IgA and/or IgG antibodies towards deamidated gliadin peptide epitopes of wheat barley and rye proteins. Diagnostic criteria currently require small intestinal biopsy to confirm disease. The only available treatment is a strict gluten-free diet.

Patient Samples

A total of 32 celiac disease and 28 control serum samples (500 µl/sample) were analyzed. Patients were diagnosed with active celiac disease based on symptoms and gluten challenge testing, as well as using a positive result from 1 of the following criteria: 1) small intestinal biopsies with a Marsh 3a-3c histological lesion, and 2) seropositive for tissue transglutaminase 2 (TG2) and/or endomysial antigen (EMA) autoantibodies. Healthy individuals were asymptomatic for celiac disease and tested seronegative for TG2 and EMA autoantibodies. Deamidated gliadin peptide (dGP) ELISA was also performed for the control and disease samples.

Sample CD92 was diagnosed as non-celiac after screening was completed therefore this sample was removed from the CD sample cohort for downstream analysis. After performing discovery, CD88 was also diagnosed as non-celiac, and having been treated with olmesartan.

Serum samples were stored at −80° C. and aliquoted to reduce freeze/thaw cycles. On the day of use, 32 µL were thawed for dilution and remaining serum was marked and re-frozen for future use. Sixteen celiac disease (including CD88) and thirteen control sera were used as an initial discovery set. The validation set consisted of fifteen celiac disease samples and fifteen control samples (i.e., non-CD).

Experimental Protocol for Celiac Disease Biomarker Discovery

A summary of the general processing and sequencing methods used for the celiac and control serum samples are detailed as follows:

1) Serum depletion step: Antibodies targeting E. coli cells are removed by incubating serum diluted in PBS with an E. coli strain expressing the library scaffold alone. After an overnight incubation, the bacteria along with any bound antibodies are removed using centrifugation and collection of the supernatant (unbound antibodies).

2) Library clearing step: Peptide libraries are first cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

3) Antibody binding step: Collected (E. coli depleted) serum diluted in PBS is incubated with Protein A and G cleared cells expressing the peptide library. Antibodies from serum bound to expressed peptides on the cells are harvested using centrifugation followed by washing with PB ST to eliminate non-specific interactions.

4) Library enrichment step: Washed cells are then incubated with magnetic beads coated with protein A and protein G to capture antibodies from the serum along with the cells expressing peptides the antibodies are interacting with. The beads are washed 5 times with PBS while magnetized to remove cells captured non-specifically.

6) Growth step: The final enriched library (bound to washed beads) is resuspended in Luria broth (LB) and the captured cells are allowed to grow overnight for replication.

7) Repeat enrichment step: This serum antibody-library peptide enrichment step can be repeated a second time to further enrich for peptide members of the library that interact with antibodies from serum and reduce non-specific binding cells that may have come through the first round of the screen. However, a single enrichment step may be sufficient.

8) Enrichment analysis step: After the second enrichment is completed, the final enriched library is analyzed by FACS to confirm and quantify binding of library members to patient serum antibodies.

9) DNA isolation from enriched library step: Plasmid is isolated from the enriched library for each serum sample for preparation for deep sequencing analysis.

10) Amplicon preparation step: The region of interest (random/peptide region from the library) is amplified using the plasmid as template with forward and reverse primers that flank the random region. The primers contain adaptors specific for use on the Illumina NextSeq next-generation sequencing platform (Illumina, Inc, San Diego, CA). The PCR product is cleaned using magnetic beads that bind DNA and the resulting product is subjected to a second PCR using primers specific to the adaptors from the first PCR. The primers are provided by the Illumina Nextera XT indexing kit. The second PCR primers contain 8 nucleotide indices to provide a unique index combination specific to the amplicon from each sample for tracking of the sample during the sequencing.

11) Amplicon quality control step: After cleaning the second PCR product, the purity is confirmed using gel electrophoresis and the quantity of the DNA is determined. Amplicons specific for the enriched libraries from all serum samples screened are normalized and pooled at equal molar concentrations for running on the NextSeq instrument.

12) Sequencing step: The amplicon pool is run on the NextSeq instrument through a paid service following instructions from the manufacturer (Illumina). A 75 cycle high-output flow cell is used with single read ("forward" direction) and dual indexing (both 5 prime and 3 prime indices are sequenced). After sequencing is complete, the samples are automatically de-multiplexed using imputed sample identities with Nextera XT indices. These specifications allow for approximately 300 million total indexed sequences per run.

13) Sequence de-multiplexing step: Resulting sequences are de-multiplexed using the index codes to identify which serum samples the sequences originated from. Indexed sequences are sorted for each sample and subjected to bioinformatics analysis.

Sample Analysis Via Display-Seq.

Display-seq was used to identify millions of antibody-binding peptides per specimen as follows. A large high-quality 12-mer peptide library (diversity=$8\times10^9$), constructed using triplet-phosphoramidites to remove stop codons and normalize amino acid frequencies was used. The library is self-renewing, and ~100M unique peptides was determined to establish baseline statistics, thereby providing a long-term supply of stable, quantified diversity. Before peptide library selection, clinically characterized sera were depleted of E. coli binding antibodies using cells that display the scaffold without a peptide. Selections were performed as described [19, 20]. In brief, after library growth and induction of expression for display, antibody binding library members were enriched using two cycles of magnetic-activated cell sorting (MACS) to >85% pure binders as measured/confirmed using flow cytometry.

E. coli Specific Serum Antibody Depletion.

To remove E. coli binding antibodies from serum samples prior to library screening, an induced culture of cells expressing the library scaffold alone (eCPX) was incubated with diluted sera. Escherichia coli strain MC1061 [FaraΔ 139 D(ara-leu)7696 GalE15 GalK16 Δ (lac)X74 rpsL (StrR) hsdR2 (rK−mK+) mcrA mcrB1] was used with surface display vector pB33eCPX. eCPX cultures grown overnight at 37° C. with vigorous shaking (250 rpm) in LB (10 g tryptone, 5 g yeast extract, 10 g/L NaCl) supplemented with 34 µg/mL chloramphenicol (CM) and 0.2% glucose were collected by centrifugation, inoculated in fresh LB+CM, grown to an $OD_{600}$=0.6, and induced for 1 hr at 37° C. with 0.02% wt/vol L(+)-arabinose. After induction, the cells were centrifuged at 3,000 relative centrifugal force (rcf) for 5 min., washed once with cold PBST (PBS+0.1% Tween and resuspended in 1 mL PBS containing serum diluted 1:25 ($1\times10^6$ cells per µL depletion sample). Samples were incubated overnight at 4° C. with gentle mixing on an orbital shaker (20 rpm). Antibodies that bound to E. coli or the eCPX scaffold were removed by centrifugation of the incubated culture at 5,000 rcf for 5 min. twice, recovering the serum supernatant after each centrifugation. The depleted serum was stored at 4° C. for up to 2 weeks during use.

Bacterial Display Library Screening.

An X12 bacterial display library was used to screen and isolate peptide binders to antibodies in individual serum samples through two rounds of selection.

First Round Selection Using Magnetic Assisted Cell Sorting (MACS):

The first selection round employed MACS to enrich the library for antibody binding peptides. A frozen aliquot of the $X_{12}$ library containing $1\times10^{11}$ cells (10× the expected diversity) was thawed and inoculated into 500 mL LB+CM. After growth to an $OD_{600}$=0.6 at 37° C. with 250 rpm shaking, the cells were induced with 0.02% wt/vol L(+)-arabinose for 1 hour using the same growth conditions. Cells ($1\times10^{11}$ per sample) were collected by centrifugation (3,000×g for 10 min.) and resuspended in 1 mL cold PBS. Prior to incubation with serum, cells were cleared of peptide clones that bind proteins A/G by incubating cells with washed protein A/G magnetic beads (Pierce) at a ratio of one bead per 50 cells for 45 min. at 4° C. with gentle mixing. Magnetic separation for 5 min. (×2) was used to recover the unbound cells. Recovered cells from the supernatant were centrifuged, resuspended in 500 µL diluted sera (1:25 in PBS), and incubated for min. at 4° C. with gentle mixing. Following serum incubation, cells were washed by centrifugation, and resuspended in 1 mL cold PBST (×3). After the final resuspension, washed protein A/G magnetic beads were added at a ratio of one bead per 50 cells. After a 45 min. incubation with protein A/G beads at 4° C. with gently mixing, a second magnetic separation was performed to isolate cells expressing peptides that bind to serum antibodies. The supernatant (unbound cells) was discarded and the separated cells/beads were washed with 1 mL cold PBST. Five repeat washes were performed while the tube was being magnetized. After the last wash, the beads were resuspended in 1 mL of LB and inoculated into 25 mL LB+CM+glucose to suppress expression. The flask was grown overnight at 37° C. with shaking at 250 rpm. A 10 uL sample was removed prior to inoculation for dilution and plating on LB-agar to estimate the diversity of the enriched library.

Second Round Selection Using Magnetic Assisted Cell Sorting (MACS):

A second round of affinity selection was carried out using MACS to further enrich the library for antibody binding peptides. After overnight growth of the first round MACS enriched library, cells were inoculated (>20× estimated diversity) at 1:50 into 10 mL LB+CM and grown to an $OD_{600}$=0.6. After induction with arabinose for 1 hour, a volume of cells >20× the library diversity was centrifuged and resuspended in 100 □L cold PBST. Prior to incubation with serum, cells were cleared again of peptide clones that bind protein A/G by incubating cells with washed protein A/G magnetic beads (Pierce) at a ratio of one bead per cell for 45 min. at 4° C. with gentle mixing. After clearing the cells of protein A/G binding peptides, the library was incubated with 100 μL diluted sera (1:25 in PBS) for 45 min. at 4° C. Following serum incubation, cells were washed by centrifugation, and resuspended in 100 μL cold PBST (×3). After the final resuspension, washed protein A/G magnetic beads were added at a ratio of one bead per cell. After a 45 min. incubation with protein A/G beads at 4° C. with gently mixing, a second magnetic separation was performed to isolate cells expressing peptides that bind to serum antibodies. The supernatant (unbound cells) was discarded and the separated cells/beads were washed with 500 μL cold PBST. Five repeat washes were performed while the tube was being magnetized. After the last wash, the beads were resuspended in 1 mL of LB and inoculated into 10 mL LB+CM+glucose to suppress expression. The flask was grown overnight at 37° C. with shaking at 250 rpm. A 10 uL sample was removed prior to inoculation for dilution and plating on LB-agar to estimate the diversity of the enriched library.

Analysis of Enriched Library Using Fluorescence Activated Cell Sorting (FACS):

The following day, cells were analyzed for reactivity to the individual serum they were screened against to assess enrichment levels via FACS. After overnight growth of the MACS×2 enriched library (i.e., the library after the two rounds of MACS described above; "MACS X2"), cells were inoculated (>20× estimated diversity) at 1:50 into 5 mL LB+CM and grown to an $OD_{600}$=0.6. After induction with arabinose for 1 hour, a volume of cells >20× the library diversity was centrifuged and resuspended in 50 □L diluted sera (1:25 in PBS) for 45 min. at 4° C. Cells were washed as described in the second round enrichment section (100 uL PBST) and resuspended in □-IgA-PE diluted 1:200 in 100 □L cold PBS. Following a 45 min. incubation at 4° C., the cells were washed again and finally resuspended in 500 μL PBS for FACS sorting. Cells were analyzed for % of the cells with fluorescence signal greater than background (eCPX scaffold) by setting a gate to exclude 99% of the signal from serum incubated with cells containing eCPX scaffold lacking peptide (negative control). Libraries with ~80% or greater enrichment (percent of cells that are above background/percent of peptides that bind serum antibodies) were processed for deep sequencing analysis (next-generation sequencing; NGS).

Enrichment Analysis.

The majority of samples demonstrated >90% enrichment values (percent above background) with the lowest enrichment values at ~78%. In contrast, the background binding (eCPX scaffold percent above background) is minimal. The majority of the samples have background binding at <1% with the highest background at 3.4%. These data demonstrate the MACS X2 enrichment strategy effectively isolated a population of cells that express peptides that bind to serum antibodies and that this procedure collects minimal background (non-specific) binding cells.

Serum dilutions of 1:25 were used in this Example to maximize coverage of the repertoire (including lower titer antibodies), and to simultaneously minimize antibody-mediated cell death (e.g. due to residual complement activation), and non-specific binding. However, serum may be used at any appropriate dilution, including without dilution, as desired. Plasmid DNA was isolated from each enriched specimen-specific library, and used to generate bar-coded amplicon DNA libraries using a two-step PCR with the Illumina Nextera index kit. Amplicon preparations were cleaned using Ampure beads, diluted to a final concentration of 4 nM each for library pooling and sequenced on the Illumina NextSeq 500 1×75 high-output flow cell. To maximize the number of usable reads obtained, we used a i) forward primer in the first PCR step having five degenerate bases, and ii) using 30% spiked PhiX reference DNA. At least one reference specimen from one healthy individual was included in each NGS run to quantify run-to-run variability in read depth and quality, and longitudinal assay stability over 10 months.

Amplicon Preparation and Next Generation Sequencing on the Illumina Platform:

Amplicon Preparation: Cells grown overnight after the second round of MACS sorting were collected and plasmid was extracted using a plasmid miniprep kit (Qiagen). The random peptide region was amplified using a two-step PCR. For the first PCR step, the primers included adaptors specific to the Illumina platform with annealing regions that flank the random section (peptide library) of the eCPX scaffold (sequences indicated below):

Forward primer:
(SEQ ID NO: 870)
TCGTCGGCAGCGTCAGATGTGTATAAGAGACAGnnnnnCAGTCTGGCC
AGGG. Bold and underlined region is the annealing region. nnnnn is 5 random degenerate bases.

Reverse primer:
(SEQ ID NO: 871)
CCAGTACTACGGCATCACTGCTGTCTCTTATACACATCTCCGAGCCCAC
GAGAC. Bold and underlined region is the annealing region.

Products from the first PCR were purified after 25 rounds of PCR amplification (65° C. annealing temp) using Agencourt Ampure XP (Beckman Coulter) clean up beads. Resulting product was subjected to a second round of PCR using Illumina Nextera XT indexing primers. These primers provide unique 8 base pair indices on the 3 prime and 5 prime ends of the amplicons for tracking the sequences back to the sample used for screening and amplicon preparation. Amplicons were cleaned up as before after 12 rounds of PCR amplification (70° C. annealing temp). The final PCR product (amplicon) was analyzed using a DNA high sensitivity chip on a Bioanalyzer 2100 (Agilent) for purity, and DNA concentration was measured using DNA high sensitivity reagent on a Qbit instrument (Life Technologies). All samples were normalized to 4 nM and pooled together into a sequencing library.

Sequencing on Illumina NextSeq:

After quantification quality control of the pool was performed, the sample was diluted and loaded on to the NextSeq instrument. A 75 cycle high-output flow cell was used with single read (one direction) and dual indexing (both 5 prime and 3 prime indices are sequenced). After sequencing was complete, the samples were automatically de-multiplexed using imputed sample identities with Illumina Nextera XT indices.

NGS Quality Control

After construction, each amplicon was run on an agarose gel to confirm amplification of the correct product (254 bp) and absence of contaminating bands. Amplicons were quantified and pooled at a final concentration of 4 nM. The final amplicon pool was run on the bioanalyzer as a second quality control (QC) step to confirm the pool represented a single amplified band of the appropriate DNA size and concentration.

NGS Results

NGS results are summarized using data provided from Illumina BaseSpace software and from bioinformatics results using a computational algorithm for peptide motif discover in NGS datasets (hereafter referred to as "IMUNE"). The overall run summary indicates the "quality" of the full run in terms of number of sequences, the average number of sequences returned for each patient, and the standard deviation (SD) of the sequences for each patient. Low patient sequences (and total sequences) suggest potential problems with a sequencing run and may trigger repeat sequencing of that pool. A large SD for the sequences indicate poor pooling and may trigger a new quantification measurement and pool creation for a repeat sequencing run. Sequences that are read and assigned to a sample on BaseSpace must meet further quality control criteria for IMUNE. This is noted by comparing the total sequences given by BaseSpace to the total given by IMUNE for each sample. Consistently, ~94% of the indexed sequences for a given sample are recognized by IMUNE. The remaining sequences are often too short (<36 base pairs) to match correctly with an X12 peptide that is displayed. As a result, shorter sequences are filtered and not used for downstream motif analysis. At least 3 million total sequences were obtained from NGS for each CD specimen.

Bioinformatic Analysis

Identification of Celiac-Specific Motifs Using IMUNE Software

Motif discovery algorithms that utilize pairwise sequence comparisons are not amenable to large NGS datasets such as created by the Display-Seq discovery platform. For instance, motif discovery in 10,000 peptides using the MEME algorithm can require one week on a single processor, and computation time scales more than quadratically. To address this limitation, we developed a computational algorithm for Identification of Motifs Using Next-generation sequencing Experiments (IMUNE). IMUNE calculates the enrichments of all possible 4, 5, and 6 amino acid patterns (~8.5 billion) in a window of 10 positions, identifies patterns that are significantly enriched (p<0.001), and clusters these patterns using the PAM30 similarity scoring matrix to build motifs.

IMUNE was used to identify patterns and motifs specific to celiac samples in the discovery set. The discovered motifs were dominated by gliadin motif variants as these sequences were the most abundant in the celiac samples and absent in the control samples. The gliadin motif variants can be mapped to a single gliadin peptide QPEQPFPE (SEQ ID NO: 933). The 8-mer gliadin motif encompasses all the gliadin variant motifs obtained from bioinformatics analysis by sequence alignment and clustering.

Using either IMUNE or MEME 79 redundant motifs were discovered. The 79 redundant motifs associated with gliadin variants clustered into 4 motifs. Diagnostic motifs for Celiac Disease include namely QXXXPF[PS]E (SEQ ID NO: 6), PFSEM (SEQ ID NO: 7), PFSEX[FW] (SEQ ID NO: 8), QPXXPFX[ED] (SEQ ID NO: 4).

Motif Analysis in Validation Sample Set

Figure 5:
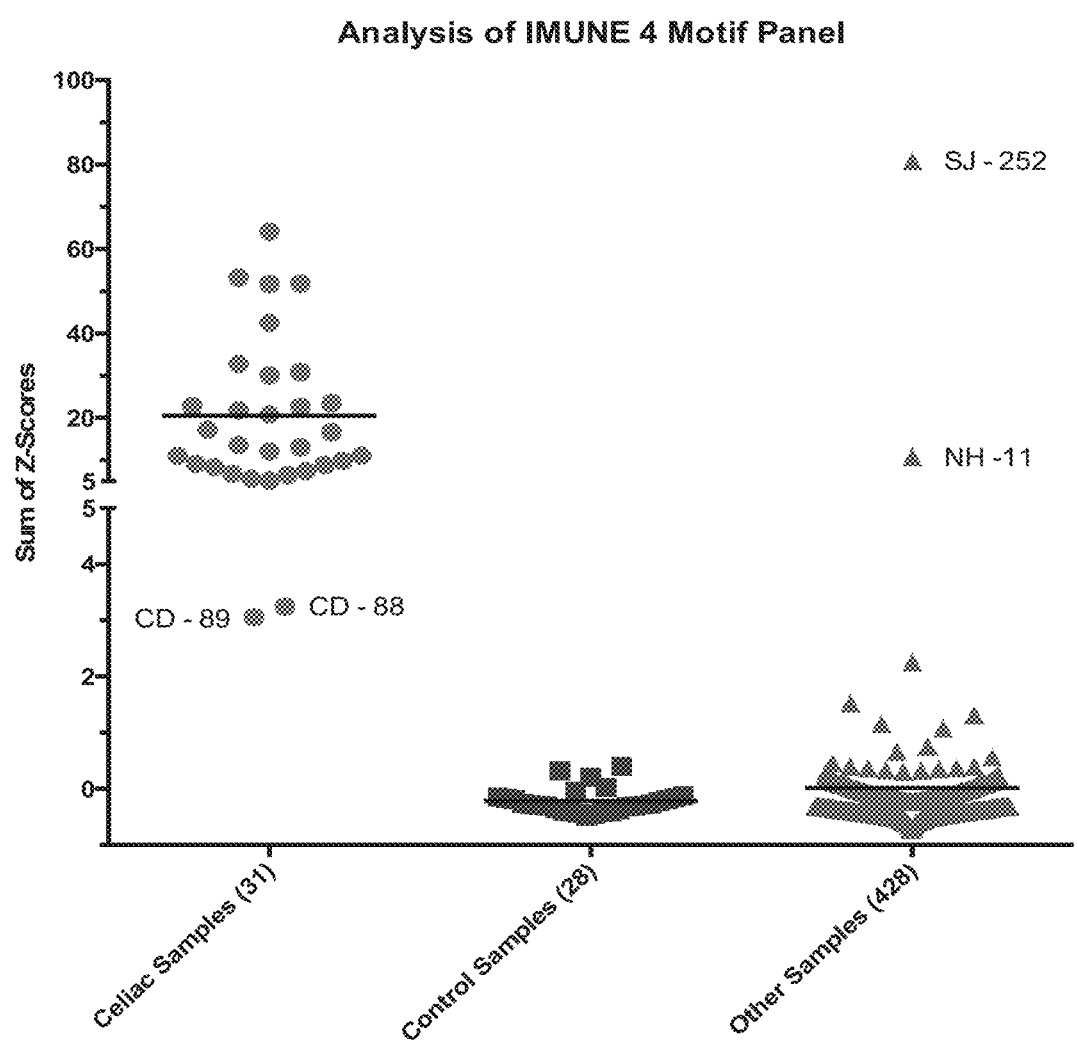
FIG. 5 illustrates the sum of z-scores (Standardized enrichment) for a four motif panel for Celiac disease discovery and validation samples.

The motifs discovered using the discovery set were further analyzed in the validation sample set. Enrichment values in the validation set for the motifs from IMUNE analysis are shown in FIG. 5. Of note, the panel of independent (non-gliadin) motifs performed poorly in the validation sample set while the gliadin variant motifs performed well.

IMUNE and MEME both identified gliadin variant motifs that were sensitive and specific in the validation sample set. The non-gliadin (additional) motifs from both IMUNE and MEME analysis failed to validate and are likely artifacts of common motifs that demonstrated enrichment in the discovery celiac samples.

Both IMUNE and MEME identified multiple motifs that were specific (i.e. occur in <1% of non-celiacs) and sensitive (i.e., in >95% of individuals with celiac disease) to celiac disease and that also correspond to a single gliadin motif.

In FIG. 5. enrichments for all samples were used to calculate z-scores for each motif in the 4-gliadin motif panel (a=IMUNE and b=MEME). Each z-score indicates the enrichment value minus the mean enrichment for all samples divided by the standard deviation of all samples. The summed z-scores are graphed comparing celiac samples to control and additional samples with datasets archived in HASRD. Note the IMUNE panel would correctly diagnose all celiac cases and the two additional samples while the MEME panel would misdiagnose two celiac samples and four additional samples. The celiac diagnostic panel generated by IMUNE was 100% sensitive (31 of 31 celiac samples are positive) with a specificity of at least 99.6% (2 of 456 control samples are positive). These two positive specimens may be from individuals with celiac disease.

Example 2. Discovery of Motifs Diagnostic of Chagas Disease

Chagas disease, also known as American trypanosomiasis, is a tropical parasitic disease caused by the protozoan *Trypanosoma cruzi* (*T. cruzi*). It is mainly spread by insects known as Triatominae, or kissing bugs, but may also be spread through blood transfusion, organ transplantation, contaminated food, and by vertical transmission from mother to fetus. Medication is effective if given early. However, most people infected with the disease do not realize they have the disease and treatment becomes less effective the longer a person has had Chagas disease. Untreated, Chagas can result in death.

Patient Samples

Serum samples (100 μl/sample) from 30 confirmed Chagas patients and 30 confirmed healthy donors were provided by the United States Center for Disease Control (CDC). Chagas diagnosis was made on the basis of two serological tests, the Wiener Chagatest ELISA and the CDC Laboratory Developed Test (LDT) TESA-Immunoblot. If both tests produced discrepancy, a third immunofluorescence assay was used as a tie-breaker test. Serum samples were stored at −80° C. upon receipt and thawed on the day of use.

Experimental Protocol for Chagas Disease Biomarker Discovery

Experiments were performed as described in Example 1.

Serum was diluted 1:25 in PBS at the *E. coli* depletion step and maintained at 4 Deg C. after depletion. For standard ecpx depletion, 1 mL each of *E. coli* cells induced to express ecpx 357 and 428 scaffolds (2 mL total) was used/ul of neat serum for depletion. Both MACS steps were performed at a 1:25 final serum dilution.

FACS Analysis of Enrichment of Chagas and Control Serum after MACS X2 for Discovery and Down Selection The effective removal of E. coli antibodies and the reactivity of each serum sample to its enriched library pool were analyzed by Flow cytometry as a quality control step in the screening process. Samples generally exhibit >75% reactivity of above background indicating that the libraries are highly enriched for patient specific peptides.

NGS Quality Control

Each amplicon was run on an agarose gel to confirm amplification of the correct product (254 bp) and absence of other bands representing non-specific PCR products. Amplicons were quantified and pooled at a final concentration of 4 nM each. The final amplicon pool was run on the bioanalyzer as a second QC step to confirm the pool represented a single amplified band of the appropriate amplicon concentration.

NGS Results

NGS raw sequence data from BaseSpace provides a breakdown of the total sequences obtained for each patient based on their unique barcode identifier. In the initial IMUNE processing step, sequences that met the quality criteria including: 1) upstream and downstream annealing regions contain <25% insertions, deletions and/or mutations, 2) the random region is of the expected length 3) no base throughout the read is unassigned (i.e. N). Unique reads are the number of sequences per patient after removal of duplicates, combination of similar sequences with few mutations (i.e. 3 or fewer) and removal of sequences that contain stop codons. The percentage of sequences that meet the above criteria relative to the total number of raw sequences is another measure of the quality of the NGS run. After processing, ~95% of the raw sequences from Basespace for each patient contain useable sequence information.

Bioinformatic Analysis

Disease specific motifs were identified using MEME and IMUNE as described in Example 1.

Preliminary IMUNE analysis of the discovery set epitope repertoires from 30 Chagas and 30 control sera discovered 1476 non-redundant motifs. Of those we considered the 200 motifs constructed using the largest number of contributing patterns. All of those motifs were specific and sensitive relative to the Chagas controls. We used HASRD (see Example 1) as a down-selection tool to identify motifs that were highly specific for Chagas based on their lack of enrichment in ~300 additional "control" samples. Additionally, we removed motifs that, while non-redundant were variations on the same epitope. This process revealed at least 39 distinct Chagas-specific motifs with varying sensitivities for Chagas disease in the discovery set Table 1.

TABLE 1

Motifs and peptides comprising panel for the diagnosis of Chagas panel

| ID | Panel motif | Antigen(s); peptide sequence(s) |
|---|---|---|
| 1 | [RK]MRxID (SEQ ID NO: 104) | |
| 2 | QHxGHP (SEQ ID NO: 105) | Glutathione peroxidase, 60S ribosomal protein L2; QHKGHP(SEQ ID NO: 143), QHIGHP(SEQ ID NO: 144) |
| 3 | KxxLPED (SEQ ID NO: 106) | Gim5A protein, Phosphatidylinositol kinase domain protein, Dynein intermediate chain, Trans-splicing factor, G-actin binding protein; KalLPED (SEQ ID NO: 145), KkhLPED (SEQ ID NO: 146), KitLPED (SEQ ID NO: 147), KtiLPED (SEQ ID NO: 148), KvILPED (SEQ ID NO: 149) |
| 4 | [IV]LxxFGY (SEQ ID NO: 107) | 60S ribosomal protein L13a, DNA polymerase, Alpha-adaptin, Mucin-associated surface protein (MASP); VLkkFGY (SEQ ID NO: 150), VLhIFGY (SEQ ID NO: 151), VLgeFGY (SEQ ID NO: 152), VLepFGY (SEQ ID NO: 153) |
| 5 | PLDxxxxIS (SEQ ID NO: 108) | Kinesin, Kinetoplast-associated protein Tcp22; PLDvekeIS (SEQ ID NO: 154), PLDIIkyIS (SEQ ID NO: 155) |
| 6 | ETXIPXE (SEQ ID NO: 109) | Complement regulatory protein, Trans-sialidase, FL-160-1 epitope, OSM3-like kinesin; ETKIPsE (SEQ ID NO: 156), ETelPsE (SEQ ID NO: 157), ETgIPfE (SEQ ID NO: 158) |
| 7 | [VI]Nx[DE][ML]YxP (SEQ ID NO: 110) | 40S ribosomal protein S21; VNvDLYiP (SEQ ID NO: 159) |
| 8 | FLxxIGA (SEQ ID NO: 111) | Flagellum-Associated Protein, Membrane protein, Dispersed gene family protein 1 (DGF-1), 60S ribosomal protein L14; FLgaIGA (SEQ ID NO: 160), FLIfIGA (SEQ ID NO: 161), FLkaIGA (SEQ ID NO: 162) |
| 9 | D[VI]x[MI][IL V]x[KR] (SEQ ID NO: 112) | UDP-GlcNAc:polypeptide N-acetylglucosaminyltransferase, Oculocerebrorenal Lowe syndrome protein, Dynein heavy chain, cytosolic, R27-2 protein, Myosin heavy chain; DIKMIeR (SEQ ID NO: 163), DIiIVsR (SEQ ID NO: 164), DVhMLvR (SEQ ID NO: 165), DVdILeR (SEQ ID NO: 166) |

TABLE 1-continued

Motifs and peptides comprising panel for the diagnosis of Chagas panel

| ID | Panel motif | Antigen(s); peptide sequence(s) |
|---|---|---|
| 10 | RxSPYx[IL]F (SEQ ID NO: 113) | Kinetoplast DNA-associated protein 3; RvSPYsIF (SEQ ID NO: 167) |
| 11 | VGPRH (SEQ ID NO: 114) | Microtubule associated protein homolog, Antigen DNA; VGPRH (SEQ ID NO: 168) |
| 12 | PQxQH[ED] (SEQ ID NO: 115) | Helicase, putative, Phosphatidylinositol 3-kinase; PQKQHE (SEQ ID NO: 169), PQgQHD (SEQ ID NO: 170) |
| 13 | PxxGGFG (SEQ ID NO: 116) | |
| 14 | KxEGxxMG (SEQ ID NO: 117) | 60S ribosomal protein L6, Adenosine 5'-monophosphoramidase; KsEGefMG (SEQ ID NO: 171), KdEGlaMG (SEQ ID NO: 172) |
| 15 | KxxGxTxxLS (SEQ ID NO: 118) | 85 kDa surface antigen, Trans-sialidase-like protein, Glycoprotein 82 kDa; KdnGsTwsLS (SEQ ID NO: 173), KddGsTwaLS (SEQ ID NO: 174) |
| 16 | EMG[FW]Q (SEQ ID NO: 119) | |
| 17 | [VI]KxGxxDxP (SEQ ID NO: 120) | ADP, ATP carrier protein 1, mitochondrial; IKqGrlDrP (SEQ ID NO: 175) |
| 18 | PE[DN]ExYP (SEQ ID NO: 121) | |
| 19 | HYEWA (SEQ ID NO: 122) | Lanosterol cyclase, Terpene cyclase/mutase family member; HYEWA (SEQ ID NO: 176) |
| 20 | [HR]SNMxF (SEQ ID NO: 123) | |
| 21 | M[TV]GxxYE (SEQ ID NO: 124) | Lanosterol cyclase, 3-methylcrotonoyl-CoA carboxylase beta subunit; MVGehYE (SEQ ID NO: 177), MVGkaYE (SEQ ID NO: 178) |
| 22 | Dxx[KH]ExxLL (SEQ ID NO: 125) | 40S ribosomal protein S8, Neurobeachin/beige protein, Kinesin, ATP-dependent DNA helicase; DqlKEgrLL (SEQ ID NO: 179), DvvKEImLL (SEQ ID NO: 180), DleKEneLL (SEQ ID NO: 181), DldKEvsLL (SEQ ID NO: 182) |
| 23 | RxxWx[EDA]x[IV][AR] (SEQ ID NO: 126) | 40S ribosomal protein S3a-1, Dynein heavy chain, Protein kinase, Eukaryotic translation initiation factor 4E (EIF4E) interacting protein, AAA ATPase; Mucin-associated surface protein (MASP); RhqWyAvVA (SEQ ID NO: 183), RhsWfDdVR (SEQ ID NO: 184), RkeWyDvVA (SEQ ID NO: 185), RdrWtEsIA (SEQ ID NO: 186), RatWIDqVR (SEQ ID NO: 187), RyvWnEwVA (SEQ ID NO: 188) |
| 24 | PxDxxAx[GPA][TS] (SEQ ID NO: 127) | Shed-acute-phase-antigen, Translation factor GUF1 homolog 1, mitochondrial, Trans-sialidase, Mucin-associated surface protein (MASP), Mucin TcMUCII; PvDstAhGT (SEQ ID NO: 189), PIDcpAIGS (SEQ ID NO: 190), PaDssAhGT (SEQ ID NO: 191), PkDvkAtGS (SEQ ID NO: 192), PpDvsAsGT (SEQ ID NO: 193), PgDlpAkAT (SEQ ID NO: 194), PaDvsAqAT (SEQ ID NO: 195), PpDvpAsGT (SEQ ID NO: 196) |
| 25 | PDxxSxT[ARG] (SEQ ID NO: 128) | UDP-GlcNAc:PI a1-6 GlcNAc-transferase, Small GTP-binding protein RAB6, 90 kDa surface protein, Mucin TcMUCII; PDpaSiTA (SEQ ID NO: 197), PDasSsTA (SEQ ID NO: 198), PDsrSiTA (SEQ ID NO: 199), PDsrSvTA (SEQ ID NO: 200), PDskSpTA (SEQ ID NO: 201), PDseSpTA (SEQ ID NO: 202) |
| 26 | GRExDG (SEQ ID NO: 129) | Mucin-associated surface protein (MASP), Trypanothione synthetase-like protein; GREsDG (SEQ ID NO: 203), GREaDG (SEQ ID NO: 204) |
| 27 | GVPGxxxK (SEQ ID NO: 130) | 60S ribosomal protein L18, Calpain-like cysteine peptidase; GVPGshaK (SEQ ID NO: 205), GVPGcviK (SEQ ID NO: 206) |

TABLE 1-continued

Motifs and peptides comprising panel for the diagnosis of Chagas panel

| ID | Panel motif | Antigen(s); peptide sequence(s) |
|----|-------------|--------------------------------|
| 28 | [LM]xxx[EDQ]VxxIM (SEQ ID NO: 131) | Sterol 14-alpha demethylase, 60S ribosomal protein L4, GTP-binding protein, Stress-induced protein sti1; LsprEVytIM (SEQ ID NO: 207), LtntDVtrIM (SEQ ID NO: 208), LedeDVIqIM (SEQ ID NO: 209), MadpEVaaIM (SEQ ID NO: 210) |
| 29 | SxxxVSGG (SEQ ID NO: 132) | Putative surface protein TASV-B-25, Aquaporin-like protein, Mucin-associated surface protein (MASP), Calcium-transporting ATPase; SqadVSGG (SEQ ID NO: 211), SvgsVSGG (SEQ ID NO: 212), SpsgVSGG (SEQ ID NO: 213), SwfdVSGG (SEQ ID NO: 214) |
| 30 | A[KR]AG[DN]K (SEQ ID NO: 133) | |
| 31 | F[RN]xIN[RQ] (SEQ ID NO: 134) | Dynein heavy chain, Eukaryotic translation initiation factor 3 subunit 8; FRiINQ (SEQ ID NO: 215), FRaINR (SEQ ID NO: 216) |
| 32 | YXPVXPXSY (SEQ ID NO: 135) | |
| 33 | KxTFPD (SEQ ID NO: 136) | Trans-sialidase, Neurobeachin/beige protein; KqTFPD (SEQ ID NO: 217), KaTFPD (SEQ ID NO: 218) |
| 34 | PFM[FVM]xxR (SEQ ID NO: 137) | Cation-transporting ATPase; PFMVqmR (SEQ ID NO: 219) |
| 35 | EFWEP (SEQ ID NO: 138) | |
| 36 | [FY]GALS (SEQ ID NO: 139) | Kinetoplast-associated protein Tcp22, Protein kinase, ABC transporter; FGALS (SEQ ID NO: 220), YGALS (SEQ ID NO: 221) |
| 37 | PxGTEN (SEQ ID NO: 140) | Trypomastigote small surface antigen; PsGTEN (SEQ ID NO: 222) |
| 38 | Gx[KE]PWE (SEQ ID NO: 141) | Metacaspase; GfKPWE (SEQ ID NO: 223) |
| 39 | D[IV]Tx[YF][WN] (SEQ ID NO: 142) | Intraflagellar transport protein component, Cyclophilin-like protein; DITdYN (SEQ ID NO: 224), DVTgFN (SEQ ID NO: 225) |

Of the final 39 motifs that comprise the panel, IMUNE identified twenty-six motifs that were highly sensitive and specific to Chagas that were not discovered by MEME. In particular, these included motifs with greater than 40% sensitivity in the Chagas discovery set.

Panel Development

Figure 6:
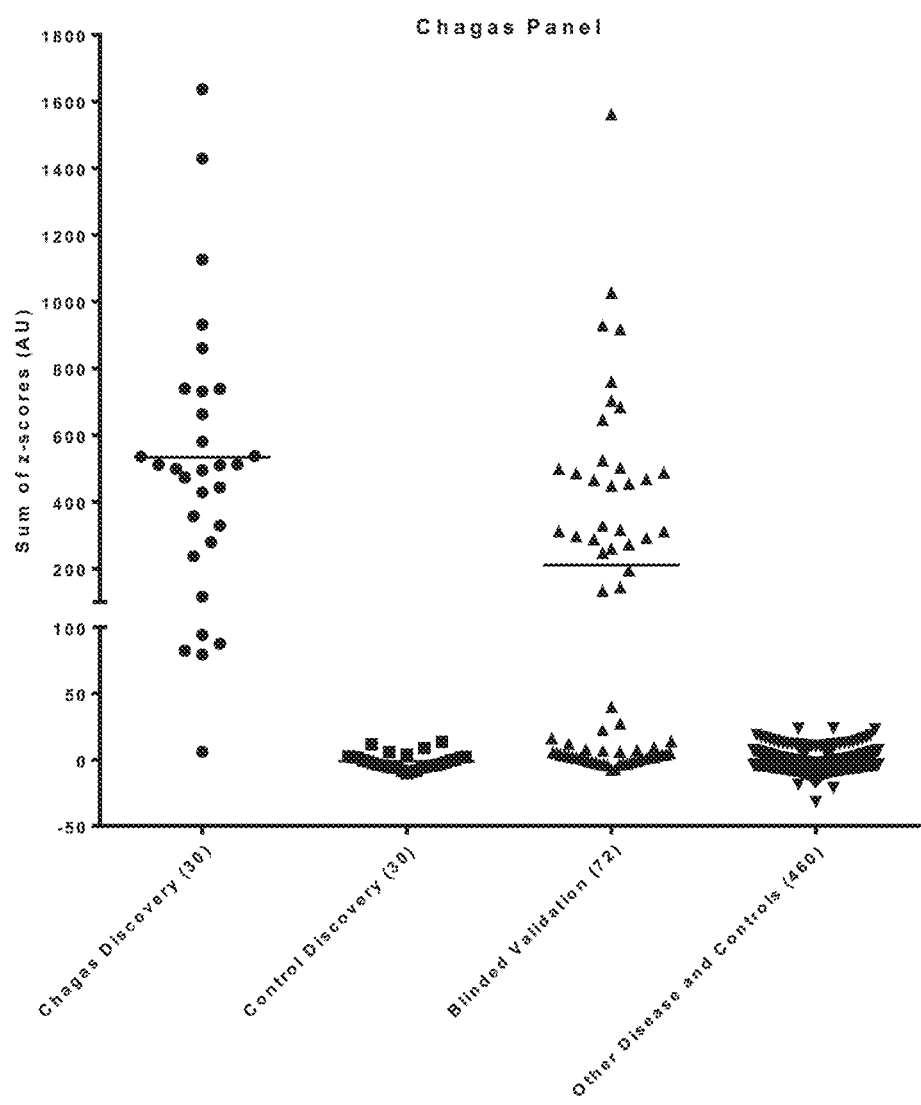
FIG. 6 illustrates the performance of *Trypanosoma cruzi* infection (Chagas disease) motif panel in a discovery and validation sample sets, exhibiting a sensitivity of 100% and specificity of 100% in the validation set.

Two methods were used to generate a panel of motifs that are diagnostic for Chagas disease. In the first method, the average enrichment and standard deviation for the 33 motifs in 416 non-Chagas samples were calculated. A positive signal in a motif is at least 4 standard deviations above the controls. A patient is diagnosed as positive for Chagas if they have a positive signal in at least 3 motifs, indeterminate if they are positive for two motifs and negative if they are positive in one or fewer motifs. Using these criteria, all thirty Chagas disease samples were positive (FIG. 6) and all the Chagas controls were negative. Additionally, all 460 controls in HASRD not used for discovery were also negative. In the second method, the sum of the z scores is calculated for all motifs and a cut off is determined based on the desired sensitivity and specificity. As shown in FIG. 6, using a cut off of 23 yields a sensitivity of 100% and a specificity of 99.5% for all 30 Chagas disease samples and all 460 controls.

Mapping of Chagas Motifs to *Trypansoma Cruzi* Antigens

Motifs identified by IMUNE often carry sufficient information content to identify organisms, antigens, and epitopes without prior knowledge of which organism or antigens may be important. About 80% of motifs that IMUNE identified that were sensitive and specific could be associated with a single *T. cruzi* antigen epitope, by performing degenerate motif searches within the entire Swissprot/TrEMBL databases using Scanprosite. See Table 1. Notably, i) three antigens (Surface antigen-2, microtubule associated protein, and small surface antigen/mucin-like protein) have been validated previously, several epitopes were from ribosomal proteins, one ribosomal epitope is identical between *T. cruzi* and *Leishmania* sp, an organism that generates false positives in available Chagas tests. The majority of Chagas antigens are novel and have not been described or characterized previously.

Example 3. Discovery of Motifs for the Diagnosis of Lyme Disease (*Borrelia Burgdorferi* Infection Lyme disease, also known as Lyme borreliosis, is an infectious disease caused by bacteria of the *Borrelia* genus. Lyme disease is transmitted to humans by the bite of infected ticks. Diagnosis is based upon a combination of symptoms, history of tick exposure, and possibly testing for specific antibodies in the blood. However, blood tests are often negative in the early stages of the disease. If untreated, symptoms may include loss of the ability to move one or both sides of the face, joint pains, severe headaches with neck stiffness, and heart palpitations. Symptoms can persist for months after treatment and may reoccur years later. The disease affects several hundred thousand people a year in the United States.

Patient Samples

Serum samples (100 ul/sample) from 20 confirmed late stage Lyme patients (L1-20) with Lyme Arthritis and 20 controls (L21-40) were provided. Lyme diagnosis was made on the basis of 2-tier testing via ELISA with reflex to Western blot. Serum samples were stored at −80° C. upon receipt and thawed on the day of use.

Experimental Protocol for Lyme Disease Biomarker Discovery

Experiments and analysis were as described in Example 1.

Serum was diluted 1:25 in PBS at the *E. coli* depletion step and maintained at 4° C. after depletion. For standard ecpx depletion, 1 mL each of *E. coli* cells induced to express eCPX 357 and 428 scaffolds (2 mL total) was used per microliter of neat serum for depletion. Both MACS steps were performed at a 1:25 final serum dilution.

FACS Analysis of Enrichment of Lyme and Control Serum after MACS X2 for Discovery and Down Selection The effective removal of *E. coli* antibodies from serum and the effective enrichment of serum antibody binders after two rounds of MACS (M2) was analyzed by Flow cytometry as a quality control step in the screening process. Samples generally exhibit 75% reactivity of above background to M2 library pool, indicating that the libraries are highly enriched for patient-specific peptides.

NGS Quality Control

Each amplicon was run on an agarose gel to confirm amplification of the correct product (254 bp) and absence of other bands representing non-specific PCR products. Amplicons were quantified and pooled at a final concentration of 4 nM each. The final amplicon pool was run on the bioanalyzer as a second QC step to confirm the pool represented a single amplified band of the appropriate amplicon concentration. Half of the disease set and half of the control set sequenced per run (20 samples per chip).

NGS Results

NGS raw sequence data from BaseSpace provides a breakdown of the total sequences obtained for each patient based on their unique barcode identifier. In the initial IMUNE processing step, sequences that met the quality criteria including: 1) upstream and downstream annealing regions contain <25% insertions, deletions and/or mutations, 2) the random region is of the expected length 3) no base throughout the read is unassigned (i.e. N). Unique reads are the number of sequences per patient after removal of duplicates, combination of similar sequences with few mutations (i.e. 3 or fewer) and removal of sequences that contain stop codons. The percentage of sequences that meet the above criteria relative to the total number of raw sequences is another measure of the quality of the NGS run. NGS runs for the 60 Lyme and control samples typically resulted in more 5-12 million total sequences, and 2-5 million unique sequences. After processing, ~95% of the raw sequences from Basespace for each patient contain useable sequence information.

Bioinformatic analysis was performed as described in Example 1.

Identification of Lyme-Specific Motifs Using IMUNE Software

Motif discovery algorithms that utilize pairwise sequence comparisons are slow and not amenable to the large NGS datasets created by the methods described herein. For instance, motif discovery in 10,000 peptides using the MEME algorithm can require one week on a single processor, and computation time scales more than quadratically. To address this limitation, a computational algorithm for Identification of Motifs Using Next-generation sequencing Experiments (IMUNE) was developed. IMUNE calculates the enrichments of all possible 4, 5, and (optionally) 6 amino acid patterns (~8.5 billion) in a window of 10 positions, identifies patterns that are significantly enriched (e.g., p<0.001), and clusters these patterns using a similarity scoring matrix (e.g., PAM30) to build motifs.

Identification of Lyme-Specific Motifs Using MEME

MEME is currently the dominant tool in motif finding. We wished to determine whether IMUNE outperforms MEME in terms of the number and specificity of the disease motifs it identifies. For the MEME motif discovery, we compiled a list of all peptides that appeared in at least 11 Lyme disease samples and in zero controls samples. MEME was used to analyze the top 4980 of these peptides that appeared in these Lyme samples, to identify the motifs in Table 30.

Candidate Motifs

Lyme Motifs Discovered by IMUNE

Preliminary IMUNE analysis of the discovery set epitope repertoires from 20 Lyme and 20 control sera discovered 296 non-redundant motifs that were at least 40% sensitive and 100% specific. To identify a subset of these motifs that together are 100% sensitive and specific for Lyme disease following steps were performed:

1) Down-Selection of Motifs Based on Specificity Using HASRD

Figure 7:
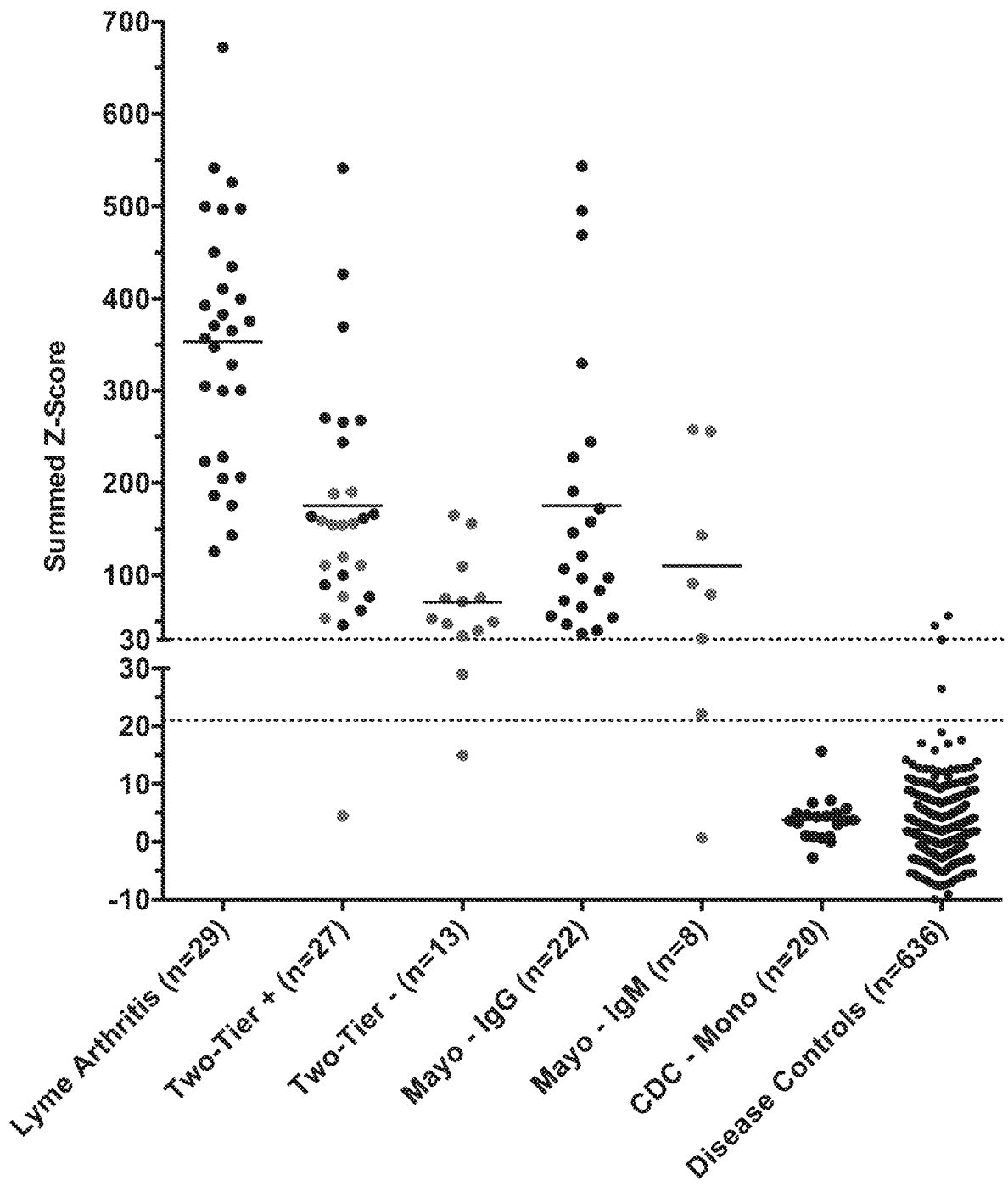
FIG. 7 illustrates the performance of *Borrelia burgdorferi* infection motif panel in a discovery and validation sets of early, early disseminated, and late Lyme disease, exhibiting a sensitivity of 97% and specificity of 99.8%.

We used a database containing hundreds of distinct epitope repertoires (i.e., peptide datasets) as a down-selection tool to identify motifs that were highly specific for Lyme disease based on their lack of enrichment in 636 additional untested, non-Lyme samples. Twenty-eight motifs were highly specific for Lyme disease (significant enrichment in <2 of the 20 Lyme controls and 636 additional non-Lyme controls (FIG. 7)) and were considered for further analysis.

2) Grouping of Motifs into Families

Many of the motifs, while non-redundant, were variations on the same epitope and thus were grouped together into families. At least 16 Lyme specific motif families were identified.

3) Down-Selection Based on Motif Sensitivity and Patient Coverage

We further down-selected the motifs based on sensitivity and patient coverage. If two highly specific motifs were present in the same family, the motif that demonstrated the highest sensitivity was selected. Motifs from each family were compared to identify those that captured distinct patient subsets. Of the initial 27 motifs we considered, the final panel includes 14 motifs, each from a distinct motif family, that together exhibit the greatest breadth of patient coverage. A sample was considered positive for any motif if it was >4 standard deviations (SD) above the mean of the controls, indeterminate if it was >3 SD and negative if it was less than 3 SD.

Lyme Motifs Discovered Using MEME

MEME identified a total of twenty-five motifs. To evaluate the performance of the two algorithms, MEME motifs were compared with all IMUNE motifs. Of the twenty-five motifs, eight were redundant within the MEME list. IMUNE identified all of the 17 remaining motifs. See Table 2. Thus, IMUNE identified 15/15 of the motifs identified by MEME.

In contrast, of the final 14 motifs that comprise the panel, IMUNE identified five motifs that were highly sensitive and specific to Lyme that were not discovered by MEME. In particular, these included motifs with <60% sensitivity in the Lyme discovery set.

Panel Development

Two methods were used to generate a panel of motifs that are diagnostic for Lyme disease. In the first method, the average enrichment and standard deviation for the 14 motifs in 419 non-Lyme samples were calculated. A positive signal in a motif is at least 4 standard deviations above the controls. A patient is diagnosed as positive for Lyme if they have a positive signal in at least 3 motifs, indeterminate if they are positive for two motifs and negative if they are positive for one or fewer motifs. Using this criteria, all twenty late Lyme disease samples in the discovery set were positive and all the non-Lyme controls were negative. Additionally, 636 Disease controls not used for discovery were also negative.

In the second method, the sum of the z scores is calculated for all motifs and a cut off is determined based on the desired sensitivity and specificity. Using a cut off of 30 yields a sensitivity of 100% and a specificity of 100% for all 20 Lyme disease samples and all 419 controls.

Mapping of Lyme Motifs to Putative *Borrelia burgdorferi* Antigens

Motifs identified by IMUNE often carry sufficient information content to identify organisms, antigens, and epitopes without prior knowledge of which organism or antigens may be important. About 80% of motifs that IMUNE identified that were sensitive and specific could be associated with a *B. burgdorferi* antigen epitope, by performing degenerate motif searches within the entire Swissprot/TrEMBL databases using Scanprosite. See Table 2.

TABLE 2

Motifs and peptides comprising panel for the diagnosis of Lyme Disease.

| ID | Panel motif | Antigen(s); peptide sequence(s) |
|---|---|---|
| 1 | VQQExxxxxP (SEQ ID NO: 358) | Flagellin (Fragment); VQQEgaqqqP (SEQ ID NO: 392) |
| 2 | QQEGxxxx[YC] (SEQ ID NO: 359) | |
| 3 | QEG[IV]Q (SEQ ID NO: 360) | Flagellar filament 41 kDa core protein (Flagellin); QEGVQ (SEQ ID NO: 393) |
| 4 | G[IV]QxEG (SEQ ID NO: 361) | Flagellar filament 41 kDa core protein (Flagellin); GVQqEG (SEQ ID NO: 394) |
| 5 | [LI]xxA[ILV]xxRG (SEQ ID NO: 362) | Flagellar hook-basal body complex protein FliE; IlkAVveRG (SEQ ID NO: 395)<br>Outer surface protein VlsE; IaaAIvIRG (SEQ ID NO: 396) |
| 6 | [ATNSD]xxxxAI[LAM]xR (SEQ ID NO: 363) | Outer surface protein VlsE; DqiaaAIAIR (SEQ ID NO: 397)<br>Flagellar M-ring protein; AkkmrAILvR (SEQ ID NO: 398)<br>Telomere resolvase ResT; AenhkAILfR (SEQ ID NO: 399) |
| 7 | Ix[LM]xGFxK (SEQ ID NO: 364) | Uncharacterized protein; IklLpGFkK (SEQ ID NO: 400)<br>Transglycosylase SLT domain protein; IfLeGFIK (SEQ ID NO: 401) |
| 8 | LxGM[RQ]K (SEQ ID NO: 365) | Uncharacterized protein; LrGMRK (SEQ ID NO: 402) |
| 9 | [HR]xDxTNxF (SEQ ID NO: 366) | |
| 10 | [DA]DPTN (SEQ ID NO: 367) | Outer surface protein VlsE1; DDPTN (SEQ ID NO: 403) |
| 11 | [KR]x[DE]xTNxF (SEQ ID NO: 368) | Borrelia ORF-A superfamily protein; KtDrTNdF (SEQ ID NO: 404)<br>Outer surface protein VlsE; KdDpTNkF (SEQ ID NO: 405)<br>CdsJ; KtDrTNdF (SEQ ID NO: 406) BBD14-like protein (Fragment); KtDkTNdF |
| 12 | [ET][ML]HKF (SEQ ID NO: 369) | PF-32 protein; TLHKF (SEQ ID NO: 407) |
| 13 | [ML]xxEFHK (SEQ ID NO: 370) | |
| 14 | Q[TI]EQxxxxxK (SEQ ID NO: 371) | Integral outer membrane protein P66; QTEQsststK (SEQ ID NO: 408) |
| 15 | DxSP[IL]E (SEQ ID NO: 372) | Uncharacterized protein; DlSPIE (SEQ ID NO: 409) |
| 16 | PFx[AP]YxK (SEQ ID NO: 373) | Integral outer membrane protein P66; PFsAYIK (SEQ ID NO: 410) |
| 17 | VxxYFxx[LV]xK (SEQ ID NO: 374) | VlsE (Fragment); VkdYFdsLaK (SEQ ID NO: 411) |

TABLE 2-continued

Motifs and peptides comprising panel for the diagnosis of Lyme Disease.

| ID | Panel motif | Antigen(s); peptide sequence(s) |
|---|---|---|
| 18 | KxVDxDR (SEQ ID NO: 375) | |
| 19 | [DN][AS]A[AG]F (SEQ ID NO: 376) | VlsE (Fragment); DAAAF (SEQ ID NO: 412) |
| 20 | Cx[NA]xKFC (SEQ ID NO: 377) | |
| 21 | Kx[GRST]AE[YF] (SEQ ID NO: 378) | Flagellar basal-body rod protein FlgG (Distal rod protein); KIRAEF<br>Putative lipoprotein; KfRAEF (SEQ ID NO: 413)<br>Na+/H+ antiporter family protein; KsSAEF(SEQ ID NO: 414)<br>VlsE (Fragment); KgGAEF(SEQ ID NO: 415) |
| 22 | HQV[PA]xxx[DHE] (SEQ ID NO: 379) | |
| 23 | IPxx V[IF]xxR (SEQ ID NO: 380) | |
| 24 | Cx[ALT]xWEx[CA] (SEQ ID NO: 381) | |
| 25 | CxxxCA[IL]xxR (SEQ ID NO: 382) | |
| 26 | I[IV]Ixx[MT]xK (SEQ ID NO: 383) | Lectin; IIIidTsK (SEQ ID NO: 416)<br>CdsC; IIIngMtK (SEQ ID NO: 417)<br>Mlp; IIItnMeK (SEQ ID NO: 418) |
| 27 | QG[ITL]x[KN][FY] (SEQ ID NO: 384) | Dephospho-CoA kinase; QGIiNY (SEQ ID NO: 419)<br>Phosphomannomutase; QGIcNY (SEQ ID NO: 420) |
| 28 | KxxPPxIN (SEQ ID NO: 385) | Outer surface protein VlsE1; KetPPaLN (SEQ ID NO: 421) |
| 29 | G[YF][FY]FxxK (SEQ ID NO: 386) | Pts system, iibc component; GFYFifK (SEQ ID NO: 422) |
| 30 | DKNVx[IV] (SEQ ID NO: 387) | Putative lipoprotein; DKNVKI (SEQ ID NO: 423) |
| 31 | [QE][KR][ND]xSG (SEQ ID NO: 388) | Outer surface protein B (OspB); EKNsSG (SEQ ID NO: 424) |
| 32 | K[RK]PGD (SEQ ID NO: 389) | Outer surface protein VlsE; KKPGD (SEQ ID NO: 425) |
| 33 | EGAxQP (SEQ ID NO: 390) | Flagellar filament 41 kDa core protein (Flagellin); EGAqQP (SEQ ID NO: 426) |
| 34 | GSPEY (SEQ ID NO: 391) | Outer membrane protein; GSPEY (SEQ ID NO: 427) |

Example 4. Discovery of Motifs for the Diagnosis of Acute or Active *Toxoplasma gondii* Infection

Figure 8:
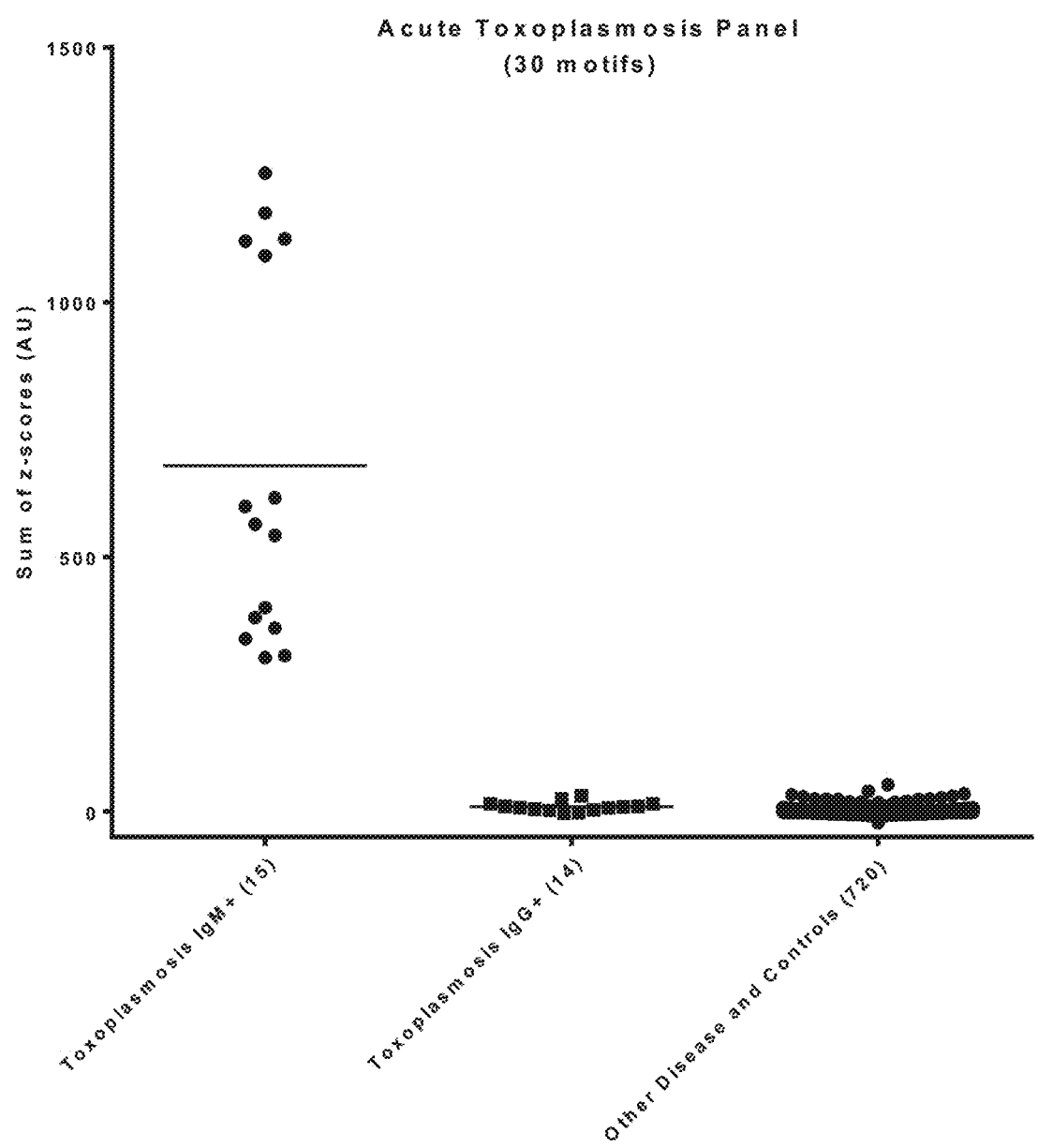
FIG. 8 illustrates the performance of an acute *Toxoplasma gondii* infection motif panel in a discovery sample set, exhibiting a sensitivity of 100% and specificity of 100%.
Figure 9:
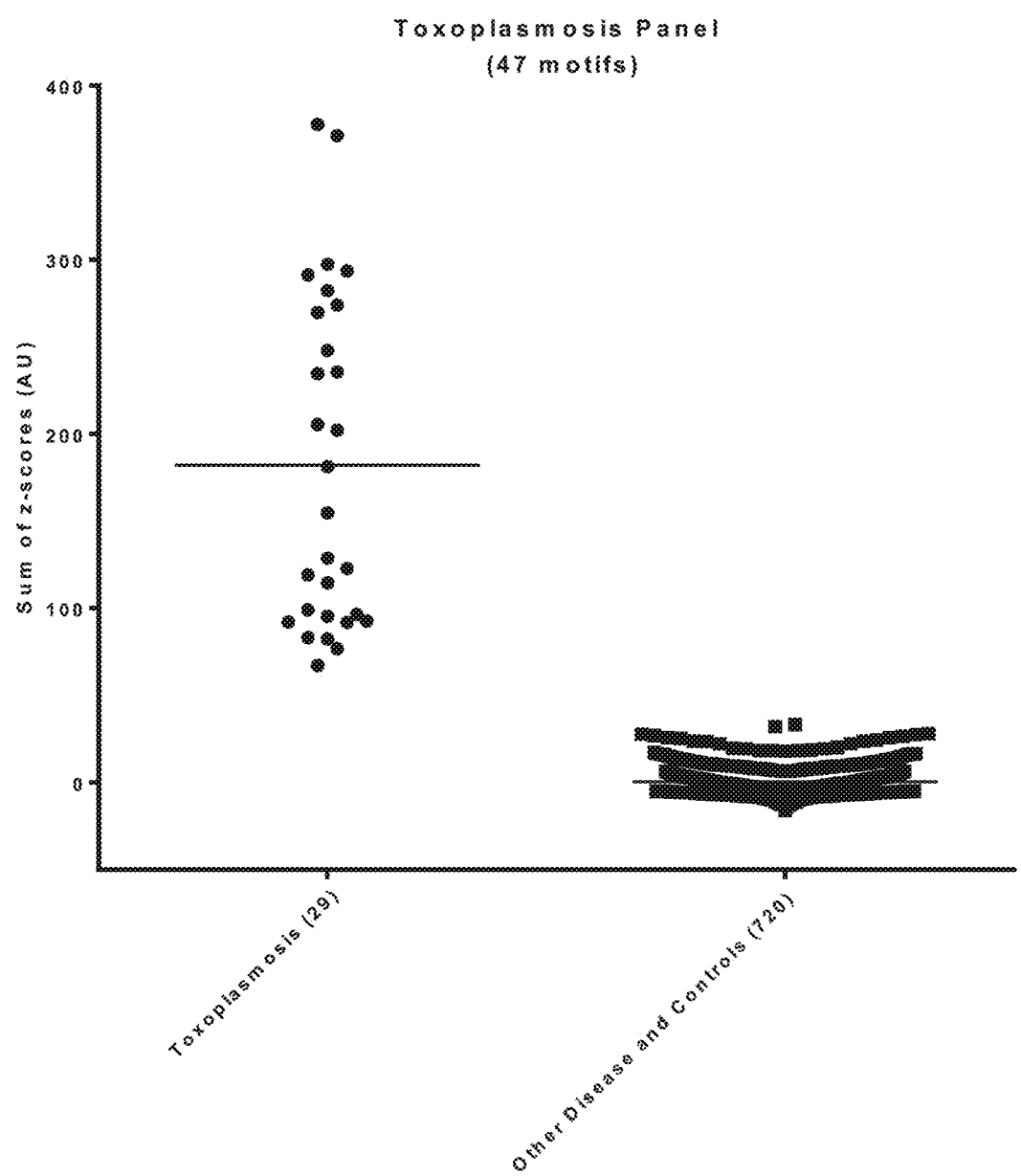
FIG. 9 illustrates the performance of (chronic or acute) *Toxoplasma gondii* infection motif panel in a discovery sample set, exhibiting a sensitivity of 100% and specificity of 100%.

*Toxoplasma gondii* is a common infectious parasite with a seroprevalence of about 20% in the US population. Acute infections can in some cases result in significant morbidities, for example during pregnancy. The method of Example 1 above was applied to a set of 30 sera from individuals that were either positive for IgG or IgM antibodies by enzyme immunoassay or immunoblot. A panel of 30 motifs indicated of Acute *Toxoplasma* infection is shown in Table 3. The panel is capable of correctly detecting 30 specimens in the discovery set (FIG. 8, FIG. 9).

TABLE 3

Motifs and peptides comprising panel for the diagnosis of acute Toxoplasmosis.

| ID | Panel motif | Antigen(s); peptide sequence(s) |
|---|---|---|
| 1 | HEXE[FY]Q (SEQ ID NO: 74) | Apical membrane antigen 1 (TgAMA-1); HEhEFQ (SEQ ID NO: 428) |
| 2 | LD[MLF]WxE (SEQ ID NO: 75) | DNA polymerase, TLD protein, Putative transmembrane protein; LDFWrE (SEQ ID NO: 429, LDFWqE (SEQ ID NO: 430), LDMWeE (SEQ ID NO: 431) |

TABLE 3-continued

Motifs and peptides comprising panel for the diagnosis of acute Toxoplasmosis.

| ID | Panel motif | Antigen(s); peptide sequence(s) |
|---|---|---|
| 3 | HCSAC (SEQ ID NO: 76) | Putative anaphase promoting complex subunit 11, Palmitoyltransferase, Sulfite exporter TauE/SafE protein; HCSAC (SEQ ID NO: 432) |
| 4 | [FY]xGVVN (SEQ ID NO: 77) | Dense granule protein 2 (Protein GRA 2) (28 kDa antigen) (GP28.5), Dynein, axonemal, heavy chain 2 family protein; FsGVVN (SEQ ID NO: 433), YpGVVN (SEQ ID NO: 434) |
| 5 | KxxxGRGxI (SEQ ID NO: 78) | NOL1/NOP2/sun family protein; KgshGRGfI (SEQ ID NO: 435) |
| 6 | GPH[LA]E (SEQ ID NO: 79) | Zinc finger (CCCH type) motif-containing protein, Glycogen synthase, Uncharacterized protein; GPHAE (SEQ ID NO: 436) |
| 7 | PRREP (SEQ ID NO: 80) | Dense granule protein 7 (Protein GRA 7) (29 kDa excretory dense granule protein), Putative transmembrane protein, Dense granule protein GRA9; 1,3-beta-glucan synthase component protein; PRREP (SEQ ID NO: 437) |
| 8 | CNxxxECY (SEQ ID NO: 81) | |
| 9 | KxCQPxxC (SEQ ID NO: 82) | |
| 10 | PxPD[FH][TS] (SEQ ID NO: 83) | Dense granule protein 2 (Protein GRA 2) (28 kDa antigen) and SAG-related sequence protein SRS15A; Uncharacterized protein; Tetratricopeptide repeat-containing protein; Flagellar/basal body protein, PGAP1 family protein; PvPDFS (SEQ ID NO: 438), PvPDFT (SEQ ID NO: 439), PIPDFT (SEQ ID NO: 440), PIPDFS (SEQ ID NO: 441), PaPDFS (SEQ ID NO: 442 |
| 11 | NxxxEx Y[AG]xD (SEQ ID NO: 84) | O-linked N-acetylglucosamine transferase, Zinc knuckle protein; NaglEvYAeD (SEQ ID NO: 443, NrrrErYGeD (SEQ ID NO: 444 |
| 12 | P[AG]AxxLD (SEQ ID NO: 85) | Dense granule protein 3 (P30), Uncharacterized protein, GRAM domain-containing protein, Concanavalin A-like lectin/glucanase family protein; PGAVILD (SEQ ID NO: 445, PAAskLD (SEQ ID NO: 446), PAAesLD (SEQ ID NO: 447), PGAarLD (SEQ ID NO: 448), PGAIdLD (SEQ ID NO: 449) |
| 13 | MPSxSxE (SEQ ID NO: 86) | Uncharacterized protein, Toxoplasma gondii family A protein, Putative Tbc domain related protein; MPSwSnE (SEQ ID NO: 450), MPStSdE (SEQ ID NO: 451, MPSeStE (SEQ ID NO: 452), MPSaSpE (SEQ ID NO: 453) |
| 14 | [RK]x YxHR[TS] (SEQ ID NO: 87) | Putative 5'-3' exoribonuclease, Glycosyltransferase, Ribosomal protein RPL3; RIYvHRS (SEQ ID NO: 454), RIYrHRT (SEQ ID NO: 455), KgYfHRT (SEQ ID NO: 456) |
| 15 | K[PA]xFxFxK (SEQ ID NO: 88) | Micronemal protein 6, GCC2 and GCC3 domain-containing protein; KPpFeFgK (SEQ ID NO: 457), KPgFvFIK (SEQ ID NO: 458) |
| 16 | DD[CST]xGxR (SEQ ID NO: 89) | Dense granule protein 5 (Protein GRA 5) (p21), Uncharacterized protein, RNA pseudouridine synthase superfamily protein, AP2 domain transcription factor AP2XI-5; DDSeGaR (SEQ ID NO: 459), DDScGrR (SEQ ID NO: 460), DDSkGdR (SEQ ID NO: 461), DDSsGyR (SEQ ID NO: 462) |
| 17 | P[ML]xxHxMY (SEQ ID NO: 90) | |
| 18 | Kx[ASQ][SAT]xRG (SEQ ID NO: 91) | Dense granule protein 2 (Protein GRA 2) (28 kDa antigen), Alpha/beta hydrolase family protein, Putative transmembrane protein, Radical SAM domain-containing protein, Rhoptry neck protein RON8; KeAAgRG (SEQ ID NO: 463), KdASIRG (SEQ ID NO: 464), KgSSgRG (SEQ ID NO: 465), KtSSrRG (SEQ ID NO: 466), KtQTvRG (SEQ ID NO: 467), KrSTIRG (SEQ ID NO: 468) |

TABLE 3-continued

Motifs and peptides comprising panel for the diagnosis of acute Toxoplasmosis.

| ID | Panel motif | Antigen(s); peptide sequence(s) |
|---|---|---|
| 19 | [DG]QPEN (SEQ ID NO: 92) | Dense granule protein 3 (P30), FHA domain-containing protein, Uncharacterized protein; DQPEN (SEQ ID NO: 469), GQPEN (SEQ ID NO: 470) |
| 20 | [KHR]N[QN]DG (SEQ ID NO: 93) | Calcium-dependent protein kinase CDPK1, La domain protein, DNA polymerase, SAG-related sequence SRS34A, Surface antigen 2 (p22); KNNDG (SEQ ID NO: 471), RNNDG (SEQ ID NO: 472) |
| 21 | Nx[EVS]GExY (SEQ ID NO: 94) | EGF family domain-containing protein, Kringle domain-containing protein; NIVGEeY (SEQ ID NO: 473), NdSGEiY (SEQ ID NO: 474) |
| 22 | EP[VI]TG (SEQ ID NO: 95) | Dense granule protein 3 (P30), Corepressor complex CRC230, Cpw-wpc domain-containing protein; EPVTG (SEQ ID NO: 475) |
| 23 | HGM[PA][KR] (SEQ ID NO: 96) | Dense granule protein GRA8, Tetratricopeptide repeat-containing protein; HGMPK (SEQ ID NO: 476), HGMAK (SEQ ID NO: 477) |
| 24 | [VIT]PWIF (SEQ ID NO: 97) | SAG-related sequence SRS57, Putative zinc finger protein; VPWIF SEQ ID NO: 478) |
| 25 | Kx[STN]VxFQ (SEQ ID NO: 98) | Putative cell-cycle-control protein (Translation regulation), MaoC family domain-containing protein, Hydrolase, NUDIX family protein; KsSVpFQ (SEQ ID NO: 479), KeTVnFQ (SEQ ID NO: 480) |
| 26 | [VAI]WSGS (SEQ ID NO: 99 | Sma protein, Ribosomal protein L9, N-terminal domain-containing protein; VWSGS (SEQ ID NO: 481), IWSGS (SEQ ID NO: 482) |
| 27 | FS[LIAM]xxWG (SEQ ID NO: 100) | Pyruvate carboxylase, AP2 domain transcription factor AP2IX-5, Putative transmembrane protein, Putative major facilitator family transporter, Tub family protein; FSLenWG (SEQ ID NO: 483), FSMgrWG (SEQ ID NO: 484), FSLvIWG (SEQ ID NO: 485), FSLvIWG (SEQ ID NO: 486), FSLtnWG (SEQ ID NO: 487) |
| 28 | PTN[PQ]G (SEQ ID NO: 101) | Uncharacterized protein; PTNQG (SEQ ID NO: 488), PTNPG (SEQ ID NO: 489) |
| 29 | [RK]Kxx[YW]xHx[TS] (SEQ ID NO: 102) | Putative type I fatty acid synthase, O-phosphoseryl-tRNA(Sec) selenium transferase, NAD(+)/NADH kinase domain-containing protein; RKlhWnHrT (SEQ ID NO: 490), KKyrYrHpT (SEQ ID NO: 491), RKavYqHnT (SEQ ID NO: 492) |
| 30 | [HRW]xxHPRF (SEQ ID NO: 103) | Uncharacterized protein, Putative calcium signaling protein kinase RAD53, Glutamate 5-kinase domain-containing protein; RtlHPRF (SEQ ID NO: 493), HfrHPRF (SEQ ID NO: 494), RvaHPRF (SEQ ID NO: 495), WqaHPRF (SEQ ID NO: 496) |

Figure 10:
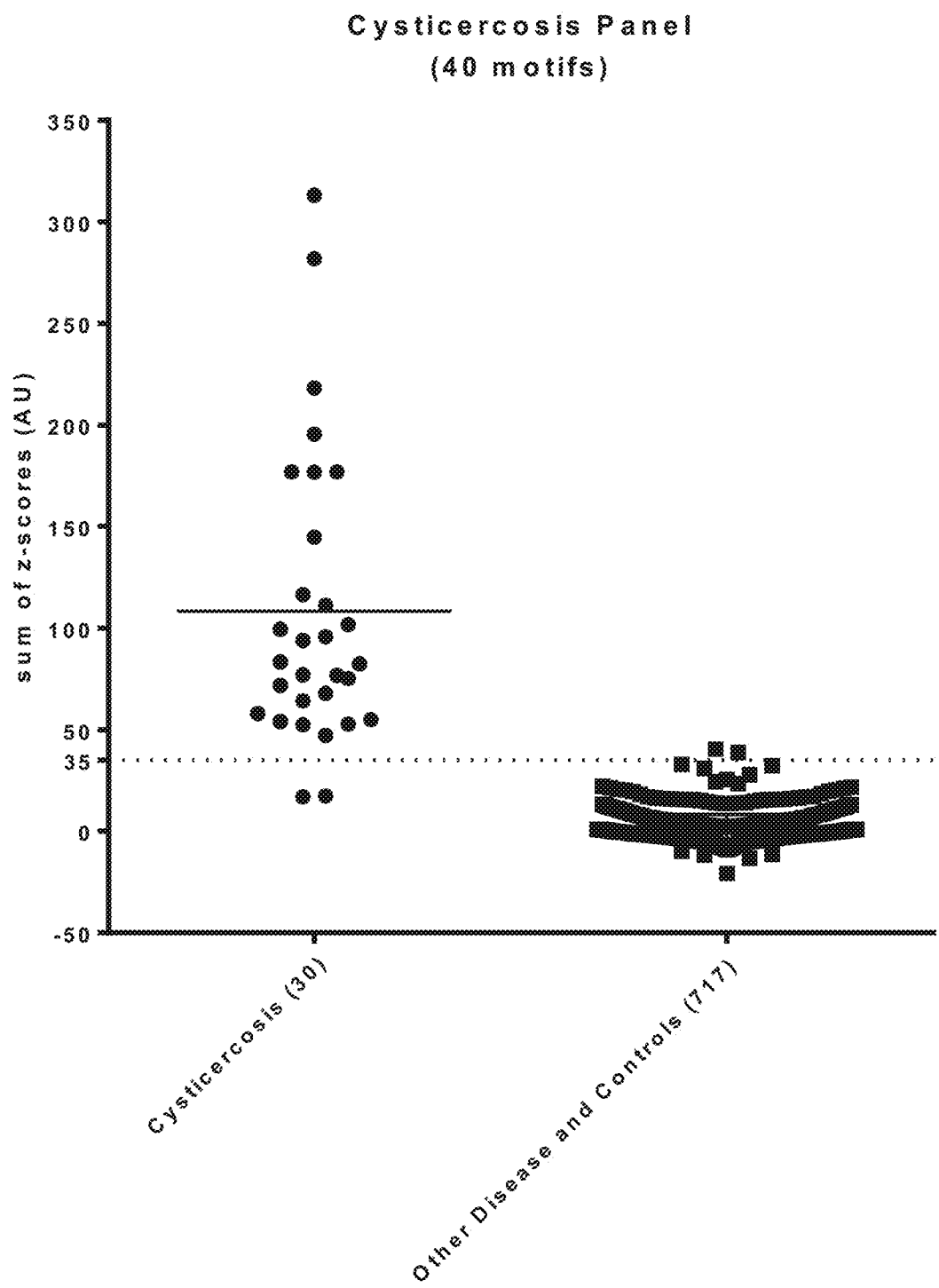
FIG. 10 illustrates the performance of *Taenia solium* (Cysticercosis) infection motif panel in a discovery sample set, exhibiting a sensitivity of >95%% and specificity of 99.5%.

Example 5. Discovery of Motifs for the Diagnosis of *Taenia solium* Infection (Cysticercosis Cysticercosis cause by the tapeworm *Taenia solium*, is considered a US neglected parasitic infection is a cause of cerebral parasitosis, and the single most common cause of epilepsy of unknown etiology. Diagnosis currently requires costly imaging studies to determine the presence, and number, of cysts present in the brain. A total of 30 samples from individuals diagnosed with Cysticercosis, with 1 or more cysts, were analyzed to determine their epitope repertoires. The method of Example 4 was applied to identify infection specific motifs (Table 4). A panel of motifs was capable of identifying Cysticercosis specimens (FIG. 10) with high specificity.

TABLE 4

Motifs and peptides comprising panel for the diagnosis of Cysticercosis.

| ID | Panel motif or Peptides |
|---|---|
| 1 | AxSPN[QEA]; (SEQ ID NO: 226) Huntingtin interacting protein 1; Trypsin-like protein, ArSPN(SEQ ID NO: 265), AgSpNri (SEQ ID NO: 266) |
| 2 | [RP]xAxSxNx[IFMLV] (SEQ ID NO: 227) |

TABLE 4-continued

Motifs and peptides comprising panel for the diagnosis of Cysticercosis.

| ID | Panel motif or Peptides |
|---|---|
| 3 | PDxGVxP (SEQ ID NO: 869); Putative DSCR5 protein, PDgGVmP (SEQ ID NO: 267) |
| 4 | NxxLGL[VT](SEQ ID NO: 228); Protein Wnt, NpkLGLT (SEQ ID NO: 268) |
| 5 | [YF]x[DE]IxxFF (SEQ ID NO: 229) |
| 6 | IxHFFxG(SEQ ID NO: 230) |
| 7 | [ILM][ILM][RK]H[ED]XQ (SEQ ID NO: 231) |
| 8 | [ILM][RK]HExQ(SEQ ID NO: 232) |
| 9 | KPxx[IL]xLx[KR](SEQ ID NO: 233) |
| 10 | NxDxxYYxx[WF](SEQ ID NO: 234) |
| 11 | GLDGP(SEQ ID NO: 235) |
| 12 | RSxHDxxN(SEQ ID NO: 236) |
| 13 | FDxFN[IL](SEQ ID NO: 237) |
| 14 | TIFxGK(SEQ ID NO: 238) |
| 15 | R[AV]xS[TQ]H(SEQ ID NO: 239) |
| 16 | KWHGxY(SEQ ID NO: 240) |
| 17 | MPEDK(SEQ ID NO: 241) |
| 18 | Exxx[FY]x[AS]D[NT](SEQ ID NO: 242) |
| 19 | NQSxxKx[VI](SEQ ID NO: 243) |
| 20 | KxY[NAS]PY (SEQ ID NO: 244) |
| 21 | [PQ][VL]HPRI(SEQ ID NO: 245) |
| 22 | EDGMxxW(SEQ ID NO: 246) |
| 23 | YASXQE(SEQ ID NO: 247) |
| 24 | KQxQ[QK]E(SEQ ID NO: 248) |
| 25 | K[AS]VFD[IVM](SEQ ID NO: 249) |
| 26 | PN[QE]x[DN]P(SEQ ID NO: 250) |
| 27 | P[QA]XM[DN]I(SEQ ID NO: 251) |
| 28 | [WR]x[RKH][ST]xFD(SEQ ID NO: 252) |
| 29 | KxEPGxK(SEQ ID NO: 253) |
| 30 | DDCLP(SEQ ID NO: 254) |
| 31 | NXXXXGXHLE(SEQ ID NO: 255) |
| 32 | DxxHLEG(SEQ ID NO: 256) |
| 33 | RPxx[TS]HN(SEQ ID NO: 257) |
| 34 | KxHS[IV]Y(SEQ ID NO: 258) |
| 35 | KxHSx[IV]S(SEQ ID NO: 259) |
| 36 | MSGYE(SEQ ID NO: 260) |
| 37 | YXIWGP(SEQ ID NO: 261) |

TABLE 4-continued

Motifs and peptides comprising panel for the diagnosis of Cysticercosis.

| ID | Panel motif or Peptides |
|---|---|
| 38 | RxxWxMN[RK](SEQ ID NO: 262) |
| 39 | QPxxT[FY]E(SEQ ID NO: 263) |
| 40 | YGYNQ(SEQ ID NO: 264) |

Figure 11A:
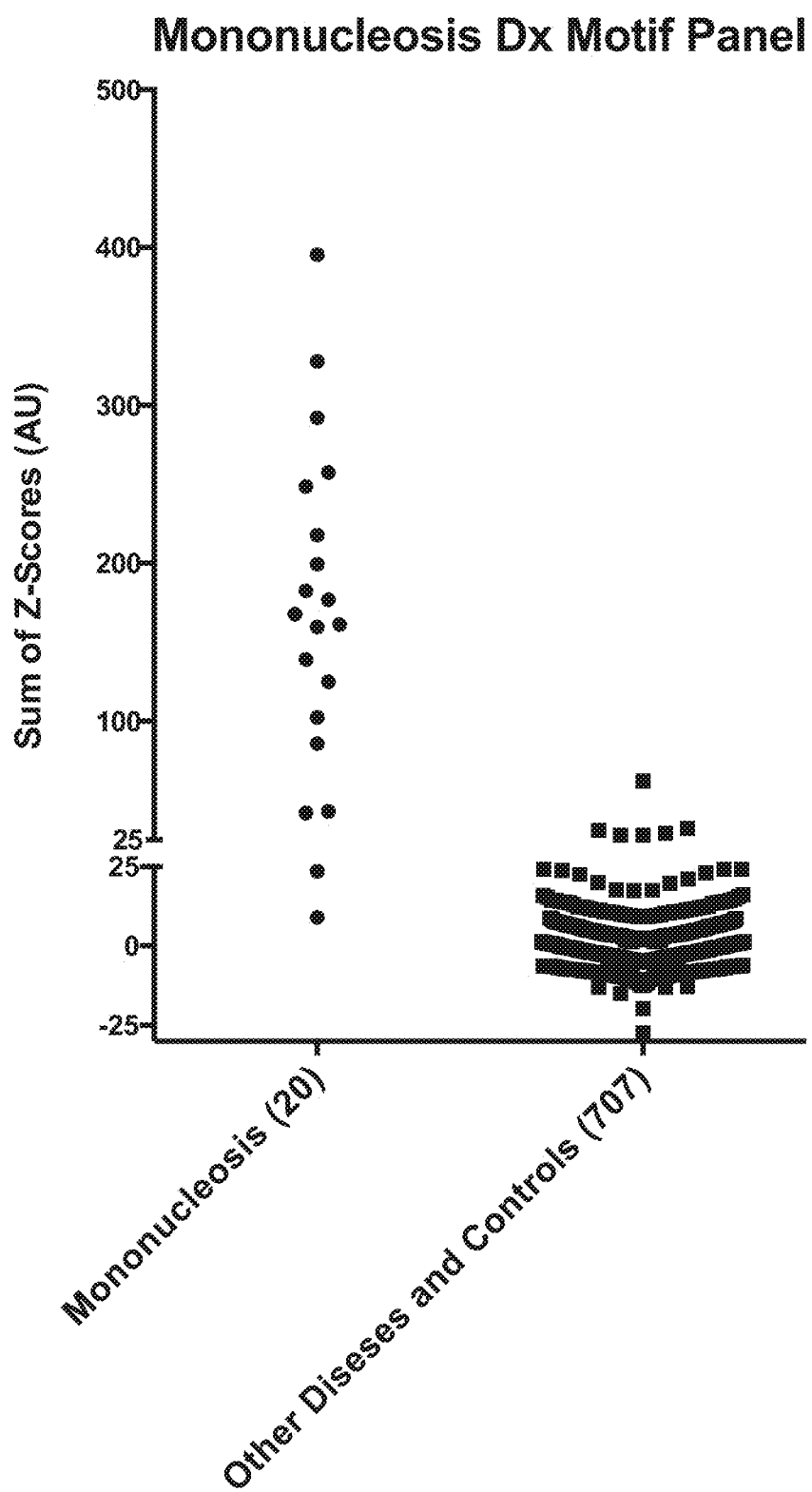
FIG. 11A illustrates the performance of an Esptein Barr Virus Mononucleosis infection motif panel in a discovery and validation sample sets, exhibiting a sensitivity of 90% and specificity of 99%.

Example 6. Discovery of Motifs for the Diagnosis of Mononucleosis by EBV Infection Mononucleosis caused by EBV can be difficult to diagnosis and discriminate from prior EBV exposure and/or viral reactivation. Twenty samples from individuals with confirmed EBV mononucleosis were characterized according to the Method of Example 1. Motifs discovered (Table 5) were capable of identifying all specimens from EBV infection Mono cases, with high specificity (FIG. 11). The absence of a particular motif (for example the RRPFF (SEQ ID NO: 937) epitope of EBNA-1) was helpful as an aid to identify individuals with prior infections, or with prolonged course of primary infection.

TABLE 5

Motifs and peptides comprising panel for the diagnosis of Mononucleosis.

| ID | Panel motif and Antigen(s); peptide sequence(s) |
|---|---|
| 1 | LFGxx[LM]N(SEQ ID NO: 9); BKRF2 (Envelope glycoprotein L); LFGanLN (SEQ ID NO: 44) |
| 2 | GELxGQ(SEQ ID NO: 852) |
| 3 | EWVxx[YF]D(SEQ ID NO: 10) |
| 4 | P[LM]ALxL(SEQ ID NO: 11 |
| 5 | KxNExWxV(SEQ ID NO: 12 |
| 6 | P[AG]xRTxK(SEQ ID NO: 13; BFLF1 (Packaging protein UL32 homolog); PGpRTcK (SEQ ID NO: 45) BZLF1 (Viral immediate early antigen); PArRTrK (SEQ ID NO: 46) |
| 7 | AYTxVN(SEQ ID NO: 14) |
| 8 | WN[AS]YxxxN (SEQ ID NO: 15) |
| 9 | [RKE]xxWxP[LM]Q (SEQ ID NO: 16) |
| 10 | [AS]YxSx[SA][YF](SEQ ID NO: 17) |
| 11 | ExYxSPS(SEQ ID NO: 18) |
| 12 | MNIxDD (SEQ ID NO: 19) |
| 13 | EH[ANK]FW(SEQ ID NO: 20) |
| 14 | VHNAY (SEQ ID NO: 21) |
| 15 | HG[EA]xLN (SEQ ID NO: 22) |
| 16 | [GD]xx[LF]xxP[ML]Q (SEQ ID NO: 23) |

TABLE 5-continued

Motifs and peptides comprising panel for the diagnosis of Mononucleosis.

| ID | Panel motif and Antigen(s); peptide sequence(s) |
|---|---|
| 17 | [LVMI]xNAx[TS][FGI] (SEQ ID NO: 24); BPLF2 (Large tegument protein); IaNAgSI (SEQ ID NO: 47) |
| 18 | PxNSYT (SEQ ID NO: 25) |
| 19 | RxxPLAxxL (SEQ ID NO: 26) |
| 20 | CPKxNxT (SEQ ID NO: 27) |
| 21 | Q[PA]H[AM]F (SEQ ID NO: 28) |
| 22 | PAxENxxx[GSP] (SEQ ID NO: 29) |
| 23 | NID[DE]D (SEQ ID NO: 30) |
| 24 | RxQx[VS]D[NA] (SEQ ID NO: 31) |
| 25 | Wx[DP]PxHL (SEQ ID NO: 32) |
| 26 | TWA[FI][FI] (SEQ ID NO: 33) |
| 27 | EDxGHP (SEQ ID NO: 34) |
| 28 | [ETA]xxx[YF]xxP[SR]Q (SEQ ID NO: 35) |
| 29 | GMxP[RK]Q (SEQ ID NO: 36) |
| 30 | Wxx[VI]RxxPxQ (SEQ ID NO: 37); EBNA-3B nuclear protein; WaqIRhiPyQ (SEQ ID NO: 48) |
| 31 | [NE][AG]Y[SAT]xxW (SEQ ID NO: 38) |
| 32 | KxI[ST]xYW (SEQ ID NO: 39) |
| 33 | YYxYRxxK (SEQ ID NO: 40) |
| 34 | KxHExG[FY] (SEQ ID NO: 41) |
| 35 | [MLF]xNPQQ (SEQ ID NO: 853); Major capsid protein (MCP); MrNPQQ (SEQ ID NO: 49) |
| 36 | HHFL[VI] (SEQ ID NO: 42) |
| 37 | [LV]CNAY (SEQ ID NO: 43) |

Example 7. Discovery of Motifs for the Diagnosis of Zika Virus Infection

Figure 12A:
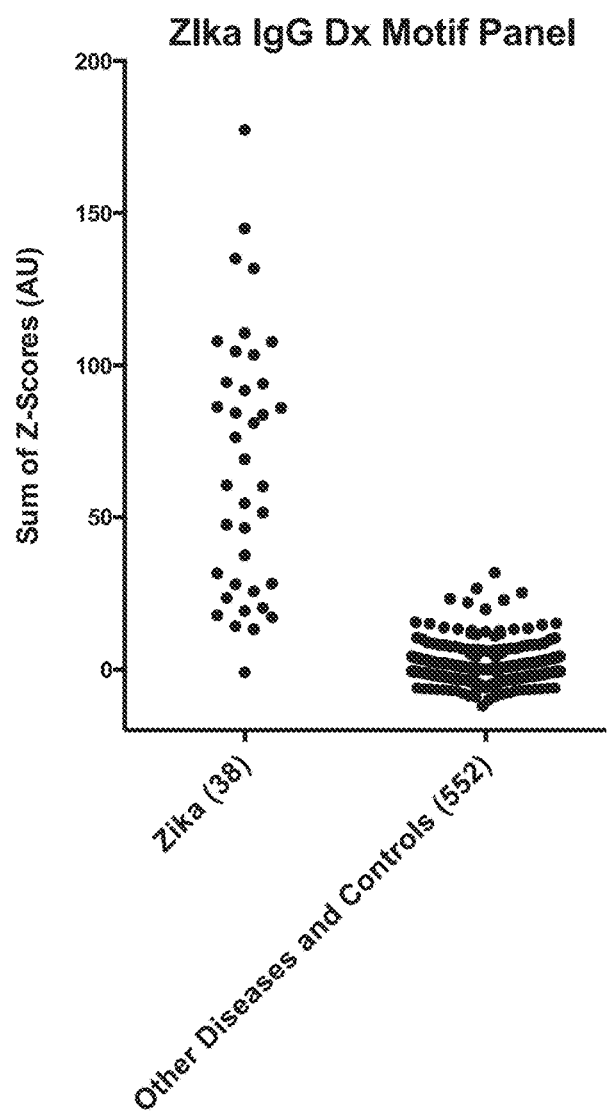
FIG. 12A illustrates the performance of IgG ZIKA virus infection motif panel in a discovery sample set.
Figure 12B:
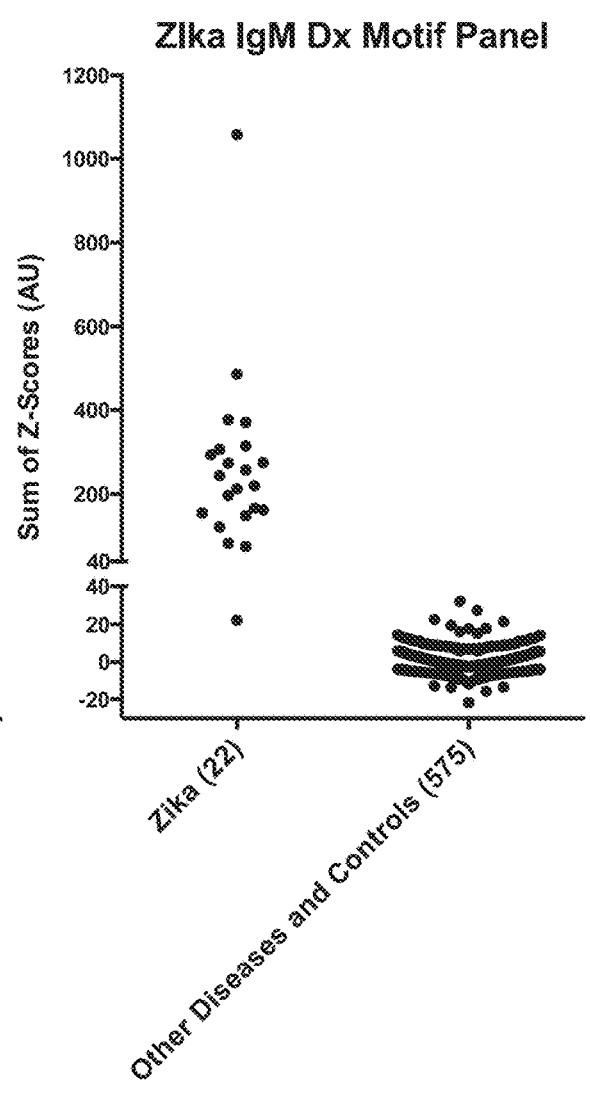
FIG. 12B illustrates the performance of an IgM motif panel for diagnosis of Zika virus infection, exhibiting a sensitivity of 95% and specificity of 100%.

A total of 38 specimens from individuals positive for Zika virus infection by IgG and/or IgM serology and clinical criteria (e.g. red eyes, fatigue, joint pain, etc) using an enzyme immunoassay were analyzed. The method of Example 1 was to identify IgG and IgM motifs specific to Zika virus infection (Table 6, Table 7) Motif panels were capable of identifying individuals with Zika virus infections (FIG. 12). Similarly, the method of example 1, with the following modifications was used to identify IgM motifs indicative of Zika infection. Rather than using protein A/G beads, peptide displaying cells complexed with IgM were separated and enriched from non-binders using a biotinylated monoclonal antibody specific for human IgM, followed by cell capture on streptavidin-conjugated magnetic beads.

TABLE 6

IgG motifs comprising IgG panel for the diagnosis of Zika

| ID | Panel motif |
|---|---|
| 1 | VRxxYxQH (SEQ ID NO: 319) |
| 2 | CEDxxxHxC (SEQ ID NO: 320) |
| 3 | DAEQxxR (SEQ ID NO: 321) |
| 4 | WPGIF (SEQ ID NO: 322) |
| 5 | CCYDxE (SEQ ID NO: 323) |
| 6 | LxPDNxT (SEQ ID NO: 324) |
| 7 | FxWGQxY (SEQ ID NO: 325) |
| 8 | KxEGHxxxxA (SEQ ID NO: 326) |
| 9 | CxxGxCQxK (SEQ ID NO: 327) |
| 10 | CCxDxx[DE][ED] (SEQ ID NO: 328) |
| 11 | RNGxED (SEQ ID NO: 329) |
| 12 | [DE]xRxIYxQ (SEQ ID NO: 330) |
| 13 | WxRCGL (SEQ ID NO: 331) |
| 14 | D[ED]xRxx YxxH (SEQ ID NO: 332) |
| 15 | WCxLx[AV]N (SEQ ID NO: 333) |
| 16 | LXTPWI (SEQ ID NO: 334) |
| 17 | CWxxxGL[CA] (SEQ ID NO: 335) |
| 18 | ID[AV]EP (SEQ ID NO: 336) |
| 19 | HF[NK][VT]xK (SEQ ID NO: 337) |
| 20 | QxNHQxK (SEQ ID NO: 338) |

TABLE 7

IgM motifs comprising IgM panel for the diagnosis of Zika.

| ID | Panel motif |
|---|---|
| 1 | FExKEP (SEQ ID NO: 339) |
| 2 | [FYW]DA[VI] (SEQ ID NO: 340) |
| 3 | DFDKR (SEQ ID NO: 341) |
| 4 | WETC (SEQ ID NO: 342) |
| 5 | KLDGP (SEQ ID NO: 343) |
| 6 | WIYPxK (SEQ ID NO: 344) |
| 7 | V[HS]DSK (SEQ ID NO: 345) |
| 8 | EQCGT (SEQ ID NO: 346) |
| 9 | [KE][MVIT]PYA (SEQ ID NO: 347) |
| 10 | [DE]xxML[RP]W (SEQ ID NO: 348) |
| 11 | YExLHx[FY] (SEQ ID NO: 349) |
| 12 | WY[TSN]xEK (SEQ ID NO: 350) |
| 13 | [YF]H[DNS]AV (SEQ ID NO: 351) |

TABLE 7-continued

IgM motifs comprising IgM panel for the diagnosis of Zika.

| ID | Panel motif |
|---|---|
| 14 | DxTG[VI]P (SEQ ID NO: 352) |
| 15 | FDxxGEH (SEQ ID NO: 353) |
| 16 | QC[AK]xx[HE]C (SEQ ID NO: 354) |
| 17 | LW[FY]xPxE (SEQ ID NO: 355) |
| 18 | C[MI][PA]GxxC (SEQ ID NO: 356) |
| 19 | Cxxxx[AVS]ADC (SEQ ID NO: 357) |
| 20 | TTESxV (SEQ ID NO: 854) |
| 21 | KDV[GA]E (SEQ ID NO: 855) |
| 22 | KPxD[FWM]GxK (SEQ ID NO: 856) |
| 23 | VxADGT (SEQ ID NO: 857) |
| 24 | M[AP][AT]AD (SEQ ID NO: 858) |
| 25 | VPxPK[DG] (SEQ ID NO: 859) |
| 26 | QxKP[TS]D (SEQ ID NO: 860) |
| 27 | F[TS]xDGF (SEQ ID NO: 861) |
| 28 | Wx[RK]VY[VA] (SEQ ID NO: 862) |
| 29 | [CS]T[TS]Exxx[YF] (SEQ ID NO: 863) |
| 30 | YxETC[TI] (SEQ ID NO: 864) |

Example 8. Discovery of Motifs for the Diagnosis for HIV Infection

Figure 13:
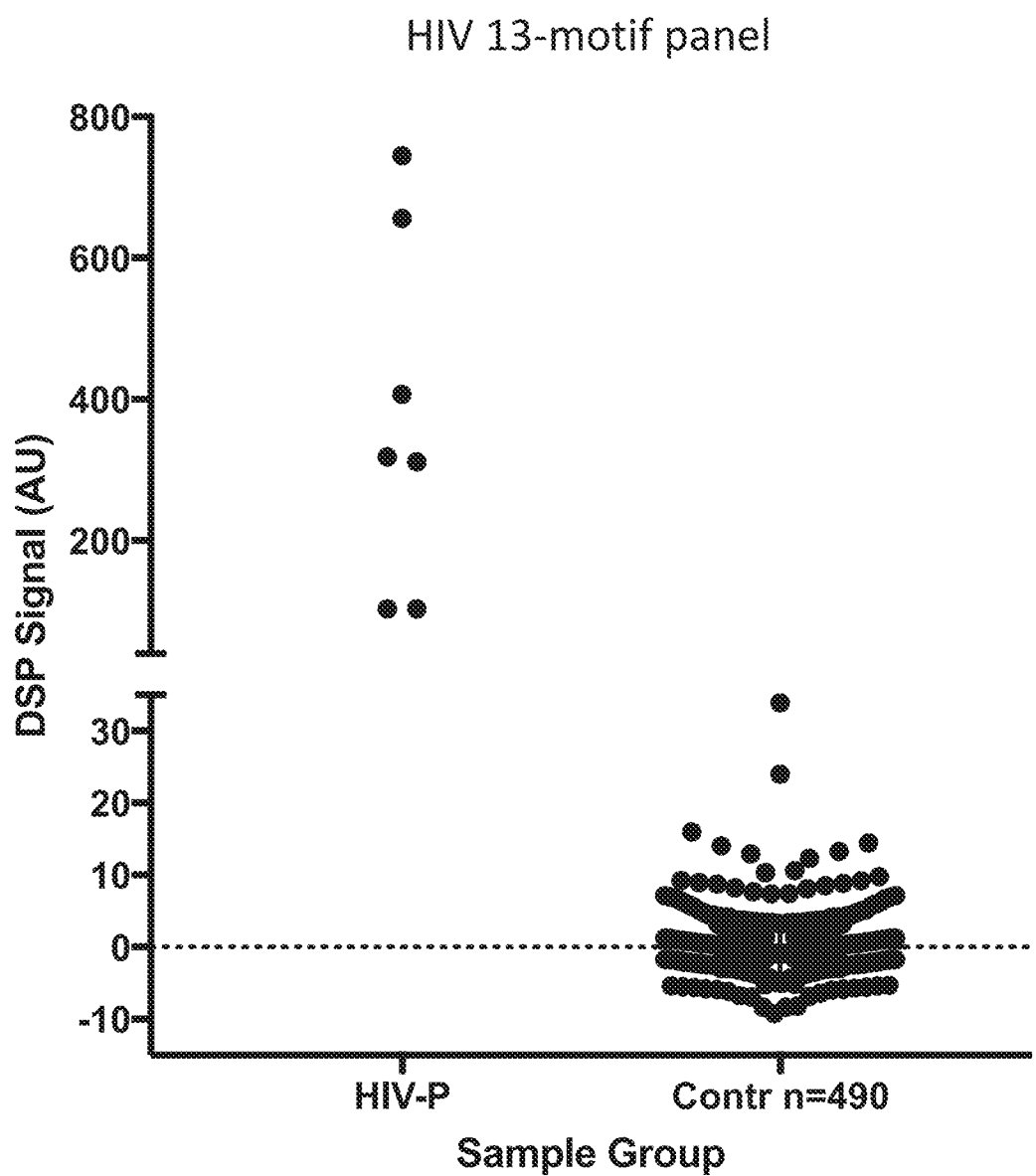
FIG. 13 illustrates the performance of HIV infection motif panel in a discovery and validation sample sets, exhibiting a sensitivity of 100% and specificity of 100%.

Sera from seven individuals with HIV infection were analyzed as described for Example 1. Motifs specific to HIV infection are as shown in Table 8. A panel of motifs was capable of identifying individuals with HIV (FIG. 13), and discriminating those with infections from those without infections.

TABLE 8

Motifs and peptides comprising panel for the diagnosis of HIV infection.

| ID | Panel motif | Antigen(s); peptide sequence(s) |
|---|---|---|
| 1 | CxGxLIC (SEQ ID NO: 290 | Envelope glycoprotein gp160; CSGKLIC (SEQ ID NO: 306) |
| 2 | CxxKx[IV]C[IV] (SEQ ID NO: 291 | Envelope glycoprotein gp160; CSGKLICT (SEQ ID NO: 306) |
| 3 | W[GAS]CxGxxxC (SEQ ID NO: 292) | Envelope glycoprotein gp160; WGCSGKLIC (SEQ ID NO: 308) |
| 4 | [RK]KL[IV]E (SEQ ID NO: 293 | |
| 5 | KLIMT (SEQ ID NO: 294) | |
| 6 | [QE]xxPFRY (SEQ ID NO: 295) | |
| 7 | CxxKx[IV]C[IV] (SEQ ID NO: 296) | Envelope glycoprotein gp160; CSGKLICT (SEQ ID NO: 309) |
| 8 | [LF]xx[LIV][ND]KW (SEQ ID NO: 297) | Envelope glycoprotein gp160; LLALDKW (SEQ ID NO: 310) |
| 9 | [AP][GC]GFG (SEQ ID NO: 298) | Envelope glycoprotein gp160; AVGMG (SEQ ID NO: 311) |
| 10 | LIx[TS]TY (SEQ ID NO: 299) | Envelope glycoprotein gp160; LICTT (SEQ ID NO: 312) |
| 11 | [RK]KLxx[MV]Y (SEQ ID NO: 300) | |
| 12 | GF[GA][AQ][AYV] (SEQ ID NO: 301) | Envelope glycoprotein gp160; GFGAV (SEQ ID NO: 313) |
| 13 | GFG[RQ]x[FNY] (SEQ ID NO: 302) | |
| 14 | [KR]KxIH[VIM] (SEQ ID NO: 303) | Envelope glycoprotein gp160; RKgIrI (SEQ ID NO: 314) KKgIaI (SEQ ID NO: 315), RKgIhM (SEQ ID NO: 316), RKsIhM (SEQ ID NO: 317) |

TABLE 8-continued

Motifs and peptides comprising panel for the diagnosis of HIV infection.

| ID | Panel motif | Antigen(s); peptide sequence(s) |
|---|---|---|
| 15 | R[IV]PFG (SEQ ID NO: 304) | |
| 16 | KLIxx[TY]T (SEQ ID NO: 305) | Envelope glycoprotein gp160; KLICTT (SEQ ID NO: 318) |

Example 9: Sjogren's Syndrome—Discovery of Diagnostic Motifs and Peptides

Primary Sjogren's Syndrome (SS) is a chronic, highly prevalent autoimmune disease affecting about 0.3-0.5% of people in the western world. The hallmark symptoms are dry eyes and mouth, which are a result of T cell and autoantibody infiltration of the exocrine glands leading to loss of secretory function and, over time, eventual gland destruction. The gradual destruction of the exocrine glands underscores the importance of early diagnosis and treatment to patient quality of life. The heterogeneity of symptoms, their association with aging and lack of specific diagnostic tests all contribute to delayed diagnosis with an average time of 4.7 years. Serological testing for autoantibodies including La/SS-B, Ro/SS-A, Anti-nuclear antibodies (ANAs) and rheumatoid factor (RE) are used to aid in SS diagnosis, however, they do not provide sufficient specificity to be used as a stand-alone diagnostic test. Identification of novel SS specific biomarkers is thus an important unmet diagnostic need. The heterogeneity of SS may reflect different subcategories of SS with unique sets of autoantibodies, posing an additional diagnostic challenge. In this Example, we identified biomarkers that are specific to SS and defined their association with specific disease subpopulations. The tests can be combined into a single multiplex assay having greater overall specificity and sensitivity than current tests.

Until recently, no SS classification criteria have been universally accepted because of the subjective and non-specific nature of SS diagnostics. The new criteria, endorsed by the American College of Rheumatology, requires a positive result in 2 out of 3 of the following objective tests:
1. Positive serum anti-SSA/Ro and/or anti-SSB/La or (positive rheumatoid factor (RF) and ANA titer 1:320), requiring 3 separate ELISAs and an indirect immunofluorescence assay (WA).
2. Labial salivary gland biopsy exhibiting focal lymphocytic sialadenitis (focus score 1 focus/4 mm2)
3. Dry eye as measured by staining on the surface of the eye with ocular staining score 3.

The need for multiple testing modalities is redundant, costly and labor intensive. Identification of a panel of biomarkers that could identify SS with high sensitivity and specificity as a single serological test could streamline and expedite SS diagnosis and improve patient outcomes.

In this Example, we identified motifs, patterns and peptides specific for primary Sjogren's Syndrome (pSS). The experiment procedure is as described in Example 1.

Figure 14:
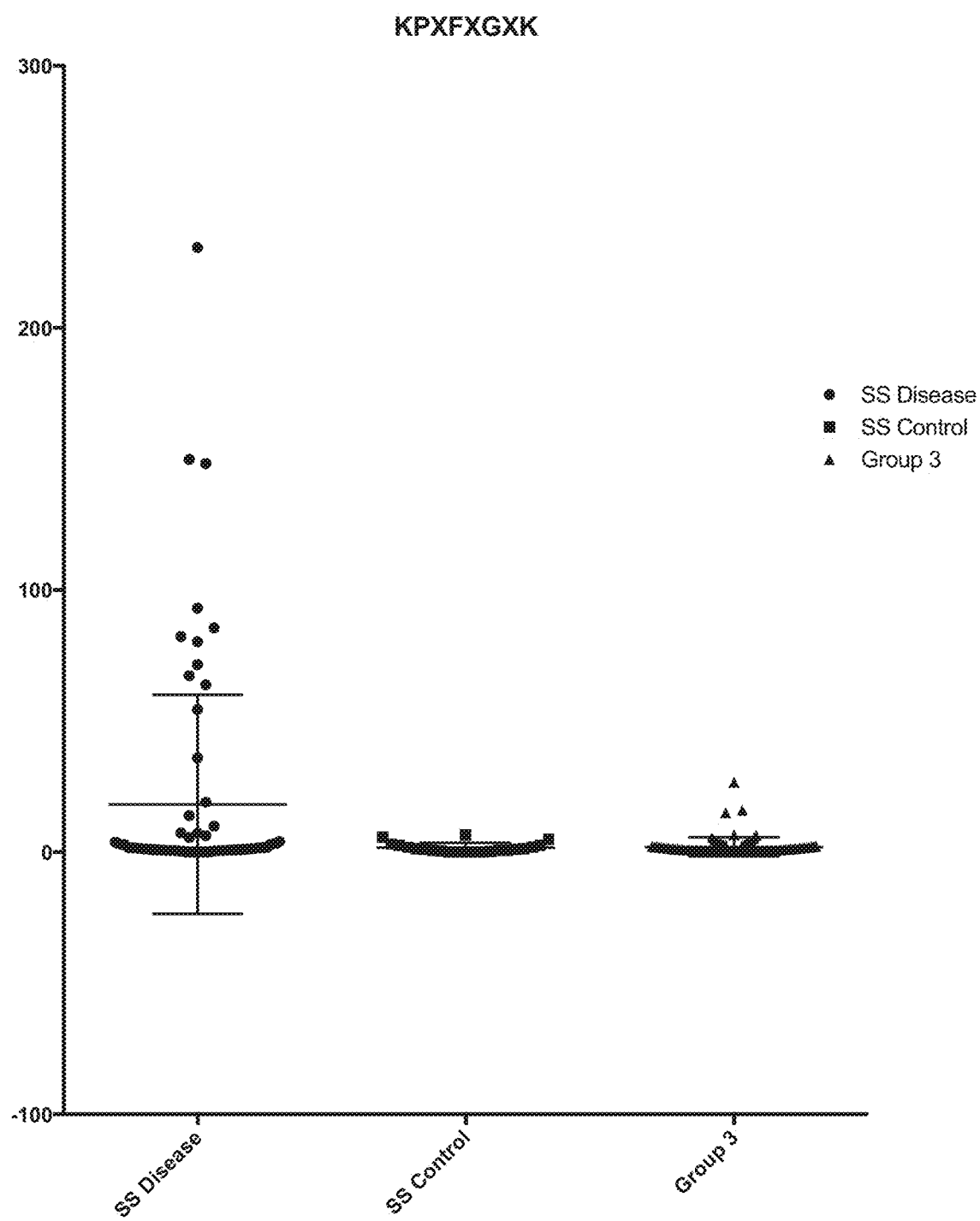
FIG. 14 illustrates the performance of an individual Sjogren's syndrome diagnostic motif (SEQ ID NO: 929) in a discovery and validation sample sets.

Examples of motifs specific to pSS include KPXFXGXK (SEQ ID NO: 929). Specificity of individual motifs (e.g., KPXFXGXK (SEQ ID NO: 929)) is also evident in dot plots (FIG. 14).

To use the pSS motifs for diagnosis of pSS, one obtains a serum or blood sample, screens a peptide display library using that sample, determines the resulting enriched sequences, and then queries for the enrichment of disease specific motifs. If one or more disease specific motif is present, then enrichment values for the pSS specific motifs are determined, and compared to a reference cutoff value.

Example 10. Discovery of Motifs Indicating Latent Epstein-Barr Virus Infection

Epstein-Barr virus (EBV) is a ubiquitous latent infection in the human population, with B-cells being the primary host for the virus. Despite being ubiquitous active EBV is associated with mononucleosis, and reactivation of latent EBV has been associated with various autoimmune diseases. Furthermore, EBV serology has shown to a risk factor for autoimmune diseases, since negative serology for EBV dramatically lowers the risk of multiple sclerosis. For these reasons, EBV serology is clinically useful.

To identify diagnostic motifs and epitopes useful for EBV serology, 20 samples from samples obtained from individuals with EBV mononucleosis were analyzed for peptide motifs using the methods described above. Peptide motifs were discovered by pattern clustering (e.g. using IMUNE algorithm).

Among the top 40 most abundant motifs, motifs corresponding to EBV epitopes were identified by searching the motif against the non-redundant protein database for all exact matches. Nine EBV motifs were identified that exactly matched a corresponding epitope in an EBV protein. See Table 9. Multiple motifs were experimentally validated to correspond to the indicated epitope within EBV.

To diagnose active infection, one or more of the motifs in Table 9 are searched within an epitope repertoire from any individual to determine serological status for EBV infection. For each motif, an enrichment of 3-fold or greater is indicative of infection See FIG. 25. Active infection can be ascertained by measuring the enrichment for motifs corresponding to BFRF2, GP42, and BVRF2, which correspond to epitopes in viral capsid antigens (VCA).

TABLE 9

Exemplary motifs and peptides for serological detection of latent EBV infection.

| EBV Motif ID | Motif | Peptide epitope in EBV protein |
|---|---|---|
| EBV.EBNA-1.1 | GRRPFF (SEQ ID NO: 269) | GRRPFF (SEQ ID NO: 281) |
| EBV.EBNA-1.2 | GGGxGAGGG (SEQ ID NO: 270) | GGGAGAGGG (SEQ ID NO: 282) |
| EBV.EBNA-1.3 | EG[PA]ST[GA]R (SEQ ID NO: 271) | EGPSTGPR (SEQ ID NO: 283) |
| EBV.EBNA-1.4 | KXXSC[IVL]GC[RK] (SEQ ID NO: 272), SCIGCK | KRPSCIGCK (SEQ ID NO: 284) |

TABLE 9-continued

Exemplary motifs and peptides for serological detection of latent EBV infection.

| EBV Motif ID | Motif | Peptide epitope in EBV protein |
|---|---|---|
| | (SEQ ID NO: 273), CIGC (SEQ ID NO: 274) | |
| EBV.GP42.1 | VxLPHW (SEQ ID NO: 275), LPHW (SEQ ID NO: 276) | KEVKLPHWTPT (SEQ ID NO: 285) |
| EBV.BFRF2 | PQDT[GA]PR (SEQ ID NO: 277) | PQDTAPR (SEQ ID NO: 286) |
| EBV.EBNA-2.1 | GPPWWP (SEQ ID NO: 278) | GPPWWP (SEQ ID NO: 287) |
| EBV.BVRF2/ BdRF1 | QQPTTXGW (SEQ ID NO: 279) | QQPTTEGH (SEQ ID NO: 288) |
| EBV.EBNA-2.2 | [LMIV]FDXDWYP (SEQ ID NO: 280) | LFPDDWYP (SEQ ID NO: 289) |

Example 11. Discovery of Motifs Related to Rhinovirus Virus Infection, and Determination of Prior Rhinovirus Infection Human rhinovirus is a common upper respiratory infection in humans, and is associated with a robust immune response. Recent infections typically increase the titer of Rhinovirus specific antibodies. Thus, by measuring the titer of antibodies towards Rhinovirus motifs or patterns, one can identify prior or recent infection with Rhinovirus.

Motifs indicative of Rhinovirus are shown in Table 10, searching epitope repertoires for rhinovirus patterns, peptides, and motifs identifies individuals with a humoral immune response against these epitopes, which can provide a measure of whom has been infected, and whether their infection was recent (by the magnitude of the enrichment signal).

TABLE 10

Exemplary motifs and peptides for serological detection of Rhinovirus infection or exposure

| Motif ID | Motif | Peptide epitope in protein |
|---|---|---|
| Rhinovirus. VP1.1 | L[EDQ]EV[LIV][IV][DE]K (SEQ ID NO: 50), E[VI][VIL][IV][DEN]K (SEQ ID NO: 51), E[VI][VI][VI]XK (SEQ ID NO: 52) | ELEEV[IV]VDK (SEQ ID NO: 58) |
| Rhinovirus. VP1.2 | VXPNI (SEQ ID NO: 53), VVPN (SEQ ID NO: 54), LXEVLVVVP (SEQ ID NO: 55) | LNEVLVVVPNI (SEQ ID NO: 59) |
| Rhinovirus. VP1.3 | GPXHTXKV (SEQ ID NO: 56) | GPKHTQKV (SEQ ID NO: 60) |
| Rhinovirus A. VP1 | EXY[VI]DX[VT]LN (SEQ ID NO: 57) | EEYVDQVLN (SEQ ID NO: 61) |

Example 12. Discovery of Motifs Related to Cytomegalovirus Infection

Human cytomegalovirus (CMV) is a common infectious herpes virus (HHV-5), often infecting salivary glands. CMV can remain dormant or latent in tissues for long periods of time, but can be reactivated by various stimuli. Infections can be life threatening in immunocompromised individuals, for instance when infected with human immunodeficiency virus (HIV) or after organ transplantation. CMV has been associated with cancers, diabetes, arterial hypertension, and other diseases. See [41, 42]. Given this, there is need to identify those infected with CMV and determine whether infected individuals are at higher risk of developing specific diseases.

Diagnosis of CMV infection can be made by looking for the presence of anti-CMV antibodies although not all of the protein and peptide antigen epitopes are known. Epitope specific detection of prior CMV infection can also be useful, for example, to associate clinical phenotypes and risks to specific antibody species.

To identify motifs indicative of latent CMV infection, epitope repertoires were determined using laboratory analysis as described above for 40 individuals with Sjogren's syndrome and 40 healthy controls, wherein a subset of each group are positive for CMV infection. Peptides present in five or more pSS and five or more healthy control epitope repertoires were then extracted from the sequence files in order to perform motif discovery via clustering with MEME. Among the resulting motifs were KXDPDXXW[ST] (SEQ ID NO: 62) and KPXLGGK (SEQ ID NO: 63), both of which occur in CMV proteins. See Table 11. These CMV associated motifs can be detected in individual epitope repertoires to assess CMV serology and exposure.

TABLE 11

Exemplary motifs and peptides for serological detection of Cytomegalovirus infection or exposure.

| Motif ID | Motif | Peptide epitope in protein |
|---|---|---|
| CMV.RL13.1 | KXDPDXXW[ST] (SEQ ID NO: 62) | KXDPDXXWT (X = variable positions in viral protein) (SEQ ID NO: 64) |
| CMV.Teg.1 | KPXLGGK (SEQ ID NO: 63) | KPtLGGK (SEQ ID NO: 65) |

Example 13. Discovery of Motifs Related to *Streptococcus* Infection

*Streptococcus pyogenes* and other *Streptococcus* species are common pathogens in humans, and accurate diagnosis can help to identify proper treatments. Antibody titer can increase in response to ongoing or recent infection. Several motifs were identified by using the methodology described herein in a set of individuals with and without autoimmune disease, grouping peptides present in >30% of samples, and then performing motif discovery. See Table 12. Motifs identified were used to search for proteins containing these motifs in the non-redundant protein database using Scanprosite. Three motifs identified primarily *Streptococcus* associated antigens, including PspC, Streptolysin 0, the later of which is a known target of the human immune response. Here, however, we have identified the protein site targeted by antibodies, and specific motifs and peptides useful for the detection of these antibodies in an epitope repertoire, or serum sample, respectively.

TABLE 12

Exemplary motifs and peptides for serological detection of *Streptococcus* infection

| Motif ID | Motif | Peptide epitope in protein |
|---|---|---|
| *Streptococcus*. PspC.1 | [IV]X[PR]QPEKP (SEQ ID NO: 66) | VKPQPEKP (SEQ ID NO: 71) |
| *Streptococcus*. Streptolysin 0.1 | KXDDMLN (SEQ ID NO: 67), KXDXMLN (SEQ ID NO: 68) | KTDDMLN (SEQ ID NO: 72) |
| *Streptococcus*. Streptolysin 0.2 | LW]XSAEXEEK (SEQ ID NO: 69), SAEXEXK (SEQ ID NO: 70) | LESAEKEEK (SEQ ID NO: 73) |

Example 14. Discovery of Motifs Diagnostic of *Haemophilus* Influenza Infection

*Haemophilus influenza* is a gram positive bacteria that infects humans, and is associated with pneumonia, meningitis, sinusitis, and other conditions. Determination of infection or of specific serotypes or species can help to determine proper antibiotic therapy.

To identify motifs indicative of *Haemophilus* influenza infection or exposure, the methods provided herein were used to determine epitope repertoires in 40 individuals with Sjogren's syndrome, and 40 healthy controls. Peptides present in five or more pSS and five or more healthy control epitope repertoires were then extracted from the sequence files in order to perform motif discovery via clustering with MEME. Clustering identified the motif MKEAX[SA]EK (SEQ ID NO: 497) which as an epitope MKEAASEK (SEQ ID NO: 498) in an poorly characterized protein antigen of *Haemophilus* influenza.

Example 15. Discovery of Motifs Diagnostic of Leishmani Infection

Figure 15:
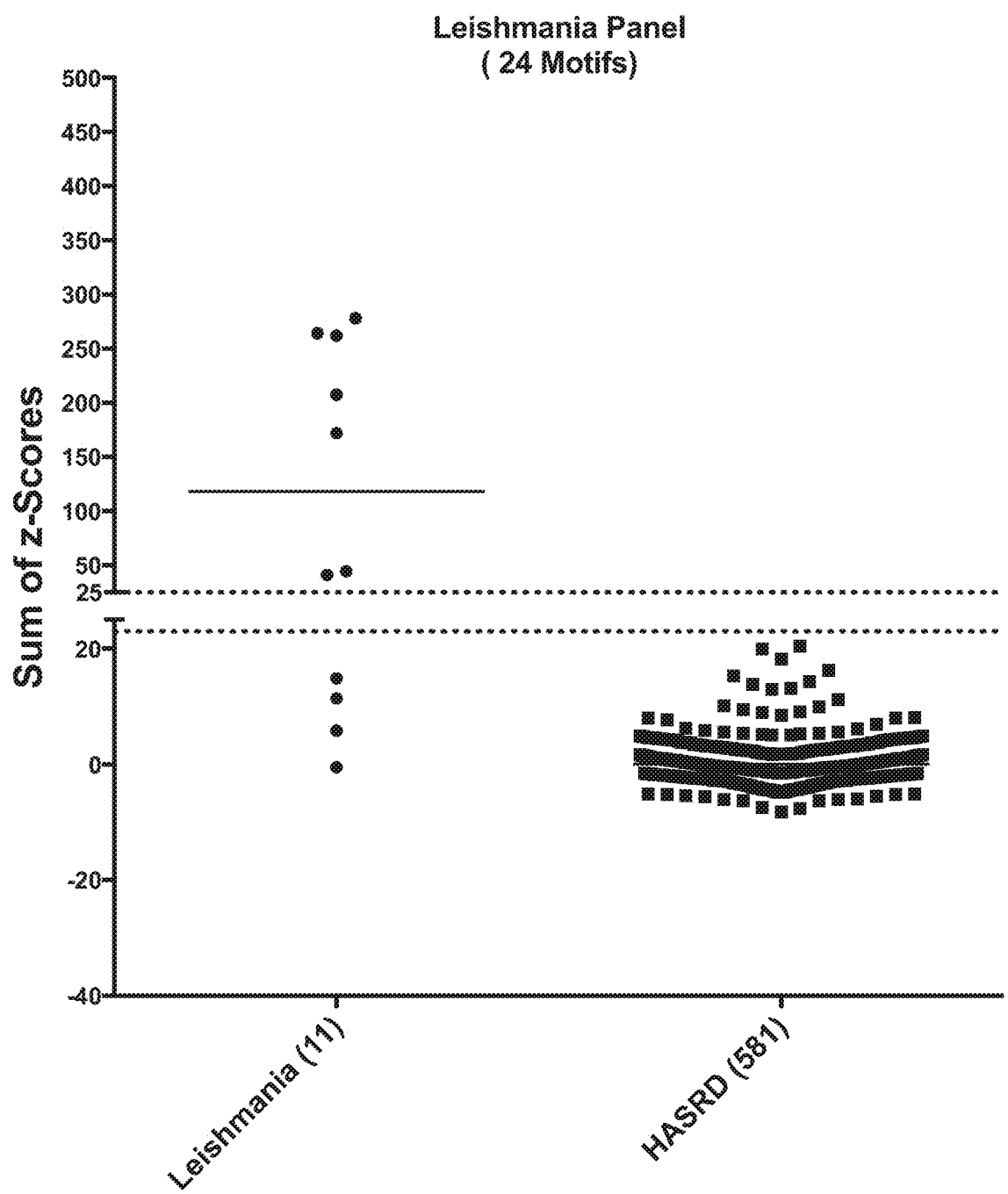
FIG. 15 illustrates the performance of *Leishmania* infection motif panel in a discovery and validation sample sets, exhibiting a sensitivity of 65% and specificity of 100%.

Samples from individuals (n=11) with Leishmani infections were analyzed by the methods described herein resulting in the motif panel in Table 13. A panel of motifs from Table 13 was capable of identifying individuals with *Leishmania* infections (FIG. 15).

TABLE 13

Motifs indicative of *Leishmania* infection.

| *Leishmania* motif | Peptide Hit(s) | Putative Antigen |
|---|---|---|
| R[IV]PFG (SEQ ID NO: 499) | RVPFG (SEQ ID NO: 519) | Uncharacterized protein. *Leishmania panamensis* and other sp |
| | RIPFG (SEQ ID NO: 520) | DNA-directed RNA polymerase subunit *Leishmania panamensis* |
| | RIPFG (SEQ ID NO: 521) | DNA-directed RNA polymerase subunit (EC 2.7.7.6). *Leishmania braziliensis* |
| | GGIfRVPFG (SEQ ID NO: 522) | 1-acyl-sn-glycerol-3-phosphateacyltransferase-like protein, putative *Leishmania panamensis* |
| KGXATP (SEQ ID NO: 500) | KGKATPS (SEQ ID NO: 523) | Histone H2A.1. *Leishmania infantum* |
| | KGKATPS (SEQ ID NO: 524) | Histone H2A. *Leishmania donovani* |
| P[ML]xVGP (SEQ ID NO: 501) | PL[VSPLR]VGP (SEQ ID NO: 525) | Uncharacterized protein. *Leishmania panamensis* and other sp |
| PKxDG[RY] (SEQ ID NO: 502) | PKvDGR (SEQ ID NO: 526) | Protein kinase, putative (EC 2.7.11.1). *Leishmania panamensis* |
| | PKaDGR (SEQ ID NO: 527) | Uncharacterized protein. *Leishmania panamensis* |
| | PKaDGY (SEQ ID NO: 528) | Uncharacterized protein. *Leishmania panamensis* |

TABLE 13-continued

Motifs indicative of Leishmania infection.

| Leishmania motif | Peptide Hit(s) | Putative Antigen |
| --- | --- | --- |
| | PKeDGR (SEQ ID NO: 529) | Hydrophilic acylated surface protein b. Leishmania infantum peptide has multiple repeats |
| Leishmania motif | Peptide Hit(s) | Putative Antigen |
| | PKeDGR (SEQ ID NO: 530) | K26 protein (Fragment). Leishmania infantum peptide has multiple repeats |
| KxDGH[ES] (SEQ ID NO: 503) | KyDGHS (SEQ ID NO: 531) | Uncharacterized protein. Leishmania panamensis |
| | KcDGHE (SEQ ID NO: 532) | Uncharacterized protein. Leishmania panamensis |
| VQx[FY]Mx[RK] (SEQ ID NO: 504) | VQhYMhR (SEQ ID NO: 865) | Uncharacterized protein. Leishmania panamensis and other sp |
| | VQIFMIR (SEQ ID NO: 533) | " |
| | VQiYMaK (SEQ ID NO: 534) | " |
| | VQIFMrR (SEQ ID NO: 535) | " |
| DRxPx[GA]x[VA] (SEQ ID NO: 505) | VQsYMIR (SEQ ID NO: 536) | " |
| | VQIYMdK (SEQ ID NO: 537) | " |
| | VQIYMdK (SEQ ID NO: 538) | Aquaglyceroporin. Leishmania donovani |
| DXIDX[VL]W (SEQ ID NO: 506) | DdIDILW (SEQ ID NO: 539) | ATPase domain protein, putative. Leishmania panamensis and other sp |
| RQPxG[RQ] (SEQ ID NO: 507) | RQPcGQ (SEQ ID NO: 540) | Mitochondrial chaperone BCS1, putative. Leishmania panamensis |
| | RQPqGR (SEQ ID NO: 866) | Protein kinase, putative (EC 2.7.11.1). Leishmania panamensis |
| | RQPIGR (SEQ ID NO: 541) | ENOL protein (EC 4.2.1.11) (Fragment). Leishmania braziliensis |
| PxHGIH (SEQ ID NO: 508) | | |
| DGDGP (SEQ ID NO: 509) | DGDGP (SEQ ID NO: 509) | Inositol polyphosphate phosphatase, putative (EC 3.1.3.36). Leishmania panamensis |
| | DGDGP (SEQ ID NO: 509) | Putative inositol polyphosphate phosphatase (EC 3.1.3.36). Leishmania braziliensis |
| | DGDGP (SEQ ID NO: 509) | Hydrophilic acylated surface protein b. Leishmania infantum |
| Hxx[NQ]TPx[KR] (SEQ ID NO: 510) | HptNTPeK (SEQ ID NO: 542) | Uncharacterized protein. Leishmania panamensis and other sp |
| | HpvNTPdK (SEQ ID NO: 543) | " |
| | HavQTPsK (SEQ ID NO: 544) | " |
| | HtfQTPqR (SEQ ID NO: 545) | " |
| | HvnQTPyR (SEQ ID NO: 546) | " |
| | HdgNTPaK (SEQ ID NO: 547) | Putative kinesin (EC 3.6.4.4). Leishmania infantum |
| Leishmania motif | Peptide Hit(s) | Putative Antigen |
| K[SA]xNP[HE] (SEQ ID NO: 511) | KSaNPE (SEQ ID NO: 548) | Uncharacterized protein. Leishmania panamensis |

TABLE 13-continued

Motifs indicative of *Leishmania* infection.

| *Leishmania* motif | Peptide Hit(s) | Putative Antigen |
|---|---|---|
| | KSINPE (SEQ ID NO: 549) | RNase III domain-containing protein. *Leishmania panamensis* |
| [EQDN]xLPHE (SEQ ID NO: 512) | KASNPH (SEQ ID NO: 550) NaLPHE (SEQ ID NO: 551) | Histone H2B. *Leishmania donovani* Uncharacterized protein. *Leishmania panamensis* |
| | DaLPHE (SEQ ID NO: 552) | " |
| | EpLPHE (SEQ ID NO: 553) | " |
| | EmLPHE (SEQ ID NO: 554) | 2-oxoglutarate dehydrogenase subunit, putative (EC 1.2.4.2). *Leishmania panamensis* |
| | QpLPHE (SEQ ID NO: 555) | |
| GQYG[VIM] (SEQ ID NO: 513) | GQYGV (SEQ ID NO: 556) | Uncharacterized protein. *Leishmania panamensis* |
| PR[ML]x[DN]K (SEQ ID NO: 514) | | |
| FGQ[GQ]xxxD (SEQ ID NO: 515) | | |
| DD[GRS]xTxK (SEQ ID NO: 516) | | |
| IxT[FP]DR (SEQ ID NO: 517) | | |
| KxxNIGxx[FY] (SEQ ID NO: 518) | KipNIGdkF (SEQ ID NO: 557) | DNA-directed RNA polymerase subunit beta (EC 2.7.7.6). *Leishmania panamensis* |

Example 16. Discovery of Motifs Diagnostic of *Babesia microti* Infection

Figure 16:
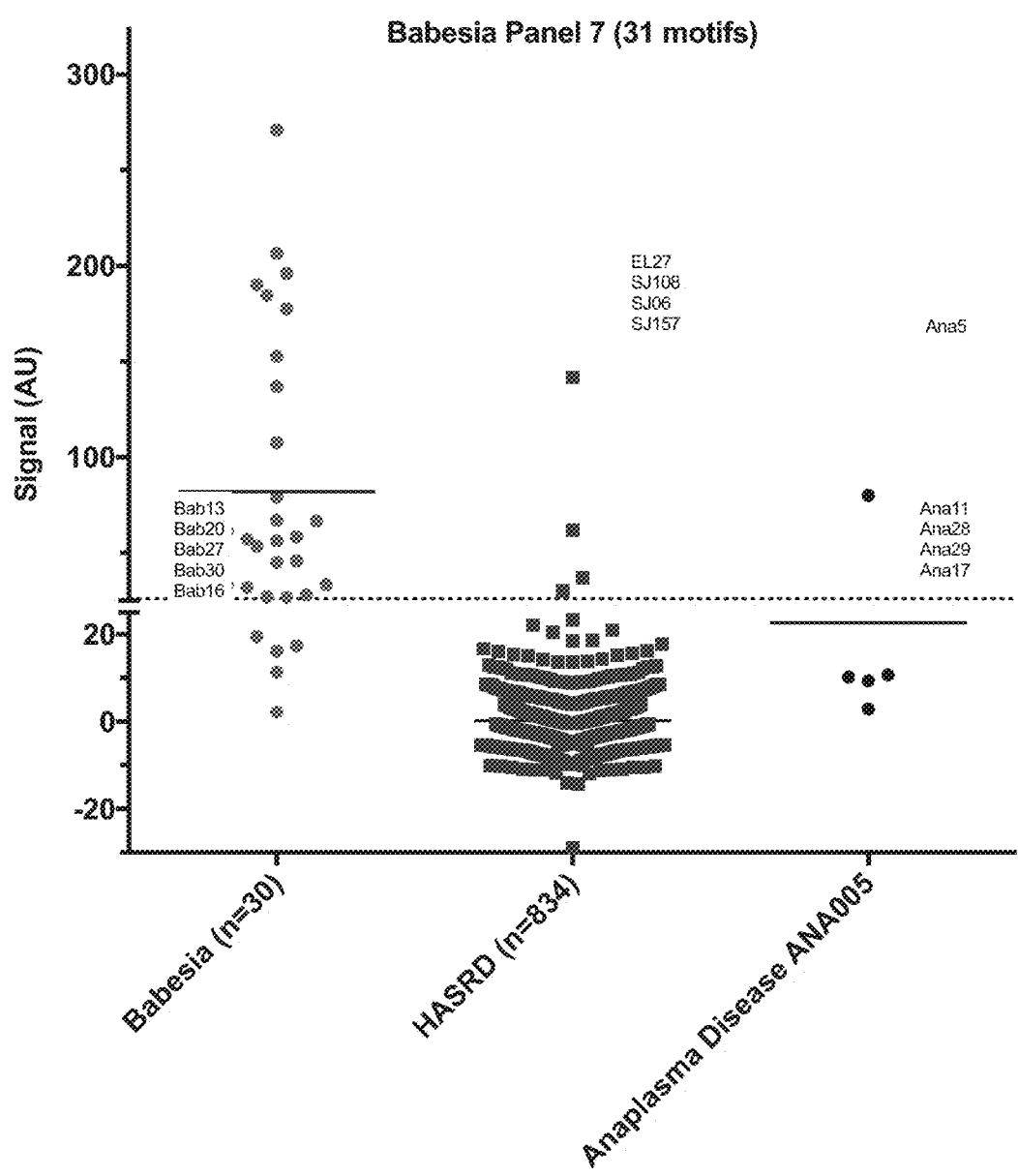
FIG. 16 illustrates the performance of *Babesia* infection motif panel in a discovery and validation sample sets, exhibiting a specificity of >99.5%.

*Babesia* infections are one of the most common infections transmitted by blood transfusions. *Babesia* can be spread by ticks and is commonly a co-infection in individuals infected with Lyme disease. A total of 30 samples with confirmed serology for *Babesia* infections, were analyzed according to the methods of Example 1. Motifs specific to individuals with probable or confirmed *Babesia* infections are shown in Table 14. A panel of motifs was capable of identifying individuals with Babesiosis (FIG. 16), and discriminting those with infections from those without infections.

TABLE 14

Exemplary motifs and peptides for serological detection of Babesia infection

| ID | Panel motif |
|---|---|
| 1 | [ML]L[AS][TA]xK (SEQ ID NO: 558) |
| 2 | [VL]x[AS]xDPxxP (SEQ ID NO: 559) |
| 3 | [KR]x[IL]x[ST][MLF]N (SEQ ID NO: 560) |
| 4 | TG[KR]MxxxxQ (SEQ ID NO: 561) |
| 5 | GxPY[STA]xxxx[ML] (SEQ ID NO: 562) |
| 6 | WE[EDA]x[PA]JI (SEQ ID NO: 563) |
| 7 | E[IV]xHxxFxR (SEQ ID NO: 564) |
| 8 | Kxx[TS]HRxK (SEQ ID NO: 565) |
| 9 | TFExGxK (SEQ ID NO: 566) |
| 10 | WENx[RA]xxx[FI] (SEQ ID NO: 567) |
| 11 | [NT][MF]FxxxxWxD (SEQ ID NO: 568) |
| 12 | [PA][GA][IV][MITV]xxP (SEQ ID NO: 569) |
| 13 | KxxRxS[YWH]D (SEQ ID NO: 570) |
| 14 | EKxxRxx[YF][DN] (SEQ ID NO: 571) |
| 15 | DTxTPxE (SEQ ID NO: 572) |
| 16 | WL[DA]QW (SEQ ID NO: 573) |
| 17 | K[EN]xxDxWN (SEQ ID NO: 574) |
| 18 | [GT]GNGG (SEQ ID NO: 575) |
| 19 | G[YFW]Dxx[QT]P (SEQ ID NO: 576) |
| 20 | [IV]GxS[RK]x[CR] (SEQ ID NO: 577) |
| 21 | [SAT]TPx[MLJE] (SEQ ID NO: 578) |

TABLE 14-continued

Exemplary motifs and peptides for serological detection of Babesia infection

| ID | Panel motif |
|---|---|
| 22 | S[DQ]WxWE (SEQ ID NO: 579) |
| 23 | Dxx Y[IT]xx[HF]K (SEQ ID NO: 580) |
| 24 | K[YF]xxxL[IVT]K (SEQ ID NO: 581) |
| 25 | P[VI]x YMQ (SEQ ID NO: 582) |
| 26 | WPTGxxx[SN] (SEQ ID NO: 583) |
| 27 | Kx[IM][VN]xWA (SEQ ID NO: 584) |
| 28 | W[AP]TG[KR] (SEQ ID NO: 585) |

Example 17. Discovery of Motifs Diagnostic of *Ehrlichia* Infection

Figure 17:
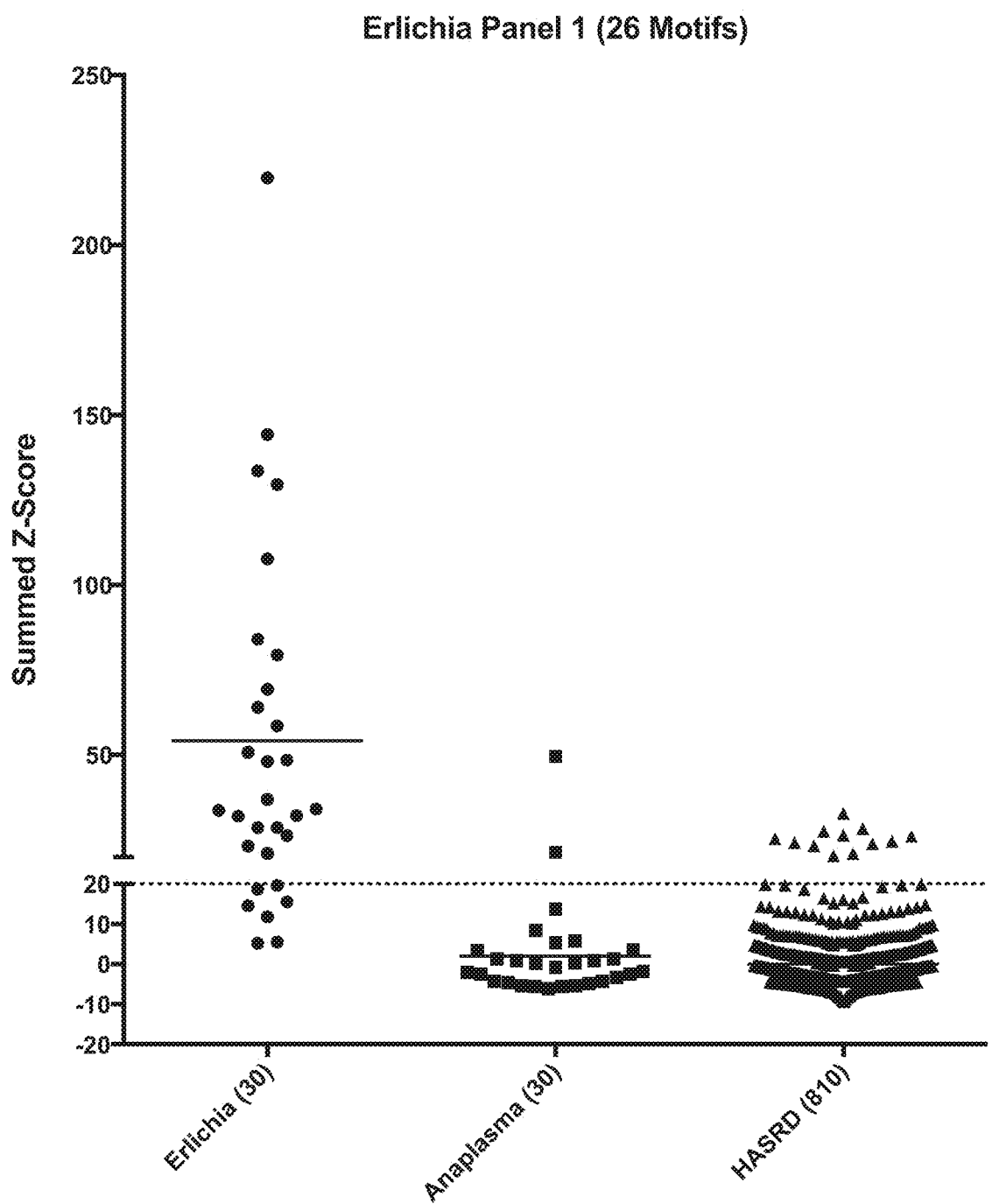
FIG. 17 illustrates the performance of *Ehrlichia* infection motif panel in a discovery and sample set.

A total of 30 specimens with positive IgG or IgM serology for *Ehrlichia* infection were analyzed according to the method of Example 1. Motifs specific to *Ehrlichia* infection are shown in Table 15. A panel of motifs was capable of identifying individuals with Ehrlichiosis (FIG. 17), and discriminating those with infections from those without infections.

TABLE 15

Exemplary motifs and peptides for serological detection of Erhlichia infection

| ID | Panel motif |
|---|---|
| 1 | YxxL[IV]xP[KR] (SEQ ID NO: 586) |
| 2 | [SA]Nx[ML]FY (SEQ ID NO: 587) |
| 3 | WDGSx[IV] (SEQ ID NO: 588) |
| 4 | PxxL[IV]KP (SEQ ID NO: 589) |
| 5 | KxDWDG (SEQ ID NO: 590) |
| 6 | RxxxxKxD[HY]D (SEQ ID NO: 591) |
| 7 | VDVMGN (SEQ ID NO: 592) |
| 8 | Ex[NQ][QN]xFY (SEQ ID NO: 593) |
| 9 | Vx[TS][TS]N (SEQ ID NO: 594) |
| 10 | KLHDP (SEQ ID NO: 595) |
| 11 | KxDxDT[GN] (SEQ ID NO: 596) |
| 12 | Y[HA]GWx[SAE] (SEQ ID NO: 597) |
| 13 | NPEH[DTE] (SEQ ID NO: 598) |
| 14 | NPAxQ[HR] (SEQ ID NO: 599) |
| 15 | [KR]MNKxx[TP] (SEQ ID NO: 600) |
| 16 | DWxxx[FY][VK]K (SEQ ID NO: 601) |
| 17 | GVN[APTS]xK (SEQ ID NO: 602) |
| 18 | [IV]x[PR]EGxK (SEQ ID NO: 603) |
| 19 | RVF[ST][MA] (SEQ ID NO: 604) |

TABLE 15-continued

Exemplary motifs and peptides for serological detection of Erhlichia infection

| ID | Panel motif |
|---|---|
| 20 | NxRxx[VI]W[YF] (SEQ ID NO: 605) |
| 21 | Yxx[MTL]x YNA (SEQ ID NO: 606) |
| 22 | Kx[VI]x[ND][IV]W (SEQ ID NO: 607) |
| 23 | [ED][YF]Q[LQ]H (SEQ ID NO: 608) |
| 24 | FGxPSI (SEQ ID NO: 609) |
| 25 | QLVGxxK (SEQ ID NO: 610) |
| 26 | YxxL[IV]xP[KR] (SEQ ID NO: 611) |

Example 18. Discovery of Motifs Diagnostic of *Anaplasma* Infection

Figure 18:
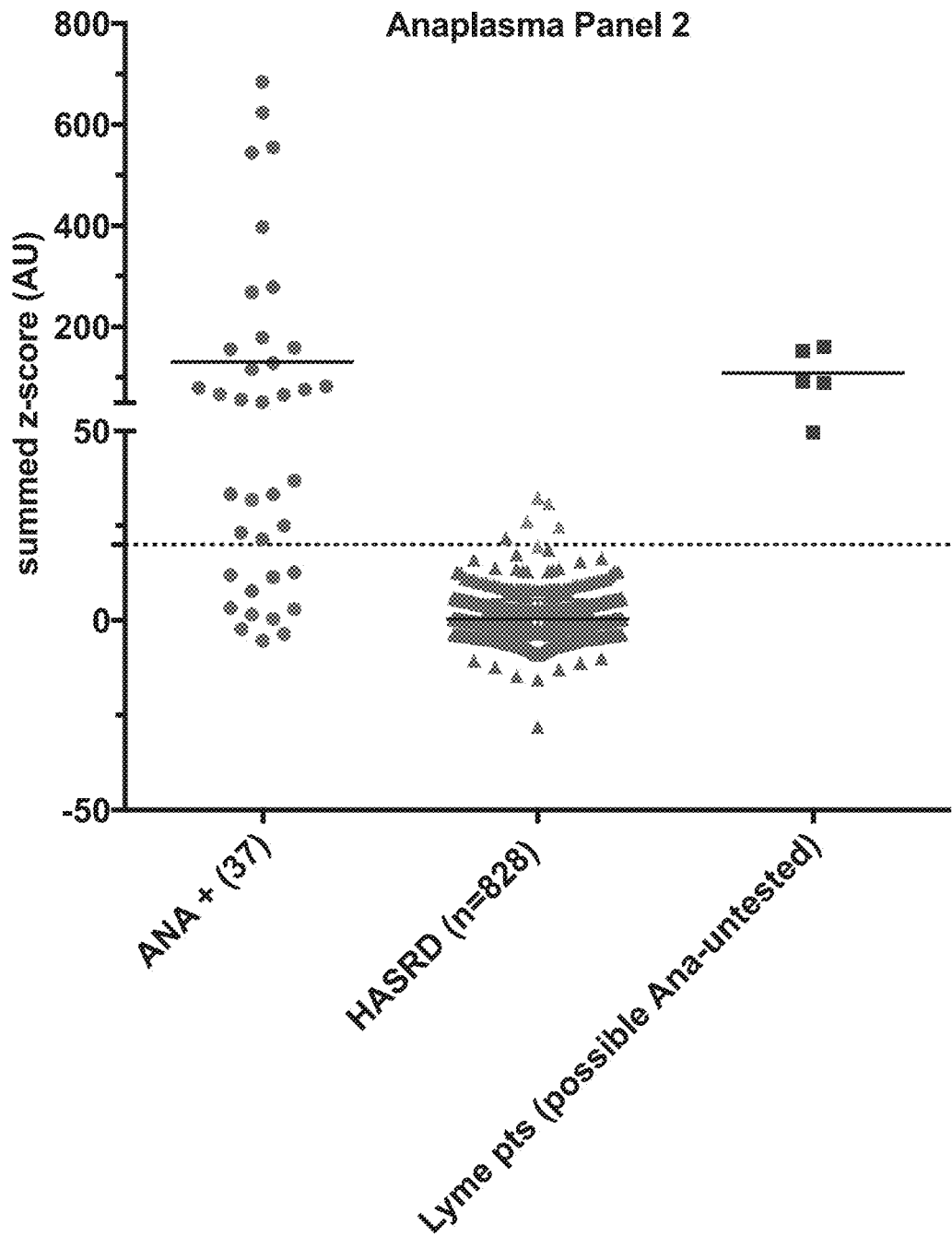
FIG. 18 illustrates the performance of *Anaplasma phagocytophilum* infection motif panel in a discovery sets, exhibiting a specificity of >99.5%.

A total of 30 specimens with positive IgG serology for *Anaplasma phagocytophilum* were analyzed according to the method of Example 1. Motifs specific to *Anaplasma* infection are shown in Table 16. A panel of motifs was capable of identifying individuals with Anaplasmosis (FIG. 18), and discriminating those with infections from those without infections.

TABLE 16

Exemplary motifs and peptides for serological detection of Anaplasma infection.

| ID | Panel motif |
|---|---|
| 1 | W[YK]Wx[PA]K (SEQ ID NO: 612) |
| 2 | KxExH[NK]F (SEQ ID NO: 613) |
| 3 | QxxxWPYxK (SEQ ID NO: 614) |
| 4 | YxFDxNxR (SEQ ID NO: 615) |
| 5 | FxWN[VI]P (SEQ ID NO: 616) |
| 6 | [FW][LM]EXAH (SEQ ID NO: 617) |
| 7 | DF[LI]xAT (SEQ ID NO: 618) |
| 8 | KxMSxFV (SEQ ID NO: 619) |
| 9 | W[YK]Wx[PA]K (SEQ ID NO: 620) |
| 10 | KxExH[NK]F (SEQ ID NO: 621) |
| 11 | QxxxWPYxK (SEQ ID NO: 622) |
| 12 | WPT[SF]T (SEQ ID NO: 623) |
| 13 | WP[TA]GR (SEQ ID NO: 624) |
| 14 | KNWPx[GF] (SEQ ID NO: 625) |
| 15 | KxxP[LI]FA (SEQ ID NO: 626) |
| 16 | WPxGQV (SEQ ID NO: 627) |
| 17 | [VI][LR]KDF (SEQ ID NO: 628) |
| 18 | WPT[SF]T (SEQ ID NO: 629) |
| 19 | Kx[IM][VN]xWA (SEQ ID NO: 630) |

TABLE 16-continued

Exemplary motifs and peptides for serological detection of Anaplasma infection.

| ID | Panel motif |
|---|---|
| 20 | [YW]TxEPF (SEQ ID NO: 631) |
| 21 | [AM][PTS]WExF (SEQ ID NO: 632) |
| 22 | R[PT][RTK]F[NS] (SEQ ID NO: 633) |
| 23 | VY[SA]HW (SEQ ID NO: 634) |
| 24 | [WF]xxKPxWxxM (SEQ ID NO: 635) |
| 25 | KGx[SA]HxF (SEQ ID NO: 636) |
| 26 | KGxVxF[AS] (SEQ ID NO: 637) |
| 27 | [IV]xHxTID (SEQ ID NO: 638) |
| 28 | MLSXXVN (SEQ ID NO: 639) |
| 29 | KxYSxxVR (SEQ ID NO: 640) |
| 30 | Kx[VK]VNP (SEQ ID NO: 641) |

Example 19. Discovery of Motifs for the Diagnosis of *Toxocara canis* Infection

Figure 19:
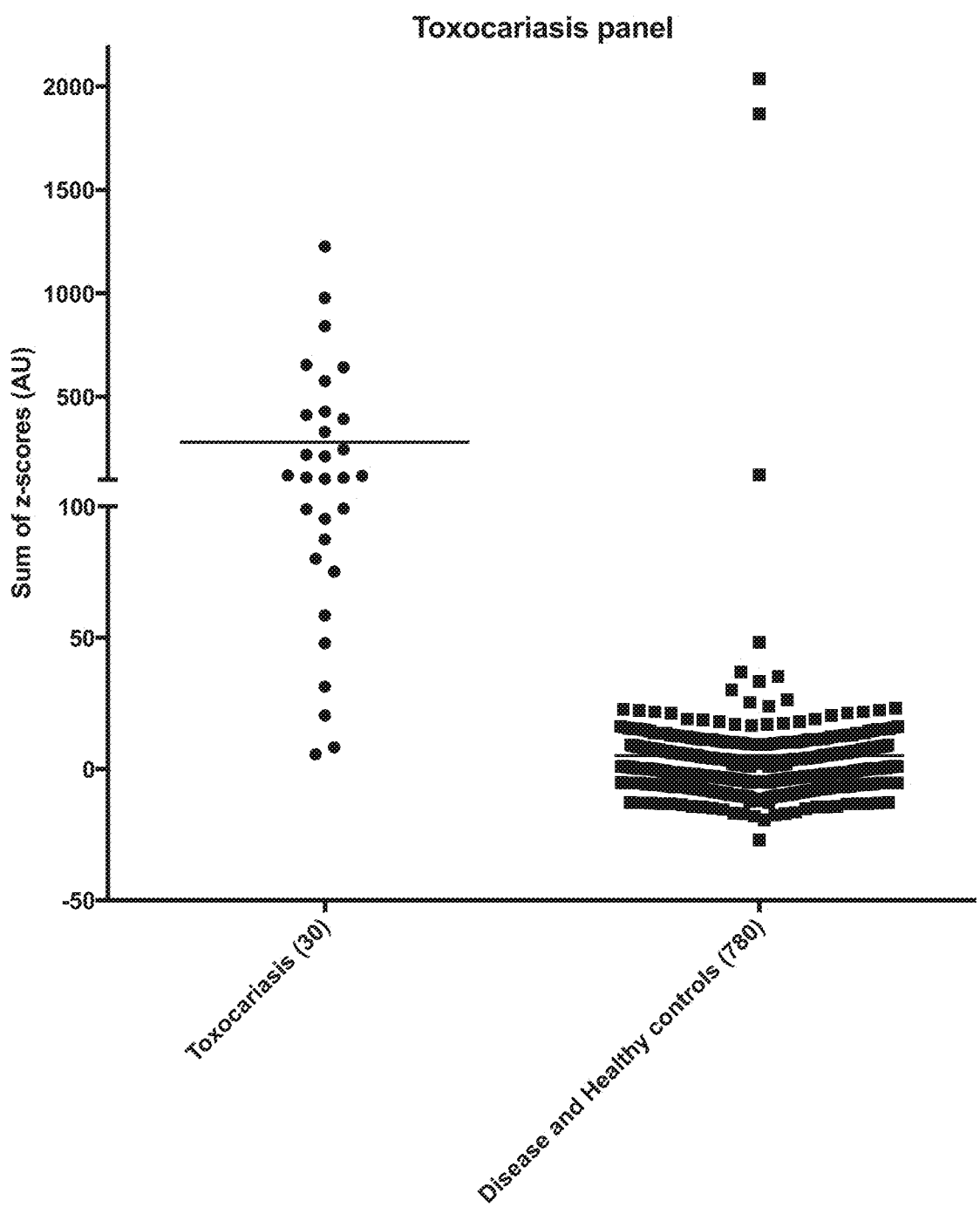
FIG. 19 illustrates the performance of a *Toxocara canis* infection motif panel in a discovery sample set, exhibiting a specificity of >99.5%.

*Toxocara canis* is a common parasitic infection, present in 5-20% of individuals in the United states. Diagnosis is dependent upon the use of serology to detect antibodies present in blood or other body fluids. The methods of Example 1 were used to develop a panel of motifs (Table 17), which correctly identified individuals with *Toxocara canis* infections (FIG. 19).

TABLE 17

Exemplary motifs and peptides for serological detection of *Toxocara canis* infection.

| ID | Panel motif | Antigen(s); peptide sequence(s) |
|---|---|---|
| 1 | [RKH]EPGD (SEQ ID NO: 642) | Putative ubiquitin-conjugating enzyme E2 7, Alpha/beta hydrolase domain-containing protein 14A, Multidrug resistance protein pgp-1, Filamin-A; HEPGD (SEQ ID NO: 680), REPGD (SEQ ID NO: 681), KEPGD (SEQ ID NO: 682), REPGD (SEQ ID NO: 683) |
| 2 | CxxIxNExC (SEQ ID NO: 643) | Uncharacterized protein; CkkIvNEtC (SEQ ID NO: 684) |
| 3 | ESR[SN]I (SEQ ID NO: 644) | Disintegrin and metalloproteinase domain-containing protein 12, 5-formyltetrahydrofolate cyclo-ligase, Putative neurobeachin-like protein, Putative glycogen [starch] synthase; ESRSI (SEQ ID NO: 685), ESRNI (SEQ ID NO: 686) |
| 4 | HPDx[QN]L (SEQ ID NO: 645) | Acetylcholinesterase 1, Sex comb on midleg-like protein 2, Cysteine string protein, Transport and Golgi organization 2-like protein, Secreted frizzled-related protein 5; HPDvNL(SEQ ID NO: 687), HPDgNL(SEQ ID NO: 688), HPDKNL(SEQ ID NO: 689), HPDeQL(SEQ ID NO: 690),HPDtQL(SEQ ID NO: 691) |
| 5 | RYxH[FY][ED] (SEQ ID NO: 646) | Uncharacterized protein, G2/M phase-specific E3 ubiquitin-protein ligase, Sorting nexin-33; RYCHFD (SEQ ID NO: 692), RYyHYD (SEQ ID NO: 693), RYKHFD (SEQ ID NO: 694) |
| 6 | F[AS]xRQxP (SEQ ID NO: 647) | Uncharacterized protein; Methyltransferase-like protein 13, Choline transporter-like protein 1, WD repeat-containing protein 46; FSfRQqP (SEQ ID NO: 695), FAHRQqP(SEQ ID NO: 696), FAHRQrP(SEQ ID NO: 697), FAtRQgP(SEQ ID NO: 698) |
| 7 | QD[AP]RN (SEQ ID NO: 648) | Voltage-dependent T-type calcium channel subunit alpha-1H; QDPRN (SEQ ID NO: 699) |
| 8 | Lxx[ILM]NQQ (SEQ ID NO: 649) | Uncharacterized protein, Putative U5 small nuclear ribonucleoprotein helicase, Cullin-5, Signal recognition particle 54 kDa protein, Soluble guanylate cyclase gcy-36; LlqLNQQ (SEQ ID NO: 700), LsIMNQQ (SEQ ID NO: 701), LfwINQQ (SEQ ID NO: 702), LqkLNQQ (SEQ ID NO: 703), LiILNQQ (SEQ ID NO: 704) |

TABLE 17-continued

Exemplary motifs and peptides for serological detection of *Toxocara canis* infection.

| ID | Panel motif | Antigen(s); peptide sequence(s) |
|---|---|---|
| 9 | [VA]xDGA[WF] (SEQ ID NO: 650) | Disintegrin and metalloproteinase domain-containing protein 12, Chondroadherin-like protein, Eukaryotic translation initiation factor 4E transporter, Zinc finger A20 and AN1 domain-containing stress-associated protein 9, Ras-related protein Rab-21; ApDGAF (SEQ ID NO: 705), VqDGAF (SEQ ID NO: 706), AgDGAF (SEQ ID NO: 707), AcDGAF (SEQ ID NO: 708), AiDGAF(SEQ ID NO: 709) |
| 10 | CxLPE[MTS] (SEQ ID NO: 651) | Leucine-rich repeat-containing protein 57, Odorant response abnormal protein 4, Transforming protein v-Fos/v-Fox, Choline kinase alpha, Neprilysin-2, Kynurenine formamidase; CsLPES (SEQ ID NO: 710), CpLPET(SEQ ID NO: 711), CvLPES(SEQ ID NO: 712), CrLPET(SEQ ID NO: 713), CpLPET(SEQ ID NO: 714), CdLPET(SEQ ID NO: 715) |
| 11 | FxxMQ[THS]K (SEQ ID NO: 652) | 2-acylglycerol O-acyltransferase 1, Melanoma-associated antigen G1; FkkMQSK(SEQ ID NO: 716), FIfMQHK(SEQ ID NO: 717) |
| 12 | GH[GAS]xLR (SEQ ID NO: 653) | Hemicentin-2, PX domain-containing protein kinase-like protein, Putative UDP-glucuronosyltransferase ugt-47, Zinc finger and BTB domain-containing protein 16; GHStLR(SEQ ID NO: 718), GHSaLR(SEQ ID NO: 719), GHGtLR(SEQ ID NO: 720), GHGrLR(SEQ ID NO: 721), GHGfLR(SEQ ID NO: 722) |
| 13 | Wxx[DE]YxxL[VE] (SEQ ID NO: 654) | Guanylate cyclase receptor-type gcy-1; WqiDYtsLV (SEQ ID NO: 723) |
| 14 | F[HND][YF]PR (SEQ ID NO: 655) | Nuclear hormone receptor family member nhr-6, Laminin-like protein epi-1, Striatin-interacting protein 2, ATP-dependent RNA helicase cgh-1, Metal tolerance protein 4, IST1-like protein, FERM domain-containing protein 4A; FDFPR (SEQ ID NO: 724), FDYPR (SEQ ID NO: 725), FNYPR (SEQ ID NO: 726) |
| 15 | PE[FY]TS (SEQ ID NO: 656) | Lysine-tRNA ligase, Sodium bicarbonate transporter-like protein 11; PEFTS (SEQ ID NO: 727) |
| 16 | CDxPSxxxC (SEQ ID NO: 657) | Tripartite motif-containing protein 2; CDaPStrsC |
| 17 | [FY]xxNGHxF (SEQ ID NO: 658) | Protein kinase C-binding protein NELL1, Protein kinase C; YyqNGHeF(SEQ ID NO: 728), YhvNGHrF(SEQ ID NO: 729) |
| 18 | YxICxExxC (SEQ ID NO: 659) | |
| 19 | DCMGxxC (SEQ ID NO: 660) | Dynein heavy chain-like protein; DCMGtfC (SEQ ID NO: 867) |
| 20 | [ML]xTGLx[DE] (SEQ ID NO: 661) | TBC1 domain family member 9B, Synaptobrevin-like protein YKT6, Acyl-CoA dehydrogenase family member 10, Cohesin subunit SA-1, Geranylgeranyl transferase type-1 subunit beta, Methyltransferase-like protein 13; LiTGLpD (SEQ ID NO: 730), MyTGLpE(SEQ ID NO: 731), LwTGLeE(SEQ ID NO: 732), LITGLaD(SEQ ID NO: 733), LITGLID(SEQ ID NO: 734), MdTGLvD(SEQ ID NO: 735) |
| 21 | MxLGYY (SEQ ID NO: 662) | Latrophilin-3; MrLGYY (SEQ ID NO: 736) |
| 22 | MP[LT]Gx[YH] (SEQ ID NO: 663) | Epoxide hydrolase 1; MPTGgH (SEQ ID NO: 737) |
| 23 | [FL]QTGx[IL] (SEQ ID NO: 664) | Protein FAM43A, Protein NDNF, 4-coumarate--CoA ligase 1; LQTGtL(SEQ ID NO: 738), LQTGkL(SEQ ID NO: 739), FQTGdI(SEQ ID NO: 740) |
| 24 | Kx[TS]CPC (SEQ ID NO: 665) | |

TABLE 17-continued

Exemplary motifs and peptides for serological detection of Toxocara canis infection.

| ID | Panel motif | Antigen(s); peptide sequence(s) |
|---|---|---|
| 25 | CKD[TSD]C (SEQ ID NO: 666) | |
| 26 | CG[VA]F[EQ] (SEQ ID NO: 667) | C-type lectin Tc-ctl-4, Collectin-12, Thyroid adenoma-associated-like protein; CGAFE(SEQ ID NO: 741), CGVFQ(SEQ ID NO: 742) |
| 27 | SNx[IVAE]Axx[IML] (SEQ ID NO: 668) | E3 ubiquitin-protein ligase UBR5, Hyaluronidase-1, DNA repair protein RAD2, Seipin, Ectopic P granules protein 5, Serpentine receptor class alpha/beta-14; SNrVAsfL(SEQ ID NO: 743), SNKAArqM(SEQ ID NO: 744), SNsAAvdL(SEQ ID NO: 745), SNdVAkiI(SEQ ID NO: 746), SNaVAqvL(SEQ ID NO: 747), SNn VAfeI(SEQ ID NO: 748) |
| 28 | PTxLxHx[KR] (SEQ ID NO: 669) | Putative thiosulfate sulfurtransferase, Sodium/hydrogen exchanger, F-box/WD repeat-containing protein 5; PTgLdHhR(SEQ ID NO: 749), PTyLiHeR(SEQ ID NO: 750) |
| 29 | WPVNN (SEQ ID NO: 670) | |
| 30 | [VIA]CN[GD]xxxxC (SEQ ID NO: 671) | Anoctamin-5, Laminin subunit alpha-2, Laminin-like protein epi-1, Vacuolar protein sorting-associated protein 45; ICNDssrrC(SEQ ID NO: 751), ACNGhsitC(SEQ ID NO: 752), VCNGhadtC(SEQ ID NO: 753), ACNGehsqC(SEQ ID NO: 754) |
| 31 | [KR]NP[YS]L (SEQ ID NO: 672) | ATP synthase lipid-binding protein, mitochondrial, Transmembrane cell adhesion receptor mua-3, Putative 39S ribosomal protein L49, mitochondrial, Nuclear distribution protein nudE-like 1, Putative serine protease, Cytosolic non-specific dipeptidase; RNPSL(SEQ ID NO: 755), KNPSL(SEQ ID NO: 756) |
| 32 | CXXXPMXVXC (SEQ ID NO: 673) | |
| 33 | G[LM][KQT]FxxD (SEQ ID NO: 674) | Meiotic recombination protein DMC1/LIM15-like protein, Serine/threonine-protein kinase WNK1, 40S ribosomal protein S3a, Epidermal growth factor receptor kinase substrate 8, WD repeat-containing protein 82, Dipeptidyl peptidase family member 6; GLTFqaD(SEQ ID NO: 757), GLQFafD(SEQ ID NO: 758), GMKFtrD(SEQ ID NO: 759), GLQFpsD(SEQ ID NO: 760), GLKFspD(SEQ ID NO: 761), GLTFtpD(SEQ ID NO: 762) |
| 34 | [IA]PMx[PAK]N (SEQ ID NO: 675) | Phosphopantothenoylcysteine decarboxylase, Protein kinase C, Achaete-scute-like protein 5, Small nuclear ribonucleoprotein Sm D3; APMdAN(SEQ ID NO: 763), IPMdPN(SEQ ID NO: 764), APMpKN(SEQ ID NO: 765), APMfKN(SEQ ID NO: 766) |
| 35 | WxWCx[HT]xxxC (SEQ ID NO: 676) | |
| 36 | FxxM[QMHE][TH]K (SEQ ID NO: 677) | Melanoma-associated antigen G1, Uncharacterized protein; FlfMQHK(SEQ ID NO: 767), FfdMETK(SEQ ID NO: 768), FeeMQTK(SEQ ID NO: 769) |
| 37 | KxEx[VI]xWR (SEQ ID NO: 678) | Uncharacterized protein; KrEiVfWR( SEQ ID NO: 868) |
| 38 | CH[NT]GxC (SEQ ID NO: 679) | Transcriptional repressor NF-X1-like protein; CHTGpC(SEQ ID NO: 770) |

Example 20. Agents for the Removal or Depletion of Commonly Occurring Antibodies from a Sample Circulating antibody biomarkers have multiple applications in medicine, including without limitation the diagnosis and monitoring of infections, autoimmunity and cancer, as well as therapeutic and vaccine development and validation. One of the greatest challenges in the unbiased discovery of disease-specific antibody biomarkers is the sorting and filtering of the vast number ($10^5$-$10^8$) of unique antibody specificities in any individual repertoire to identify those shared antibody specificities associated with disease.

Although each person's antibody repertoire is unique, a large proportion of antibodies react with common environmental antigens to which people are routinely exposed. Many of these antibodies map to one or a few common epitopes on a given antigen. Removal of these common antibodies from serum prior to biomarker discovery could, in principle, substantially narrow the individual antibody repertoire "noise" allowing for more sensitive and streamlined discovery of disease specific antibodies.

The purpose of this Example is to create a library of peptides that bind to common shared antibody specificities that can be used to remove these antibodies from serum to facilitate improved biomarker discovery. For Display-seq analysis, this "Depletion reagent" could be used in addition to or in lieu of standard E. coli cell depletion as described in the Examples above. The resulting depleted serum would contain a smaller, more patient specific subset of each person's antibody repertoire and would eliminate noise from high titer, non-disease specific antibodies.

Experimental Design Summary

Serum was pooled (3 samples/pool) and used to iteratively sort the X12 peptide library for 14 rounds of affinity selection by a combination of Magnetic activated cell sorting (MACS) and Fluorescence activated cell sorting (FACS). To establish whether this process would converge on a similar set of peptides, two tracks were performed in parallel, each containing a unique set of sera (no overlap). Sorting was stopped when the libraries demonstrated a similar reactivity to serum pools used for screening and naïve pools not used for screening.

Serum Sample Preparation

Each pool was comprised of serum samples from a combination of healthy, Sjogren's syndrome, Myasthenia Gravis and Systemic Lupus Erythematosa sera. Each pool was diluted to a final pooled serum concentration of 1:100 (1:300 individual serum concentration). The pooling strategy and serum dilution were chosen to favor common specificities that would be at a higher titer and/or present in more than one patient in a given pool. Serum pools were depleted of E. coli binding antibodies by incubation with E. coli expressing scaffold only (standard E. coli depletion protocol, see Example 1).

X12 Library Screen

E. coli depleted serum pools were used to screen a naïve bacterial display peptide library with twelve random positions (X12 naïve library) to enrich for peptide mimitopes representing common, abundant antibody specificities. A total of fourteen rounds of screening were performed using a combination of MACS and FACS. The final four rounds of sorting were performed using pools composed exclusively of serum from healthy donors to reduce the likelihood of selecting for a disease-specific antibody specificity that may have been enriched in an earlier sort with a disease-containing serum pool.

The X12 library (diversity $7 \times 10^9$) was grown, induced to express peptides and sorted by MACS and FACS using standard protocols. A summary of the steps is given below:

Library Propagation step: The X12 library was grown to OD 0.4-0.6 in LB medium with chloramphenicol, and peptide expression was induce with 0.02% arabinose for 1 hour.

Library clearing step: Peptide libraries were first cleared of protein A and protein G binders by incubating the induced library with magnetic beads coated with protein A and protein G. Magnetic separation captures the beads along with any cells that are bound to the protein coating the beads. The unbound fraction is collected for screening for serum antibody binders.

MACS Enrichment

Antibody binding step: A pool of (E. coli depleted) serum diluted in PBS was incubated with Protein A and G cleared cells expressing the peptide library. Antibodies from serum that bound to expressed peptides on the cells were harvested using centrifugation followed by washing with PB ST to eliminate non-specific interactions.

Library enrichment step: Washed cells were then incubated with magnetic beads coated with protein A and protein G to capture antibodies from the serum along with the cells expressing peptides the antibodies are interacting with. The beads were washed 5 times with PBST while magnetized to remove cells captured non-specifically.

Growth step: The enriched library (bound to washed beads) was resuspended in LB medium and grown overnight to amplify the library.

Repeat MACS enrichment: MACS enrichment was repeated (×3) with a new serum pool until the estimated library diversity was in the ~$10^5$ range and could be sorted using FACS.

FACS Enrichment and Analysis

Antibody binding step: A different serum pool was used for each subsequent round of enrichment. A pellet of induced cells from the previous enrichment round representing 10× the predicted library diversity was incubated with serum, the sample was centrifuged, unbound antibodies in the supernatant were removed and the pellet was washed to remove non-specific antibody binders.

Library enrichment step: The cell pellet was resuspended in PBS containing a secondary anti-human IgG antibody labeled with Phycoerythrin and incubated to allow for binding to serum antibody-peptide complexes. Cells were centrifuged, the supernatant was removed and the pellet was resuspended in PBS. Cells with bound secondary antibody above background fluorescence were sorted. A minimum of 10 fold over the predicted library diversity was sorted for each round for enrichment steps.

Growth step: The enriched library was resuspended in LB medium and the captured cells were grown overnight to amplify the library.

Next Generation Sequencing to Identify Peptide Sequences

To identify the peptides that were enriched in each of the libraries, the plasmids were purified from the final round of sorting of each library and the amplicons prepared for next-generation sequencing using established Illumina protocols. Briefly, the peptide-encoding region of the plasmid DNA was amplified and barcoded using two rounds of PCR. Samples were pooled and run on the Illumina NextSeq Platform. Parallel tracks were run with separate bar codes to enable a comparison of total sequence diversity in each library and evaluate the motif overlap and determine whether both tracks converged on a set of similar motifs.

Depletion Library Analysis

The Depletion Screen Enriched for Common Antibody Specificities

To evaluate whether the screening process was effective and establish an endpoint for the screen, enriched library pools were analyzed for reactivity to naïve serum pools at various points throughout the screening process. Results are the combined data from both tracks. The final libraries showed >75% binding to ten naïve serum pools indicating that the libraries are highly enriched for cross-reactive antibody mimitopes.

NGS Results and Motif Analysis

The Screening Process Identified a Highly Overlapping Set of Motifs from Two Independent Screens Each library track contained a similar number of unique sequences (Track 1—49,413 Track 2—51,956). To identify enriched motifs and determine whether the screening process selected for a similar set antibody specificities, peptide sequences were compared between the two libraries using IMUNE software, and separated into those that were present in both tracks versus those that were unique to one or the other track. The two tracks shared a total of 1605 full peptides, representing ~3% of the individual library diversities. Next, the peptide sequences that were present in both libraries versus those unique to Track 1 or Track 2 were ranked according to the number of times they appeared in the NGS data. Motifs were generated from the top 5000 peptides from Track 1 only, Track 2 only or both Tracks using MEME. The MEME motifs discovered from each of these analyses are in data room/Depletion Reagent/MEME. A total of 81 unique motifs were identified from the three MEME analyses. See Table 18.

The degree of motif overlap between the two libraries was quantified using the Human Antibody Specificity Repertoire Database (HASRD). The NGS sequence data for the libraries was uploaded and samples were queried with all identified MEME motifs. Of the 81 motifs identified, 91% were present in both libraries indicating a high degree of motif overlap between the two Tracks. Thus, even though the libraries primarily contained unique peptides, the two separate screens both selected for a common set of highly cross-reactive antibody specificities. The peptide and motif overlap is summarized in Table 19.

TABLE 18

Top Depletion Reagent Motifs Identified by MEME

| | | |
|---|---|---|
| [VI]PEFXG[SA](SEQ ID NO: 771) | Y[IVM]DXX[LM]N(SEQ ID NO: 772) | DDKGK(SEQ ID NO: 773) |
| KXPEEP(SEQ ID NO: 774) | [LM]XLPDK(SEQ ID NO: 775) | [IVY]DXXGN(SEQ ID NO: 776) |
| E[VI][VI][VI]DK(SEQ ID NO: 777) | [ML][WY]WMDK(SEQ ID NO: 778) | NPVE(SEQ ID NO: 779) |
| CMNXXC(SEQ ID NO: 780) | [RK]DX[ML]GR(SEQ ID NO: 781) | [IV]XXPXY[DE]K(SEQ ID NO: 782) |
| PXG[TV]LXK(SEQ ID NO: 783) | [VI]XXQPXKP(SEQ ID NO: 784) | DTXP[RK](SEQ ID NO: 785) |
| CXXPWXXEXC(SEQ ID NO: 786) | W[WF]X[QIV]PDK(SEQ ID NO: 787) | PPWW(SEQ ID NO: 788) |
| [LI]N[KR]P(SEQ ID NO: 789) | P[IL]XNX[HP]XW(SEQ ID NO: 790) | [FY]XHXX[LIM]N(SEQ ID NO: 791) |
| [PW]FXXM[DN]KP(SEQ ID NO: 792) | K[FYW]THP (SEQ ID NO: 793) | YXPTXX[WY](SEQ ID NO: 794) |
| PXAIXD[LMI] [LVI](SEQ ID NO: 795) | YXDXX[LM]N(SEQ ID NO: 796) | C[WN]X[WR]XC(SEQ ID NO: 797) |
| KXDPDXXW(SEQ ID NO: 798) | [RK]C[YF][LIVM]C[ED](SEQ ID NO: 799) | WCWK[DE](SEQ ID NO: 800) |
| [VI]X[LFM]PHW(SEQ ID NO: 801) | PXL[ST]XXE(SEQ ID NO: 8020) | PX[IV]XEXXM[FW](SEQ ID NO: 803) |
| DPYQXX[WF](SEQ ID NO: 804) | [VI]PXLXXXE(SEQ ID NO: 805) | YNPF(SEQ ID NO: 806) |
| PVXF[ND]K(SEQ ID NO: 807) | PXXFYN(SEQ ID NO: 808) | PYXXYQ(SEQ ID NO: 809) |
| [RH][RK][PW]FF(SEQ ID NO: 810) | KXRPXW(SEQ ID NO: 811) | CXNWXXXC(SEQ ID NO: 812) |
| C[IWML]NXXDC(SEQ ID NO: 813) | KXDXMXN(SEQ ID NO: 814) | WXKXXGXW(SEQ ID NO: 815) |
| PXDT[SA]PR(SEQ ID NO: 816) | PPT[YFW][LM]G(SEQ ID NO: 817) | [YF]X[YF]XXFN(SEQ ID NO: 818) |
| [LM]XXGWNXKP(SEQ ID NO: 819) | KX[IVF]PXYL(SEQ ID NO: 820) | YXX[IV]PW[ML](SEQ ID NO: 821) |
| GAGGG(SEQ ID NO: 822) | CX[ND]XPXXC(SEQ ID NO: 823) | HXP[ML][FMY]Y(SEQ ID NO: 824) |
| PDDI[SG]K(SEQ ID NO: 825) | FPXXWYP(SEQ ID NO: 826) | DMNXH(SEQ ID NO: 827) |
| [KR][LMI]VXQS[SN](SEQ ID NO: 828) | WDXXDG(SEQ ID NO: 829) | PXXNXX[LI][TS](SEQ ID NO: 830) |

TABLE 18-continued

Top Depletion Reagent Motifs Identified by MEME

| | | |
|---|---|---|
| [VMI]VPEXK(SEQ ID NO: 831) | PX[VI][FYW]XNXP(SEQ ID NO: 832) | SGP[KR][HY](SEQ ID NO: 833) |
| KXXFPQ(SEQ ID NO: 834) | PDXXWXK(SEQ ID NO: 835) | QP[LM][FM]Y (SEQ ID NO: 836) |
| [YF]XCT[FYM]MC(SEQ ID NO: 837) | [FW]XPXX[LMI][QN][RK] (SEQ ID NO: 838) | [IV]CWSX[PC] (SEQ ID NO: 839) |
| PDXP[VI]S(SEQ ID NO: 840) | P[LI]XGXPW(SEQ ID NO: 841) | ELPRX[YML](SEQ ID NO: 842) |
| PESHN[DW](SEQ ID NO: 843) | YXXTLX[YW](SEQ ID NO: 844) | [VI]XWNXP (SEQ ID NO: 845) |
| G[WYF]DXXD[GP](SEQ ID NO: 846) | KX[TSN]HPG[ED](SEQ ID NO: 847) | MMXHI(SEQ ID NO: 848) |
| KPXLGX[KR](SEQ ID NO: 849) | N[SD]SMN(SEQ ID NO: 850) | WXXWF(SEQ ID NO: 851) |

TABLE 19

Full peptides versus motif overlap in Depletion reagent tracks

| | Track I | Track II |
|---|---|---|
| NGS Unique sequences | 49413 | 51956 |
| # unique peptides common to both libraries | | 1605 (~3%) |
| # of motifs common to both libraries | | 74/81 (91%) |

Figure 20:
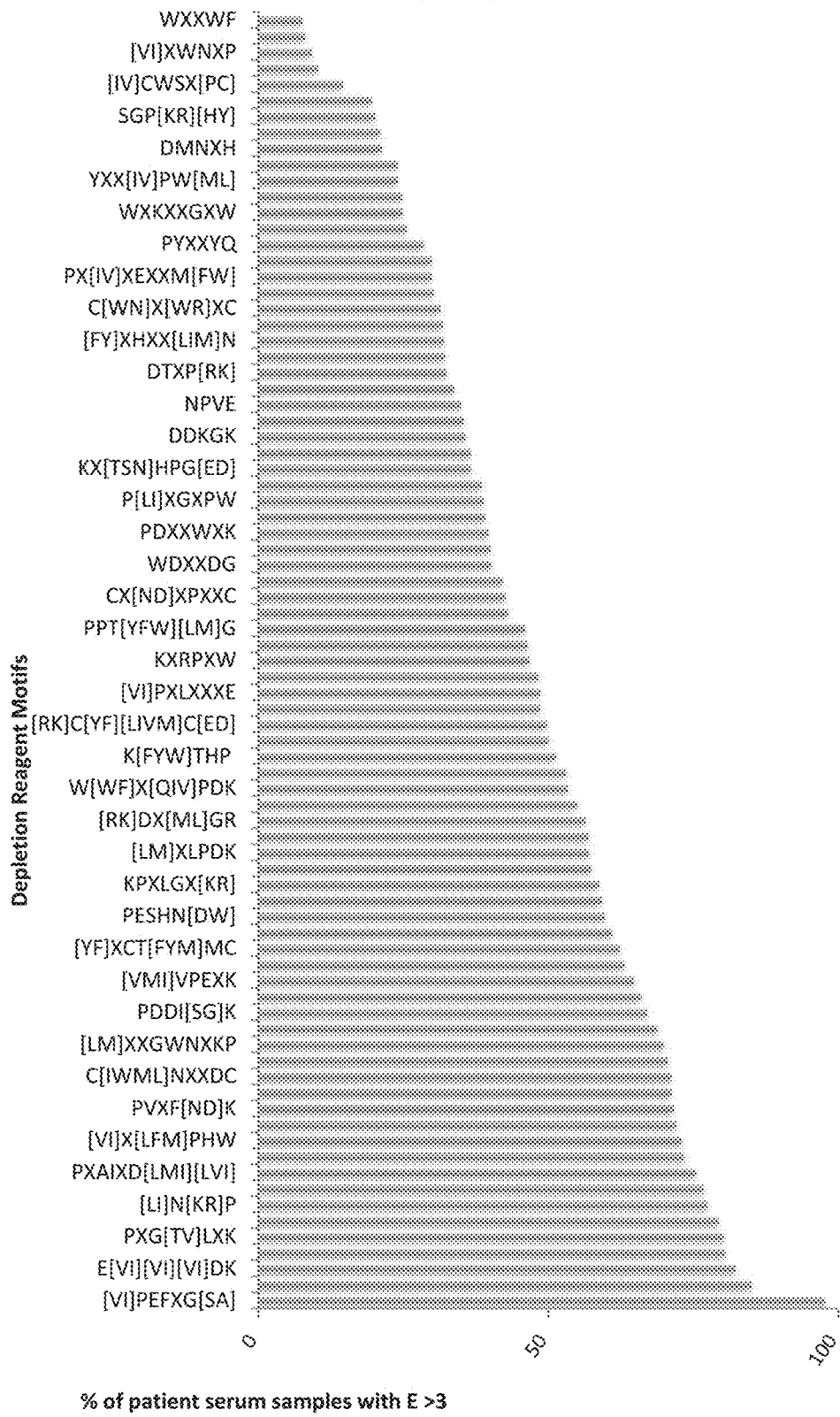
FIG. 20: Percentage of subjects with >3 fold enrichment of depletion reagent motifs in HASRD (n=358 subjects) (SEQ ID NOS 845, 839, 833, 827, 821, 815, 809, 803, 797, 791, 785, 779, 773, 847, 841, 835, 829, 823, 817, 811, 805, 799, 793, 787, 781, 775, 849, 843, 837, 831, 825, 819, 813, 807, 801, 795, 789, 783, 777, and 771, respectively, in order of appearance).

The Depletion Library Enriched for Motifs that are Well Represented in the General Population To establish the cross-reactivity of the Depletion reagent motifs in the general population, 358 serum samples (including healthy, Sjogren's syndrome, Systemic Lupus Erythmatosus, Myasthenia Gravis, Celiac and Chagas disease sera) that had been screened using Display Seq were queried for motif enrichment in HASRD. Display seq recovers between ~0.5-3×10⁶ unique antibody binding peptides per serum sample representing the diversity of each subject's antibody repertoire. These sequences were uploaded to HASRD and the percentage of subjects that showed enrichment for each motif was tabulated. "Enrichment" was defined as an E value of ≥3 where an E=1 is background (the number of unique peptides observed for a given motifs is equal to what would be expected by random chance). The percentage of patient serum samples that showed ≥3-fold enrichment for each of the 81 motifs queried is shown in FIG. 20. Serum cross-reactivity ranged from 8-98% with an average of 48% of subjects showing motif enrichment. Ninety four percent of the motifs were enriched in at least 20% of the samples queried and enrichment was evenly distributed between healthy and disease sera.

Depletion Reagent Validation

Figure 21:
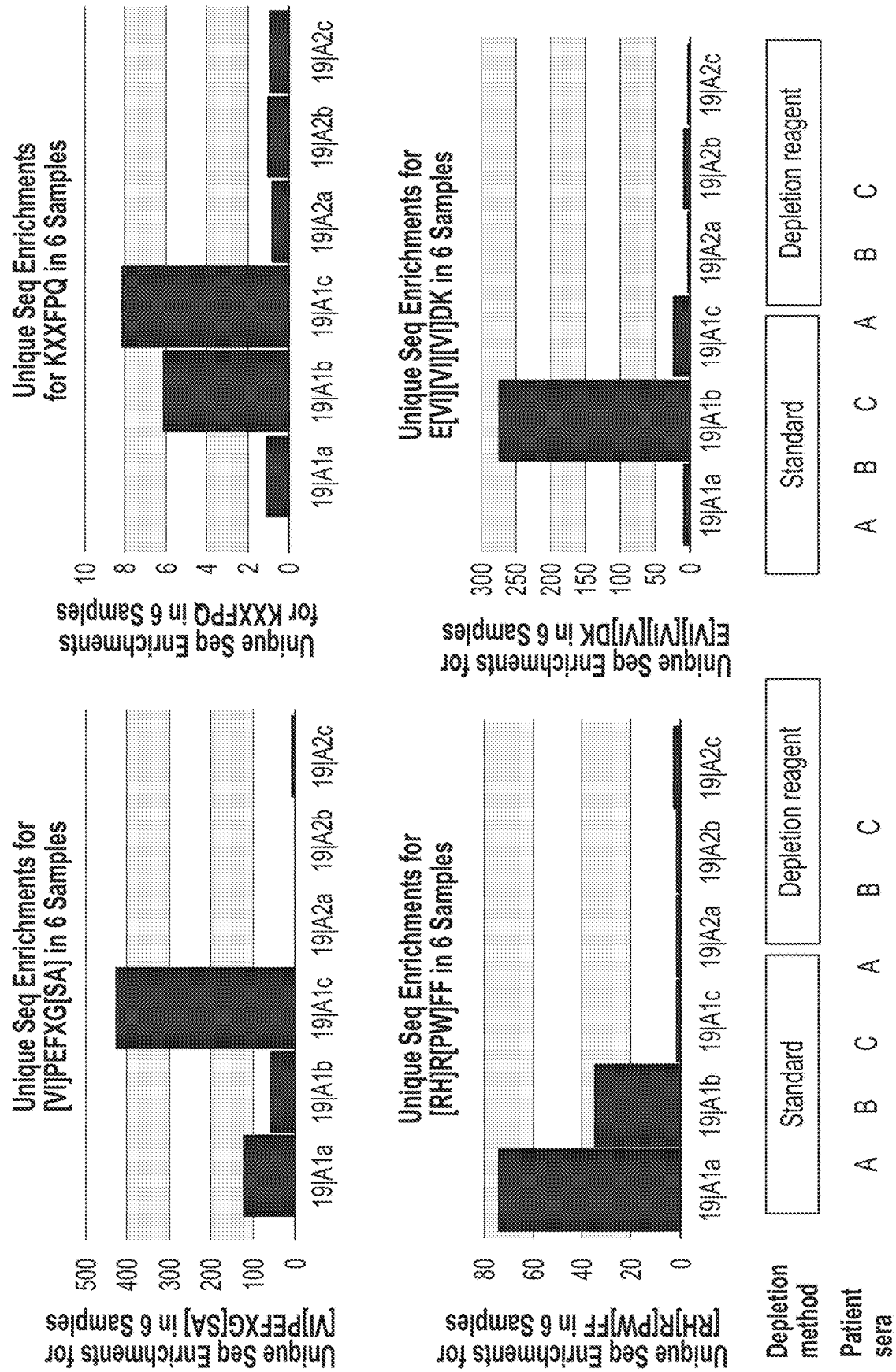
FIG. 21 illustrates that the depletion reagent and method effectively removes antibodies from serum prior to screening. Three separate motifs are shown. On each graph, first 3 bars represent the enrichment value for the given motif in 3 separate patients after standard depletion. The second three bars are the enrichment values for the same 3 patients after depletion with the depletion reagent. "[VI]PEFXG[SA]" is disclosed as SEQ ID NO: 771, "[RH]R[PW]FF" is disclosed as SEQ ID NO: 930, "KXXFPQ" is disclosed as SEQ ID NO: 834, and "E[VI][VI][VI]DK" is disclosed as SEQ ID NO: 777.

The Depletion Reagent Effectively Removes Common Antibody Specificities from Serum In order to be a useful tool in biomarker discovery, the Depletion Reagent should effectively remove common antibodies from serum, thereby enhancing biomarker discovery. To test the ability of the library to effectively deplete sera of common antibody specificities, three healthy serum samples were depleted using either standard conditions with E. coli expressing eCPX scaffold alone, or with the Depletion reagent consisting of both Track 1 and Track 2 pooled libraries, according to established protocols. Depleted serum was then used to screen the X12 bacterial display library at a final serum dilution of 1:25 by the Display Seq method. Samples were processed for NGS as described previously and the unique peptide sequences returned for each sample were uploaded to HASRD and queried with motifs known to be present in the Depletion Reagent. The enrichment values for several common motifs from serum depleted using standard conditions or with the Depletion reagent are shown in FIG. 21. Motifs spanned a large range of enrichment values (~6 to 400 fold enrichment). Regardless of the level of enrichment, the Depletion reagent effectively removed antibodies from the serum, resulting in reduction in enrichment to or near background levels.

Figure 22:
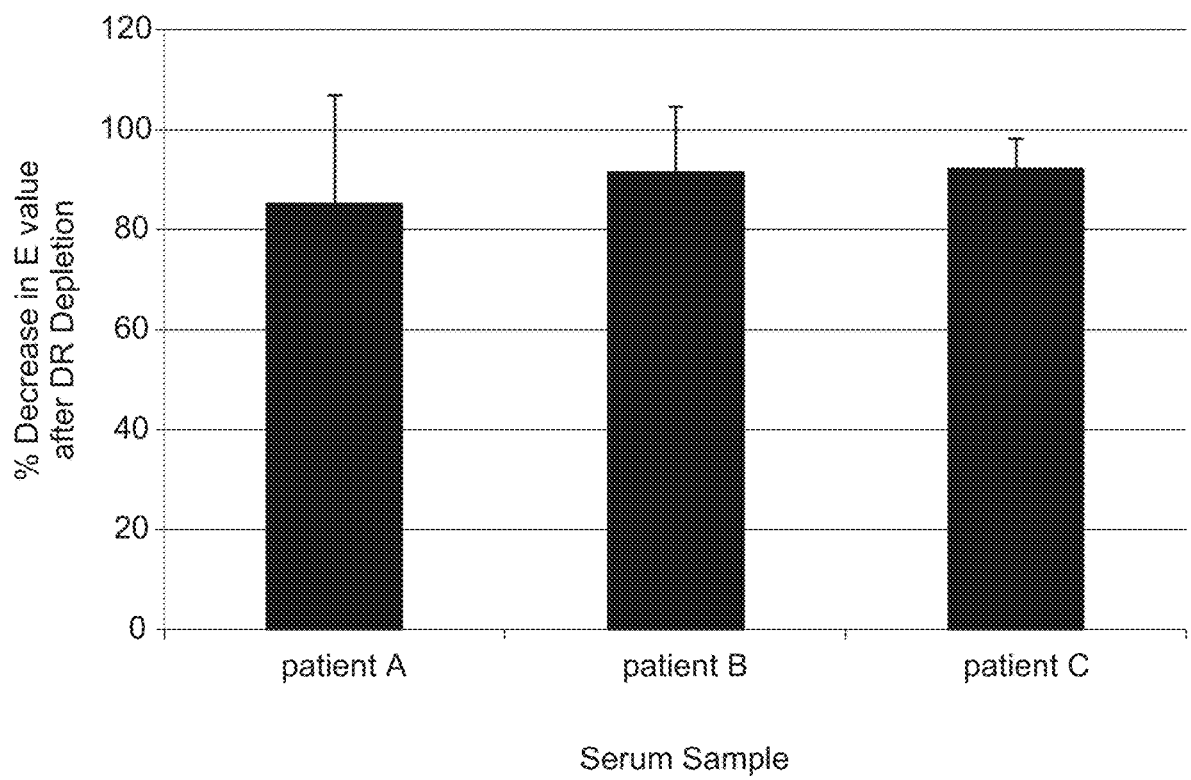
FIG. 22: The depletion reagent removed 80-90% of antibodies associated with 11 motifs for each patient. The enrichment for each motif was determined on sera that had been processed for display seq using both depletion methods. The percent decrease for each motif after treatment with the depletion reagent was calculated. All motifs included in the analysis were known to be present in the depletion reagent.

The ability of the Depletion Reagent to remove common antibodies was further quantified by calculating the percent decrease in motif enrichment after treatment with the Depletion reagent. See FIG. 22. In three separate patients, the average enrichment decreased by ~80-90%.

Figure 23:
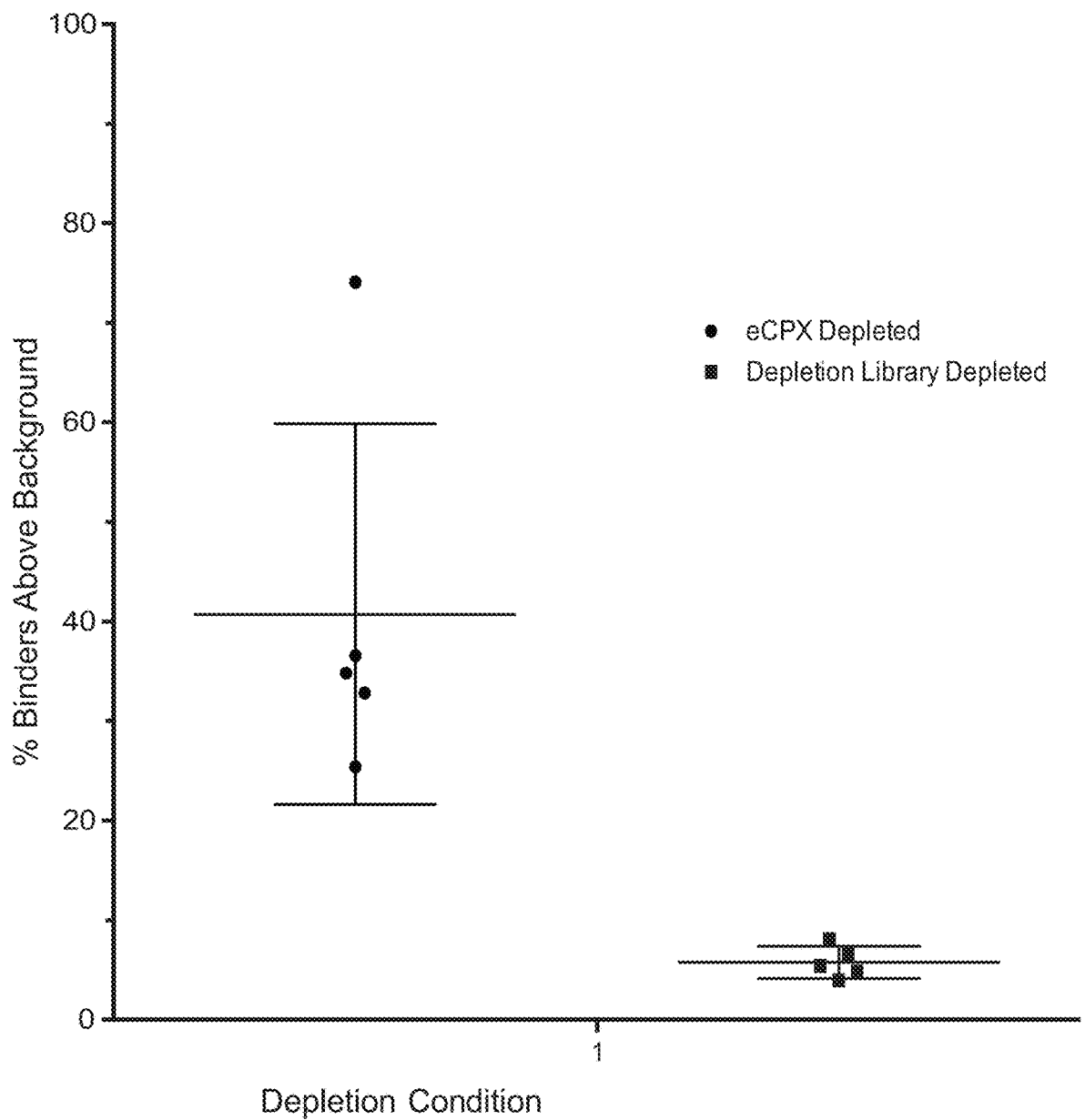
FIG. 23: The depletion reagent reduces reactivity of serum to the X12 library by 5-10 fold. The results are the average and standard deviation of 5 serum samples. The reactivity of the serum samples to the eCPX scaffold only represents background binding of serum in the absence of peptides.

To understand the effect of the Depletion reagent on reducing the diversity of the antibody repertoire in depleted serum, we compared the reactivity of five serum samples that had been depleted using standard conditions or with the Depletion reagent to the naïve X12 library. The depletion reagent reduced the reactivity by ~5-10-fold, indicating that a significant fraction of antibodies are removed. See FIG. 23.

Figure 24:
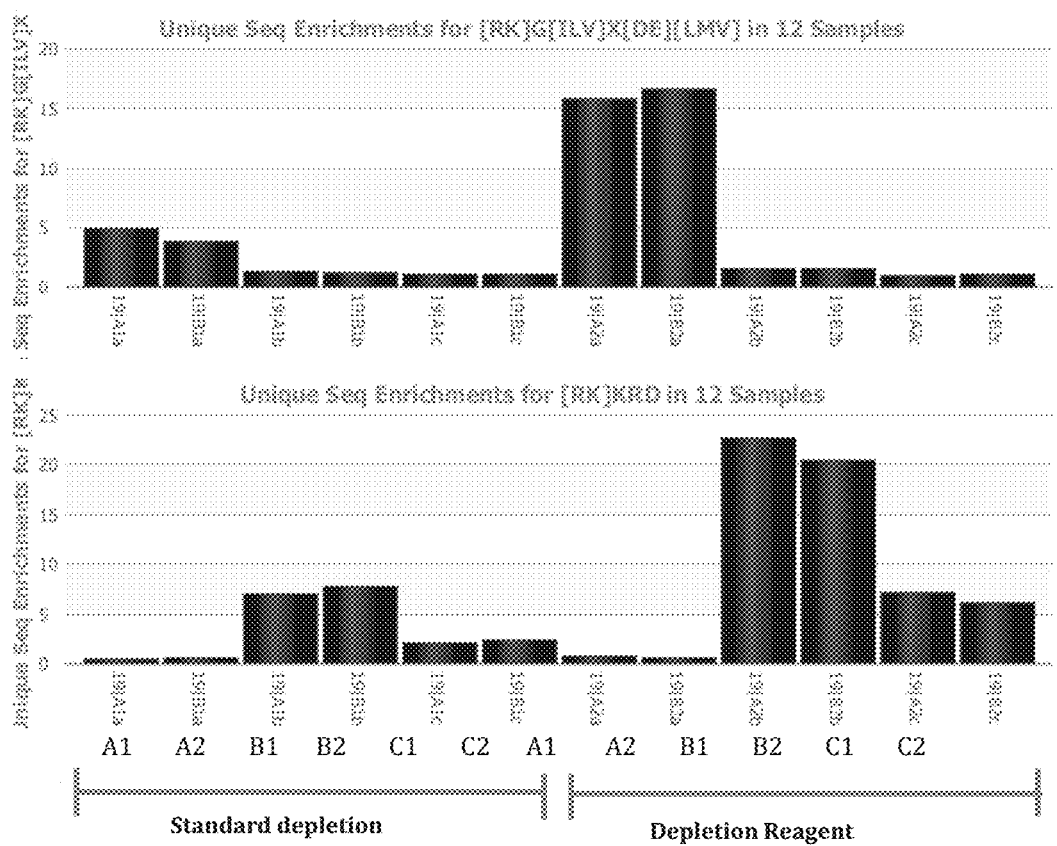
FIG. 24: Two motifs that were not present in the depletion reagent demonstrate increased enrichment in serum treated with the depletion reagent as compared with eCPX depleted sera. Three serum samples are shown and each was run in duplicate. The depletion reagent enhances enrichment by ~3 fold as compared with standard depletion. "[RK]G[ILV]X[DE][LMV]" is disclosed as SEQ ID NO: 931 and "[RK]KRD" is disclosed as SEQ ID NO: 932.

Removal of Common Antibody Specificities by the Depletion Reagent Improves Detection of Other Antibody Specificities We wanted to determine whether the Depletion reagent also enhances the ability to detect the remaining antibody specificities and/or allows for capture of a wider diversity of an individuals' antibody repertoire. To ask this question, we queried the serum samples that had been depleted under both conditions with motifs not present in the Depletion reagent. An example of this analysis, shown in FIG. 24, indicates that removal of common antibody specificities by the Depletion reagent can enhance detection of remaining antibody specificities. Motif enrichment increased an average of 3-fold after DR depletion.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

References referred to throughout this disclosure by bracketed numbers (e.g., [1], [2], etc.) are listed below. Each reference is incorporated herein by reference in its entirety.
1. Carmona, S. J., et al., *Towards high-throughput immunomics for infectious diseases: use of next-generation peptide microarrays for rapid discovery and mapping of antigenic determinants*. Mol Cell Proteomics, 2015.
2. Plebani, M., et al., *Recent advances in diagnostic technologies for autoimmune diseases*. Autoimmun Rev, 2009. 8 (3): p. 238-43.
3. Maynard, J. and G. Georgiou, *Antibody engineering*. Annu Rev Biomed Eng, 2000. 2: p. 339-76.
4. Anderson, K. S., et al., *Protein microarray signature of autoantibody biomarkers for the early detection of breast cancer*. J Proteome Res, 2011. 10 (1): p. 85-96.
5. Wang, X., et al., *Autoantibody signatures in prostate cancer*. N Engl J Med, 2005. 353 (12): p. 1224-35.
6. Spatola, B. N., et al., *Antibody Repertoire Profiling Using Bacterial Display Identifies Reactivity Signatures of Celiac Disease*. Analytical Chemistry, 2012. 85 (2): p. 1215-1222.
7. Johansen Taber, K. A., B. D. Dickinson, and M. Wilson, *The promise and challenges of next-generation genome sequencing for clinical care*. JAMA Intern Med, 2014. 174 (2): p. 275-80.
8. Georgiou, G., et al., *The promise and challenge of high-throughput sequencing of the antibody repertoire*. Nat Biotechnol, 2014. 32 (2): p. 158-68.
9. Larman, H. B., et al., *PhIP-Seq characterization of autoantibodies from patients with multiple sclerosis, type 1 diabetes and rheumatoid arthritis*. J Autoimmun, 2013. 43: p. 1-9.
10. Xu, G. J., et al., *Viral immunology. Comprehensive serological profiling of human populations using a synthetic human virome*. Science, 2015. 348 (6239): p. aaa0698.
11. Borrebaeck, C. A. K., *Antibody engineering*. 2nd ed. Breakthroughs in molecular biology. 1995, New York: Oxford University Press. xv, 390 p.
12. Daugherty, P. S., *Protein engineering with bacterial display*. Curr Opin Struct Biol, 2007. 17 (4): p. 474-80.
13. Andreatta, M., O. Lund, and M. Nielsen, *Simultaneous alignment and clustering of peptide data using a Gibbs sampling approach*. Bioinformatics, 2013. 29 (1): p. 8-14.
14. Bailey, T. L. and C. Elkan, *The value of prior knowledge in discovering motifs with MEME*. Proc Int Conf Intell Syst Mol Biol, 1995. 3: p. 21-9.
15. Bailey, T. L. and C. Elkan, *Fitting a mixture model by expectation maximization to discover motifs in biopolymers*. Proc Int Conf Intell Syst Mol Biol, 1994. 2: p. 28-36.
16. Amstutz, P., et al., *In vitro display technologies: novel developments and applications*. Curr Opin Biotechnol, 2001. 12 (4): p. 400-5.
17. Gould Rothberg, B. E. and J. M. Rothberg, *Massively parallel ("next-generation") DNA sequencing*. Clin Chem, 2015. 61 (7): p. 997-8.
18. Rice, J. J. and P. S. Daugherty, *Directed evolution of a biterminal bacterial display scaffold enhances the display of diverse peptides*. Protein Eng Des Sel, 2008. 21 (7): p. 435-42.
19. Getz, J. A., T. D. Schoep, and P. S. Daugherty, *Peptide discovery using bacterial display and flow cytometry*. Methods Enzymol. 503: p. 75-97.
15. Ballew, J. T., et al., *Antibody biomarker discovery through in vitro directed evolution of consensus recognition epitopes*. Proc Natl Acad Sci USA, 2013. 110 (48): p. 19330-5.
21. Wallis, A. B., et al., *Secular trends in the rates of preeclampsia, eclampsia, and gestational hypertension, United States, 1987-2004*. Am J Hypertens, 2008. 21 (5): p. 521-6.
22. Samadi, A. R., et al., *Maternal hypertension and associated pregnancy complications among African-American and other women in the United States*. Obstet Gynecol, 1996. 87 (4): p. 557-63.
23. Wagner, L. K., *Diagnosis and management of preeclampsia*. Am Fam Physician, 2004. p. 2317-24.
24. Hadker, N., et al., *Financial impact of a novel preeclampsia diagnostic test versus standard practice: a decision-analytic modeling analysis from a UK healthcare payer perspective*. J Med Econ. 13(4): p. 728-37.
25. MacKay, A. P., C. J. Berg, and H. K. Atrash, *Pregnancy-related mortality from preeclampsia and eclampsia*. Obstet Gynecol, 2001. 97 (4): p. 533-8.
26. Masoura, S., et al., *Biomarkers in pre-eclampsia: a novel approach to early detection of the disease*. J Obstet Gynaecol, 2012. 32 (7): p. 609-16.
27. Kleinrouweler, C. E., et al., *Accuracy of circulating placental growth factor, vascular endothelial growth factor, soluble fms-like tyrosine kinase 1 and soluble endoglin in the prediction of pre-eclampsia: a systematic review and meta-analysis*. BJOG, 2012. 119 (7): p. 778-87.
28. Levine, R. J., et al., *Circulating angiogenic factors and the risk of preeclampsia*. N Engl J Med, 2004. 350 (7): p. 672-83.
29. Schiettecatte, J., et al., *Multicenter evaluation of the first automated Elecsys sFlt-1 and P1GF assays in normal pregnancies and preeclampsia*. Clin Biochem. 43(9): p. 768-70.
30. Ohkuchi, A., et al., *Evaluation of a new and automated electrochemiluminescence immunoassay for plasma sFlt-1 and P1GF levels in women with preeclampsia*. Hypertens Res. 33(5): p. 422-7.
31. Lain, K. Y. and J. M. Roberts, *Contemporary concepts of the pathogenesis and management of preeclampsia*. JAMA, 2002. 287 (24): p. 3183-6.
32. Walther, T., et al., *Angiotensin II type 1 receptor agonistic antibodies reflect fundamental alterations in the uteroplacental vasculature*. Hypertension, 2005. 46 (6): p. 1275-9.
33. Roberts, J. M., *Angiotensin-1 receptor autoantibodies: A role in the pathogenesis of preeclampsia?* Circulation, 2000. 101 (20): p. 2335-7.
34. Wallukat, G., et al., *Patients with preeclampsia develop agonistic autoantibodies against the angiotensin AT1 receptor*. J Clin Invest, 1999. 103 (7): p. 945-52.
35. Rossitto, G., et al., *Elevation of Angiotensin-II Type-1-Receptor Autoantibodies Titer in Primary Aldosteronism as a Result of Aldosterone-Producing Adenoma*. Hypertension, 2013. 61 (2): p. 526-33.
36. Zhou, C. C., et al., *Autoantibody from women with preeclampsia induces soluble Fms-like tyrosine kinase-1

*production via angiotensin type 1 receptor and calcineurin/nuclear factor of activated T-cells signaling.* Hypertension, 2008. 51 (4): p. 1010-9.
37. Parrish, M. R., et al., *The effect of immune factors, tumor necrosis factor-alpha, and agonistic autoantibodies to the angiotensin II type I receptor on soluble fms-like tyrosine-1 and soluble endoglin production in response to hypertension during pregnancy.* Am J Hypertens. 23(8): p. 911-6.
38. Zhou, C. C., et al., *Angiotensin receptor agonistic autoantibodies induce pre-eclampsia in pregnant mice.* Nat Med, 2008. 14 (8): p. 855-62.
39. Herse, F., et al., *Prevalence of agonistic autoantibodies against the angiotensin II type 1 receptor and soluble fms-like tyrosine kinase 1 in a gestational age-matched case study.* Hypertension, 2009. 53 (2): p. 393-8.
40. Wallukat, G., et al., *Spontaneously beating neonatal rat heart myocyte culture-a model to characterize angiotensin II at(I) receptor autoantibodies in patients with preeclampsia.* In Vitro Cell Dev Biol Anim, 2002. 38 (7): p. 376-7.
41. Griffiths, P. and S. Lumley, *Cytomegalovirus.* Curr Opin Infect Dis, 2014. 27 (6): p. 554-9.
42. Halenius, A. and H. Hengel, *Human cytomegalovirus and autoimmune disease.* Biomed Res Int, 2014. 2014: p. 472978.

The present application and invention further includes the subject matter of the following numbered clauses:

1. A method of identifying a plurality of peptides, comprising: providing a biological sample comprising a plurality of antibodies; contacting the biological sample with a plurality of peptides; and identifying members of the plurality of peptides that form a complex with members of the plurality of antibodies.
2. The method of clause 1, wherein the biological sample comprises a bodily fluid.
3. The method of clause 2, wherein the bodily fluid comprises peripheral blood, lymphatic fluid, sweat, saliva, mucus, or a derivative of any thereof.
4. The method of any preceding clauses, wherein identifying members of the plurality of peptides that form a complex members of the plurality of antibodies comprises sequencing a nucleic acid that encodes the peptide.
5. The method of clause 4, wherein the sequencing comprises next generation sequencing (NGS), Sanger sequencing, real-time PCR, or pyrosequencing.
6. The method of any of clauses 4-5, wherein each member of the plurality of peptides is coupled to a nucleic acid molecule encoding that peptide.
7. The method of any of clauses 4-5, wherein the nucleic acid molecule comprises deoxyribonucleic acid (DNA), ribonucleic acid (RNA), or a derivative of any thereof.
8. The method of clause 6, wherein each peptide is directly coupled to its corresponding nucleic acid molecule.
9. The method of clause 6, wherein each peptide is indirectly coupled to its corresponding nucleic acid molecule.
10. The method of clause 9, wherein the corresponding nucleic acid molecule is within a vector that encodes the peptide.
11. The method of clause 10, wherein the vector is configured to express the peptide.
12. The method of clause 10, wherein the vector is comprised in a host cell.
13. The method of clause 12, wherein the host cell expresses the peptide.
14. The method of clause 13, wherein the peptide is expressed on the surface of the host cell.
15. The method of any of clauses 12-14, wherein the host cell comprises a microbial cell, a bacterial cell, an *E. coli* cell, a eukaryotic cell, a yeast cell, or a mammalian cell.
16. The method of any one of clauses 1-15, further comprising capturing members of the plurality of peptides that form a complex with members of the plurality of antibodies prior to identifying members of the plurality of peptides that form a complex with members of the plurality of antibodies.
17. The method of clause 16, wherein the capturing comprises capturing the peptide-bound members of the plurality of antibodies.
18. The method of clause 17, wherein the peptide-bound members of the plurality of antibodies are captured to a substrate.
19. The method of clause 18, wherein the substrate comprises a planar surface or a plurality of microbeads.
20. The method of clause 19, wherein the plurality of microbeads are magnetic or fluorescent.
21. The method of any one of clauses 17-20, wherein the bound members of the plurality of antibodies are captured using Protein A, Protein G, Protein L and/or an anti-immunoglobulin antibody or aptamer.
22. The method of any one of clauses 1-21, further comprising filtering the plurality of antibodies prior to contacting the biological sample with a plurality of peptides.
23. The method of clause 22, wherein the filtering comprises contacting the plurality of antibodies with at least one reagent configured to deplete antibodies that bind to assay components other than the plurality of peptides.
24. The method of clause 23, wherein the at least one reagent comprises the host cell.
25. The method of any one of clauses 1-24, further comprising filtering the plurality of peptides prior to contacting the biological sample with a plurality of peptides.
26. The method of clause 25, wherein the filtering the plurality of peptides comprises contacting the plurality of peptides with at least one reagent configured to deplete peptides that form a complex with assay components other than the plurality of antibodies.
27. The method of clause 26, wherein the at least one reagent configured to deplete peptides comprises Protein A, Protein G, Protein L, and/or an anti-immunoglobulin antibody or aptamer.
28. The method of any of clauses 1-27, further comprising determining at least one peptide motif from the members of the plurality of peptides identified in c).
29. The method of clause 28, wherein determining the at least one peptide motif comprises aligning the sequences of the members of the plurality of peptides identified in c).
30. The method of clause 29, wherein the aligning comprises using a computational alignment algorithm.
31. A method of identifying at least one peptide indicative of a phenotype in a biological sample comprising: (a) identifying a plurality of peptides in the biological sample according to any one of clauses 1-30; (b) comparing the presence or level of each member of the plurality of peptides identified in a) to a reference value; and (c) identifying a peptide with a presence or level that differs from the reference based on the comparison in b), thereby identifying the at least peptide indicative of the phenotype.

32. The method of clause 31, wherein the reference value for each member of the plurality of peptides comprises a presence or level of that member of the plurality of peptides in a control sample.

33. A method of identifying at least one peptide motif indicative of a phenotype in a biological sample comprising: (a) identifying at least one peptide motif in the biological sample according to any one of clauses 28-30; (b) comparing the presence or level of the at least one peptide motif identified in step a) to a reference value; and (c) identifying at least one peptide motif with a presence or level that differs from the reference based on the comparison in b), thereby identifying the at least one peptide motif indicative of the phenotype.

34. The method of clause 33, wherein the reference value comprises a presence or level of the same peptide motif in a control sample.

35. A method of characterizing a phenotype in a biological sample comprising: (a) identifying a plurality of peptides in the biological sample according to any one of clauses 1-30; (b) comparing the presence or level of each member of the plurality of peptides identified in a) to a reference value; and (c) identifying a peptide with a presence or level that differs from the reference based on the comparison in b), thereby characterizing the phenotype.

36. The method of clause 35, wherein the reference value for each member of the plurality of peptides comprises a presence or level of that member of the plurality of peptides in a control sample.

37. A method of characterizing a phenotype in a biological sample comprising: (a) identifying at least one peptide motif in the biological sample according to any one of clauses 28-30; (b) comparing the presence or level of the at least one peptide motif identified in step a) to a reference value; and (c) identifying at least one peptide motif with a presence or level that differs from the reference based on the comparison in b), thereby identifying the at least one peptide motif indicative of the phenotype.

38. The method of clause 37, wherein the reference value comprises a presence or level of the same peptide motif in a control sample.

39. The method of any one of clause 32, 34, 36 or 38, wherein the control sample has a different phenotype than the biological sample.

40. A method comprising detecting at least one peptide in a biological sample, wherein optionally the detecting is used to characterize a phenotype.

41. The method of clause 39 or clause 40, wherein the phenotype comprises a disease or disorder.

42. The method of any one of clauses 35, 37 or 40, wherein the characterizing comprises a diagnosis, prognosis or theranosis of the disease or disorder.

43. The method of any of clauses 35, 37 or 40, wherein the characterizing comprises determining a stage, grade, progression, treatment regimen and/or treatment response of the disease or disorder.

44. The method of any one of clauses 41-43, wherein the disease or disorder comprises an infectious, autoimmune, parasitic, allergic, oncological, neurological, cardiovascular, pregnancy-related or endocrine disease or disorder.

45. The method of any one of clauses 41-43, wherein the disease or disorder comprises an infectious disease or an autoimmune disease.

46. The method of any one of clauses 41-43, wherein the disease or disorder comprises Celiac disease (CD), Sjogren's Syndrome (SS), Myasthenia Gravis (MG), preeclampsia (PE), systemic lupus erythematosis (SLE), Epstein-Barr virus (EBV), rhinovirus, cytomegalovirus (CMV), *Streptococcus*, human immunodeficiency virus (HIV), *Haemophilus* influenza, Chagas disease or Lyme disease.

47. The method of any one of clauses 41-43, wherein the disease or disorder comprises a microbial infection, viral infection, bacterial infection or fungal infection.

48. A peptide comprising a sequence in any of SEQ ID NOs.1-868.

49. A composition comprising at least one peptide of clause 48.

50. Use of at least one reagent to carry out the method of any of clauses 1-47.

51. The use of clause 50, wherein the at least one reagent comprises at least one of: at least one peptide from any of SEQ ID NOs.1-868; a peptide library display system; an antibody binding agent; a primer set; and a depletion reagent.

52. The use clause 51, wherein the peptide library display system comprises an *E. coli* display system.

53. The use of clause 51, wherein the peptide library display system comprises a naïve peptide library.

54. The use of clause 51, wherein the peptide library display system is configured to characterize a phenotype 55. A kit comprising at least one reagent to carry out the method of any of clauses 1-47.

56. The kit of clause 55, wherein the at least one reagent comprises at least one of: at least one peptide from any of SEQ ID NOs.1-868; a peptide library display system; an antibody binding agent; a primer set; and a depletion reagent.

57. The kit of clause 56, wherein the peptide library display system comprises an *E. coli* display system.

58. The kit of clause 69, wherein the peptide library display system comprises a naïve peptide library.

59. The kit of clause 69, wherein the peptide library display system is configured to characterize a phenotype.

60. A composition comprising at least 1, 2, 3, 4, 5, 6, 7, 8, 9, 10, 11, 12, 13, 14, 15, 16, 17, 18, 19, 20, 25, 30, 35, 40, 45, 50, 65, 70, 75, 80, 90, 100, 200, 300, 400, 500, 600, 700, 800, 900, 1000, 10000, or at least 100000 peptides matching a peptide sequence in SEQ ID NOs.1-868.

61. A composition comprising a library of nucleic acids having sequences encoding at least 1, 2, 3, 4, 5, 6, 7, 8, 9, 10, 11, 12, 13, 14, 15, 16, 17, 18, 19, 20, 25, 30, 35, 40, 45, 50, 65, 75, 80, 90, 100, 200, 300, 400, 500, 600, 700, 800, 900, 1000, 10000, or at least 100000 peptides matching a peptide sequence in SEQ ID NOs.1-868.

62. A composition comprising host cells comprising a library of nucleic acids having sequences encoding at least 1, 2, 3, 4, 5, 6, 7, 8, 9, 10, 11, 12, 13, 14, 15, 16, 17, 18, 19, 20, 30, 35, 40, 45, 50, 65, 70, 75, 80, 90, 100, 200, 300, 400, 500, 600, 700, 800, 900, 1000, 10000, or at least 100000 peptides matching a peptide sequence in SEQ ID NOs.1-868.

63. The composition of clause 62, wherein the host cells comprise microbial cells, bacterial cells, *E. coli* cells, eukaryotic cells, yeast cells, or mammalian cells.

64. The composition of clause 62, wherein the host cells express the peptides on their surface.

65. A method of depleting a biological sample of an antibody repertoire, comprising: (a) contacting the biological sample with a composition of clauses 60 or 61; (b) separating the host cells from the biological sample, thereby depleting the biological sample of the antibody repertoire.

A method comprising using the depleted biological sample of clause 65 as the biological sample in step a) of clause 65.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

SEQUENCE LISTING

```
Sequence total quantity: 937
SEQ ID NO: 1            moltype = AA  length = 5
FEATURE                 Location/Qualifiers
source                  1..5
                        mol_type = protein
                        organism = synthetic construct
VARIANT                 3
                        note = X can be any amino acid
VARIANT                 1
                        note = D can be replaced by E
VARIANT                 4
                        note = F can be replaced by Y or L
SEQUENCE: 1
DTXFK                                                              5

SEQ ID NO: 2            moltype = AA  length = 5
FEATURE                 Location/Qualifiers
REGION                  1..5
                        note = Synthetic peptide
VARIANT                 3
                        note = X can be any amino acid
source                  1..5
                        mol_type = protein
```

```
                         organism = synthetic construct
SEQUENCE: 2
DTXFK                                                                    5

SEQ ID NO: 3             moltype = AA   length = 8
FEATURE                  Location/Qualifiers
REGION                   1..8
                         note = Synthetic peptide
VARIANT                  2
                         note = X can be any amino acid
VARIANT                  4
                         note = X can be any amino acid
VARIANT                  6..7
                         note = X can be any amino acid
source                   1..8
                         mol_type = protein
                         organism = synthetic construct
SEQUENCE: 3
DXTXFXXK                                                                 8

SEQ ID NO: 4             moltype = AA   length = 8
FEATURE                  Location/Qualifiers
REGION                   1..8
                         note = Synthetic peptide
VARIANT                  3..4
                         note = X can be any amino acid
VARIANT                  7
                         note = X can be any amino acid
VARIANT                  8
                         note = X can be E or D
source                   1..8
                         mol_type = protein
                         organism = synthetic construct
SEQUENCE: 4
QPXXPFXX                                                                 8

SEQ ID NO: 5             moltype = AA   length = 6
FEATURE                  Location/Qualifiers
REGION                   1..6
                         note = Synthetic peptide
VARIANT                  3..4
                         note = X can be any amino acid
source                   1..6
                         mol_type = protein
                         organism = synthetic construct
SEQUENCE: 5
QPXXPF                                                                   6

SEQ ID NO: 6             moltype = AA   length = 8
FEATURE                  Location/Qualifiers
REGION                   1..8
                         note = Synthetic peptide
VARIANT                  2..4
                         note = X can be any amino acid
VARIANT                  7
                         note = X can be P or S
source                   1..8
                         mol_type = protein
                         organism = synthetic construct
SEQUENCE: 6
QXXXPFXE                                                                 8

SEQ ID NO: 7             moltype = AA   length = 5
FEATURE                  Location/Qualifiers
REGION                   1..5
                         note = Synthetic peptide
source                   1..5
                         mol_type = protein
                         organism = synthetic construct
SEQUENCE: 7
PFSEM                                                                    5

SEQ ID NO: 8             moltype = AA   length = 6
FEATURE                  Location/Qualifiers
REGION                   1..6
                         note = Synthetic peptide
VARIANT                  5
                         note = X can be any amino acid
VARIANT                  6
```

```
                           note = X can be F or W
source                     1..6
                           mol_type = protein
                           organism = synthetic construct
SEQUENCE: 8
PFSEXX                                                                    6

SEQ ID NO: 9               moltype = AA  length = 7
FEATURE                    Location/Qualifiers
REGION                     1..7
                           note = Synthetic peptide
VARIANT                    4..5
                           note = X can be any amino acid
VARIANT                    6
                           note = X can be L or M
source                     1..7
                           mol_type = protein
                           organism = synthetic construct
SEQUENCE: 9
LFGXXXN                                                                   7

SEQ ID NO: 10              moltype = AA  length = 7
FEATURE                    Location/Qualifiers
REGION                     1..7
                           note = Synthetic peptide
VARIANT                    4..5
                           note = X can be any amino acid
VARIANT                    6
                           note = X can be Y or F
source                     1..7
                           mol_type = protein
                           organism = synthetic construct
SEQUENCE: 10
EWVXXXD                                                                   7

SEQ ID NO: 11              moltype = AA  length = 6
FEATURE                    Location/Qualifiers
REGION                     1..6
                           note = Synthetic peptide
VARIANT                    2
                           note = X can be L or M
VARIANT                    5
                           note = X can be any amino acid
source                     1..6
                           mol_type = protein
                           organism = synthetic construct
SEQUENCE: 11
PXALXL                                                                    6

SEQ ID NO: 12              moltype = AA  length = 8
FEATURE                    Location/Qualifiers
REGION                     1..8
                           note = Synthetic peptide
VARIANT                    2
                           note = X can be any amino acid
VARIANT                    5
                           note = X can be any amino acid
VARIANT                    7
                           note = X can be any amino acid
source                     1..8
                           mol_type = protein
                           organism = synthetic construct
SEQUENCE: 12
KXNEXWXV                                                                  8

SEQ ID NO: 13              moltype = AA  length = 7
FEATURE                    Location/Qualifiers
REGION                     1..7
                           note = Synthetic peptide
VARIANT                    2
                           note = X can be A or G
VARIANT                    3
                           note = X can be any amino acid
VARIANT                    6
                           note = X can be any amino acid
source                     1..7
                           mol_type = protein
                           organism = synthetic construct
SEQUENCE: 13
```

```
PXXRTXK                                                                  7

SEQ ID NO: 14          moltype = AA  length = 6
FEATURE                Location/Qualifiers
REGION                 1..6
                       note = Synthetic peptide
VARIANT                4
                       note = X can be any amino acid
source                 1..6
                       mol_type = protein
                       organism = synthetic construct
SEQUENCE: 14
AYTXVN                                                                   6

SEQ ID NO: 15          moltype = AA  length = 8
FEATURE                Location/Qualifiers
REGION                 1..8
                       note = Synthetic peptide
VARIANT                3
                       note = X can be A or S
VARIANT                5..7
                       note = X can be any amino acid
source                 1..8
                       mol_type = protein
                       organism = synthetic construct
SEQUENCE: 15
WNXYXXXN                                                                 8

SEQ ID NO: 16          moltype = AA  length = 8
FEATURE                Location/Qualifiers
source                 1..8
                       mol_type = protein
                       organism = synthetic construct
VARIANT                1
                       note = R can be replaced by K or E
VARIANT                2..3
                       note = X can be any amino acid
VARIANT                7
                       note = L can be replaced by M
VARIANT                5
                       note = X can be any amino acid
SEQUENCE: 16
RXXWXPLQ                                                                 8

SEQ ID NO: 17          moltype = AA  length = 7
FEATURE                Location/Qualifiers
source                 1..7
                       mol_type = protein
                       organism = synthetic construct
VARIANT                1
                       note = A can be replaced by S
VARIANT                3
                       note = X can be any amino acid
VARIANT                5
                       note = X can be any amino acid
VARIANT                6
                       note = S can be replaced by A
VARIANT                7
                       note = Y can be replaced by F
SEQUENCE: 17
AYXSXSY                                                                  7

SEQ ID NO: 18          moltype = AA  length = 7
FEATURE                Location/Qualifiers
REGION                 1..7
                       note = Synthetic peptide
VARIANT                2
                       note = X can be any amino acid
VARIANT                4
                       note = X can be any amino acid
source                 1..7
                       mol_type = protein
                       organism = synthetic construct
SEQUENCE: 18
EXYXSPS                                                                  7

SEQ ID NO: 19          moltype = AA  length = 6
FEATURE                Location/Qualifiers
REGION                 1..6
```

-continued

```
                     note = Synthetic peptide
VARIANT              4
                     note = X can be any amino acid
source               1..6
                     mol_type = protein
                     organism = synthetic construct
SEQUENCE: 19
MNIXDD                                                                        6

SEQ ID NO: 20        moltype = AA  length = 5
FEATURE              Location/Qualifiers
REGION               1..5
                     note = Synthetic peptide
VARIANT              3
                     note = X can be A, N or K
source               1..5
                     mol_type = protein
                     organism = synthetic construct
SEQUENCE: 20
EHXFW                                                                         5

SEQ ID NO: 21        moltype = AA  length = 5
FEATURE              Location/Qualifiers
REGION               1..5
                     note = Synthetic peptide
source               1..5
                     mol_type = protein
                     organism = synthetic construct
SEQUENCE: 21
VHNAY                                                                         5

SEQ ID NO: 22        moltype = AA  length = 6
FEATURE              Location/Qualifiers
REGION               1..6
                     note = Synthetic peptide
VARIANT              3
                     note = X can be E or A
VARIANT              4
                     note = X can be any amino acid
source               1..6
                     mol_type = protein
                     organism = synthetic construct
SEQUENCE: 22
HGXXLN                                                                        6

SEQ ID NO: 23        moltype = AA  length = 9
FEATURE              Location/Qualifiers
source               1..9
                     mol_type = protein
                     organism = synthetic construct
VARIANT              1
                     note = G can be replaced by D
VARIANT              2..3
                     note = X can be any amino acid
VARIANT              4
                     note = L can be replaced by F
VARIANT              5..6
                     note = X can be any amino acid
VARIANT              8
                     note = M can be replaced by L
SEQUENCE: 23
GXXLXXPMQ                                                                     9

SEQ ID NO: 24        moltype = AA  length = 7
FEATURE              Location/Qualifiers
source               1..7
                     mol_type = protein
                     organism = synthetic construct
VARIANT              1
                     note = L can be replaced by V, M or I
VARIANT              2
                     note = X can be any amino acid
VARIANT              5
                     note = X can be any amino acid
VARIANT              6
                     note = T can be replaced by S
VARIANT              7
                     note = F can be replaced by G or I
SEQUENCE: 24
```

```
LXNAXTF                                                                   7

SEQ ID NO: 25        moltype = AA  length = 6
FEATURE              Location/Qualifiers
REGION               1..6
                     note = Synthetic peptide
VARIANT              2
                     note = X can be any amino acid
source               1..6
                     mol_type = protein
                     organism = synthetic construct SEQUENCE: 25
PXNSYT                                                                    6

SEQ ID NO: 26        moltype = AA  length = 9
FEATURE              Location/Qualifiers
REGION               1..9
                     note = Synthetic peptide
VARIANT              2..3
                     note = X can be any amino acid
VARIANT              7..8
                     note = X can be any amino acid
source               1..9
                     mol_type = protein
                     organism = synthetic construct SEQUENCE: 26
RXXPLAXXL                                                                 9

SEQ ID NO: 27        moltype = AA  length = 7
FEATURE              Location/Qualifiers
REGION               1..7
                     note = Synthetic peptide
VARIANT              4
                     note = X can be any amino acid
VARIANT              6
                     note = X can be any amino acid
source               1..7
                     mol_type = protein
                     organism = synthetic construct SEQUENCE: 27
CPKXNXT                                                                   7

SEQ ID NO: 28        moltype = AA  length = 5
FEATURE              Location/Qualifiers
source               1..5
                     mol_type = protein
                     organism = synthetic construct
VARIANT              2
                     note = P can be replaced by A
VARIANT              4
                     note = A can be replaced by M SEQUENCE: 28
QPHAF                                                                     5

SEQ ID NO: 29        moltype = AA  length = 9
FEATURE              Location/Qualifiers
REGION               1..9
                     note = Synthetic peptide
VARIANT              3
                     note = X can be any amino acid
VARIANT              6..8
                     note = X can be any amino acid
VARIANT              9
                     note = X can be G, S or P
source               1..9
                     mol_type = protein
                     organism = synthetic construct SEQUENCE: 29
PAXENXXXX                                                                 9

SEQ ID NO: 30        moltype = AA  length = 5
FEATURE              Location/Qualifiers
REGION               1..5
                     note = Synthetic peptide
VARIANT              4
                     note = X can be D or E
source               1..5
                     mol_type = protein
                     organism = synthetic construct
```

```
SEQUENCE: 30
NIDXD                                                                    5

SEQ ID NO: 31           moltype = AA  length = 7
FEATURE                 Location/Qualifiers
source                  1..7
                        mol_type = protein
                        organism = synthetic construct
VARIANT                 2
                        note = X can be any amino acid
VARIANT                 4
                        note = X can be any amino acid
VARIANT                 5
                        note = V can be replaced by S
VARIANT                 7
                        note = N can be replaced by A
SEQUENCE: 31
RXQXVDN                                                                  7

SEQ ID NO: 32           moltype = AA  length = 7
FEATURE                 Location/Qualifiers
REGION                  1..7
                        note = Synthetic peptide
VARIANT                 2
                        note = X can be any amino acid
VARIANT                 3
                        note = X can be D or P
VARIANT                 5
                        note = X can be any amino acid
source                  1..7
                        mol_type = protein
                        organism = synthetic construct
SEQUENCE: 32
WXXPXHL                                                                  7

SEQ ID NO: 33           moltype = AA  length = 5
FEATURE                 Location/Qualifiers
source                  1..5
                        mol_type = protein
                        organism = synthetic construct
VARIANT                 4..5
                        note = F can be replaced by I
SEQUENCE: 33
TWAFF                                                                    5

SEQ ID NO: 34           moltype = AA  length = 6
FEATURE                 Location/Qualifiers
REGION                  1..6
                        note = Synthetic peptide
VARIANT                 3
                        note = X can be any amino acid
source                  1..6
                        mol_type = protein
                        organism = synthetic construct
SEQUENCE: 34
EDXGHP                                                                   6

SEQ ID NO: 35           moltype = AA  length = 10
FEATURE                 Location/Qualifiers
source                  1..10
                        mol_type = protein
                        organism = synthetic construct
VARIANT                 1
                        note = E can be replaced by T or A
VARIANT                 2..4
                        note = X can be any amino acid
VARIANT                 5
                        note = Y can be replaced by F
VARIANT                 6..7
                        note = X can be any amino acid
VARIANT                 9
                        note = S can be replaced by R
SEQUENCE: 35
EXXXYXXPSQ                                                              10

SEQ ID NO: 36           moltype = AA  length = 6
FEATURE                 Location/Qualifiers
REGION                  1..6
                        note = Synthetic peptide
```

```
VARIANT              3
                     note = X can be any amino acid
VARIANT              5
                     note = X can be R or K
source               1..6
                     mol_type = protein
                     organism = synthetic construct
SEQUENCE: 36
GMXPXQ                                                                           6

SEQ ID NO: 37        moltype = AA  length = 10
FEATURE              Location/Qualifiers
REGION               1..10
                     note = Synthetic peptide
VARIANT              2..3
                     note = X can be any amino acid
VARIANT              4
                     note = X can be V or I
VARIANT              6..7
                     note = X can be any amino acid
VARIANT              9
                     note = X can be any amino acid
source               1..10
                     mol_type = protein
                     organism = synthetic construct
SEQUENCE: 37
WXXXRXXPXQ                                                                      10

SEQ ID NO: 38        moltype = AA  length = 7
FEATURE              Location/Qualifiers
source               1..7
                     mol_type = protein
                     organism = synthetic construct
VARIANT              1
                     note = N can be replaced by E
VARIANT              2
                     note = A can be replaced by G
VARIANT              4
                     note = S can be replaced by A or T
VARIANT              5..6
                     note = X can be any amino acid
SEQUENCE: 38
NAYSXXW                                                                          7

SEQ ID NO: 39        moltype = AA  length = 7
FEATURE              Location/Qualifiers
REGION               1..7
                     note = Synthetic peptide
VARIANT              2
                     note = X can be any amino acid
VARIANT              4
                     note = X can be S or T
VARIANT              5
                     note = X can be any amino acid
source               1..7
                     mol_type = protein
                     organism = synthetic construct
SEQUENCE: 39
KXIXXYW                                                                          7

SEQ ID NO: 40        moltype = AA  length = 8
FEATURE              Location/Qualifiers
REGION               1..8
                     note = Synthetic peptide
VARIANT              3
                     note = X can be any amino acid
VARIANT              6..7
                     note = X can be any amino acid
source               1..8
                     mol_type = protein
                     organism = synthetic construct
SEQUENCE: 40
YYXYRXXK                                                                         8

SEQ ID NO: 41        moltype = AA  length = 7
FEATURE              Location/Qualifiers
REGION               1..7
                     note = Synthetic peptide
VARIANT              2
```

|   |   |   |
|---|---|---|
| VARIANT | note = X can be any amino acid<br>5 | |
| VARIANT | note = X can be any amino acid<br>7 | |
| source | note = X can be F or Y<br>1..7<br>mol_type = protein<br>organism = synthetic construct | |
| SEQUENCE: 41 | | |
| KXHEXGX | | 7 |
| SEQ ID NO: 42<br>FEATURE<br>REGION | moltype = AA  length = 5<br>Location/Qualifiers<br>1..5<br>note = Synthetic peptide | |
| VARIANT | 5<br>note = X can be V or I | |
| source | 1..5<br>mol_type = protein<br>organism = synthetic construct | |
| SEQUENCE: 42 | | |
| HHFLX | | 5 |
| SEQ ID NO: 43<br>FEATURE<br>REGION | moltype = AA  length = 5<br>Location/Qualifiers<br>1..5<br>note = Synthetic peptide | |
| VARIANT | 1<br>note = X can be L or V | |
| source | 1..5<br>mol_type = protein<br>organism = synthetic construct | |
| SEQUENCE: 43 | | |
| XCNAY | | 5 |
| SEQ ID NO: 44<br>FEATURE<br>REGION | moltype = AA  length = 7<br>Location/Qualifiers<br>1..7<br>note = Synthetic peptide | |
| source | 1..7<br>mol_type = protein<br>organism = synthetic construct | |
| SEQUENCE: 44 | | |
| LFGANLN | | 7 |
| SEQ ID NO: 45<br>FEATURE<br>REGION | moltype = AA  length = 7<br>Location/Qualifiers<br>1..7<br>note = Synthetic peptide | |
| source | 1..7<br>mol_type = protein<br>organism = synthetic construct | |
| SEQUENCE: 45 | | |
| PGPRTCK | | 7 |
| SEQ ID NO: 46<br>FEATURE<br>REGION | moltype = AA  length = 7<br>Location/Qualifiers<br>1..7<br>note = Synthetic peptide | |
| source | 1..7<br>mol_type = protein<br>organism = synthetic construct | |
| SEQUENCE: 46 | | |
| PARRTRK | | 7 |
| SEQ ID NO: 47<br>FEATURE<br>REGION | moltype = AA  length = 7<br>Location/Qualifiers<br>1..7<br>note = Synthetic peptide | |
| source | 1..7<br>mol_type = protein<br>organism = synthetic construct | |
| SEQUENCE: 47 | | |
| IANAGSI | | 7 |
| SEQ ID NO: 48<br>FEATURE<br>REGION | moltype = AA  length = 10<br>Location/Qualifiers<br>1..10<br>note = Synthetic peptide | |

```
                       -continued source                 1..10
                       mol_type = protein
                       organism = synthetic construct
SEQUENCE: 48
WAQIRHIPYQ                                                              10

SEQ ID NO: 49          moltype = AA  length = 6
FEATURE                Location/Qualifiers
REGION                 1..6
                       note = Synthetic peptide
source                 1..6
                       mol_type = protein
                       organism = synthetic construct
SEQUENCE: 49
MRNPQQ                                                                  6

SEQ ID NO: 50          moltype = AA  length = 8
FEATURE                Location/Qualifiers
REGION                 1..8
                       note = Synthetic peptide
VARIANT                2
                       note = X can be E, D or Q
VARIANT                5
                       note = X can be L, I or V
VARIANT                6
                       note = X can be I or V
VARIANT                7
                       note = X can be D or E
source                 1..8
                       mol_type = protein
                       organism = synthetic construct
SEQUENCE: 50
LXEVXXXK                                                                8

SEQ ID NO: 51          moltype = AA  length = 6
FEATURE                Location/Qualifiers
source                 1..6
                       mol_type = protein
                       organism = synthetic construct
VARIANT                2
                       note = V can be replaced by I
VARIANT                3
                       note = V can be replaced by I or L
VARIANT                4
                       note = I can be replaced by V
VARIANT                5
                       note = D can be replaced by E or N
SEQUENCE: 51
EVVIDK                                                                  6

SEQ ID NO: 52          moltype = AA  length = 6
FEATURE                Location/Qualifiers
source                 1..6
                       mol_type = protein
                       organism = synthetic construct
VARIANT                2..4
                       note = V can be replaced by I
VARIANT                5
                       note = X can be any amino acid
SEQUENCE: 52
EVVVXK                                                                  6

SEQ ID NO: 53          moltype = AA  length = 5
FEATURE                Location/Qualifiers
REGION                 1..5
                       note = Synthetic peptide
VARIANT                2
                       note = X can be any amino acid
source                 1..5
                       mol_type = protein
                       organism = synthetic construct
SEQUENCE: 53
VXPNI                                                                   5

SEQ ID NO: 54          moltype = AA  length = 4
FEATURE                Location/Qualifiers
REGION                 1..4
                       note = Synthetic peptide
source                 1..4
```

```
                        mol_type = protein
                        organism = synthetic construct
SEQUENCE: 54
VVPN                                                                    4

SEQ ID NO: 55           moltype = AA   length = 9
FEATURE                 Location/Qualifiers
REGION                  1..9
                        note = Synthetic peptide
VARIANT                 2
                        note = X can be any amino acid
source                  1..9
                        mol_type = protein
                        organism = synthetic construct
SEQUENCE: 55
LXEVLVVVP                                                               9

SEQ ID NO: 56           moltype = AA   length = 8
FEATURE                 Location/Qualifiers
REGION                  1..8
                        note = Synthetic peptide
VARIANT                 3
                        note = X can be any amino acid
VARIANT                 6
                        note = X can be any amino acid
source                  1..8
                        mol_type = protein
                        organism = synthetic construct
SEQUENCE: 56
GPXHTXKV                                                                8

SEQ ID NO: 57           moltype = AA   length = 9
FEATURE                 Location/Qualifiers
REGION                  1..9
                        note = Synthetic peptide
VARIANT                 2
                        note = X can be any amino acid
VARIANT                 4
                        note = X can be V or I
VARIANT                 6
                        note = X can be any amino acid
VARIANT                 7
                        note = X can be V or T
source                  1..9
                        mol_type = protein
                        organism = synthetic construct
SEQUENCE: 57
EXYXDXXLN                                                               9

SEQ ID NO: 58           moltype = AA   length = 9
FEATURE                 Location/Qualifiers
REGION                  1..9
                        note = Synthetic peptide
VARIANT                 6
                        note = X can be I or V
source                  1..9
                        mol_type = protein
                        organism = synthetic construct
SEQUENCE: 58
ELEEVXVDK                                                               9

SEQ ID NO: 59           moltype = AA   length = 11
FEATURE                 Location/Qualifiers
REGION                  1..11
                        note = Synthetic peptide
source                  1..11
                        mol_type = protein
                        organism = synthetic construct
SEQUENCE: 59
LNEVLVVVPN I                                                           11

SEQ ID NO: 60           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 60
```

```
GPKHTQKV                                                                          8

SEQ ID NO: 61           moltype = AA  length = 9
FEATURE                 Location/Qualifiers
REGION                  1..9
                        note = Synthetic peptide
source                  1..9
                        mol_type = protein
                        organism = synthetic construct
SEQUENCE: 61
EEYVDQVLN                                                                         9

SEQ ID NO: 62           moltype = AA  length = 9
FEATURE                 Location/Qualifiers
REGION                  1..9
                        note = Synthetic peptide
VARIANT                 2
                        note = X can be any amino acid
VARIANT                 6..7
                        note = X can be any amino acid
VARIANT                 9
                        note = X can be S or T
source                  1..9
                        mol_type = protein
                        organism = synthetic construct
SEQUENCE: 62
KXDPDXXWX                                                                         9

SEQ ID NO: 63           moltype = AA  length = 7
FEATURE                 Location/Qualifiers
REGION                  1..7
                        note = Synthetic peptide
VARIANT                 3
                        note = X can be any amino acid
source                  1..7
                        mol_type = protein
                        organism = synthetic construct
SEQUENCE: 63
KPXLGGK                                                                           7

SEQ ID NO: 64           moltype = AA  length = 9
FEATURE                 Location/Qualifiers
REGION                  1..9
                        note = Synthetic peptide
VARIANT                 2
                        note = X can be any amino acid
VARIANT                 6..7
                        note = X can be any amino acid
source                  1..9
                        mol_type = protein
                        organism = synthetic construct
SEQUENCE: 64
KXDPDXXWT                                                                         9

SEQ ID NO: 65           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 65
KPTLGGK                                                                           7

SEQ ID NO: 66           moltype = AA  length = 8
FEATURE                 Location/Qualifiers
REGION                  1..8
                        note = Synthetic peptide
VARIANT                 1
                        note = X can be I or V
VARIANT                 2
                        note = X can be any amino acid
VARIANT                 3
                        note = X can be P or R
source                  1..8
                        mol_type = protein
                        organism = synthetic construct
SEQUENCE: 66
XXXQPEKP                                                                          8
```

```
SEQ ID NO: 67            moltype = AA   length = 7
FEATURE                  Location/Qualifiers
REGION                   1..7
                         note = Synthetic peptide
VARIANT                  2
                         note = X can be any amino acid
source                   1..7
                         mol_type = protein
                         organism = synthetic construct
SEQUENCE: 67
KXDDMLN                                                                   7

SEQ ID NO: 68            moltype = AA   length = 7
FEATURE                  Location/Qualifiers
REGION                   1..7
                         note = Synthetic peptide
VARIANT                  2
                         note = X can be any amino acid
VARIANT                  4
                         note = X can be any amino acid
source                   1..7
                         mol_type = protein
                         organism = synthetic construct
SEQUENCE: 68
KXDXMLN                                                                   7

SEQ ID NO: 69            moltype = AA   length = 9
FEATURE                  Location/Qualifiers
REGION                   1..9
                         note = Synthetic peptide
VARIANT                  1
                         note = X can be L or W
VARIANT                  2
                         note = X can be any amino acid
VARIANT                  6
                         note = X can be any amino acid
source                   1..9
                         mol_type = protein
                         organism = synthetic construct
SEQUENCE: 69
XXSAEXEEK                                                                 9

SEQ ID NO: 70            moltype = AA   length = 7
FEATURE                  Location/Qualifiers
REGION                   1..7
                         note = Synthetic peptide
VARIANT                  4
                         note = X can be any amino acid
VARIANT                  6
                         note = X can be any amino acid
source                   1..7
                         mol_type = protein
                         organism = synthetic construct
SEQUENCE: 70
SAEXEXK                                                                   7

SEQ ID NO: 71            moltype = AA   length = 8
FEATURE                  Location/Qualifiers
REGION                   1..8
                         note = Synthetic peptide
source                   1..8
                         mol_type = protein
                         organism = synthetic construct
SEQUENCE: 71
VKPQPEKP                                                                  8

SEQ ID NO: 72            moltype = AA   length = 7
FEATURE                  Location/Qualifiers
REGION                   1..7
                         note = Synthetic peptide
source                   1..7
                         mol_type = protein
                         organism = synthetic construct
SEQUENCE: 72
KTDDMLN                                                                   7

SEQ ID NO: 73            moltype = AA   length = 9
FEATURE                  Location/Qualifiers
```

```
REGION                  1..9
                        note = Synthetic peptide
source                  1..9
                        mol_type = protein
                        organism = synthetic construct
SEQUENCE: 73
LESAEKEEK                                                                         9

SEQ ID NO: 74           moltype = AA  length = 6
FEATURE                 Location/Qualifiers
REGION                  1..6
                        note = Synthetic peptide
VARIANT                 3
                        note = X can be any amino acid
VARIANT                 5
                        note = X can be F or Y
source                  1..6
                        mol_type = protein
                        organism = synthetic construct
SEQUENCE: 74
HEXEXQ                                                                            6

SEQ ID NO: 75           moltype = AA  length = 6
FEATURE                 Location/Qualifiers
REGION                  1..6
                        note = Synthetic peptide
VARIANT                 3
                        note = X can be M, L or F
VARIANT                 5
                        note = X can be any amino acid
source                  1..6
                        mol_type = protein
                        organism = synthetic construct
SEQUENCE: 75
LDXWXE                                                                            6

SEQ ID NO: 76           moltype = AA  length = 5
FEATURE                 Location/Qualifiers
REGION                  1..5
                        note = Synthetic peptide
source                  1..5
                        mol_type = protein
                        organism = synthetic construct
SEQUENCE: 76
HCSAC                                                                             5

SEQ ID NO: 77           moltype = AA  length = 6
FEATURE                 Location/Qualifiers
REGION                  1..6
                        note = Synthetic peptide
VARIANT                 1
                        note = X can be F or Y
VARIANT                 2
                        note = X can be any amino acid
source                  1..6
                        mol_type = protein
                        organism = synthetic construct
SEQUENCE: 77
XXGVVN                                                                            6

SEQ ID NO: 78           moltype = AA  length = 9
FEATURE                 Location/Qualifiers
REGION                  1..9
                        note = Synthetic peptide
VARIANT                 2..4
                        note = X can be any amino acid
VARIANT                 8
                        note = X can be any amino acid
source                  1..9
                        mol_type = protein
                        organism = synthetic construct
SEQUENCE: 78
KXXXGRGXI                                                                         9

SEQ ID NO: 79           moltype = AA  length = 5
FEATURE                 Location/Qualifiers
REGION                  1..5
                        note = Synthetic peptide
VARIANT                 4
```

```
                            note = X can be L or A
source                      1..5
                            mol_type = protein
                            organism = synthetic construct
SEQUENCE: 79
GPHXE                                                                        5

SEQ ID NO: 80               moltype = AA  length = 5
FEATURE                     Location/Qualifiers
REGION                      1..5
                            note = Synthetic peptide
source                      1..5
                            mol_type = protein
                            organism = synthetic construct
SEQUENCE: 80
PRREP                                                                        5

SEQ ID NO: 81               moltype = AA  length = 8
FEATURE                     Location/Qualifiers
REGION                      1..8
                            note = Synthetic peptide
VARIANT                     3..5
                            note = X can be any amino acid
source                      1..8
                            mol_type = protein
                            organism = synthetic construct
SEQUENCE: 81
CNXXXECY                                                                     8

SEQ ID NO: 82               moltype = AA  length = 8
FEATURE                     Location/Qualifiers
REGION                      1..8
                            note = Synthetic peptide
VARIANT                     2
                            note = X can be any amino acid
VARIANT                     6..7
                            note = X can be any amino acid
source                      1..8
                            mol_type = protein
                            organism = synthetic construct
SEQUENCE: 82
KXCQPXXC                                                                     8

SEQ ID NO: 83               moltype = AA  length = 6
FEATURE                     Location/Qualifiers
source                      1..6
                            mol_type = protein
                            organism = synthetic construct
VARIANT                     2
                            note = X can be any amino acid
VARIANT                     5
                            note = F can be replaced by H
VARIANT                     6
                            note = T can be replaced by S
SEQUENCE: 83
PXPDFT                                                                       6

SEQ ID NO: 84               moltype = AA  length = 10
FEATURE                     Location/Qualifiers
REGION                      1..10
                            note = Synthetic peptide
VARIANT                     2..4
                            note = X can be any amino acid
VARIANT                     6
                            note = X can be any amino acid
VARIANT                     8
                            note = X can be A or G
VARIANT                     9
                            note = X can be any amino acid
source                      1..10
                            mol_type = protein
                            organism = synthetic construct
SEQUENCE: 84
NXXXEXYXXD                                                                  10

SEQ ID NO: 85               moltype = AA  length = 7
FEATURE                     Location/Qualifiers
REGION                      1..7
                            note = Synthetic peptide
```

```
                        VARIANT               2
                                              note = X can be A or G
                        VARIANT               4..5
                                              note = X can be any amino acid
                        source                1..7
                                              mol_type = protein
                                              organism = synthetic construct
SEQUENCE: 85
PXAXXLD                                                                                              7

SEQ ID NO: 86           moltype = AA  length = 7
FEATURE                 Location/Qualifiers
REGION                  1..7
                        note = Synthetic peptide
VARIANT                 4
                        note = X can be any amino acid
VARIANT                 6
                        note = X can be any amino acid
source                  1..7
                        mol_type = protein
                        organism = synthetic construct
SEQUENCE: 86
MPSXSXE                                                                                              7

SEQ ID NO: 87           moltype = AA  length = 7
FEATURE                 Location/Qualifiers
source                  1..7
                        mol_type = protein
                        organism = synthetic construct
VARIANT                 1
                        note = R can be replaced by K
VARIANT                 2
                        note = X can be any amino acid
VARIANT                 4
                        note = X can be any amino acid
VARIANT                 7
                        note = T can be replaced by S
SEQUENCE: 87
RXYXHRT                                                                                              7

SEQ ID NO: 88           moltype = AA  length = 8
FEATURE                 Location/Qualifiers
REGION                  1..8
                        note = Synthetic peptide
VARIANT                 2
                        note = X can be P or A
VARIANT                 3
                        note = X can be any amino acid
VARIANT                 5
                        note = X can be any amino acid
VARIANT                 7
                        note = X can be any amino acid
source                  1..8
                        mol_type = protein
                        organism = synthetic construct
SEQUENCE: 88
KXXFXFXK                                                                                             8

SEQ ID NO: 89           moltype = AA  length = 7
FEATURE                 Location/Qualifiers
REGION                  1..7
                        note = Synthetic peptide
VARIANT                 3
                        note = X can be C, S or T
VARIANT                 4
                        note = X can be any amino acid
VARIANT                 6
                        note = X can be any amino acid
source                  1..7
                        mol_type = protein
                        organism = synthetic construct
SEQUENCE: 89
DDXXGXR                                                                                              7

SEQ ID NO: 90           moltype = AA  length = 8
FEATURE                 Location/Qualifiers
REGION                  1..8
                        note = Synthetic peptide
VARIANT                 2
```

```
                            note = X can be M or L
VARIANT                     3..4
                            note = X can be any amino acid
VARIANT                     6
                            note = X can be any amino acid
source                      1..8
                            mol_type = protein
                            organism = synthetic construct
SEQUENCE: 90
PXXXHXMY                                                                       8

SEQ ID NO: 91               moltype = AA  length = 7
FEATURE                     Location/Qualifiers
source                      1..7
                            mol_type = protein
                            organism = synthetic construct
VARIANT                     2
                            note = X can be any amino acid
VARIANT                     3
                            note = A can be replaced by S or Q
VARIANT                     4
                            note = S can be replaced by A or T
VARIANT                     5
                            note = X can be any amino acid
SEQUENCE: 91
KXASXRG                                                                        7

SEQ ID NO: 92               moltype = AA  length = 5
FEATURE                     Location/Qualifiers
REGION                      1..5
                            note = Synthetic peptide
VARIANT                     1
                            note = X can be D or G
source                      1..5
                            mol_type = protein
                            organism = synthetic construct
SEQUENCE: 92
XQPEN                                                                          5

SEQ ID NO: 93               moltype = AA  length = 5
FEATURE                     Location/Qualifiers
source                      1..5
                            mol_type = protein
                            organism = synthetic construct
VARIANT                     1
                            note = K can be replaced by H or R
VARIANT                     3
                            note = Q can be replaced by N
SEQUENCE: 93
KNQDG                                                                          5

SEQ ID NO: 94               moltype = AA  length = 7
FEATURE                     Location/Qualifiers
REGION                      1..7
                            note = Synthetic peptide
VARIANT                     2
                            note = X can be any amino acid
VARIANT                     3
                            note = X can be E, V or S
VARIANT                     6
                            note = X can be any amino acid
source                      1..7
                            mol_type = protein
                            organism = synthetic construct
SEQUENCE: 94
NXXGEXY                                                                        7

SEQ ID NO: 95               moltype = AA  length = 5
FEATURE                     Location/Qualifiers
REGION                      1..5
                            note = Synthetic peptide
VARIANT                     3
                            note = X can be V or I
source                      1..5
                            mol_type = protein
                            organism = synthetic construct
SEQUENCE: 95
EPXTG                                                                          5
```

```
SEQ ID NO: 96          moltype = AA  length = 5
FEATURE                Location/Qualifiers
source                 1..5
                       mol_type = protein
                       organism = synthetic construct
VARIANT                4
                       note = P can be replaced by A
VARIANT                5
                       note = K can be replaced by R
SEQUENCE: 96
HGMPK                                                                       5

SEQ ID NO: 97          moltype = AA  length = 5
FEATURE                Location/Qualifiers
REGION                 1..5
                       note = Synthetic peptide
VARIANT                1
                       note = X can be V, I or T
source                 1..5
                       mol_type = protein
                       organism = synthetic construct
SEQUENCE: 97
XPWIF                                                                       5

SEQ ID NO: 98          moltype = AA  length = 7
FEATURE                Location/Qualifiers
REGION                 1..7
                       note = Synthetic peptide
VARIANT                2
                       note = X can be any amino acid
VARIANT                3
                       note = X can be S, T or N
VARIANT                5
                       note = X can be any amino acid
source                 1..7
                       mol_type = protein
                       organism = synthetic construct
SEQUENCE: 98
KXXVXFQ                                                                     7

SEQ ID NO: 99          moltype = AA  length = 5
FEATURE                Location/Qualifiers
REGION                 1..5
                       note = Synthetic peptide
VARIANT                1
                       note = X can be V, A or I
source                 1..5
                       mol_type = protein
                       organism = synthetic construct
SEQUENCE: 99
XWSGS                                                                       5

SEQ ID NO: 100         moltype = AA  length = 7
FEATURE                Location/Qualifiers
REGION                 1..7
                       note = Synthetic peptide
VARIANT                3
                       note = X can be L, I, A or M
VARIANT                4..5
                       note = X can be any amino acid
source                 1..7
                       mol_type = protein
                       organism = synthetic construct
SEQUENCE: 100
FSXXXWG                                                                     7

SEQ ID NO: 101         moltype = AA  length = 5
FEATURE                Location/Qualifiers
REGION                 1..5
                       note = Synthetic peptide
VARIANT                4
                       note = X can be P or Q
source                 1..5
                       mol_type = protein
                       organism = synthetic construct
SEQUENCE: 101
PTNXG                                                                       5

SEQ ID NO: 102         moltype = AA  length = 9
```

```
FEATURE                 Location/Qualifiers
source                  1..9
                        mol_type = protein
                        organism = synthetic construct
VARIANT                 1
                        note = R can be replaced by K
VARIANT                 3..4
                        note = X can be any amino acid
VARIANT                 5
                        note = Y can be replaced by W
VARIANT                 6
                        note = X can be any amino acid
VARIANT                 8
                        note = X can be any amino acid
VARIANT                 9
                        note = T can be replaced by S
SEQUENCE: 102
RKXXYXHXT                                                                          9

SEQ ID NO: 103          moltype = AA   length = 7
FEATURE                 Location/Qualifiers
REGION                  1..7
                        note = Synthetic peptide
VARIANT                 1
                        note = X can be H, R or W
VARIANT                 2..3
                        note = X can be any amino acid
source                  1..7
                        mol_type = protein
                        organism = synthetic construct
SEQUENCE: 103
XXXHPRF                                                                            7

SEQ ID NO: 104          moltype = AA   length = 6
FEATURE                 Location/Qualifiers
REGION                  1..6
                        note = Synthetic peptide
VARIANT                 1
                        note = X can be R or K
VARIANT                 4
                        note = X can be any amino acid
source                  1..6
                        mol_type = protein
                        organism = synthetic construct
SEQUENCE: 104
XMRXID                                                                             6

SEQ ID NO: 105          moltype = AA   length = 6
FEATURE                 Location/Qualifiers
REGION                  1..6
                        note = Synthetic peptide
VARIANT                 3
                        note = X can be any amino acid
source                  1..6
                        mol_type = protein
                        organism = synthetic construct
SEQUENCE: 105
QHXGHP                                                                             6

SEQ ID NO: 106          moltype = AA   length = 7
FEATURE                 Location/Qualifiers
REGION                  1..7
                        note = Synthetic peptide
VARIANT                 2..3
                        note = X can be any amino acid
source                  1..7
                        mol_type = protein
                        organism = synthetic construct
SEQUENCE: 106
KXXLPED                                                                            7

SEQ ID NO: 107          moltype = AA   length = 7
FEATURE                 Location/Qualifiers
REGION                  1..7
                        note = Synthetic peptide
VARIANT                 1
                        note = X can be I or V
VARIANT                 3..4
                        note = X can be any amino acid
```

```
source                    1..7
                          mol_type = protein
                          organism = synthetic construct
SEQUENCE: 107
XLXXFGY                                                                    7

SEQ ID NO: 108            moltype = AA  length = 9
FEATURE                   Location/Qualifiers
REGION                    1..9
                          note = Synthetic peptide
VARIANT                   4..7
                          note = X can be any amino acid
source                    1..9
                          mol_type = protein
                          organism = synthetic construct
SEQUENCE: 108
PLDXXXXIS                                                                  9

SEQ ID NO: 109            moltype = AA  length = 7
FEATURE                   Location/Qualifiers
REGION                    1..7
                          note = Synthetic peptide
VARIANT                   3
                          note = X can be any amino acid
VARIANT                   6
                          note = X can be any amino acid
source                    1..7
                          mol_type = protein
                          organism = synthetic construct
SEQUENCE: 109
ETXIPXE                                                                    7

SEQ ID NO: 110            moltype = AA  length = 8
FEATURE                   Location/Qualifiers
source                    1..8
                          mol_type = protein
                          organism = synthetic construct
VARIANT                   1
                          note = V can be replaced by I
VARIANT                   3
                          note = X can be any amino acid
VARIANT                   4
                          note = D can be replaced by E
VARIANT                   5
                          note = M can be replaced by L
VARIANT                   7
                          note = X can be any amino acid
SEQUENCE: 110
VNXDMYXP                                                                   8

SEQ ID NO: 111            moltype = AA  length = 7
FEATURE                   Location/Qualifiers
REGION                    1..7
                          note = Synthetic peptide
VARIANT                   3..4
                          note = X can be any amino acid
source                    1..7
                          mol_type = protein
                          organism = synthetic construct
SEQUENCE: 111
FLXXIGA                                                                    7

SEQ ID NO: 112            moltype = AA  length = 7
FEATURE                   Location/Qualifiers
source                    1..7
                          mol_type = protein
                          organism = synthetic construct
VARIANT                   2
                          note = V can be replaced by I
VARIANT                   3
                          note = X can be any amino acid
VARIANT                   4
                          note = M can be replaced by I
VARIANT                   5
                          note = I can be replaced by L or V
VARIANT                   6
                          note = X can be any amino acid
VARIANT                   7
                          note = K can be replaced by R
```

```
SEQUENCE: 112
DVXMIXK                                                                    7

SEQ ID NO: 113          moltype = AA  length = 8
FEATURE                 Location/Qualifiers
REGION                  1..8
                        note = Synthetic peptide
VARIANT                 2
                        note = X can be any amino acid
VARIANT                 6
                        note = X can be any amino acid
source                  1..8
                        mol_type = protein
                        organism = synthetic construct
SEQUENCE: 113
RXSPYXJF                                                                   8

SEQ ID NO: 114          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 114
VGPRH                                                                      5

SEQ ID NO: 115          moltype = AA  length = 6
FEATURE                 Location/Qualifiers
REGION                  1..6
                        note = Synthetic peptide
VARIANT                 3
                        note = X can be any amino acid
VARIANT                 6
                        note = X can be E or D
source                  1..6
                        mol_type = protein
                        organism = synthetic construct
SEQUENCE: 115
PQXQHX                                                                     6

SEQ ID NO: 116          moltype = AA  length = 7
FEATURE                 Location/Qualifiers
REGION                  1..7
                        note = Synthetic peptide
VARIANT                 2..3
                        note = X can be any amino acid
source                  1..7
                        mol_type = protein
                        organism = synthetic construct
SEQUENCE: 116
PXXGGFG                                                                    7

SEQ ID NO: 117          moltype = AA  length = 8
FEATURE                 Location/Qualifiers
REGION                  1..8
                        note = Synthetic peptide
VARIANT                 2
                        note = X can be any amino acid
VARIANT                 5..6
                        note = X can be any amino acid
source                  1..8
                        mol_type = protein
                        organism = synthetic construct
SEQUENCE: 117
KXEGXXMG                                                                   8

SEQ ID NO: 118          moltype = AA  length = 10
FEATURE                 Location/Qualifiers
REGION                  1..10
                        note = Synthetic peptide
VARIANT                 2..3
                        note = X can be any amino acid
VARIANT                 5
                        note = X can be any amino acid
VARIANT                 7..8
                        note = X can be any amino acid
source                  1..10
                        mol_type = protein
```

```
                        organism = synthetic construct
SEQUENCE: 118
KXXGXTXXLS                                                              10

SEQ ID NO: 119          moltype = AA   length = 5
FEATURE                 Location/Qualifiers
REGION                  1..5
                        note = Synthetic peptide
VARIANT                 4
                        note = X can be F or W
source                  1..5
                        mol_type = protein
                        organism = synthetic construct
SEQUENCE: 119
EMGXQ                                                                   5

SEQ ID NO: 120          moltype = AA   length = 9
FEATURE                 Location/Qualifiers
REGION                  1..9
                        note = Synthetic peptide
VARIANT                 1
                        note = X can be V or I
VARIANT                 3
                        note = X can be any amino acid
VARIANT                 5..6
                        note = X can be any amino acid
VARIANT                 8
                        note = X can be any amino acid
source                  1..9
                        mol_type = protein
                        organism = synthetic construct
SEQUENCE: 120
XKXGXXDXP                                                               9

SEQ ID NO: 121          moltype = AA   length = 7
FEATURE                 Location/Qualifiers
REGION                  1..7
                        note = Synthetic peptide
VARIANT                 5
                        note = X can be any amino acid
source                  1..7
                        mol_type = protein
                        organism = synthetic construct
SEQUENCE: 121
PEBEXYP                                                                 7

SEQ ID NO: 122          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 122
HYEWA                                                                   5

SEQ ID NO: 123          moltype = AA   length = 6
FEATURE                 Location/Qualifiers
REGION                  1..6
                        note = Synthetic peptide
VARIANT                 1
                        note = X can be H or R
VARIANT                 5
                        note = X can be any amino acid
source                  1..6
                        mol_type = protein
                        organism = synthetic construct
SEQUENCE: 123
XSNMXF                                                                  6

SEQ ID NO: 124          moltype = AA   length = 7
FEATURE                 Location/Qualifiers
REGION                  1..7
                        note = Synthetic peptide
VARIANT                 2
                        note = X can be T or V
VARIANT                 4..5
                        note = X can be any amino acid
source                  1..7
```

```
                        mol_type = protein
                        organism = synthetic construct
SEQUENCE: 124
MXGXXYE                                                                 7

SEQ ID NO: 125          moltype = AA   length = 9
FEATURE                 Location/Qualifiers
REGION                  1..9
                        note = Synthetic peptide
VARIANT                 2..3
                        note = X can be any amino acid
VARIANT                 4
                        note = X can be K or H
VARIANT                 6..7
                        note = X can be any amino acid
source                  1..9
                        mol_type = protein
                        organism = synthetic construct
SEQUENCE: 125
DXXXEXXLL                                                               9

SEQ ID NO: 126          moltype = AA   length = 9
FEATURE                 Location/Qualifiers
source                  1..9
                        mol_type = protein
                        organism = synthetic construct
VARIANT                 2..3
                        note = X can be any amino acid
VARIANT                 5
                        note = X can be any amino acid
VARIANT                 6
                        note = E can be replaced by D or A
VARIANT                 7
                        note = X can be any amino acid
VARIANT                 8
                        note = I can be replaced by V
VARIANT                 9
                        note = A can be replaced by R
SEQUENCE: 126
RXXWXEXIA                                                               9

SEQ ID NO: 127          moltype = AA   length = 9
FEATURE                 Location/Qualifiers
source                  1..9
                        mol_type = protein
                        organism = synthetic construct
VARIANT                 2
                        note = X can be any amino acid
VARIANT                 4..5
                        note = X can be any amino acid
VARIANT                 7
                        note = X can be any amino acid
VARIANT                 8
                        note = G can be replaced by P or A
VARIANT                 9
                        note = T can be replaced by S
SEQUENCE: 127
PXDXXAXGT                                                               9

SEQ ID NO: 128          moltype = AA   length = 8
FEATURE                 Location/Qualifiers
REGION                  1..8
                        note = Synthetic peptide
VARIANT                 3..4
                        note = X can be any amino acid
VARIANT                 6
                        note = X can be any amino acid
VARIANT                 8
                        note = X can be A, R or G
source                  1..8
                        mol_type = protein
                        organism = synthetic construct
SEQUENCE: 128
PDXXSXTX                                                                8

SEQ ID NO: 129          moltype = AA   length = 6
FEATURE                 Location/Qualifiers
REGION                  1..6
                        note = Synthetic peptide
```

```
                         VARIANT          4
                                          note = X can be any amino acid
                         source           1..6
                                          mol_type = protein
                                          organism = synthetic construct
                         SEQUENCE: 129
                         GREXDG                                                                 6

SEQ ID NO: 130   moltype = AA   length = 8
                         FEATURE          Location/Qualifiers
                         REGION           1..8
                                          note = Synthetic peptide
                         VARIANT          5..7
                                          note = X can be any amino acid
                         source           1..8
                                          mol_type = protein
                                          organism = synthetic construct
                         SEQUENCE: 130
                         GVPGXXXK                                                               8

SEQ ID NO: 131   moltype = AA   length = 10
                         FEATURE          Location/Qualifiers
                         source           1..10
                                          mol_type = protein
                                          organism = synthetic construct
                         VARIANT          1
                                          note = L can be replaced by M
                         VARIANT          2..4
                                          note = X can be any amino acid
                         VARIANT          5
                                          note = E can be replaced by D or Q
                         VARIANT          7..8
                                          note = X can be any amino acid
                         SEQUENCE: 131
                         LXXXEVXXIM                                                             10

SEQ ID NO: 132   moltype = AA   length = 8
                         FEATURE          Location/Qualifiers
                         REGION           1..8
                                          note = Synthetic peptide
                         VARIANT          2..4
                                          note = X can be any amino acid
                         source           1..8
                                          mol_type = protein
                                          organism = synthetic construct
                         SEQUENCE: 132
                         SXXXVSGG                                                               8

SEQ ID NO: 133   moltype = AA   length = 6
                         FEATURE          Location/Qualifiers
                         REGION           1..6
                                          note = Synthetic peptide
                         VARIANT          2
                                          note = X can be K or R
                         source           1..6
                                          mol_type = protein
                                          organism = synthetic construct
                         SEQUENCE: 133
                         AXAGBK                                                                 6

SEQ ID NO: 134   moltype = AA   length = 6
                         FEATURE          Location/Qualifiers
                         source           1..6
                                          mol_type = protein
                                          organism = synthetic construct
                         VARIANT          2
                                          note = R can be replaced by N
                         VARIANT          3
                                          note = X can be any amino acid
                         VARIANT          6
                                          note = R can be replaced by Q
                         SEQUENCE: 134
                         FRXINR                                                                 6

SEQ ID NO: 135   moltype = AA   length = 9
                         FEATURE          Location/Qualifiers
                         REGION           1..9
                                          note = Synthetic peptide
                         VARIANT          2
```

```
                    note = X can be any amino acid
VARIANT             5
                    note = X can be any amino acid
VARIANT             7
                    note = X can be any amino acid
source              1..9
                    mol_type = protein
                    organism = synthetic construct
SEQUENCE: 135
YXPVXPXSY                                                                        9

SEQ ID NO: 136      moltype = AA  length = 6
FEATURE             Location/Qualifiers
REGION              1..6
                    note = Synethetic peptide
VARIANT             2
                    note = X can be any amino acid
source              1..6
                    mol_type = protein
                    organism = synthetic construct
SEQUENCE: 136
KXTFPD                                                                           6

SEQ ID NO: 137      moltype = AA  length = 7
FEATURE             Location/Qualifiers
REGION              1..7
                    note = Synethetic peptide
VARIANT             4
                    note = X can be F, V or M
VARIANT             5..6
                    note = X can be any amino acid
source              1..7
                    mol_type = protein
                    organism = synthetic construct
SEQUENCE: 137
PFMXXXR                                                                          7

SEQ ID NO: 138      moltype = AA  length = 5
FEATURE             Location/Qualifiers
REGION              1..5
                    note = Synethetic peptide
source              1..5
                    mol_type = protein
                    organism = synthetic construct
SEQUENCE: 138
EFWEP                                                                            5

SEQ ID NO: 139      moltype = AA  length = 5
FEATURE             Location/Qualifiers
REGION              1..5
                    note = Synethetic peptide
VARIANT             1
                    note = X can be F or Y
source              1..5
                    mol_type = protein
                    organism = synthetic construct
SEQUENCE: 139
XGALS                                                                            5

SEQ ID NO: 140      moltype = AA  length = 6
FEATURE             Location/Qualifiers
REGION              1..6
                    note = Synethetic peptide
VARIANT             2
                    note = X can be any amino acid
source              1..6
                    mol_type = protein
                    organism = synthetic construct
SEQUENCE: 140
PXGTEN                                                                           6

SEQ ID NO: 141      moltype = AA  length = 6
FEATURE             Location/Qualifiers
REGION              1..6
                    note = Synethetic peptide
VARIANT             2
                    note = X can be any amino acid
VARIANT             3
                    note = X can be K or E
```

```
                       -continued source                  1..6
                        mol_type = protein
                        organism = synthetic construct
SEQUENCE: 141
GXXPWE                                                              6

SEQ ID NO: 142          moltype = AA  length = 6
FEATURE                 Location/Qualifiers
source                  1..6
                        mol_type = protein
                        organism = synthetic construct
VARIANT                 2
                        note = I can be replaced by V
VARIANT                 4
                        note = X can be any amino acid
VARIANT                 5
                        note = Y can be replaced by F
VARIANT                 6
                        note = W can be replaced by N
SEQUENCE: 142
DITXYW                                                              6

SEQ ID NO: 143          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 143
QHKGHP                                                              6

SEQ ID NO: 144          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 144
QHIGHP                                                              6

SEQ ID NO: 145          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 145
KALLPED                                                             7

SEQ ID NO: 146          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 146
KKHLPED                                                             7

SEQ ID NO: 147          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 147
KITLPED                                                             7

SEQ ID NO: 148          moltype = AA  length = 7
FEATURE                 Location/Qualifiers
REGION                  1..7
                        note = Synthetic peptide
source                  1..7
                        mol_type = protein
                        organism = synthetic construct
```

```
SEQUENCE: 148
KTILPED                                                                          7

SEQ ID NO: 149          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 149
KVLLPED                                                                          7

SEQ ID NO: 150          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 150
VLKKFGY                                                                          7

SEQ ID NO: 151          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 151
VLHLFGY                                                                          7

SEQ ID NO: 152          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 152
VLGEFGY                                                                          7

SEQ ID NO: 153          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 153
VLEPFGY                                                                          7

SEQ ID NO: 154          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 154
PLDVEKEIS                                                                        9

SEQ ID NO: 155          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 155
PLDLLKYIS                                                                        9

SEQ ID NO: 156          moltype = AA  length = 7
FEATURE                 Location/Qualifiers
REGION                  1..7
                        note = Synthetic peptide
source                  1..7
                        mol_type = protein
```

```
                        organism = synthetic construct
SEQUENCE: 156
ETKIPSE                                                                 7

SEQ ID NO: 157          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 157
ETEIPSE                                                                 7

SEQ ID NO: 158          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 158
ETGIPFE                                                                 7

SEQ ID NO: 159          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 159
VNVDLYIP                                                                8

SEQ ID NO: 160          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 160
FLGAIGA                                                                 7

SEQ ID NO: 161          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 161
FLLFIGA                                                                 7

SEQ ID NO: 162          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 162
FLKAIGA                                                                 7

SEQ ID NO: 163          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 163
DIKMIER                                                                 7

SEQ ID NO: 164          moltype = AA  length = 7
FEATURE                 Location/Qualifiers
REGION                  1..7
                        note = Synthetic peptide
source                  1..7
```

```
                            mol_type = protein
                            organism = synthetic construct
SEQUENCE: 164
DIIIVSR                                                                 7

SEQ ID NO: 165              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 165
DVHMLVR                                                                 7

SEQ ID NO: 166              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 166
DVDILER                                                                 7

SEQ ID NO: 167              moltype = AA   length = 8
FEATURE                     Location/Qualifiers
REGION                      1..8
                            note = Synthetic peptide
source                      1..8
                            mol_type = protein
                            organism = synthetic construct
SEQUENCE: 167
RVSPYSIF                                                                8

SEQ ID NO: 168              moltype = AA   length = 5
FEATURE                     Location/Qualifiers
REGION                      1..5
                            note = Synthetic peptide
source                      1..5
                            mol_type = protein
                            organism = synthetic construct
SEQUENCE: 168
VGPRH                                                                   5

SEQ ID NO: 169              moltype = AA   length = 6
FEATURE                     Location/Qualifiers
REGION                      1..6
                            note = Synthetic peptide
source                      1..6
                            mol_type = protein
                            organism = synthetic construct
SEQUENCE: 169
PQKQHE                                                                  6

SEQ ID NO: 170              moltype = AA   length = 6
FEATURE                     Location/Qualifiers
REGION                      1..6
                            note = Synthetic peptide
source                      1..6
                            mol_type = protein
                            organism = synthetic construct
SEQUENCE: 170
PQGQHD                                                                  6

SEQ ID NO: 171              moltype = AA   length = 8
FEATURE                     Location/Qualifiers
REGION                      1..8
                            note = Synthetic peptide
source                      1..8
                            mol_type = protein
                            organism = synthetic construct
SEQUENCE: 171
KSEGEFMG                                                                8

SEQ ID NO: 172              moltype = AA   length = 8
FEATURE                     Location/Qualifiers
REGION                      1..8
                            note = Synthetic peptide
```

```
source                      1..8
                            mol_type = protein
                            organism = synthetic construct
SEQUENCE: 172
KDEGLAMG                                                                        8

SEQ ID NO: 173              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 173
KDNGSTWSLS                                                                     10

SEQ ID NO: 174              moltype = AA  length = 10
FEATURE                     Location/Qualifiers
REGION                      1..10
                            note = Synthetic peptide
source                      1..10
                            mol_type = protein
                            organism = synthetic construct
SEQUENCE: 174
KDDGSTWALS                                                                     10

SEQ ID NO: 175              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 175
IKQGRLDRP                                                                       9

SEQ ID NO: 176              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 176
HYEWA                                                                           5

SEQ ID NO: 177              moltype = AA  length = 7
FEATURE                     Location/Qualifiers
REGION                      1..7
                            note = Synthetic peptide
source                      1..7
                            mol_type = protein
                            organism = synthetic construct
SEQUENCE: 177
MVGEHYE                                                                         7

SEQ ID NO: 178              moltype = AA  length = 7
FEATURE                     Location/Qualifiers
REGION                      1..7
                            note = Synthetic peptide
source                      1..7
                            mol_type = protein
                            organism = synthetic construct
SEQUENCE: 178
MVGKAYE                                                                         7

SEQ ID NO: 179              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 179
DQLKEGRLL                                                                       9

SEQ ID NO: 180              moltype = AA  length = 9
FEATURE                     Location/Qualifiers
REGION                      1..9
```

```
                        note = Synthetic peptide
source                  1..9
                        mol_type = protein
                        organism = synthetic construct
SEQUENCE: 180
DVVKELMLL                                                                        9

SEQ ID NO: 181          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 181
DLEKENELL                                                                        9

SEQ ID NO: 182          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 182
DLDKEVSLL                                                                        9

SEQ ID NO: 183          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 183
RHQWYAVVA                                                                        9

SEQ ID NO: 184          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 184
RHSWFDDVR                                                                        9

SEQ ID NO: 185          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 185
RKEWYDVVA                                                                        9

SEQ ID NO: 186          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 186
RDRWTESIA                                                                        9

SEQ ID NO: 187          moltype = AA   length = 9
FEATURE                 Location/Qualifiers
REGION                  1..9
                        note = Synthetic peptide
source                  1..9
                        mol_type = protein
                        organism = synthetic construct
SEQUENCE: 187
RATWLDQVR                                                                        9

SEQ ID NO: 188          moltype = AA   length = 9
FEATURE                 Location/Qualifiers
```

```
REGION                 1..9
                       note = Synthetic peptide
source                 1..9
                       mol_type = protein
                       organism = synthetic construct
SEQUENCE: 188
RYVWNEWVA                                                                        9

SEQ ID NO: 189         moltype = AA  length = 9
FEATURE                Location/Qualifiers
REGION                 1..9
                       note = Synthetic peptide
source                 1..9
                       mol_type = protein
                       organism = synthetic construct
SEQUENCE: 189
PVDSAHGT                                                                         9

SEQ ID NO: 190         moltype = AA  length = 9
FEATURE                Location/Qualifiers
REGION                 1..9
                       note = Synthetic peptide
source                 1..9
                       mol_type = protein
                       organism = synthetic construct
SEQUENCE: 190
PLDCPALGS                                                                        9

SEQ ID NO: 191         moltype = AA  length = 9
FEATURE                Location/Qualifiers
REGION                 1..9
                       note = Synthetic peptide
source                 1..9
                       mol_type = protein
                       organism = synthetic construct
SEQUENCE: 191
PADSSAHGT                                                                        9

SEQ ID NO: 192         moltype = AA  length = 9
FEATURE                Location/Qualifiers
REGION                 1..9
                       note = Synthetic peptide
source                 1..9
                       mol_type = protein
                       organism = synthetic construct
SEQUENCE: 192
PKDVKATGS                                                                        9

SEQ ID NO: 193         moltype = AA  length = 9
FEATURE                Location/Qualifiers
REGION                 1..9
                       note = Synthetic peptide
source                 1..9
                       mol_type = protein
                       organism = synthetic construct
SEQUENCE: 193
PPDVSASGT                                                                        9

SEQ ID NO: 194         moltype = AA  length = 9
FEATURE                Location/Qualifiers
REGION                 1..9
                       note = Synthetic peptide
source                 1..9
                       mol_type = protein
                       organism = synthetic construct
SEQUENCE: 194
PGDLPAKAT                                                                        9

SEQ ID NO: 195         moltype = AA  length = 9
FEATURE                Location/Qualifiers
REGION                 1..9
                       note = Synthetic peptide
source                 1..9
                       mol_type = protein
                       organism = synthetic construct
SEQUENCE: 195
PADVSAQAT                                                                        9

SEQ ID NO: 196         moltype = AA  length = 9
```

```
FEATURE               Location/Qualifiers
REGION                1..9
                      note = Synthetic peptide
source                1..9
                      mol_type = protein
                      organism = synthetic construct
SEQUENCE: 196
PPDVPASGT                                                                        9

SEQ ID NO: 197        moltype = AA   length = 8
FEATURE               Location/Qualifiers
REGION                1..8
                      note = Synthetic peptide
source                1..8
                      mol_type = protein
                      organism = synthetic construct
SEQUENCE: 197
PDPASITA                                                                         8

SEQ ID NO: 198        moltype = AA   length = 8
FEATURE               Location/Qualifiers
REGION                1..8
                      note = Synthetic peptide
source                1..8
                      mol_type = protein
                      organism = synthetic construct
SEQUENCE: 198
PDASSSTA                                                                         8

SEQ ID NO: 199        moltype = AA   length = 8
FEATURE               Location/Qualifiers
REGION                1..8
                      note = Synthetic peptide
source                1..8
                      mol_type = protein
                      organism = synthetic construct
SEQUENCE: 199
PDSRSITA                                                                         8

SEQ ID NO: 200        moltype = AA   length = 8
FEATURE               Location/Qualifiers
REGION                1..8
                      note = Synthetic peptide
source                1..8
                      mol_type = protein
                      organism = synthetic construct
SEQUENCE: 200
PDSRSVTA                                                                         8

SEQ ID NO: 201        moltype = AA   length = 8
FEATURE               Location/Qualifiers
REGION                1..8
                      note = Synthetic peptide
source                1..8
                      mol_type = protein
                      organism = synthetic construct
SEQUENCE: 201
PDSKSPTA                                                                         8

SEQ ID NO: 202        moltype = AA   length = 8
FEATURE               Location/Qualifiers
REGION                1..8
                      note = Synthetic peptide
source                1..8
                      mol_type = protein
                      organism = synthetic construct
SEQUENCE: 202
PDSESPTA                                                                         8

SEQ ID NO: 203        moltype = AA   length = 6
FEATURE               Location/Qualifiers
REGION                1..6
                      note = Synthetic peptide
source                1..6
                      mol_type = protein
                      organism = synthetic construct
SEQUENCE: 203
GRESDG                                                                           6
```

| | | |
|---|---|---|
| SEQ ID NO: 204<br>FEATURE<br>REGION<br><br>source<br><br><br><br>SEQUENCE: 204<br>GREADG | moltype = AA   length = 6<br>Location/Qualifiers<br>1..6<br>note = Synthetic peptide<br>1..6<br>mol_type = protein<br>organism = synthetic construct<br><br> | <br><br><br><br><br><br><br><br>6 |
| SEQ ID NO: 205<br>FEATURE<br>REGION<br><br>source<br><br><br><br>SEQUENCE: 205<br>GVPGSHAK | moltype = AA   length = 8<br>Location/Qualifiers<br>1..8<br>note = Synthetic peptide<br>1..8<br>mol_type = protein<br>organism = synthetic construct<br><br> | <br><br><br><br><br><br><br><br>8 |
| SEQ ID NO: 206<br>FEATURE<br>REGION<br><br>source<br><br><br><br>SEQUENCE: 206<br>GVPGCVIK | moltype = AA   length = 8<br>Location/Qualifiers<br>1..8<br>note = Synthetic peptide<br>1..8<br>mol_type = protein<br>organism = synthetic construct<br><br> | <br><br><br><br><br><br><br><br>8 |
| SEQ ID NO: 207<br>FEATURE<br>REGION<br><br>source<br><br><br><br>SEQUENCE: 207<br>LSPREVYTIM | moltype = AA   length = 10<br>Location/Qualifiers<br>1..10<br>note = Synthetic peptide<br>1..10<br>mol_type = protein<br>organism = synthetic construct<br><br> | <br><br><br><br><br><br><br><br>10 |
| SEQ ID NO: 208<br>FEATURE<br>REGION<br><br>source<br><br><br><br>SEQUENCE: 208<br>LTNTDVTRIM | moltype = AA   length = 10<br>Location/Qualifiers<br>1..10<br>note = Synthetic peptide<br>1..10<br>mol_type = protein<br>organism = synthetic construct<br><br> | <br><br><br><br><br><br><br><br>10 |
| SEQ ID NO: 209<br>FEATURE<br>REGION<br><br>source<br><br><br><br>SEQUENCE: 209<br>LEDEDVLQIM | moltype = AA   length = 10<br>Location/Qualifiers<br>1..10<br>note = Synthetic peptide<br>1..10<br>mol_type = protein<br>organism = synthetic construct<br><br> | <br><br><br><br><br><br><br><br>10 |
| SEQ ID NO: 210<br>FEATURE<br>REGION<br><br>source<br><br><br><br>SEQUENCE: 210<br>MADPEVAAIM | moltype = AA   length = 10<br>Location/Qualifiers<br>1..10<br>note = Synthetic peptide<br>1..10<br>mol_type = protein<br>organism = synthetic construct<br><br> | <br><br><br><br><br><br><br><br>10 |
| SEQ ID NO: 211<br>FEATURE<br>REGION<br><br>source<br><br><br><br>SEQUENCE: 211<br>SQADVSGG | moltype = AA   length = 8<br>Location/Qualifiers<br>1..8<br>note = Synthetic peptide<br>1..8<br>mol_type = protein<br>organism = synthetic construct<br><br> | <br><br><br><br><br><br><br><br>8 |

```
SEQ ID NO: 212          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 212
SVGSVSGG                                                                    8

SEQ ID NO: 213          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 213
SPSGVSGG                                                                    8

SEQ ID NO: 214          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 214
SWFDVSGG                                                                    8

SEQ ID NO: 215          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 215
FRIINQ                                                                      6

SEQ ID NO: 216          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 216
FRAINR                                                                      6

SEQ ID NO: 217          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 217
KQTFPD                                                                      6

SEQ ID NO: 218          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 218
KATFPD                                                                      6

SEQ ID NO: 219          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 219
```

```
                                          -continued

PFMVQMR                                                                   7

SEQ ID NO: 220          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 220
FGALS                                                                     5

SEQ ID NO: 221          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 221
YGALS                                                                     5

SEQ ID NO: 222          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 222
PSGTEN                                                                    6

SEQ ID NO: 223          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 223
GFKPWE                                                                    6

SEQ ID NO: 224          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 224
DITDYN                                                                    6

SEQ ID NO: 225          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 225
DVTGFN                                                                    6

SEQ ID NO: 226          moltype = AA  length = 6
FEATURE                 Location/Qualifiers
REGION                  1..6
                        note = Synthetic peptide
VARIANT                 2
                        note = X can be any amino acid
VARIANT                 6
                        note = X can be Q, E or A
source                  1..6
                        mol_type = protein
                        organism = synthetic construct
SEQUENCE: 226
AXSPNX                                                                    6

SEQ ID NO: 227          moltype = AA  length = 9
FEATURE                 Location/Qualifiers
source                  1..9
```

```
                        mol_type = protein
                        organism = synthetic construct
VARIANT                 1
                        note = R can be replaced by P
VARIANT                 2
                        note = X can be any amino acid
VARIANT                 4
                        note = X can be any amino acid
VARIANT                 6
                        note = X can be any amino acid
VARIANT                 8
                        note = X can be any amino acid
VARIANT                 9
                        note = I can be replaced by F, M, L or V
SEQUENCE: 227
RXAXSXNXI                                                                9

SEQ ID NO: 228          moltype = AA   length = 7
FEATURE                 Location/Qualifiers
REGION                  1..7
                        note = Synthetic peptide
VARIANT                 2..3
                        note = X can be any amino acid
VARIANT                 7
                        note = X can be V or T
source                  1..7
                        mol_type = protein
                        organism = synthetic construct
SEQUENCE: 228
NXXLGLX                                                                  7

SEQ ID NO: 229          moltype = AA   length = 8
FEATURE                 Location/Qualifiers
source                  1..8
                        mol_type = protein
                        organism = synthetic construct
VARIANT                 1
                        note = Y can be replaced by F
VARIANT                 2
                        note = X can be any amino acid
VARIANT                 3
                        note = D can be replaced by E
VARIANT                 5..6
                        note = X can be any amino acid
SEQUENCE: 229
YXDIXXFF                                                                 8

SEQ ID NO: 230          moltype = AA   length = 7
FEATURE                 Location/Qualifiers
REGION                  1..7
                        note = Synthetic peptide
VARIANT                 2
                        note = X can be any amino acid
VARIANT                 6
                        note = X can be any amino acid
source                  1..7
                        mol_type = protein
                        organism = synthetic construct
SEQUENCE: 230
IXHFFXG                                                                  7

SEQ ID NO: 231          moltype = AA   length = 7
FEATURE                 Location/Qualifiers
source                  1..7
                        mol_type = protein
                        organism = synthetic construct
VARIANT                 1..2
                        note = I can be replaced by L or M
VARIANT                 3
                        note = R can be replaced by K
VARIANT                 5
                        note = E can be replaced by D
VARIANT                 6
                        note = X can be any amino acid
SEQUENCE: 231
IIRHEXQ                                                                  7

SEQ ID NO: 232          moltype = AA   length = 6
FEATURE                 Location/Qualifiers
```

```
                        -continued source              1..6
                    mol_type = protein
                    organism = synthetic construct
VARIANT             1
                    note = I can be replaced by L or M
VARIANT             2
                    note = R can be replaced by K
VARIANT             5
                    note = X can be any amino acid
SEQUENCE: 232
IRHEXQ                                                                      6

SEQ ID NO: 233      moltype = AA  length = 9
FEATURE             Location/Qualifiers
source              1..9
                    mol_type = protein
                    organism = synthetic construct
VARIANT             3..4
                    note = X can be any amino acid
VARIANT             6
                    note = X can be any amino acid
VARIANT             8
                    note = X can be any amino acid
VARIANT             9
                    note = K can be replaced by R
SEQUENCE: 233
KPXXJXLXK                                                                   9

SEQ ID NO: 234      moltype = AA  length = 10
FEATURE             Location/Qualifiers
REGION              1..10
                    note = Synthetic peptide
VARIANT             2
                    note = X can be any amino acid
VARIANT             4..5
                    note = X can be any amino acid
VARIANT             8..9
                    note = X can be any amino acid
VARIANT             10
                    note = X can be W or F
source              1..10
                    mol_type = protein
                    organism = synthetic construct
SEQUENCE: 234
NXDXXYYXXX                                                                 10

SEQ ID NO: 235      moltype = AA  length = 5
FEATURE             Location/Qualifiers
REGION              1..5
                    note = Synthetic peptide
source              1..5
                    mol_type = protein
                    organism = synthetic construct
SEQUENCE: 235
GLDGP                                                                       5

SEQ ID NO: 236      moltype = AA  length = 8
FEATURE             Location/Qualifiers
REGION              1..8
                    note = Synthetic peptide
VARIANT             3
                    note = X can be any amino acid
VARIANT             6..7
                    note = X can be any amino acid
source              1..8
                    mol_type = protein
                    organism = synthetic construct
SEQUENCE: 236
RSXHDXXN                                                                    8

SEQ ID NO: 237      moltype = AA  length = 6
FEATURE             Location/Qualifiers
REGION              1..6
                    note = Synthetic peptide
VARIANT             3
                    note = X can be any amino acid
source              1..6
                    mol_type = protein
                    organism = synthetic construct
```

```
SEQUENCE: 237
FDXFNJ                                                                              6

SEQ ID NO: 238              moltype = AA  length = 6
FEATURE                     Location/Qualifiers
REGION                      1..6
                            note = Synthetic peptide
VARIANT                     4
                            note = X can be any amino acid
source                      1..6
                            mol_type = protein
                            organism = synthetic construct
SEQUENCE: 238
TIFXGK                                                                              6

SEQ ID NO: 239              moltype = AA  length = 6
FEATURE                     Location/Qualifiers
source                      1..6
                            mol_type = protein
                            organism = synthetic construct
VARIANT                     2
                            note = A can be replaced by V
VARIANT                     3
                            note = X can be any amino acid
VARIANT                     5
                            note = T can be replaced by Q
SEQUENCE: 239
RAXSTH                                                                              6

SEQ ID NO: 240              moltype = AA  length = 6
FEATURE                     Location/Qualifiers
REGION                      1..6
                            note = Synthetic peptide
VARIANT                     5
                            note = X can be any amino acid
source                      1..6
                            mol_type = protein
                            organism = synthetic construct
SEQUENCE: 240
KWHGXY                                                                              6

SEQ ID NO: 241              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 241
MPEDK                                                                               5

SEQ ID NO: 242              moltype = AA  length = 9
FEATURE                     Location/Qualifiers
source                      1..9
                            mol_type = protein
                            organism = synthetic construct
VARIANT                     2..4
                            note = X can be any amino acid
VARIANT                     5
                            note = F can be replaced by Y
VARIANT                     6
                            note = X can be any amino acid
VARIANT                     7
                            note = A can be replaced by S
VARIANT                     9
                            note = N can be replaced by T
SEQUENCE: 242
EXXXFXADN                                                                           9

SEQ ID NO: 243              moltype = AA  length = 8
FEATURE                     Location/Qualifiers
REGION                      1..8
                            note = Synthetic peptide
VARIANT                     4..5
                            note = X can be any amino acid
VARIANT                     7
                            note = X can be any amino acid
VARIANT                     8
                            note = X can be V or I
```

```
source                  1..8
                        mol_type = protein
                        organism = synthetic construct
SEQUENCE: 243
NQSXXKXX                                                                    8

SEQ ID NO: 244          moltype = AA   length = 6
FEATURE                 Location/Qualifiers
REGION                  1..6
                        note = Synthetic peptide
VARIANT                 2
                        note = X can be any amino acid
VARIANT                 4
                        note = X can be N, A or S
source                  1..6
                        mol_type = protein
                        organism = synthetic construct
SEQUENCE: 244
KXYXPY                                                                      6

SEQ ID NO: 245          moltype = AA   length = 6
FEATURE                 Location/Qualifiers
REGION                  1..6
                        note = Synthetic peptide
VARIANT                 1
                        note = X can be P or Q
VARIANT                 2
                        note = X can be V or L
source                  1..6
                        mol_type = protein
                        organism = synthetic construct
SEQUENCE: 245
XXHPRI                                                                      6

SEQ ID NO: 246          moltype = AA   length = 7
FEATURE                 Location/Qualifiers
REGION                  1..7
                        note = Synthetic peptide
VARIANT                 5..6
                        note = X can be any amino acid
source                  1..7
                        mol_type = protein
                        organism = synthetic construct
SEQUENCE: 246
EDGMXXW                                                                     7

SEQ ID NO: 247          moltype = AA   length = 6
FEATURE                 Location/Qualifiers
REGION                  1..6
                        note = Synthetic peptide
VARIANT                 4
                        note = X can be any amino acid
source                  1..6
                        mol_type = protein
                        organism = synthetic construct
SEQUENCE: 247
YASXQE                                                                      6

SEQ ID NO: 248          moltype = AA   length = 6
FEATURE                 Location/Qualifiers
REGION                  1..6
                        note = Synthetic peptide
VARIANT                 3
                        note = X can be any amino acid
VARIANT                 5
                        note = X can be Q or K
source                  1..6
                        mol_type = protein
                        organism = synthetic construct
SEQUENCE: 248
KQXQXE                                                                      6

SEQ ID NO: 249          moltype = AA   length = 6
FEATURE                 Location/Qualifiers
REGION                  1..6
                        note = Synthetic peptide
VARIANT                 2
                        note = X can be A or S
VARIANT                 6
```

```
                            note = X can be I, V or M
source                      1..6
                            mol_type = protein
                            organism = synthetic construct
SEQUENCE: 249
KXVFDX                                                                          6

SEQ ID NO: 250              moltype = AA  length = 6
FEATURE                     Location/Qualifiers
source                      1..6
                            mol_type = protein
                            organism = synthetic construct
VARIANT                     3
                            note = Q can be replaced by E
VARIANT                     4
                            note = X can be any amino acid
SEQUENCE: 250
PNQXBP                                                                          6

SEQ ID NO: 251              moltype = AA  length = 6
FEATURE                     Location/Qualifiers
source                      1..6
                            mol_type = protein
                            organism = synthetic construct
VARIANT                     2
                            note = Q can be replaced by A
VARIANT                     3
                            note = X can be any amino acid
SEQUENCE: 251
PQXMBI                                                                          6

SEQ ID NO: 252              moltype = AA  length = 7
FEATURE                     Location/Qualifiers
source                      1..7
                            mol_type = protein
                            organism = synthetic construct
VARIANT                     1
                            note = W can be replaced by R
VARIANT                     2
                            note = X can be any amino acid
VARIANT                     3
                            note = R can be replaced by K or H
VARIANT                     4
                            note = S can be replaced by T
VARIANT                     5
                            note = X can be any amino acid
SEQUENCE: 252
WXRSXFD                                                                         7

SEQ ID NO: 253              moltype = AA  length = 7
FEATURE                     Location/Qualifiers
REGION                      1..7
                            note = Synthetic peptide
VARIANT                     2
                            note = X can be any amino acid
VARIANT                     6
                            note = X can be any amino acid
source                      1..7
                            mol_type = protein
                            organism = synthetic construct
SEQUENCE: 253
KXEPGXK                                                                         7

SEQ ID NO: 254              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 254
DDCLP                                                                           5

SEQ ID NO: 255              moltype = AA  length = 10
FEATURE                     Location/Qualifiers
REGION                      1..10
                            note = Synthetic peptide
VARIANT                     2..5
                            note = X can be any amino acid
```

```
VARIANT            7
                   note = X can be any amino acid
source             1..10
                   mol_type = protein
                   organism = synthetic construct
SEQUENCE: 255
NXXXXGXHLE                                                                              10

SEQ ID NO: 256     moltype = AA  length = 7
FEATURE            Location/Qualifiers
REGION             1..7
                   note = Synthetic peptide
VARIANT            2..3
                   note = X can be any amino acid
source             1..7
                   mol_type = protein
                   organism = synthetic construct
SEQUENCE: 256
DXXHLEG                                                                                 7

SEQ ID NO: 257     moltype = AA  length = 7
FEATURE            Location/Qualifiers
REGION             1..7
                   note = Synthetic peptide
VARIANT            3..4
                   note = X can be any amino acid
VARIANT            5
                   note = X can be T or S
source             1..7
                   mol_type = protein
                   organism = synthetic construct
SEQUENCE: 257
RPXXXHN                                                                                 7

SEQ ID NO: 258     moltype = AA  length = 6
FEATURE            Location/Qualifiers
REGION             1..6
                   note = Synthetic peptide
VARIANT            2
                   note = X can be any amino acid
VARIANT            5
                   note = X can be I or V
source             1..6
                   mol_type = protein
                   organism = synthetic construct
SEQUENCE: 258
KXHSXY                                                                                  6

SEQ ID NO: 259     moltype = AA  length = 7
FEATURE            Location/Qualifiers
REGION             1..7
                   note = Synthetic peptide
VARIANT            2
                   note = X can be any amino acid
VARIANT            5
                   note = X can be any amino acid
VARIANT            6
                   note = X can be I or V
source             1..7
                   mol_type = protein
                   organism = synthetic construct
SEQUENCE: 259
KXHSXXS                                                                                 7

SEQ ID NO: 260     moltype = AA  length = 5
FEATURE            Location/Qualifiers
REGION             1..5
                   note = Synthetic peptide
source             1..5
                   mol_type = protein
                   organism = synthetic construct
SEQUENCE: 260
MSGYE                                                                                   5

SEQ ID NO: 261     moltype = AA  length = 6
FEATURE            Location/Qualifiers
REGION             1..6
                   note = Synthetic peptide
VARIANT            2
```

```
                        note = X can be any amino acid
source                  1..6
                        mol_type = protein
                        organism = synthetic construct
SEQUENCE: 261
YXIWGP                                                                        6

SEQ ID NO: 262          moltype = AA  length = 8
FEATURE                 Location/Qualifiers
REGION                  1..8
                        note = Synthetic peptide
VARIANT                 2..3
                        note = X can be any amino acid
VARIANT                 5
                        note = X can be any amino acid
VARIANT                 8
                        note = X can be R or K
source                  1..8
                        mol_type = protein
                        organism = synthetic construct
SEQUENCE: 262
RXXWXMNX                                                                      8

SEQ ID NO: 263          moltype = AA  length = 7
FEATURE                 Location/Qualifiers
REGION                  1..7
                        note = Synthetic peptide
VARIANT                 3..4
                        note = X can be any amino acid
VARIANT                 6
                        note = X can be F or Y
source                  1..7
                        mol_type = protein
                        organism = synthetic construct
SEQUENCE: 263
QPXXTXE                                                                       7

SEQ ID NO: 264          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 264
YGYNQ                                                                         5

SEQ ID NO: 265          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 265
ARSPN                                                                         5

SEQ ID NO: 266          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 266
AGSPNRI                                                                       7

SEQ ID NO: 267          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 267
PDGGVMP                                                                       7

SEQ ID NO: 268          moltype = AA  length = 7
FEATURE                 Location/Qualifiers
```

```
REGION                  1..7
                        note = Synthetic peptide
source                  1..7
                        mol_type = protein
                        organism = synthetic construct
SEQUENCE: 268
NPKLGLT                                                                      7

SEQ ID NO: 269          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 269
GRRPFF                                                                       6

SEQ ID NO: 270          moltype = AA  length = 9
FEATURE                 Location/Qualifiers
REGION                  1..9
                        note = Synthetic peptide
VARIANT                 4
                        note = X can be any amino acid
source                  1..9
                        mol_type = protein
                        organism = synthetic construct
SEQUENCE: 270
GGGXGAGGG                                                                    9

SEQ ID NO: 271          moltype = AA  length = 7
FEATURE                 Location/Qualifiers
REGION                  1..7
                        note = Synthetic peptide
VARIANT                 3
                        note = X can be P or A
VARIANT                 6
                        note = X can be G or A
source                  1..7
                        mol_type = protein
                        organism = synthetic construct
SEQUENCE: 271
EGXSTXR                                                                      7

SEQ ID NO: 272          moltype = AA  length = 9
FEATURE                 Location/Qualifiers
REGION                  1..9
                        note = Synthetic peptide
VARIANT                 2..3
                        note = X can be any amino acid
VARIANT                 6
                        note = X can be I, V or L
VARIANT                 9
                        note = X can be R or K
source                  1..9
                        mol_type = protein
                        organism = synthetic construct
SEQUENCE: 272
KXXSCXGCX                                                                    9

SEQ ID NO: 273          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 273
SCIGCK                                                                       6

SEQ ID NO: 274          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 274
CIGC                                                                         4
```

```
SEQ ID NO: 275          moltype = AA  length = 6
FEATURE                 Location/Qualifiers
REGION                  1..6
                        note = Synthetic peptide
VARIANT                 2
                        note = X can be any amino acid
source                  1..6
                        mol_type = protein
                        organism = synthetic construct
SEQUENCE: 275
VXLPHW                                                                    6

SEQ ID NO: 276          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 276
LPHW                                                                      4

SEQ ID NO: 277          moltype = AA  length = 7
FEATURE                 Location/Qualifiers
REGION                  1..7
                        note = Synthetic peptide
VARIANT                 5
                        note = X can be G or A
VARIANT                 5
                        note = X can be G or A
source                  1..7
                        mol_type = protein
                        organism = synthetic construct
SEQUENCE: 277
PQDTXPR                                                                   7

SEQ ID NO: 278          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 278
GPPWWP                                                                    6

SEQ ID NO: 279          moltype = AA  length = 8
FEATURE                 Location/Qualifiers
REGION                  1..8
                        note = Synthetic peptide
VARIANT                 6
                        note = X can be any amino acid
source                  1..8
                        mol_type = protein
                        organism = synthetic construct
SEQUENCE: 279
QQPTTXGW                                                                  8

SEQ ID NO: 280          moltype = AA  length = 8
FEATURE                 Location/Qualifiers
REGION                  1..8
                        note = Synthetic peptide
VARIANT                 1
                        note = X can be L, M, I or V
VARIANT                 4
                        note = X can be any amino acid
source                  1..8
                        mol_type = protein
                        organism = synthetic construct
SEQUENCE: 280
XFDXDWYP                                                                  8

SEQ ID NO: 281          moltype = AA  length = 6
FEATURE                 Location/Qualifiers
REGION                  1..6
                        note = Synthetic peptide
source                  1..6
                        mol_type = protein
```

```
                        organism = synthetic construct
SEQUENCE: 281
GRRPFF                                                                          6

SEQ ID NO: 282          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 282
GGGAGAGGG                                                                       9

SEQ ID NO: 283          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 283
EGPSTGPR                                                                        8

SEQ ID NO: 284          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 284
KRPSCIGCK                                                                       9

SEQ ID NO: 285          moltype = AA  length = 11
FEATURE                 Location/Qualifiers
REGION                  1..11
                        note = Synthetic peptide
source                  1..11
                        mol_type = protein
                        organism = synthetic construct
SEQUENCE: 285
KEVKLPHWTP T                                                                   11

SEQ ID NO: 286          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 286
PQDTAPR                                                                         7

SEQ ID NO: 287          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 287
GPPWWP                                                                          6

SEQ ID NO: 288          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 288
QQPTTEGH                                                                        8

SEQ ID NO: 289          moltype = AA  length = 8
FEATURE                 Location/Qualifiers
REGION                  1..8
                        note = Synthetic peptide
source                  1..8
```

```
                            -continued
                        mol_type = protein
                        organism = synthetic construct
SEQUENCE: 289
LFPDDWYP                                                              8

SEQ ID NO: 290          moltype = AA  length = 7
FEATURE                 Location/Qualifiers
REGION                  1..7
                        note = Synthetic peptide
VARIANT                 2
                        note = X can be any amino acid
VARIANT                 4
                        note = X can be any amino acid
source                  1..7
                        mol_type = protein
                        organism = synthetic construct
SEQUENCE: 290
CXGXLIC                                                               7

SEQ ID NO: 291          moltype = AA  length = 8
FEATURE                 Location/Qualifiers
source                  1..8
                        mol_type = protein
                        organism = synthetic construct
VARIANT                 2..3
                        note = X can be any amino acid
VARIANT                 5
                        note = X can be any amino acid
VARIANT                 6
                        note = I can be replaced by V
VARIANT                 8
                        note = I can be replaced by V
SEQUENCE: 291
CXXKXICI                                                              8

SEQ ID NO: 292          moltype = AA  length = 9
FEATURE                 Location/Qualifiers
REGION                  1..9
                        note = Synthetic peptide
VARIANT                 2
                        note = X can be G, A or S
VARIANT                 4
                        note = X can be any amino acid
VARIANT                 6..8
                        note = X can be any amino acid
source                  1..9
                        mol_type = protein
                        organism = synthetic construct
SEQUENCE: 292
WXCXGXXXC                                                             9

SEQ ID NO: 293          moltype = AA  length = 5
FEATURE                 Location/Qualifiers
source                  1..5
                        mol_type = protein
                        organism = synthetic construct
VARIANT                 1
                        note = R can be replaced by K
VARIANT                 4
                        note = I can be replaced by V
SEQUENCE: 293
RKLIE                                                                 5

SEQ ID NO: 294          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 294
KLIMT                                                                 5

SEQ ID NO: 295          moltype = AA  length = 7
FEATURE                 Location/Qualifiers
REGION                  1..7
                        note = Synthetic peptide
VARIANT                 1
                        note = X can be Q or E
```

```
                        2..3
                        note = X can be any amino acid
source                  1..7
                        mol_type = protein
                        organism = synthetic construct
SEQUENCE: 295
XXXPFRY                                                                   7

SEQ ID NO: 296          moltype = AA  length = 8
FEATURE                 Location/Qualifiers
source                  1..8
                        mol_type = protein
                        organism = synthetic construct
VARIANT                 2..3
                        note = X can be any amino acid
VARIANT                 5
                        note = X can be any amino acid
VARIANT                 6
                        note = I can be replaced by V
VARIANT                 8
                        note = I can be replaced by V
SEQUENCE: 296
CXXKXICI                                                                  8

SEQ ID NO: 297          moltype = AA  length = 7
FEATURE                 Location/Qualifiers
source                  1..7
                        mol_type = protein
                        organism = synthetic construct
VARIANT                 1
                        note = L can be replaced by F
VARIANT                 2..3
                        note = X can be any amino acid
VARIANT                 4
                        note = L can be replaced by I or V
VARIANT                 5
                        note = N can be replaced by D
SEQUENCE: 297
LXXLNKW                                                                   7

SEQ ID NO: 298          moltype = AA  length = 5
FEATURE                 Location/Qualifiers
source                  1..5
                        mol_type = protein
                        organism = synthetic construct
VARIANT                 1
                        note = A can be replaced by P
VARIANT                 2
                        note = G can be replaced by C
SEQUENCE: 298
AGGFG                                                                     5

SEQ ID NO: 299          moltype = AA  length = 6
FEATURE                 Location/Qualifiers
REGION                  1..6
                        note = Synthetic peptide
VARIANT                 3
                        note = X can be any amino acid
VARIANT                 4
                        note = X can be T or S
source                  1..6
                        mol_type = protein
                        organism = synthetic construct
SEQUENCE: 299
LIXXTY                                                                    6

SEQ ID NO: 300          moltype = AA  length = 7
FEATURE                 Location/Qualifiers
source                  1..7
                        mol_type = protein
                        organism = synthetic construct
VARIANT                 1
                        note = R can be replaced by K
VARIANT                 4..5
                        note = X can be any amino acid
VARIANT                 6
                        note = M can be replaced by V
SEQUENCE: 300
RKLXXMY                                                                   7
```

```
SEQ ID NO: 301           moltype = AA   length = 5
FEATURE                  Location/Qualifiers
source                   1..5
                         mol_type = protein
                         organism = synthetic construct
VARIANT                  3
                         note = G can be replaced by A
VARIANT                  4
                         note = A can be replaced by Q
VARIANT                  5
                         note = A can be replaced by Y or V
SEQUENCE: 301
GFGAA                                                                      5

SEQ ID NO: 302           moltype = AA   length = 6
FEATURE                  Location/Qualifiers
source                   1..6
                         mol_type = protein
                         organism = synthetic construct
VARIANT                  4
                         note = R can be replaced by Q
VARIANT                  5
                         note = X can be any amino acid
VARIANT                  6
                         note = F can be replaced by N or Y
SEQUENCE: 302
GFGRXF                                                                     6

SEQ ID NO: 303           moltype = AA   length = 6
FEATURE                  Location/Qualifiers
source                   1..6
                         mol_type = protein
                         organism = synthetic construct
VARIANT                  1
                         note = K can be replaced by R
VARIANT                  3
                         note = X can be any amino acid
VARIANT                  6
                         note = V can be replaced by I or M
SEQUENCE: 303
KKXIHV                                                                     6

SEQ ID NO: 304           moltype = AA   length = 5
FEATURE                  Location/Qualifiers
REGION                   1..5
                         note = Synthetic peptide
VARIANT                  2
                         note = X can be I or V
source                   1..5
                         mol_type = protein
                         organism = synthetic construct
SEQUENCE: 304
RXPFG                                                                      5

SEQ ID NO: 305           moltype = AA   length = 7
FEATURE                  Location/Qualifiers
REGION                   1..7
                         note = Synthetic peptide
VARIANT                  4..5
                         note = X can be any amino acid
VARIANT                  6
                         note = X can be T or Y
source                   1..7
                         mol_type = protein
                         organism = synthetic construct
SEQUENCE: 305
KLIXXXT                                                                    7

SEQ ID NO: 306           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 306
CSGKLICT                                                                   8
```

```
SEQ ID NO: 307            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 307
CSGKLICT                                                                  8

SEQ ID NO: 308            moltype = AA   length = 9
FEATURE                   Location/Qualifiers
REGION                    1..9
                          note = Synthetic peptide
source                    1..9
                          mol_type = protein
                          organism = synthetic construct
SEQUENCE: 308
WGCSGKLIC                                                                 9

SEQ ID NO: 309            moltype = AA   length = 8
FEATURE                   Location/Qualifiers
REGION                    1..8
                          note = Synthetic peptide
source                    1..8
                          mol_type = protein
                          organism = synthetic construct
SEQUENCE: 309
CSGKLICT                                                                  8

SEQ ID NO: 310            moltype = AA   length = 7
FEATURE                   Location/Qualifiers
REGION                    1..7
                          note = Synthetic peptide
source                    1..7
                          mol_type = protein
                          organism = synthetic construct
SEQUENCE: 310
LLALDKW                                                                   7

SEQ ID NO: 311            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 311
AVGMG                                                                     5

SEQ ID NO: 312            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 312
LICTT                                                                     5

SEQ ID NO: 313            moltype = AA   length = 5
FEATURE                   Location/Qualifiers
REGION                    1..5
                          note = Synthetic peptide
source                    1..5
                          mol_type = protein
                          organism = synthetic construct
SEQUENCE: 313
GFGAV                                                                     5

SEQ ID NO: 314            moltype = AA   length = 6
FEATURE                   Location/Qualifiers
REGION                    1..6
                          note = Synthetic peptide
source                    1..6
                          mol_type = protein
                          organism = synthetic construct
SEQUENCE: 314
RKGIRI                                                                    6
```

```
SEQ ID NO: 315          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 315
KKGIAI                                                                    6

SEQ ID NO: 316          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 316
RKGIHM                                                                    6

SEQ ID NO: 317          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 317
RKSIHM                                                                    6

SEQ ID NO: 318          moltype = AA   length = 6
FEATURE                 Location/Qualifiers
REGION                  1..6
                        note = Synthetic peptide
source                  1..6
                        mol_type = protein
                        organism = synthetic construct
SEQUENCE: 318
KLICTT                                                                    6

SEQ ID NO: 319          moltype = AA   length = 8
FEATURE                 Location/Qualifiers
REGION                  1..8
                        note = Synthetic peptide
VARIANT                 3..4
                        note = X can be any amino acid
VARIANT                 6
                        note = X can be any amino acid
source                  1..8
                        mol_type = protein
                        organism = synthetic construct
SEQUENCE: 319
VRXXYXQH                                                                  8

SEQ ID NO: 320          moltype = AA   length = 9
FEATURE                 Location/Qualifiers
REGION                  1..9
                        note = Synthetic peptide
VARIANT                 4..6
                        note = X can be any amino acid
VARIANT                 8
                        note = X can be any amino acid
source                  1..9
                        mol_type = protein
                        organism = synthetic construct
SEQUENCE: 320
CEDXXXHXC                                                                 9

SEQ ID NO: 321          moltype = AA   length = 7
FEATURE                 Location/Qualifiers
REGION                  1..7
                        note = Synthetic peptide
VARIANT                 5..6
                        note = X can be any amino acid
source                  1..7
                        mol_type = protein
                        organism = synthetic construct
SEQUENCE: 321
```

```
DAEQXXR                                                                 7

SEQ ID NO: 322         moltype = AA  length = 5
FEATURE                Location/Qualifiers
REGION                 1..5
                       note = Synthetic peptide
source                 1..5
                       mol_type = protein
                       organism = synthetic construct
SEQUENCE: 322
WPGIF                                                                   5

SEQ ID NO: 323         moltype = AA  length = 6
FEATURE                Location/Qualifiers
REGION                 1..6
                       note = Synthetic peptide
VARIANT                5
                       note = X can be any amino acid
source                 1..6
                       mol_type = protein
                       organism = synthetic construct
SEQUENCE: 323
CCYDXE                                                                  6

SEQ ID NO: 324         moltype = AA  length = 7
FEATURE                Location/Qualifiers
REGION                 1..7
                       note = Synthetic peptide
VARIANT                2
                       note = X can be any amino acid
VARIANT                6
                       note = X can be any amino acid
source                 1..7
                       mol_type = protein
                       organism = synthetic construct
SEQUENCE: 324
LXPDNXT                                                                 7

SEQ ID NO: 325         moltype = AA  length = 7
FEATURE                Location/Qualifiers
REGION                 1..7
                       note = Synthetic peptide
VARIANT                2
                       note = X can be any amino acid
VARIANT                6
                       note = X can be any amino acid
source                 1..7
                       mol_type = protein
                       organism = synthetic construct
SEQUENCE: 325
FXWGQXY                                                                 7

SEQ ID NO: 326         moltype = AA  length = 10
FEATURE                Location/Qualifiers
REGION                 1..10
                       note = Synthetic peptide
VARIANT                2
                       note = X can be any amino acid
VARIANT                6..9
                       note = X can be any amino acid
source                 1..10
                       mol_type = protein
                       organism = synthetic construct
SEQUENCE: 326
KXEGHXXXXA                                                             10

SEQ ID NO: 327         moltype = AA  length = 9
FEATURE                Location/Qualifiers
REGION                 1..9
                       note = Synthetic peptide
VARIANT                2..3
                       note = X can be any amino acid
VARIANT                5
                       note = X can be any amino acid
VARIANT                8
                       note = X can be any amino acid
source                 1..9
                       mol_type = protein
                       organism = synthetic construct
```

```
SEQUENCE: 327
CXXGXCQXK                                                                       9

SEQ ID NO: 328          moltype = AA  length = 8
FEATURE                 Location/Qualifiers
source                  1..8
                        mol_type = protein
                        organism = synthetic construct
VARIANT                 3
                        note = X can be any amino acid
VARIANT                 5..6
                        note = X can be any amino acid
VARIANT                 7
                        note = D can be replaced by E
VARIANT                 8
                        note = E can be replaced by D
SEQUENCE: 328
CCXDXXDE                                                                        8

SEQ ID NO: 329          moltype = AA  length = 6
FEATURE                 Location/Qualifiers
REGION                  1..6
                        note = Synthetic peptide
VARIANT                 4
                        note = X can be any amino acid
source                  1..6
                        mol_type = protein
                        organism = synthetic construct
SEQUENCE: 329
RNGXED                                                                          6

SEQ ID NO: 330          moltype = AA  length = 8
FEATURE                 Location/Qualifiers
REGION                  1..8
                        note = Synthetic peptide
VARIANT                 1
                        note = X can be D or E
VARIANT                 2
                        note = X can be any amino acid
VARIANT                 4
                        note = X can be any amino acid
VARIANT                 7
                        note = X can be any amino acid
source                  1..8
                        mol_type = protein
                        organism = synthetic construct
SEQUENCE: 330
XXRXIYXQ                                                                        8

SEQ ID NO: 331          moltype = AA  length = 6
FEATURE                 Location/Qualifiers
REGION                  1..6
                        note = Synthetic peptide
VARIANT                 2
                        note = X can be any amino acid
source                  1..6
                        mol_type = protein
                        organism = synthetic construct
SEQUENCE: 331
WXRCGL                                                                          6

SEQ ID NO: 332          moltype = AA  length = 10
FEATURE                 Location/Qualifiers
REGION                  1..10
                        note = Synthetic peptide
VARIANT                 2
                        note = X can be E or D
VARIANT                 3
                        note = X can be any amino acid
VARIANT                 5..6
                        note = X can be any amino acid
VARIANT                 8..9
                        note = X can be any amino acid
source                  1..10
                        mol_type = protein
                        organism = synthetic construct
SEQUENCE: 332
DXXRXXYXXH                                                                     10
```

```
SEQ ID NO: 333            moltype = AA   length = 7
FEATURE                   Location/Qualifiers
REGION                    1..7
                          note = Synthetic peptide
VARIANT                   3
                          note = X can be any amino acid
VARIANT                   5
                          note = X can be any amino acid
VARIANT                   6
                          note = X can be A or V
source                    1..7
                          mol_type = protein
                          organism = synthetic construct
SEQUENCE: 333
WCXLXXN                                                                   7

SEQ ID NO: 334            moltype = AA   length = 6
FEATURE                   Location/Qualifiers
REGION                    1..6
                          note = Synthetic peptide
VARIANT                   2
                          note = X can be any amino acid
source                    1..6
                          mol_type = protein
                          organism = synthetic construct
SEQUENCE: 334
LXTPWI                                                                    6

SEQ ID NO: 335            moltype = AA   length = 8
FEATURE                   Location/Qualifiers
REGION                    1..8
                          note = Synthetic peptide
VARIANT                   3..5
                          note = X can be any amino acid
VARIANT                   8
                          note = X can be C or A
source                    1..8
                          mol_type = protein
                          organism = synthetic construct
SEQUENCE: 335
CWXXXGLX                                                                  8

SEQ ID NO: 336            moltype = AA   length = 5
FEATURE                   Location/Qualifiers
REGION                    1..5
                          note = Synthetic peptide
VARIANT                   3
                          note = X can be A or V
source                    1..5
                          mol_type = protein
                          organism = synthetic construct
SEQUENCE: 336
IDXEP                                                                     5

SEQ ID NO: 337            moltype = AA   length = 6
FEATURE                   Location/Qualifiers
source                    1..6
                          mol_type = protein
                          organism = synthetic construct
VARIANT                   3
                          note = N can be replaced by K
VARIANT                   4
                          note = V can be replaced by T
VARIANT                   5
                          note = X can be any amino acid
SEQUENCE: 337
HFNVXK                                                                    6

SEQ ID NO: 338            moltype = AA   length = 7
FEATURE                   Location/Qualifiers
REGION                    1..7
                          note = Synthetic peptide
VARIANT                   2
                          note = X can be any amino acid
VARIANT                   6
                          note = X can be any amino acid
source                    1..7
                          mol_type = protein
                          organism = synthetic construct
```

```
SEQUENCE: 338
QXNHQXK                                                                    7

SEQ ID NO: 339         moltype = AA  length = 6
FEATURE                Location/Qualifiers
REGION                 1..6
                       note = Synthetic peptide
VARIANT                3
                       note = X can be any amino acid
source                 1..6
                       mol_type = protein
                       organism = synthetic construct
SEQUENCE: 339
FEXKEP                                                                     6

SEQ ID NO: 340         moltype = AA  length = 4
FEATURE                Location/Qualifiers
source                 1..4
                       mol_type = protein
                       organism = synthetic construct
VARIANT                1
                       note = F can be replaced by Y or W
VARIANT                4
                       note = V can be replaced by I
SEQUENCE: 340
FDAV                                                                       4

SEQ ID NO: 341         moltype = AA  length = 5
FEATURE                Location/Qualifiers
REGION                 1..5
                       note = Synthetic peptide
source                 1..5
                       mol_type = protein
                       organism = synthetic construct
SEQUENCE: 341
DFDKR                                                                      5

SEQ ID NO: 342         moltype = AA  length = 4
FEATURE                Location/Qualifiers
REGION                 1..4
                       note = Synthetic peptide
source                 1..4
                       mol_type = protein
                       organism = synthetic construct
SEQUENCE: 342
WETC                                                                       4

SEQ ID NO: 343         moltype = AA  length = 5
FEATURE                Location/Qualifiers
REGION                 1..5
                       note = Synthetic peptide
source                 1..5
                       mol_type = protein
                       organism = synthetic construct
SEQUENCE: 343
KLDGP                                                                      5

SEQ ID NO: 344         moltype = AA  length = 6
FEATURE                Location/Qualifiers
REGION                 1..6
                       note = Synthetic peptide
VARIANT                5
                       note = X can be any amino acid
source                 1..6
                       mol_type = protein
                       organism = synthetic construct
SEQUENCE: 344
WIYPXK                                                                     6

SEQ ID NO: 345         moltype = AA  length = 5
FEATURE                Location/Qualifiers
REGION                 1..5
                       note = Synthetic peptide
VARIANT                2
                       note = X can be H or S
source                 1..5
                       mol_type = protein
                       organism = synthetic construct
SEQUENCE: 345
```

```
VXDSK                                                                          5

SEQ ID NO: 347         moltype = AA  length = 5
FEATURE                Location/Qualifiers
source                 1..5
                       mol_type = protein
                       organism = synthetic construct
SEQ ID NO: 346         moltype = AA  length = 5
FEATURE                Location/Qualifiers
REGION                 1..5
                       note = Synthetic peptide
source                 1..5
                       mol_type = protein
                       organism = synthetic construct
SEQUENCE: 346
EQCGT                                                                          5

SEQ ID NO: 347         moltype = AA  length = 5
FEATURE                Location/Qualifiers
source                 1..5
                       mol_type = protein
                       organism = synthetic construct
VARIANT                1
                       note = K can be replaced by E
VARIANT                2
                       note = M can be replaced by V, I or T
SEQUENCE: 347
KMPYA                                                                          5

SEQ ID NO: 348         moltype = AA  length = 7
FEATURE                Location/Qualifiers
source                 1..7
                       mol_type = protein
                       organism = synthetic construct
VARIANT                1
                       note = D can be replaced by E
VARIANT                2..3
                       note = X can be any amino acid
VARIANT                6
                       note = R can be replaced by P
SEQUENCE: 348
DXXML

```
SEQ ID NO: 352          moltype = AA   length = 6
FEATURE                 Location/Qualifiers
REGION                  1..6
                        note = Synthetic peptide
VARIANT                 2
                        note = X can be any amino acid
VARIANT                 5
                        note = X can be V or I
source                  1..6
                        mol_type = protein
                        organism = synthetic construct
SEQUENCE: 352
DXTGXP                                                                    6

SEQ ID NO: 353          moltype = AA   length = 7
FEATURE                 Location/Qualifiers
REGION                  1..7
                        note = Synthetic peptide
VARIANT                 3..4
                        note = X can be any amino acid
VARIANT                 6
                        note = X can be A or V
source                  1..7
                        mol_type = protein
                        organism = synthetic construct
SEQUENCE: 353
FDXXGEH                                                                   7

SEQ ID NO: 354          moltype = AA   length = 7
FEATURE                 Location/Qualifiers
source                  1..7
                        mol_type = protein
                        organism = synthetic construct
VARIANT                 3
                        note = A can be replaced by K
VARIANT                 4..5
                        note = X can be any amino acid
VARIANT                 6
                        note = H can be replaced by E
SEQUENCE: 354
QCAXXHC                                                                   7

SEQ ID NO: 355          moltype = AA   length = 7
FEATURE                 Location/Qualifiers
REGION                  1..7
                        note = Synthetic peptide
VARIANT                 3
                        note = X can be F or Y
VARIANT                 4
                        note = X can be any amino acid
VARIANT                 6
                        note = X can be any amino acid
source                  1..7
                        mol_type = protein
                        organism = synthetic construct
SEQUENCE: 355
LWXXPXE                                                                   7

SEQ ID NO: 356          moltype = AA   length = 7
FEATURE                 Location/Qualifiers
source                  1..7
                        mol_type = protein
                        organism = synthetic construct
VARIANT                 2
                        note = M can be replaced by I
VARIANT                 3
                        note = P can be replaced by A
VARIANT                 5..6
                        note = X can be any amino acid
SEQUENCE: 356
CMPGXXC                                                                   7

SEQ ID NO: 357          moltype = AA   length = 9
FEATURE                 Location/Qualifiers
REGION                  1..9
                        note = Synthetic peptide
VARIANT                 2..5
                        note = X can be any amino acid
```

```
VARIANT                 6
                        note = X can be A, V or S
source                  1..9
                        mol_type = protein
                        organism = synthetic construct
SEQUENCE: 357
CXXXXXADC                                                                    9

SEQ ID NO: 358          moltype = AA   length = 10
FEATURE                 Location/Qualifiers
REGION                  1..10
                        note = Synthetic peptide
VARIANT                 5..9
                        note = X can be any amino acid
source                  1..10
                        mol_type = protein
                        organism = synthetic construct
SEQUENCE: 358
VQQEXXXXXP                                                                   10

SEQ ID NO: 359          moltype = AA   length = 9
FEATURE                 Location/Qualifiers
REGION                  1..9
                        note = Synthetic peptide
VARIANT                 5..8
                        note = X can be any amino acid
VARIANT                 9
                        note = X can be Y or C
source                  1..9
                        mol_type = protein
                        organism = synthetic construct
SEQUENCE: 359
QQEGXXXXX                                                                    9

SEQ ID NO: 360          moltype = AA   length = 5
FEATURE                 Location/Qualifiers
REGION                  1..5
                        note = Synthetic peptide
VARIANT                 4
                        note = X can be I or V
source                  1..5
                        mol_type = protein
                        organism = synthetic construct
SEQUENCE: 360
QEGXQ                                                                        5

SEQ ID NO: 361          moltype = AA   length = 6
FEATURE                 Location/Qualifiers
REGION                  1..6
                        note = Synthetic peptide
VARIANT                 2
                        note = X can be I or V
VARIANT                 4
                        note = X can be any amino acid
source                  1..6
                        mol_type = protein
                        organism = synthetic construct
SEQUENCE: 361
GXQXEG                                                                       6

SEQ ID NO: 362          moltype = AA   length = 9
FEATURE                 Location/Qualifiers
source                  1..9
                        mol_type = protein
                        organism = synthetic construct
VARIANT                 2..3
                        note = X can be any amino acid
VARIANT                 5
                        note = I can be replaced by L or V
VARIANT                 6..7
                        note = X can be any amino acid
SEQUENCE: 362
JXXAIXXRG                                                                    9

SEQ ID NO: 363          moltype = AA   length = 10
FEATURE                 Location/Qualifiers
source                  1..10
                        mol_type = protein
                        organism = synthetic construct
```

```
VARIANT                 1
                        note = A can be replaced by T, N, S or D
VARIANT                 2..5
                        note = X can be any amino acid
VARIANT                 8
                        note = L can be replaced by A or M
VARIANT                 9
                        note = X can be any amino acid
SEQUENCE: 363
AXXXXAILXR                                                                      10

SEQ ID NO: 364          moltype = AA  length = 8
FEATURE                 Location/Qualifiers
REGION                  1..8
                        note = Synthetic peptide
VARIANT                 2
                        note = X can be any amino acid
VARIANT                 3
                        note = X can be L or M
VARIANT                 4
                        note = X can be any amino acid
VARIANT                 7
                        note = X can be any amino acid
source                  1..8
                        mol_type = protein
                        organism = synthetic construct
SEQUENCE: 364
IXXXGFXK                                                                        8

SEQ ID NO: 365          moltype = AA  length = 6
FEATURE                 Location/Qualifiers
REGION                  1..6
                        note = Synthetic peptide
VARIANT                 2
                        note = X can be any amino acid
VARIANT                 5
                        note = X can be R or Q
source                  1..6
                        mol_type = protein
                        organism = synthetic construct
SEQUENCE: 365
LXGMXK                                                                          6

SEQ ID NO: 366          moltype = AA  length = 8
FEATURE                 Location/Qualifiers
REGION                  1..8
                        note = Synthetic peptide
VARIANT                 1
                        note = X can be H or R
VARIANT                 2
                        note = X can be any amino acid
VARIANT                 4
                        note = X can be any amino acid
VARIANT                 7
                        note = X can be any amino acid
source                  1..8
                        mol_type = protein
                        organism = synthetic construct
SEQUENCE: 366
XXDXTNXF                                                                        8

SEQ ID NO: 367          moltype = AA  length = 5
FEATURE                 Location/Qualifiers
REGION                  1..5
                        note = Synthetic peptide
VARIANT                 1
                        note = X can be D or A
source                  1..5
                        mol_type = protein
                        organism = synthetic construct
SEQUENCE: 367
XDPTN                                                                           5

SEQ ID NO: 368          moltype = AA  length = 8
FEATURE                 Location/Qualifiers
source                  1..8
                        mol_type = protein
                        organism = synthetic construct
VARIANT                 1
```

```
                        note = K can be replaced by R
VARIANT                 2
                        note = X can be any amino acid
VARIANT                 3
                        note = D can be replaced by E
VARIANT                 4
                        note = X can be any amino acid
VARIANT                 7
                        note = X can be any amino acid
SEQUENCE: 368
KXDXTNXF                                                                  8

SEQ ID NO: 369          moltype = AA   length = 5
FEATURE                 Location/Qualifiers
source                  1..5
                        mol_type = protein
                        organism = synthetic construct
VARIANT                 1
                        note = E can be replaced by T
VARIANT                 2
                        note = M can be replaced by L
SEQUENCE: 369
EMHKF                                                                     5

SEQ ID NO: 370          moltype = AA   length = 7
FEATURE                 Location/Qualifiers
REGION                  1..7
                        note = Synthetic peptide
VARIANT                 1
                        note = X can be M or L
VARIANT                 2..3
                        note = X can be any amino acid
source                  1..7
                        mol_type = protein
                        organism = synthetic construct
SEQUENCE: 370
XXXEPHK                                                                   7

SEQ ID NO: 371          moltype = AA   length = 10
FEATURE                 Location/Qualifiers
REGION                  1..10
                        note = Synthetic peptide
VARIANT                 2
                        note = X can be T or I
VARIANT                 5..9
                        note = X can be any amino acid
source                  1..10
                        mol_type = protein
                        organism = synthetic construct
SEQUENCE: 371
QXEQXXXXXK                                                               10

SEQ ID NO: 372          moltype = AA   length = 6
FEATURE                 Location/Qualifiers
REGION                  1..6
                        note = Synthetic peptide
VARIANT                 2
                        note = X can be any amino acid
source                  1..6
                        mol_type = protein
                        organism = synthetic construct
SEQUENCE: 372
DXSPJE                                                                    6

SEQ ID NO: 373          moltype = AA   length = 7
FEATURE                 Location/Qualifiers
REGION                  1..7
                        note = Synthetic peptide
VARIANT                 3
                        note = X can be any amino acid
VARIANT                 4
                        note = X can be A or P
VARIANT                 6
                        note = X can be any amino acid
source                  1..7
                        mol_type = protein
                        organism = synthetic construct
SEQUENCE: 373
PFXXYXK                                                                   7
```

```
SEQ ID NO: 374            moltype = AA  length = 10
FEATURE                   Location/Qualifiers
REGION                    1..10
                          note = Synthetic peptide
VARIANT                   2..3
                          note = X can be any amino acid
VARIANT                   6..7
                          note = X can be any amino acid
VARIANT                   8
                          note = X can be L or V
VARIANT                   9
                          note = X can be any amino acid
source                    1..10
                          mol_type = protein
                          organism = synthetic construct
SEQUENCE: 374
VXXYFXXXXK                                                                    10

SEQ ID NO: 375            moltype = AA  length = 7
FEATURE                   Location/Qualifiers
REGION                    1..7
                          note = Synthetic peptide
VARIANT                   2
                          note = X can be any amino acid
VARIANT                   5
                          note = X can be any amino acid
source                    1..7
                          mol_type = protein
                          organism = synthetic construct
SEQUENCE: 375
KXVDXDR                                                                        7

SEQ ID NO: 376            moltype = AA  length = 5
FEATURE                   Location/Qualifiers
source                    1..5
                          mol_type = protein
                          organism = synthetic construct
VARIANT                   2
                          note = A can be replaced by S
VARIANT                   4
                          note = A can be replaced by G
SEQUENCE: 376
BAAAF                                                                          5

SEQ ID NO: 377            moltype = AA  length = 7
FEATURE                   Location/Qualifiers
REGION                    1..7
                          note = Synthetic peptide
VARIANT                   2
                          note = X can be any amino acid
VARIANT                   3
                          note = X can be N or A
VARIANT                   4
                          note = X can be any amino acid
source                    1..7
                          mol_type = protein
                          organism = synthetic construct
SEQUENCE: 377
CXXXKFC                                                                        7

SEQ ID NO: 378            moltype = AA  length = 6
FEATURE                   Location/Qualifiers
source                    1..6
                          mol_type = protein
                          organism = synthetic construct
VARIANT                   2
                          note = X can be any amino acid
VARIANT                   3
                          note = G can be replaced by R, S or T
VARIANT                   6
                          note = Y can be replaced by F
SEQUENCE: 378
KXGAEY                                                                         6

SEQ ID NO: 379            moltype = AA  length = 8
FEATURE                   Location/Qualifiers
source                    1..8
                          mol_type = protein
```

```
                        organism = synthetic construct
VARIANT                 4
                        note = P can be replaced by A
VARIANT                 5..7
                        note = X can be any amino acid
VARIANT                 8
                        note = D can be replaced by H or E
SEQUENCE: 379
HQVPXXXD                                                                         8

SEQ ID NO: 380          moltype = AA   length = 9
FEATURE                 Location/Qualifiers
REGION                  1..9
                        note = Synthetic peptide
VARIANT                 3..4
                        note = X can be any amino acid
VARIANT                 6
                        note = X can be I or F
VARIANT                 6
VARIANT                 7..8
                        note = X can be any amino acid
source                  1..9
                        mol_type = protein
                        organism = synthetic construct
SEQUENCE: 380
IPXXVXXXR                                                                        9

SEQ ID NO: 381          moltype = AA   length = 8
FEATURE                 Location/Qualifiers
source                  1..8
                        mol_type = protein
                        organism = synthetic construct
VARIANT                 2
                        note = X can be any amino acid
VARIANT                 3
                        note = A can be replaced by L or T
VARIANT                 4
                        note = X can be any amino acid
VARIANT                 7
                        note = X can be any amino acid
VARIANT                 8
                        note = C can be replaced by A
SEQUENCE: 381
CXAXWEXC                                                                         8

SEQ ID NO: 382          moltype = AA   length = 10
FEATURE                 Location/Qualifiers
REGION                  1..10
                        note = Synthetic peptide
VARIANT                 2..4
                        note = X can be any amino acid
VARIANT                 8..9
                        note = X can be any amino acid
source                  1..10
                        mol_type = protein
                        organism = synthetic construct
SEQUENCE: 382
CXXXCAJXXR                                                                      10

SEQ ID NO: 383          moltype = AA   length = 8
FEATURE                 Location/Qualifiers
source                  1..8
                        mol_type = protein
                        organism = synthetic construct
VARIANT                 2
                        note = I can be replaced by V
VARIANT                 4..5
                        note = X can be any amino acid
VARIANT                 6
                        note = M can be replaced by T
VARIANT                 7
                        note = X can be any amino acid
SEQUENCE: 383
IIIXXMXK                                                                         8

SEQ ID NO: 384          moltype = AA   length = 6
FEATURE                 Location/Qualifiers
source                  1..6
                        mol_type = protein
```

```
                        organism = synthetic construct
VARIANT                 3
                        note = I can be replaced by T or L
VARIANT                 4
                        note = X can be any amino acid
VARIANT                 5
                        note = K can be replaced by N
VARIANT                 6
                        note = F can be replaced by Y
SEQUENCE: 384
QGIXKF                                                                        6

SEQ ID NO: 385          moltype = AA   length = 8
FEATURE                 Location/Qualifiers
REGION                  1..8
                        note = Synthetic peptide
VARIANT                 2..3
                        note = X can be any amino acid
VARIANT                 6
                        note = X can be any amino acid
source                  1..8
                        mol_type = protein
                        organism = synthetic construct
SEQUENCE: 385
KXXPPXIN                                                                      8

SEQ ID NO: 386          moltype = AA   length = 7
FEATURE                 Location/Qualifiers
source                  1..7
                        mol_type = protein
                        organism = synthetic construct
VARIANT                 2
                        note = Y can be replaced by F
VARIANT                 3
                        note = F can be replaced by Y
VARIANT                 5..6
                        note = X can be any amino acid
SEQUENCE: 386
GYFFXXK                                                                       7

SEQ ID NO: 387          moltype = AA   length = 6
FEATURE                 Location/Qualifiers
REGION                  1..6
                        note = Synthetic peptide
VARIANT                 5
                        note = X can be any amino acid
VARIANT                 6
                        note = X can be I or V
source                  1..6
                        mol_type = protein
                        organism = synthetic construct
SEQUENCE: 387
DKNVXX                                                                        6

SEQ ID NO: 388          moltype = AA   length = 6
FEATURE                 Location/Qualifiers
source                  1..6
                        mol_type = protein
                        organism = synthetic construct
VARIANT                 1
                        note = Q can be replaced by E
VARIANT                 2
                        note = K can be replaced by R
VARIANT                 4
                        note = X can be any amino acid
SEQUENCE: 388
QKBXSG                                                                        6

SEQ ID NO: 389          moltype = AA   length = 5
FEATURE                 Location/Qualifiers
REGION                  1..5
                        note = Synthetic peptide
VARIANT                 2
                        note = X can be R or K
source                  1..5
                        mol_type = protein
                        organism = synthetic construct
SEQUENCE: 389
KXPGD                                                                         5
```

```
SEQ ID NO: 390         moltype = AA   length = 6
FEATURE                Location/Qualifiers
REGION                 1..6
                       note = Synthetic peptide
VARIANT                4
                       note = X can be any amino acid
source                 1..6
                       mol_type = protein
                       organism = synthetic construct
SEQUENCE: 390
EGAXQP                                                                  6

SEQ ID NO: 391         moltype = AA   length = 5
FEATURE                Location/Qualifiers
REGION                 1..5
                       note = Synthetic peptide
source                 1..5
                       mol_type = protein
                       organism = synthetic construct
SEQUENCE: 391
GSPEY                                                                   5

SEQ ID NO: 392         moltype = AA   length = 10
FEATURE                Location/Qualifiers
REGION                 1..10
                       note = Synthetic peptide
source                 1..10
                       mol_type = protein
                       organism = synthetic construct
SEQUENCE: 392
VQQEGAQQQP                                                             10

SEQ ID NO: 393         moltype = AA   length = 5
FEATURE                Location/Qualifiers
REGION                 1..5
                       note = Synthetic peptide
source                 1..5
                       mol_type = protein
                       organism = synthetic construct
SEQUENCE: 393
QEGVQ                                                                   5

SEQ ID NO: 394         moltype = AA   length = 6
FEATURE                Location/Qualifiers
REGION                 1..6
                       note = Synthetic peptide
source                 1..6
                       mol_type = protein
                       organism = synthetic construct
SEQUENCE: 394
GVQQEG                                                                  6

SEQ ID NO: 395         moltype = AA   length = 9
FEATURE                Location/Qualifiers
REGION                 1..9
                       note = Synthetic peptide
source                 1..9
                       mol_type = protein
                       organism = synthetic construct
SEQUENCE: 395
ILKAVVERG                                                               9

SEQ ID NO: 396         moltype = AA   length = 9
FEATURE                Location/Qualifiers
REGION                 1..9
                       note = Synthetic peptide
source                 1..9
                       mol_type = protein
                       organism = synthetic construct
SEQUENCE: 396
IAAAIVLRG                                                               9

SEQ ID NO: 397         moltype = AA   length = 10
FEATURE                Location/Qualifiers
REGION                 1..10
                       note = Synthetic peptide
source                 1..10
                       mol_type = protein
```

```
                        organism = synthetic construct
SEQUENCE: 397
DQIAAAIALR                                                              10

SEQ ID NO: 398          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 398
AKKMRAILVR                                                              10

SEQ ID NO: 399          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 399
AENHKAILFR                                                              10

SEQ ID NO: 400          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 400
IKLPGFKK                                                                 8

SEQ ID NO: 401          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 401
IFLEGFLK                                                                 8

SEQ ID NO: 402          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 402
LRGMRK                                                                   6

SEQ ID NO: 403          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 403
DDPTN                                                                    5

SEQ ID NO: 404          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 404
KTDRTNDF                                                                 8

SEQ ID NO: 405          moltype = AA  length = 8
FEATURE                 Location/Qualifiers
REGION                  1..8
                        note = Synthetic peptide
source                  1..8
```

```
                    mol_type = protein
                    organism = synthetic construct
SEQUENCE: 405
KDDPTNKF                                                              8

SEQ ID NO: 406      moltype = AA   length = 8
FEATURE             Location/Qualifiers
REGION              1..8
                    note = Synthetic peptide
source              1..8
                    mol_type = protein
                    organism = synthetic construct
SEQUENCE: 406
KTDRTNDF                                                              8

SEQ ID NO: 407      moltype = AA   length = 5
FEATURE             Location/Qualifiers
REGION              1..5
                    note = Synthetic peptide
source              1..5
                    mol_type = protein
                    organism = synthetic construct
SEQUENCE: 407
TLHKF                                                                 5

SEQ ID NO: 408      moltype = AA   length = 10
FEATURE             Location/Qualifiers
REGION              1..10
                    note = Synthetic peptide
source              1..10
                    mol_type = protein
                    organism = synthetic construct
SEQUENCE: 408
QTEQSSTSTK                                                           10

SEQ ID NO: 409      moltype = AA   length = 6
FEATURE             Location/Qualifiers
REGION              1..6
                    note = Synthetic peptide
source              1..6
                    mol_type = protein
                    organism = synthetic construct
SEQUENCE: 409
DLSPIE                                                                6

SEQ ID NO: 410      moltype = AA   length = 7
FEATURE             Location/Qualifiers
REGION              1..7
                    note = Synthetic peptide
source              1..7
                    mol_type = protein
                    organism = synthetic construct
SEQUENCE: 410
PFSAYIK                                                               7

SEQ ID NO: 411      moltype = AA   length = 10
FEATURE             Location/Qualifiers
REGION              1..10
                    note = Synthetic peptide
source              1..10
                    mol_type = protein
                    organism = synthetic construct
SEQUENCE: 411
VKDYFDSLAK                                                           10

SEQ ID NO: 412      moltype = AA   length = 5
FEATURE             Location/Qualifiers
REGION              1..5
                    note = Synthetic peptide
source              1..5
                    mol_type = protein
                    organism = synthetic construct
SEQUENCE: 412
DAAAF                                                                 5

SEQ ID NO: 413      moltype = AA   length = 6
FEATURE             Location/Qualifiers
REGION              1..6
                    note = Synthetic peptide
```

```
source                  1..6
                        mol_type = protein
                        organism = synthetic construct
SEQUENCE: 413
KFRAEF                                                                     6

SEQ ID NO: 414          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 414
KSSAEF                                                                     6

SEQ ID NO: 415          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 415
KGGAEF                                                                     6

SEQ ID NO: 416          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 416
IIIIDTSK                                                                   8

SEQ ID NO: 417          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 417
IIINGMTK                                                                   8

SEQ ID NO: 418          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 418
IIITNMEK                                                                   8

SEQ ID NO: 419          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 419
QGIINY                                                                     6

SEQ ID NO: 420          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 420
QGICNY                                                                     6

SEQ ID NO: 421          moltype = AA  length = 8
FEATURE                 Location/Qualifiers
REGION                  1..8
```

```
                        note = Synthetic peptide
source                  1..8
                        mol_type = protein
                        organism = synthetic construct
SEQUENCE: 421
KETPPALN                                                                8

SEQ ID NO: 422          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 422
GFYFIFK                                                                 7

SEQ ID NO: 423          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 423
DKNVKI                                                                  6

SEQ ID NO: 424          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 424
EKNSSG                                                                  6

SEQ ID NO: 425          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 425
KKPGD                                                                   5

SEQ ID NO: 426          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 426
EGAQQP                                                                  6

SEQ ID NO: 427          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 427
GSPEY                                                                   5

SEQ ID NO: 428          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 428
HEHEFQ                                                                  6

SEQ ID NO: 429          moltype = AA  length = 6
FEATURE                 Location/Qualifiers
```

```
REGION                    1..6
                          note = Synthetic peptide
source                    1..6
                          mol_type = protein
                          organism = synthetic construct
SEQUENCE: 429
LDFWRE                                                                    6

SEQ ID NO: 430            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 430
LDFWQE                                                                    6

SEQ ID NO: 431            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 431
LDMWEE                                                                    6

SEQ ID NO: 432            moltype = AA  length = 5
FEATURE                   Location/Qualifiers
REGION                    1..5
                          note = Synthetic peptide
source                    1..5
                          mol_type = protein
                          organism = synthetic construct
SEQUENCE: 432
HCSAC                                                                     5

SEQ ID NO: 433            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 433
FSGVVN                                                                    6

SEQ ID NO: 434            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 434
YPGVVN                                                                    6

SEQ ID NO: 435            moltype = AA  length = 9
FEATURE                   Location/Qualifiers
REGION                    1..9
                          note = Synthetic peptide
source                    1..9
                          mol_type = protein
                          organism = synthetic construct
SEQUENCE: 435
KGSHGRGFI                                                                 9

SEQ ID NO: 436            moltype = AA  length = 5
FEATURE                   Location/Qualifiers
REGION                    1..5
                          note = Synthetic peptide
source                    1..5
                          mol_type = protein
                          organism = synthetic construct
SEQUENCE: 436
GPHAE                                                                     5

SEQ ID NO: 437            moltype = AA  length = 5
```

```
FEATURE                 Location/Qualifiers
REGION                  1..5
                        note = Synthetic peptide
source                  1..5
                        mol_type = protein
                        organism = synthetic construct
SEQUENCE: 437
PRREP                                                                    5

SEQ ID NO: 438          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 438
PVPDFS                                                                   6

SEQ ID NO: 439          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 439
PVPDFT                                                                   6

SEQ ID NO: 440          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 440
PLPDFT                                                                   6

SEQ ID NO: 441          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 441
PLPDFS                                                                   6

SEQ ID NO: 442          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 442
PAPDFS                                                                   6

SEQ ID NO: 443          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 443
NAGLEVYAED                                                              10

SEQ ID NO: 444          moltype = AA  length = 10
FEATURE                 Location/Qualifiers
REGION                  1..10
                        note = Synthetic peptide
source                  1..10
                        mol_type = protein
                        organism = synthetic construct
SEQUENCE: 444
NRRRERYGED                                                              10
```

| | | |
|---|---|---|
| SEQ ID NO: 445<br>FEATURE<br>REGION<br><br>source<br><br><br><br>SEQUENCE: 445<br>PGAVLLD | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 446<br>FEATURE<br>REGION<br><br>source<br><br><br><br>SEQUENCE: 446<br>PAASKLD | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 447<br>FEATURE<br>REGION<br><br>source<br><br><br><br>SEQUENCE: 447<br>PAAESLD | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 448<br>FEATURE<br>REGION<br><br>source<br><br><br><br>SEQUENCE: 448<br>PGAARLD | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 449<br>FEATURE<br>REGION<br><br>source<br><br><br><br>SEQUENCE: 449<br>PGALDLD | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 450<br>FEATURE<br>REGION<br><br>source<br><br><br><br>SEQUENCE: 450<br>MPSWSNE | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 451<br>FEATURE<br>REGION<br><br>source<br><br><br><br>SEQUENCE: 451<br>MPSTSDE | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |
| SEQ ID NO: 452<br>FEATURE<br>REGION<br><br>source<br><br><br><br>SEQUENCE: 452<br>MPSESTE | moltype = AA   length = 7<br>Location/Qualifiers<br>1..7<br>note = Synthetic peptide<br>1..7<br>mol_type = protein<br>organism = synthetic construct | <br><br><br><br><br><br><br><br><br>7 |

```
SEQ ID NO: 453           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 453
MPSASPE                                                                    7

SEQ ID NO: 454           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 454
RLYVHRS                                                                    7

SEQ ID NO: 455           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 455
RLYRHRT                                                                    7

SEQ ID NO: 456           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 456
KGYFHRT                                                                    7

SEQ ID NO: 457           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 457
KPPFEFGK                                                                   8

SEQ ID NO: 458           moltype = AA   length = 8
FEATURE                  Location/Qualifiers
REGION                   1..8
                         note = Synthetic peptide
source                   1..8
                         mol_type = protein
                         organism = synthetic construct
SEQUENCE: 458
KPGFVFLK                                                                   8

SEQ ID NO: 459           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 459
DDSEGAR                                                                    7

SEQ ID NO: 460           moltype = AA   length = 7
FEATURE                  Location/Qualifiers
REGION                   1..7
                         note = Synthetic peptide
source                   1..7
                         mol_type = protein
                         organism = synthetic construct
SEQUENCE: 460
```

```
DDSCGRR                                                                              7

SEQ ID NO: 461          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 461
DDSKGDR                                                                              7

SEQ ID NO: 462          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 462
DDSSGYR                                                                              7

SEQ ID NO: 463          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 463
KEAAGRG                                                                              7

SEQ ID NO: 464          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 464
KDASLRG                                                                              7

SEQ ID NO: 465          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 465
KGSSGRG                                                                              7

SEQ ID NO: 466          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 466
KTSSRRG                                                                              7

SEQ ID NO: 467          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 467
KTQTVRG                                                                              7

SEQ ID NO: 468          moltype = AA   length = 7
FEATURE                 Location/Qualifiers
REGION                  1..7
                        note = Synthetic peptide
source                  1..7
                        mol_type = protein
                        organism = synthetic construct
```

```
SEQUENCE: 468
KRSTLRG                                                                           7

SEQ ID NO: 469          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 469
DQPEN                                                                             5

SEQ ID NO: 470          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 470
GQPEN                                                                             5

SEQ ID NO: 471          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 471
KNNDG                                                                             5

SEQ ID NO: 472          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 472
RNNDG                                                                             5

SEQ ID NO: 473          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 473
NLVGEEY                                                                           7

SEQ ID NO: 474          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 474
NDSGEIY                                                                           7

SEQ ID NO: 475          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 475
EPVTG                                                                             5

SEQ ID NO: 476          moltype = AA  length = 5
FEATURE                 Location/Qualifiers
REGION                  1..5
                        note = Synthetic peptide
source                  1..5
                        mol_type = protein
```

```
                              organism = synthetic construct
SEQUENCE: 476
HGMPK                                                                        5

SEQ ID NO: 477           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 477
HGMAK                                                                        5

SEQ ID NO: 478           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 478
VPWIF                                                                        5

SEQ ID NO: 479           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 479
KSSVPFQ                                                                      7

SEQ ID NO: 480           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 480
KETVNFQ                                                                      7

SEQ ID NO: 481           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 481
VWSGS                                                                        5

SEQ ID NO: 482           moltype = AA  length = 5
FEATURE                  Location/Qualifiers
REGION                   1..5
                         note = Synthetic peptide
source                   1..5
                         mol_type = protein
                         organism = synthetic construct
SEQUENCE: 482
IWSGS                                                                        5

SEQ ID NO: 483           moltype = AA  length = 7
FEATURE                  Location/Qualifiers
REGION                   1..7
                         note = Synthetic peptide
source                   1..7
                         mol_type = protein
                         organism = synthetic construct
SEQUENCE: 483
FSLENWG                                                                      7

SEQ ID NO: 484           moltype = AA  length = 7
FEATURE                  Location/Qualifiers
REGION                   1..7
                         note = Synthetic peptide
source                   1..7
```

```
                            mol_type = protein
                            organism = synthetic construct
SEQUENCE: 484
FSMGRWG                                                                     7

SEQ ID NO: 485              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 485
FSLVLWG                                                                     7

SEQ ID NO: 486              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 486
FSLVLWG                                                                     7

SEQ ID NO: 487              moltype = AA   length = 7
FEATURE                     Location/Qualifiers
REGION                      1..7
                            note = Synthetic peptide
source                      1..7
                            mol_type = protein
                            organism = synthetic construct
SEQUENCE: 487
FSLTNWG                                                                     7

SEQ ID NO: 488              moltype = AA   length = 5
FEATURE                     Location/Qualifiers
REGION                      1..5
                            note = Synthetic peptide
source                      1..5
                            mol_type = protein
                            organism = synthetic construct
SEQUENCE: 488
PTNQG                                                                       5

SEQ ID NO: 489              moltype = AA   length = 5
FEATURE                     Location/Qualifiers
REGION                      1..5
                            note = Synthetic peptide
source                      1..5
                            mol_type = protein
                            organism = synthetic construct
SEQUENCE: 489
PTNPG                                                                       5

SEQ ID NO: 490              moltype = AA   length = 9
FEATURE                     Location/Qualifiers
REGION                      1..9
                            note = Synthetic peptide
source                      1..9
                            mol_type = protein
                            organism = synthetic construct
SEQUENCE: 490
RKLHWNHRT                                                                   9

SEQ ID NO: 491              moltype = AA   length = 9
FEATURE                     Location/Qualifiers
REGION                      1..9
                            note = Synthetic peptide
source                      1..9
                            mol_type = protein
                            organism = synthetic construct
SEQUENCE: 491
KKYRYRHPT                                                                   9

SEQ ID NO: 492              moltype = AA   length = 9
FEATURE                     Location/Qualifiers
REGION                      1..9
                            note = Synthetic peptide
```

```
source                  1..9
                        mol_type = protein
                        organism = synthetic construct
SEQUENCE: 492
RKAVYQHNT                                                                9

SEQ ID NO: 493          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 493
RTLHPRF                                                                  7

SEQ ID NO: 494          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 494
HFRHPRF                                                                  7

SEQ ID NO: 495          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 495
RVAHPRF                                                                  7

SEQ ID NO: 496          moltype = AA   length = 7
FEATURE                 Location/Qualifiers
REGION                  1..7
                        note = Synthetic peptide
source                  1..7
                        mol_type = protein
                        organism = synthetic construct
SEQUENCE: 496
WQAHPRF                                                                  7

SEQ ID NO: 497          moltype = AA   length = 8
FEATURE                 Location/Qualifiers
REGION                  1..8
                        note = Synthetic peptide
VARIANT                 5
                        note = X can be any amino acid
VARIANT                 6
                        note = X can be S or A
source                  1..8
                        mol_type = protein
                        organism = synthetic construct
SEQUENCE: 497
MKEAXXEK                                                                 8

SEQ ID NO: 498          moltype = AA   length = 8
FEATURE                 Location/Qualifiers
REGION                  1..8
                        note = Synthetic peptide
source                  1..8
                        mol_type = protein
                        organism = synthetic construct
SEQUENCE: 498
MKEAASEK                                                                 8

SEQ ID NO: 499          moltype = AA   length = 5
FEATURE                 Location/Qualifiers
REGION                  1..5
                        note = Synthetic peptide
VARIANT                 2
                        note = X can be I or V
source                  1..5
                        mol_type = protein
                        organism = synthetic construct
```

```
SEQUENCE: 499
RXPFG                                                                            5

SEQ ID NO: 500          moltype = AA  length = 6
FEATURE                 Location/Qualifiers
REGION                  1..6
                        note = Synthetic peptide
VARIANT                 3
                        note = X can be any amino acid
source                  1..6
                        mol_type = protein
                        organism = synthetic construct
SEQUENCE: 500
KGXATP                                                                           6

SEQ ID NO: 501          moltype = AA  length = 6
FEATURE                 Location/Qualifiers
REGION                  1..6
                        note = Synthetic peptide
VARIANT                 2
                        note = X can be M or L
VARIANT                 3
                        note = X can be any amino acid
source                  1..6
                        mol_type = protein
                        organism = synthetic construct
SEQUENCE: 501
PXXVGP                                                                           6

SEQ ID NO: 502          moltype = AA  length = 6
FEATURE                 Location/Qualifiers
REGION                  1..6
                        note = Synthetic peptide
VARIANT                 3
                        note = X can be any amino acid
VARIANT                 6
                        note = X can be R or Y
source                  1..6
                        mol_type = protein
                        organism = synthetic construct
SEQUENCE: 502
PKXDGX                                                                           6

SEQ ID NO: 503          moltype = AA  length = 6
FEATURE                 Location/Qualifiers
REGION                  1..6
                        note = Synthetic peptide
VARIANT                 2
                        note = X can be any amino acid
VARIANT                 6
                        note = X can be E or S
source                  1..6
                        mol_type = protein
                        organism = synthetic construct
SEQUENCE: 503
KXDGHX                                                                           6

SEQ ID NO: 504          moltype = AA  length = 7
FEATURE                 Location/Qualifiers
source                  1..7
                        mol_type = protein
                        organism = synthetic construct
VARIANT                 3
                        note = X can be any amino acid
VARIANT                 4
                        note = F can be replaced by Y
VARIANT                 6
                        note = X can be any amino acid
VARIANT                 7
                        note = R can be replaced by K
SEQUENCE: 504
VQXFMXR                                                                          7

SEQ ID NO: 505          moltype = AA  length = 8
FEATURE                 Location/Qualifiers
source                  1..8
                        mol_type = protein
                        organism = synthetic construct
VARIANT                 3
```

```
                        note = X can be any amino acid
VARIANT                 5
                        note = X can be any amino acid
VARIANT                 6
                        note = G can be replaced by A
VARIANT                 7
                        note = X can be any amino acid
VARIANT                 8
                        note = V can be replaced by A
SEQUENCE: 505
DRXPXGXV                                                                        8

SEQ ID NO: 506          moltype = AA  length = 7
FEATURE                 Location/Qualifiers
REGION                  1..7
                        note = Synthetic peptide
VARIANT                 2
                        note = X can be any amino acid
VARIANT                 5
                        note = X can be any amino acid
VARIANT                 6
                        note = X can be V or L
source                  1..7
                        mol_type = protein
                        organism = synthetic construct
SEQUENCE: 506
DXIDXXW                                                                         7

SEQ ID NO: 507          moltype = AA  length = 6
FEATURE                 Location/Qualifiers
REGION                  1..6
                        note = Synthetic peptide
VARIANT                 4
                        note = X can be any amino acid
VARIANT                 6
                        note = X can be R or Q
source                  1..6
                        mol_type = protein
                        organism = synthetic construct
SEQUENCE: 507
RQPXGX                                                                          6

SEQ ID NO: 508          moltype = AA  length = 6
FEATURE                 Location/Qualifiers
REGION                  1..6
                        note = Synthetic peptide
VARIANT                 2
                        note = X can be any amino acid
source                  1..6
                        mol_type = protein
                        organism = synthetic construct
SEQUENCE: 508
PXHGIH                                                                          6

SEQ ID NO: 509          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 509
DGDGP                                                                           5

SEQ ID NO: 510          moltype = AA  length = 8
FEATURE                 Location/Qualifiers
source                  1..8
                        mol_type = protein
                        organism = synthetic construct
VARIANT                 2..3
                        note = X can be any amino acid
VARIANT                 4
                        note = N can be replaced by Q
VARIANT                 7
                        note = X can be any amino acid
VARIANT                 8
                        note = K can be replaced by R
SEQUENCE: 510
HXXNTPXK                                                                        8
```

```
SEQ ID NO: 511              moltype = AA   length = 6
FEATURE                     Location/Qualifiers
source                      1..6
                            mol_type = protein
                            organism = synthetic construct
VARIANT                     2
                            note = S can be replaced by A
VARIANT                     3
                            note = X can be any amino acid
VARIANT                     6
                            note = H can be replaced by E
SEQUENCE: 511
KSXNPH                                                                    6

SEQ ID NO: 512              moltype = AA   length = 6
FEATURE                     Location/Qualifiers
REGION                      1..6
                            note = Synthetic peptide
VARIANT                     1
                            note = X can be E, Q, D or N
VARIANT                     2
                            note = X can be any amino acid
source                      1..6
                            mol_type = protein
                            organism = synthetic construct
SEQUENCE: 512
XXLPHE                                                                    6

SEQ ID NO: 513              moltype = AA   length = 5
FEATURE                     Location/Qualifiers
REGION                      1..5
                            note = Synthetic peptide
VARIANT                     5
                            note = X can be V, I or M
source                      1..5
                            mol_type = protein
                            organism = synthetic construct
SEQUENCE: 513
GQYGX                                                                     5

SEQ ID NO: 514              moltype = AA   length = 6
FEATURE                     Location/Qualifiers
source                      1..6
                            mol_type = protein
                            organism = synthetic construct
VARIANT                     3
                            note = M can be replaced by L
VARIANT                     4
                            note = X can be any amino acid
SEQUENCE: 514
PRMXBK                                                                    6

SEQ ID NO: 515              moltype = AA   length = 8
FEATURE                     Location/Qualifiers
REGION                      1..8
                            note = Synthetic peptide
VARIANT                     4
                            note = X can be G or Q
VARIANT                     5..7
                            note = X can be any amino acid
source                      1..8
                            mol_type = protein
                            organism = synthetic construct
SEQUENCE: 515
FGQXXXXD                                                                  8

SEQ ID NO: 516              moltype = AA   length = 7
FEATURE                     Location/Qualifiers
REGION                      1..7
                            note = Synthetic peptide
VARIANT                     3
                            note = X can be G, R or S
VARIANT                     3
                            note = X can be G, R or S
VARIANT                     4
                            note = X can be any amino acid
VARIANT                     6
                            note = X can be any amino acid
```

```
source                      1..7
                            mol_type = protein
                            organism = synthetic construct
SEQUENCE: 516
DDXXTXK                                                                    7

SEQ ID NO: 517              moltype = AA  length = 6
FEATURE                     Location/Qualifiers
REGION                      1..6
                            note = Synthetic peptide
VARIANT                     2
                            note = X can be any amino acid
VARIANT                     4
                            note = X can be F or P
source                      1..6
                            mol_type = protein
                            organism = synthetic construct
SEQUENCE: 517
IXTXDR                                                                     6

SEQ ID NO: 518              moltype = AA  length = 9
FEATURE                     Location/Qualifiers
REGION                      1..9
                            note = Synthetic peptide
VARIANT                     2..3
                            note = X can be any amino acid
VARIANT                     7..8
                            note = X can be any amino acid
VARIANT                     9
                            note = X can be F or Y
source                      1..9
                            mol_type = protein
                            organism = synthetic construct
SEQUENCE: 518
KXXNIGXXX                                                                  9

SEQ ID NO: 519              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 519
RVPFG                                                                      5

SEQ ID NO: 520              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 520
RIPFG                                                                      5

SEQ ID NO: 521              moltype = AA  length = 5
FEATURE                     Location/Qualifiers
REGION                      1..5
                            note = Synthetic peptide
source                      1..5
                            mol_type = protein
                            organism = synthetic construct
SEQUENCE: 521
RIPFG                                                                      5

SEQ ID NO: 522              moltype = AA  length = 9
FEATURE                     Location/Qualifiers
REGION                      1..9
                            note = Synthetic peptide
source                      1..9
                            mol_type = protein
                            organism = synthetic construct
SEQUENCE: 522
GGLFRVPFG                                                                  9

SEQ ID NO: 523              moltype = AA  length = 7
FEATURE                     Location/Qualifiers
REGION                      1..7
```

```
                        note = Synthetic peptide
source                  1..7
                        mol_type = protein
                        organism = synthetic construct
SEQUENCE: 523
KGKATPS                                                                          7

SEQ ID NO: 524          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 524
KGKATPS                                                                          7

SEQ ID NO: 525          moltype = AA  length = 6
FEATURE                 Location/Qualifiers
REGION                  1..6
                        note = Synthetic peptide
VARIANT                 3
                        note = X can be V, S, P, L or R
source                  1..6
                        mol_type = protein
                        organism = synthetic construct
SEQUENCE: 525
PLXVGP                                                                           6

SEQ ID NO: 526          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 526
PKVDGR                                                                           6

SEQ ID NO: 527          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 527
PKADGR                                                                           6

SEQ ID NO: 528          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 528
PKADGY                                                                           6

SEQ ID NO: 529          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 529
PKEDGR                                                                           6

SEQ ID NO: 530          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 530
PKEDGR                                                                           6
```

```
SEQ ID NO: 531        moltype = AA  length = 6
FEATURE               Location/Qualifiers
REGION                1..6
                      note = Synthetic peptide
source                1..6
                      mol_type = protein
                      organism = synthetic construct
SEQUENCE: 531
KYDGHS                                                                     6

SEQ ID NO: 532        moltype = AA  length = 6
FEATURE               Location/Qualifiers
REGION                1..6
                      note = Synthetic peptide
source                1..6
                      mol_type = protein
                      organism = synthetic construct
SEQUENCE: 532
KCDGHE                                                                     6

SEQ ID NO: 533        moltype = AA  length = 7
FEATURE               Location/Qualifiers
REGION                1..7
                      note = Synthetic peptide
source                1..7
                      mol_type = protein
                      organism = synthetic construct
SEQUENCE: 533
VQTFMLR                                                                    7

SEQ ID NO: 534        moltype = AA  length = 7
FEATURE               Location/Qualifiers
REGION                1..7
                      note = Synthetic peptide
source                1..7
                      mol_type = protein
                      organism = synthetic construct
SEQUENCE: 534
VQIYMAK                                                                    7

SEQ ID NO: 535        moltype = AA  length = 7
FEATURE               Location/Qualifiers
REGION                1..7
                      note = Synthetic peptide
source                1..7
                      mol_type = protein
                      organism = synthetic construct
SEQUENCE: 535
VQLFMRR                                                                    7

SEQ ID NO: 536        moltype = AA  length = 7
FEATURE               Location/Qualifiers
REGION                1..7
                      note = Synthetic peptide
source                1..7
                      mol_type = protein
                      organism = synthetic construct
SEQUENCE: 536
VQSYMLR                                                                    7

SEQ ID NO: 537        moltype = AA  length = 7
FEATURE               Location/Qualifiers
REGION                1..7
                      note = Synthetic peptide
source                1..7
                      mol_type = protein
                      organism = synthetic construct
SEQUENCE: 537
VQLYMDK                                                                    7

SEQ ID NO: 538        moltype = AA  length = 7
FEATURE               Location/Qualifiers
REGION                1..7
                      note = Synthetic peptide
source                1..7
                      mol_type = protein
                      organism = synthetic construct
SEQUENCE: 538
VQLYMDK                                                                    7
```

```
SEQ ID NO: 539        moltype = AA   length = 7
FEATURE               Location/Qualifiers
REGION                1..7
                      note = Synthetic peptide
source                1..7
                      mol_type = protein
                      organism = synthetic construct
SEQUENCE: 539
DDIDLLW                                                                    7

SEQ ID NO: 540        moltype = AA   length = 6
FEATURE               Location/Qualifiers
REGION                1..6
                      note = Synthetic peptide
source                1..6
                      mol_type = protein
                      organism = synthetic construct
SEQUENCE: 540
RQPCGQ                                                                     6

SEQ ID NO: 541        moltype = AA   length = 6
FEATURE               Location/Qualifiers
REGION                1..6
                      note = Synthetic peptide
source                1..6
                      mol_type = protein
                      organism = synthetic construct
SEQUENCE: 541
RQPIGR                                                                     6

SEQ ID NO: 542        moltype = AA   length = 8
FEATURE               Location/Qualifiers
REGION                1..8
                      note = Synthetic peptide
source                1..8
                      mol_type = protein
                      organism = synthetic construct
SEQUENCE: 542
HPTNTPEK                                                                   8

SEQ ID NO: 543        moltype = AA   length = 8
FEATURE               Location/Qualifiers
REGION                1..8
                      note = Synthetic peptide
source                1..8
                      mol_type = protein
                      organism = synthetic construct
SEQUENCE: 543
HPVNTPDK                                                                   8

SEQ ID NO: 544        moltype = AA   length = 8
FEATURE               Location/Qualifiers
REGION                1..8
                      note = Synthetic peptide
source                1..8
                      mol_type = protein
                      organism = synthetic construct
SEQUENCE: 544
HAVQTPSK                                                                   8

SEQ ID NO: 545        moltype = AA   length = 8
FEATURE               Location/Qualifiers
REGION                1..8
                      note = Synthetic peptide
source                1..8
                      mol_type = protein
                      organism = synthetic construct
SEQUENCE: 545
HTFQTPQR                                                                   8

SEQ ID NO: 546        moltype = AA   length = 8
FEATURE               Location/Qualifiers
REGION                1..8
                      note = Synthetic peptide
source                1..8
                      mol_type = protein
                      organism = synthetic construct
SEQUENCE: 546
```

```
HVNQTPYR                                                                                    8

SEQ ID NO: 547          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 547
HDGNTPAK                                                                                    8

SEQ ID NO: 548          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 548
KSANPE                                                                                      6

SEQ ID NO: 549          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 549
KSINPE                                                                                      6

SEQ ID NO: 550          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 550
KASNPH                                                                                      6

SEQ ID NO: 551          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 551
NALPHE                                                                                      6

SEQ ID NO: 552          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 552
DALPHE                                                                                      6

SEQ ID NO: 553          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 553
EPLPHE                                                                                      6

SEQ ID NO: 554          moltype = AA  length = 6
FEATURE                 Location/Qualifiers
REGION                  1..6
                        note = Synthetic peptide
source                  1..6
                        mol_type = protein
                        organism = synthetic construct
```

```
SEQUENCE: 554
EMLPHE                                                                              6

SEQ ID NO: 555          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 555
QPLPHE                                                                              6

SEQ ID NO: 556          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 556
GQYGV                                                                               5

SEQ ID NO: 557          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 557
KIPNIGDKF                                                                           9

SEQ ID NO: 558          moltype = AA  length = 6
FEATURE                 Location/Qualifiers
source                  1..6
                        mol_type = protein
                        organism = synthetic construct
VARIANT                 1
                        note = M can be replaced by L
VARIANT                 3
                        note = A can be replaced by S
VARIANT                 4
                        note = T can be replaced by A
VARIANT                 5
                        note = X can be any amino acid
SEQUENCE: 558
MLATXK                                                                              6

SEQ ID NO: 559          moltype = AA  length = 9
FEATURE                 Location/Qualifiers
source                  1..9
                        mol_type = protein
                        organism = synthetic construct
VARIANT                 1
                        note = V can be replaced by L
VARIANT                 2
                        note = X can be any amino acid
VARIANT                 3
                        note = A can be replaced by S
VARIANT                 4
                        note = X can be any amino acid
VARIANT                 7..8
                        note = X can be any amino acid
SEQUENCE: 559
VXAXDPXXP                                                                           9

SEQ ID NO: 560          moltype = AA  length = 7
FEATURE                 Location/Qualifiers
source                  1..7
                        mol_type = protein
                        organism = synthetic construct
VARIANT                 1
                        note = K can be replaced by R
VARIANT                 2
                        note = X can be any amino acid
VARIANT                 4
                        note = X can be any amino acid
VARIANT                 5
```

```
                         note = S can be replaced by T
VARIANT                  6
                         note = M can be replaced by L or F
SEQUENCE: 560
KXJXSMN                                                                       7

SEQ ID NO: 561           moltype = AA  length = 9
FEATURE                  Location/Qualifiers
REGION                   1..9
                         note = Synthetic peptide
VARIANT                  3
                         note = X can be K or R
VARIANT                  5..8
                         note = X can be any amino acid
source                   1..9
                         mol_type = protein
                         organism = synthetic construct
SEQUENCE: 561
TGXMXXXXQ                                                                     9

SEQ ID NO: 562           moltype = AA  length = 10
FEATURE                  Location/Qualifiers
source                   1..10
                         mol_type = protein
                         organism = synthetic construct
VARIANT                  2
                         note = X can be any amino acid
VARIANT                  5
                         note = S can be replaced by T or A
VARIANT                  6..9
                         note = X can be any amino acid
VARIANT                  10
                         note = M can be replaced by L
SEQUENCE: 562
GXPYSXXXXM                                                                    10

SEQ ID NO: 563           moltype = AA  length = 6
FEATURE                  Location/Qualifiers
source                   1..6
                         mol_type = protein
                         organism = synthetic construct
VARIANT                  3
                         note = E can be replaced by D or A
VARIANT                  4
                         note = X can be any amino acid
VARIANT                  5
                         note = P can be replaced by A
SEQUENCE: 563
WEEXPI                                                                        6

SEQ ID NO: 564           moltype = AA  length = 9
FEATURE                  Location/Qualifiers
REGION                   1..9
                         note = Synthetic peptide
VARIANT                  2
                         note = X can be I or V
VARIANT                  3
                         note = X can be any amino acid
VARIANT                  5..6
                         note = X can be any amino acid
VARIANT                  8
                         note = X can be any amino acid
source                   1..9
                         mol_type = protein
                         organism = synthetic construct
SEQUENCE: 564
EXXHXXFXR                                                                     9

SEQ ID NO: 565           moltype = AA  length = 8
FEATURE                  Location/Qualifiers
REGION                   1..8
                         note = Synthetic peptide
VARIANT                  2..3
                         note = X can be any amino acid
VARIANT                  4
                         note = X can be T or S
VARIANT                  7
                         note = X can be any amino acid
source                   1..8
```

```
                            mol_type = protein
                            organism = synthetic construct
SEQUENCE: 565
KXXXHRXK                                                                    8

SEQ ID NO: 566              moltype = AA   length = 7
FEATURE                     Location/Qualifiers
REGION                      1..7
                            note = Synthetic peptide
VARIANT                     4
                            note = X can be any amino acid
VARIANT                     6
                            note = X can be any amino acid
source                      1..7
                            mol_type = protein
                            organism = synthetic construct
SEQUENCE: 566
TFEXGXK                                                                     7

SEQ ID NO: 567              moltype = AA   length = 9
FEATURE                     Location/Qualifiers
source                      1..9
                            mol_type = protein
                            organism = synthetic construct
VARIANT                     4
                            note = X can be any amino acid
VARIANT                     5
                            note = R can be replaced by A
VARIANT                     6..8
                            note = X can be any amino acid
VARIANT                     9
                            note = F can be replaced by I
SEQUENCE: 567
WENXRXXXF                                                                   9

SEQ ID NO: 568              moltype = AA   length = 10
FEATURE                     Location/Qualifiers
source                      1..10
                            mol_type = protein
                            organism = synthetic construct
VARIANT                     1
                            note = N can be replaced by T
VARIANT                     2
                            note = M can be replaced by F
VARIANT                     4..7
                            note = X can be any amino acid
VARIANT                     9
                            note = X can be any amino acid
SEQUENCE: 568
NMFXXXXWXD                                                                 10

SEQ ID NO: 569              moltype = AA   length = 7
FEATURE                     Location/Qualifiers
source                      1..7
                            mol_type = protein
                            organism = synthetic construct
VARIANT                     1
                            note = P can be replaced by A
VARIANT                     2
                            note = G can be replaced by A
VARIANT                     3
                            note = I can be replaced by V
VARIANT                     4
                            note = M can be replaced by I, T or V
VARIANT                     5..6
                            note = X can be any amino acid
SEQUENCE: 569
PGIMXXP                                                                     7

SEQ ID NO: 570              moltype = AA   length = 8
FEATURE                     Location/Qualifiers
REGION                      1..8
                            note = Synthetic peptide
VARIANT                     2..3
                            note = X can be any amino acid
VARIANT                     5
                            note = X can be any amino acid
VARIANT                     7
                            note = X can be Y, W or H
```

```
source                  1..8
                        mol_type = protein
                        organism = synthetic construct
SEQUENCE: 570
KXXRXSXD                                                                8

SEQ ID NO: 571          moltype = AA  length = 9
FEATURE                 Location/Qualifiers
source                  1..9
                        mol_type = protein
                        organism = synthetic construct
VARIANT                 3..4
                        note = X can be any amino acid
VARIANT                 6..7
                        note = X can be any amino acid
VARIANT                 8
                        note = Y can be replaced by F
SEQUENCE: 571
EKXXRXXYB                                                               9

SEQ ID NO: 572          moltype = AA  length = 7
FEATURE                 Location/Qualifiers
REGION                  1..7
                        note = Synthetic peptide
VARIANT                 3
                        note = X can be any amino acid
VARIANT                 6
                        note = X can be any amino acid
source                  1..7
                        mol_type = protein
                        organism = synthetic construct
SEQUENCE: 572
DTXTPXE                                                                 7

SEQ ID NO: 573          moltype = AA  length = 5
FEATURE                 Location/Qualifiers
REGION                  1..5
                        note = Synthetic peptide
VARIANT                 3
                        note = X can be D or A
source                  1..5
                        mol_type = protein
                        organism = synthetic construct
SEQUENCE: 573
WLXQW                                                                   5

SEQ ID NO: 574          moltype = AA  length = 8
FEATURE                 Location/Qualifiers
REGION                  1..8
                        note = Synthetic peptide
VARIANT                 2
                        note = X can be E or N
VARIANT                 3..4
                        note = X can be any amino acid
VARIANT                 6
                        note = X can be any amino acid
source                  1..8
                        mol_type = protein
                        organism = synthetic construct
SEQUENCE: 574
KXXXDXWN                                                                8

SEQ ID NO: 575          moltype = AA  length = 5
FEATURE                 Location/Qualifiers
REGION                  1..5
                        note = Synthetic peptide
VARIANT                 1
                        note = X can be G or T
source                  1..5
                        mol_type = protein
                        organism = synthetic construct
SEQUENCE: 575
XGNGG                                                                   5

SEQ ID NO: 576          moltype = AA  length = 7
FEATURE                 Location/Qualifiers
source                  1..7
                        mol_type = protein
                        organism = synthetic construct
```

```
                        -continued

VARIANT                 2
                        note = Y can be replaced by F or W
VARIANT                 6
                        note = Q can be replaced by T
VARIANT                 4..5
                        note = X can be any amino acid
SEQUENCE: 576
GYDXXQP                                                                 7

SEQ ID NO: 577          moltype = AA   length = 7
FEATURE                 Location/Qualifiers
source                  1..7
                        mol_type = protein
                        organism = synthetic construct
VARIANT                 3
                        note = X can be any amino acid
VARIANT                 6
                        note = X can be any amino acid
VARIANT                 1
                        note = I can be replaced by V
VARIANT                 5
                        note = R can be replaced by K
VARIANT                 7
                        note = C can be replaced by R
SEQUENCE: 577
IGXSRXC                                                                 7

SEQ ID NO: 578          moltype = AA   length = 6
FEATURE                 Location/Qualifiers
source                  1..6
                        mol_type = protein
                        organism = synthetic construct
VARIANT                 1
                        note = S can be replaced by A or T
VARIANT                 5
                        note = M can be replaced by L
VARIANT                 4
                        note = X can be any amino acid
SEQUENCE: 578
STPXME                                                                  6

SEQ ID NO: 579          moltype = AA   length = 6
FEATURE                 Location/Qualifiers
REGION                  1..6
                        note = Synthetic peptide
VARIANT                 2
                        note = X can be D or Q
VARIANT                 4
                        note = X can be any amino acid
source                  1..6
                        mol_type = protein
                        organism = synthetic construct
SEQUENCE: 579
SXWXWE                                                                  6

SEQ ID NO: 580          moltype = AA   length = 9
FEATURE                 Location/Qualifiers
source                  1..9
                        mol_type = protein
                        organism = synthetic construct
VARIANT                 2..3
                        note = X can be any amino acid
VARIANT                 6..7
                        note = X can be any amino acid
VARIANT                 5
                        note = I can be replaced by T
VARIANT                 8
                        note = H can be replaced by F
SEQUENCE: 580
DXXYIXXHK                                                               9

SEQ ID NO: 581          moltype = AA   length = 8
FEATURE                 Location/Qualifiers
source                  1..8
                        mol_type = protein
                        organism = synthetic construct
VARIANT                 2
                        note = Y can be replaced by F
VARIANT                 7
```

```
                        note = I can be replaced by V or T
VARIANT                 3..5
                        note = X can be any amino acid
SEQUENCE: 581
KYXXXLIK                                                                        8

SEQ ID NO: 582          moltype = AA   length = 6
FEATURE                 Location/Qualifiers
REGION                  1..6
                        note = Synthetic peptide
VARIANT                 2
                        note = X can be V or I
VARIANT                 3
                        note = X can be any amino acid
source                  1..6
                        mol_type = protein
                        organism = synthetic construct
SEQUENCE: 582
PXXYMQ                                                                          6

SEQ ID NO: 583          moltype = AA   length = 8
FEATURE                 Location/Qualifiers
REGION                  1..8
                        note = Synthetic peptide
VARIANT                 5..7
                        note = X can be any amino acid
VARIANT                 8
                        note = X can be S or N
source                  1..8
                        mol_type = protein
                        organism = synthetic construct
SEQUENCE: 583
WPTGXXXX                                                                        8

SEQ ID NO: 584          moltype = AA   length = 7
FEATURE                 Location/Qualifiers
source                  1..7
                        mol_type = protein
                        organism = synthetic construct
VARIANT                 2
                        note = X can be any amino acid
VARIANT                 5
                        note = X can be any amino acid
VARIANT                 3
                        note = I can be replaced by M
VARIANT                 4
                        note = V can be replaced by N
SEQUENCE: 584
KXIVXWA                                                                         7

SEQ ID NO: 585          moltype = AA   length = 5
FEATURE                 Location/Qualifiers
source                  1..5
                        mol_type = protein
                        organism = synthetic construct
VARIANT                 2
                        note = A can be replaced by P
VARIANT                 5
                        note = K can be replaced by R
SEQUENCE: 585
WATGK                                                                           5

SEQ ID NO: 586          moltype = AA   length = 8
FEATURE                 Location/Qualifiers
source                  1..8
                        mol_type = protein
                        organism = synthetic construct
VARIANT                 5
                        note = I can be replaced by V
VARIANT                 8
                        note = K can be replaced by R
VARIANT                 2..3
                        note = X can be any amino acid
VARIANT                 6
                        note = X can be any amino acid
SEQUENCE: 586
YXXLIXPK                                                                        8

SEQ ID NO: 587          moltype = AA   length = 6
```

```
FEATURE              Location/Qualifiers
source               1..6
                     mol_type = protein
                     organism = synthetic construct
VARIANT              3
                     note = X can be any amino acid
VARIANT              1
                     note = S can be replaced by A
VARIANT              4
                     note = M can be replaced by L
SEQUENCE: 587
SNXMFY                                                                       6

SEQ ID NO: 588       moltype = AA  length = 6
FEATURE              Location/Qualifiers
REGION               1..6
                     note = Synthetic peptide
VARIANT              5
                     note = X can be any amino acid
VARIANT              6
                     note = X can be I or V
source               1..6
                     mol_type = protein
                     organism = synthetic construct
SEQUENCE: 588
WDGSXX                                                                       6

SEQ ID NO: 589       moltype = AA  length = 7
FEATURE              Location/Qualifiers
REGION               1..7
                     note = Synthetic peptide
VARIANT              2..3
                     note = X can be any amino acid
VARIANT              5
                     note = X can be I or V
source               1..7
                     mol_type = protein
                     organism = synthetic construct
SEQUENCE: 589
PXXLXKP                                                                      7

SEQ ID NO: 590       moltype = AA  length = 6
FEATURE              Location/Qualifiers
REGION               1..6
                     note = Synthetic peptide
VARIANT              2
                     note = X can be any amino acid
source               1..6
                     mol_type = protein
                     organism = synthetic construct
SEQUENCE: 590
KXDWDG                                                                       6

SEQ ID NO: 591       moltype = AA  length = 10
FEATURE              Location/Qualifiers
REGION               1..10
                     note = Synthetic peptide
VARIANT              2..5
                     note = X can be any amino acid
VARIANT              7
                     note = X can be any amino acid
VARIANT              9
                     note = X can be H or Y
source               1..10
                     mol_type = protein
                     organism = synthetic construct
SEQUENCE: 591
RXXXXKXDXD                                                                  10

SEQ ID NO: 592       moltype = AA  length = 6
FEATURE              Location/Qualifiers
REGION               1..6
                     note = Synthetic peptide
source               1..6
                     mol_type = protein
                     organism = synthetic construct
SEQUENCE: 592
VDVMGN                                                                       6
```

```
SEQ ID NO: 593          moltype = AA   length = 7
FEATURE                 Location/Qualifiers
source                  1..7
                        mol_type = protein
                        organism = synthetic construct
VARIANT                 3
                        note = N can be replaced by Q
VARIANT                 4
                        note = Q can be replaced by N
VARIANT                 2
                        note = X can be any amino acid
VARIANT                 5
                        note = X can be any amino acid
SEQUENCE: 593
EXNQXFY                                                                     7

SEQ ID NO: 594          moltype = AA   length = 5
FEATURE                 Location/Qualifiers
source                  1..5
                        mol_type = protein
                        organism = synthetic construct
VARIANT                 2
                        note = X can be any amino acid
VARIANT                 3..4
                        note = T can be replaced by S
SEQUENCE: 594
VXTTN                                                                       5

SEQ ID NO: 595          moltype = AA   length = 5
FEATURE                 Location/Qualifiers
REGION                  1..5
                        note = Synthetic peptide
source                  1..5
                        mol_type = protein
                        organism = synthetic construct
SEQUENCE: 595
KLHDP                                                                       5

SEQ ID NO: 596          moltype = AA   length = 7
FEATURE                 Location/Qualifiers
REGION                  1..7
                        note = Synthetic peptide
VARIANT                 2
                        note = X can be any amino acid
VARIANT                 4
                        note = X can be any amino acid
VARIANT                 7
                        note = X can be G or N
source                  1..7
                        mol_type = protein
                        organism = synthetic construct
SEQUENCE: 596
KXDXDTX                                                                     7

SEQ ID NO: 597          moltype = AA   length = 6
FEATURE                 Location/Qualifiers
source                  1..6
                        mol_type = protein
                        organism = synthetic construct
VARIANT                 2
                        note = H can be replaced by A
VARIANT                 6
                        note = S can be replaced by A or E
VARIANT                 5
                        note = X can be any amino acid
SEQUENCE: 597
YHGWXS                                                                      6

SEQ ID NO: 598          moltype = AA   length = 5
FEATURE                 Location/Qualifiers
REGION                  1..5
                        note = Synthetic peptide
VARIANT                 5
                        note = X can be D, T or E
source                  1..5
                        mol_type = protein
                        organism = synthetic construct
SEQUENCE: 598
NPEHX                                                                       5
```

```
SEQ ID NO: 599           moltype = AA   length = 6
FEATURE                  Location/Qualifiers
REGION                   1..6
                         note = Synthetic peptide
VARIANT                  4
                         note = X can be any amino acid
VARIANT                  6
                         note = X can be H or R
source                   1..6
                         mol_type = protein
                         organism = synthetic construct
SEQUENCE: 599
NPAXQX                                                                    6

SEQ ID NO: 600           moltype = AA   length = 7
FEATURE                  Location/Qualifiers
source                   1..7
                         mol_type = protein
                         organism = synthetic construct
VARIANT                  5..6
                         note = X can be any amino acid
VARIANT                  1
                         note = K can be replaced by R
VARIANT                  7
                         note = T can be replaced by P
SEQUENCE: 600
KMNKXXT                                                                   7

SEQ ID NO: 601           moltype = AA   length = 8
FEATURE                  Location/Qualifiers
source                   1..8
                         mol_type = protein
                         organism = synthetic construct
VARIANT                  3..5
                         note = X can be any amino acid
VARIANT                  6
                         note = F can be replaced by Y
VARIANT                  7
                         note = V can be replaced by K
SEQUENCE: 601
DWXXXFVK                                                                  8

SEQ ID NO: 602           moltype = AA   length = 6
FEATURE                  Location/Qualifiers
REGION                   1..6
                         note = Synthetic peptide
VARIANT                  4
                         note = X can be A, P, T or S
VARIANT                  5
                         note = X can be any amino acid
source                   1..6
                         mol_type = protein
                         organism = synthetic construct
SEQUENCE: 602
GVNXXK                                                                    6

SEQ ID NO: 603           moltype = AA   length = 7
FEATURE                  Location/Qualifiers
source                   1..7
                         mol_type = protein
                         organism = synthetic construct
VARIANT                  1
                         note = I can be replaced by V
VARIANT                  3
                         note = P can be replaced by R
VARIANT                  2
                         note = X can be any amino acid
VARIANT                  6
                         note = X can be any amino acid
SEQUENCE: 603
IXPEGXK                                                                   7

SEQ ID NO: 604           moltype = AA   length = 5
FEATURE                  Location/Qualifiers
source                   1..5
                         mol_type = protein
                         organism = synthetic construct
VARIANT                  4
```

```
                        note = S can be replaced by T
VARIANT                 5
                        note = M can be replaced by A
SEQUENCE: 604
RVFSM                                                                              5

SEQ ID NO: 605          moltype = AA  length = 8
FEATURE                 Location/Qualifiers
source                  1..8
                        mol_type = protein
                        organism = synthetic construct
VARIANT                 2
                        note = X can be any amino acid
VARIANT                 4..5
                        note = X can be any amino acid
VARIANT                 6
                        note = V can be replaced by I
VARIANT                 8
                        note = Y can be replaced by F
SEQUENCE: 605
NXRXXVWY                                                                           8

SEQ ID NO: 606          moltype = AA  length = 8
FEATURE                 Location/Qualifiers
REGION                  1..8
                        note = Synthetic peptide
VARIANT                 2..3
                        note = X can be any amino acid
VARIANT                 4
                        note = X can be M, T or L
VARIANT                 5
                        note = X can be any amino acid
source                  1..8
                        mol_type = protein
                        organism = synthetic construct
SEQUENCE: 606
YXXXXYNA                                                                           8

SEQ ID NO: 607          moltype = AA  length = 7
FEATURE                 Location/Qualifiers
source                  1..7
                        mol_type = protein
                        organism = synthetic construct
VARIANT                 2
                        note = X can be any amino acid
VARIANT                 3
                        note = V can be replaced by I
VARIANT                 4
                        note = X can be any amino acid
VARIANT                 6
                        note = I can be replaced by V
SEQUENCE: 607
KXVXBIW                                                                            7

SEQ ID NO: 608          moltype = AA  length = 5
FEATURE                 Location/Qualifiers
source                  1..5
                        mol_type = protein
                        organism = synthetic construct
VARIANT                 1
                        note = E can be replaced by D
VARIANT                 2
                        note = Y can be replaced by F
VARIANT                 4
                        note = L can be replaced by Q
SEQUENCE: 608
EYQLH                                                                              5

SEQ ID NO: 609          moltype = AA  length = 6
FEATURE                 Location/Qualifiers
REGION                  1..6
                        note = Synthetic peptide
VARIANT                 3
                        note = X can be any amino acid
source                  1..6
                        mol_type = protein
                        organism = synthetic construct
SEQUENCE: 609
FGXPSI                                                                             6
```

```
SEQ ID NO: 610          moltype = AA  length = 7
FEATURE                 Location/Qualifiers
REGION                  1..7
                        note = Synthetic peptide
VARIANT                 5..6
                        note = X can be any amino acid
source                  1..7
                        mol_type = protein
                        organism = synthetic construct
SEQUENCE: 610
QLVGXXK                                                                  7

SEQ ID NO: 611          moltype = AA  length = 8
FEATURE                 Location/Qualifiers
source                  1..8
                        mol_type = protein
                        organism = synthetic construct
VARIANT                 2..3
                        note = X can be any amino acid
VARIANT                 5
                        note = I can be replaced by V
VARIANT                 6
                        note = X can be any amino acid
VARIANT                 8
                        note = K can be replaced by R
SEQUENCE: 611
YXXLIXPK                                                                 8

SEQ ID NO: 612          moltype = AA  length = 6
FEATURE                 Location/Qualifiers
source                  1..6
                        mol_type = protein
                        organism = synthetic construct
VARIANT                 2
                        note = Y can be replaced by K
VARIANT                 5
                        note = P can be replaced by A
VARIANT                 4
                        note = X can be any amino acid
SEQUENCE: 612
WYWXPK                                                                   6

SEQ ID NO: 613          moltype = AA  length = 7
FEATURE                 Location/Qualifiers
REGION                  1..7
                        note = Synthetic peptide
VARIANT                 2
                        note = X can be any amino acid
VARIANT                 4
                        note = X can be any amino acid
VARIANT                 6
                        note = X can be N or K
source                  1..7
                        mol_type = protein
                        organism = synthetic construct
SEQUENCE: 613
KXEXHXF                                                                  7

SEQ ID NO: 614          moltype = AA  length = 9
FEATURE                 Location/Qualifiers
REGION                  1..9
                        note = Synthetic peptide
VARIANT                 2..4
                        note = X can be any amino acid
VARIANT                 8
                        note = X can be any amino acid
source                  1..9
                        mol_type = protein
                        organism = synthetic construct
SEQUENCE: 614
QXXXWPYXK                                                                9

SEQ ID NO: 615          moltype = AA  length = 8
FEATURE                 Location/Qualifiers
REGION                  1..8
                        note = Synthetic peptide
VARIANT                 2
                        note = X can be any amino acid
```

```
VARIANT                 5
                        note = X can be any amino acid
VARIANT                 7
                        note = X can be any amino acid
source                  1..8
                        mol_type = protein
                        organism = synthetic construct
SEQUENCE: 615
YXFDXNXR                                                                  8

SEQ ID NO: 616          moltype = AA  length = 6
FEATURE                 Location/Qualifiers
REGION                  1..6
                        note = Synthetic peptide
VARIANT                 2
                        note = X can be any amino acid
VARIANT                 5
                        note = X can be V or I
source                  1..6
                        mol_type = protein
                        organism = synthetic construct
SEQUENCE: 616
FXWNXP                                                                    6

SEQ ID NO: 617          moltype = AA  length = 6
FEATURE                 Location/Qualifiers
source                  1..6
                        mol_type = protein
                        organism = synthetic construct
VARIANT                 4
                        note = X can be any amino acid
VARIANT                 1
                        note = F can be replaced by W
VARIANT                 2
                        note = L can be replaced by M
SEQUENCE: 617
FLEXAH                                                                    6

SEQ ID NO: 618          moltype = AA  length = 6
FEATURE                 Location/Qualifiers
REGION                  1..6
                        note = Synthetic peptide
VARIANT                 4
                        note = X can be any amino acid
source                  1..6
                        mol_type = protein
                        organism = synthetic construct
SEQUENCE: 618
DFJXAT                                                                    6

SEQ ID NO: 619          moltype = AA  length = 7
FEATURE                 Location/Qualifiers
REGION                  1..7
                        note = Synthetic peptide
VARIANT                 2
                        note = X can be any amino acid
VARIANT                 5
                        note = X can be any amino acid
source                  1..7
                        mol_type = protein
                        organism = synthetic construct
SEQUENCE: 619
KXMSXFV                                                                   7

SEQ ID NO: 620          moltype = AA  length = 6
FEATURE                 Location/Qualifiers
source                  1..6
                        mol_type = protein
                        organism = synthetic construct
VARIANT                 2
                        note = Y can be replaced by K
VARIANT                 5
                        note = P can be replaced by A
VARIANT                 4
                        note = X can be any amino acid
SEQUENCE: 620
WYWXPK                                                                    6

SEQ ID NO: 621          moltype = AA  length = 7
```

```
FEATURE              Location/Qualifiers
REGION               1..7
                     note = Synthetic peptide
VARIANT              2
                     note = X can be any amino acid
VARIANT              4
                     note = X can be any amino acid
VARIANT              6
                     note = X can be N or K
source               1..7
                     mol_type = protein
                     organism = synthetic construct
SEQUENCE: 621
KXEXHXF                                                                         7

SEQ ID NO: 622       moltype = AA   length = 9
FEATURE              Location/Qualifiers
REGION               1..9
                     note = Synthetic peptide
VARIANT              2..4
                     note = X can be any amino acid
VARIANT              8
                     note = X can be any amino acid
source               1..9
                     mol_type = protein
                     organism = synthetic construct
SEQUENCE: 622
QXXXWPYXK                                                                       9

SEQ ID NO: 623       moltype = AA   length = 5
FEATURE              Location/Qualifiers
REGION               1..5
                     note = Synthetic peptide
VARIANT              4
                     note = X can be S or F
source               1..5
                     mol_type = protein
                     organism = synthetic construct
SEQUENCE: 623
WPTXT                                                                           5

SEQ ID NO: 624       moltype = AA   length = 5
FEATURE              Location/Qualifiers
REGION               1..5
                     note = Synthetic peptide
VARIANT              3
                     note = X can be T or A
source               1..5
                     mol_type = protein
                     organism = synthetic construct
SEQUENCE: 624
WPXGR                                                                           5

SEQ ID NO: 625       moltype = AA   length = 6
FEATURE              Location/Qualifiers
REGION               1..6
                     note = Synthetic peptide
VARIANT              5
                     note = X can be any amino acid
VARIANT              6
                     note = X can be G or F
source               1..6
                     mol_type = protein
                     organism = synthetic construct
SEQUENCE: 625
KNWPXX                                                                          6

SEQ ID NO: 626       moltype = AA   length = 7
FEATURE              Location/Qualifiers
REGION               1..7
                     note = Synthetic peptide
VARIANT              2..3
                     note = X can be any amino acid
source               1..7
                     mol_type = protein
                     organism = synthetic construct
SEQUENCE: 626
KXXPJFA                                                                         7
```

```
SEQ ID NO: 627          moltype = AA  length = 6
FEATURE                 Location/Qualifiers
REGION                  1..6
                        note = Synthetic peptide
VARIANT                 3
                        note = X can be any amino acid
source                  1..6
                        mol_type = protein
                        organism = synthetic construct
SEQUENCE: 627
WPXGQV                                                                    6

SEQ ID NO: 628          moltype = AA  length = 5
FEATURE                 Location/Qualifiers
source                  1..5
                        mol_type = protein
                        organism = synthetic construct
VARIANT                 1
                        note = V can be replaced by I
VARIANT                 2
                        note = L can be replaced by R
SEQUENCE: 628
VLKDF                                                                     5

SEQ ID NO: 629          moltype = AA  length = 5
FEATURE                 Location/Qualifiers
REGION                  1..5
                        note = Synthetic peptide
VARIANT                 4
                        note = X can be S or F
source                  1..5
                        mol_type = protein
                        organism = synthetic construct
SEQUENCE: 629
WPTXT                                                                     5

SEQ ID NO: 630          moltype = AA  length = 7
FEATURE                 Location/Qualifiers
source                  1..7
                        mol_type = protein
                        organism = synthetic construct
VARIANT                 2
                        note = X can be any amino acid
VARIANT                 3
                        note = I can be replaced by M
VARIANT                 4
                        note = V can be replaced by N
VARIANT                 5
                        note = X can be any amino acid
SEQUENCE: 630
KXIVXWA                                                                   7

SEQ ID NO: 631          moltype = AA  length = 6
FEATURE                 Location/Qualifiers
REGION                  1..6
                        note = Sythentic peptide
VARIANT                 1
                        note = X can be Y or W
VARIANT                 3
                        note = X can be any amino acid
source                  1..6
                        mol_type = protein
                        organism = synthetic construct
SEQUENCE: 631
XTXEPF                                                                    6

SEQ ID NO: 632          moltype = AA  length = 6
FEATURE                 Location/Qualifiers
source                  1..6
                        mol_type = protein
                        organism = synthetic construct
VARIANT                 1
                        note = A can be replaced by M
VARIANT                 2
                        note = P can be replaced by T or S
VARIANT                 5
                        note = X can be any amino acid
SEQUENCE: 632
APWEXF                                                                    6
```

```
SEQ ID NO: 633         moltype = AA  length = 5
FEATURE                Location/Qualifiers
source                 1..5
                       mol_type = protein
                       organism = synthetic construct
VARIANT                2
                       note = P can be replaced by T
VARIANT                3
                       note = R can be replaced by T or K
VARIANT                5
                       note = N can be replaced by S
SEQUENCE: 633
RPRFN                                                                     5

SEQ ID NO: 634         moltype = AA  length = 5
FEATURE                Location/Qualifiers
REGION                 1..5
                       note = Sythentic peptide
VARIANT                3
                       note = X can be S or A
source                 1..5
                       mol_type = protein
                       organism = synthetic construct
SEQUENCE: 634
VYXHW                                                                     5

SEQ ID NO: 635         moltype = AA  length = 10
FEATURE                Location/Qualifiers
REGION                 1..10
                       note = Sythentic peptide
VARIANT                1
                       note = X can be W or F
VARIANT                2..3
                       note = X can be any amino acid
VARIANT                6
                       note = X can be any amino acid
VARIANT                8..9
                       note = X can be any amino acid
source                 1..10
                       mol_type = protein
                       organism = synthetic construct
SEQUENCE: 635
XXXKPXWXXM                                                               10

SEQ ID NO: 636         moltype = AA  length = 7
FEATURE                Location/Qualifiers
REGION                 1..7
                       note = Sythentic peptide
VARIANT                3
                       note = X can be any amino acid
VARIANT                4
                       note = X can be S or A
VARIANT                6
                       note = X can be any amino acid
source                 1..7
                       mol_type = protein
                       organism = synthetic construct
SEQUENCE: 636
KGXXHXF                                                                   7

SEQ ID NO: 637         moltype = AA  length = 7
FEATURE                Location/Qualifiers
REGION                 1..7
                       note = Sythentic peptide
VARIANT                3
                       note = X can be any amino acid
VARIANT                5
                       note = X can be any amino acid
VARIANT                7
                       note = X can be A or S
source                 1..7
                       mol_type = protein
                       organism = synthetic construct
SEQUENCE: 637
KGXVXFX                                                                   7

SEQ ID NO: 638         moltype = AA  length = 7
FEATURE                Location/Qualifiers
```

```
REGION                  1..7
                        note = Sythentic peptide
VARIANT                 1
                        note = X can be I or V
VARIANT                 2
                        note = X can be any amino acid
VARIANT                 4
                        note = X can be any amino acid
source                  1..7
                        mol_type = protein
                        organism = synthetic construct
SEQUENCE: 638
XXHXTID                                                                 7

SEQ ID NO: 639          moltype = AA  length = 7
FEATURE                 Location/Qualifiers
REGION                  1..7
                        note = Sythentic peptide
VARIANT                 4..5
                        note = X can be any amino acid
source                  1..7
                        mol_type = protein
                        organism = synthetic construct
SEQUENCE: 639
MLSXXVN                                                                 7

SEQ ID NO: 640          moltype = AA  length = 8
FEATURE                 Location/Qualifiers
REGION                  1..8
                        note = Sythentic peptide
VARIANT                 2
                        note = X can be any amino acid
VARIANT                 5..6
                        note = X can be any amino acid
source                  1..8
                        mol_type = protein
                        organism = synthetic construct
SEQUENCE: 640
KXYSXXVR                                                                8

SEQ ID NO: 641          moltype = AA  length = 6
FEATURE                 Location/Qualifiers
REGION                  1..6
                        note = Synthetic peptide
VARIANT                 2
                        note = X can be any amino acid
VARIANT                 3
                        note = X can be V or K
source                  1..6
                        mol_type = protein
                        organism = synthetic construct
SEQUENCE: 641
KXXVNP                                                                  6

SEQ ID NO: 642          moltype = AA  length = 5
FEATURE                 Location/Qualifiers
REGION                  1..5
                        note = Synthetic peptide
VARIANT                 1
                        note = X can be R, K or H
source                  1..5
                        mol_type = protein
                        organism = synthetic construct
SEQUENCE: 642
XEPGD                                                                   5

SEQ ID NO: 643          moltype = AA  length = 9
FEATURE                 Location/Qualifiers
REGION                  1..9
                        note = Synthetic peptide
VARIANT                 2..3
                        note = X can be any amino acid
VARIANT                 5
                        note = X can be any amino acid
VARIANT                 8
                        note = X can be any amino acid
source                  1..9
                        mol_type = protein
                        organism = synthetic construct
```

```
SEQUENCE: 643
CXXIXNEXC                                                                        9

SEQ ID NO: 644          moltype = AA  length = 5
FEATURE                 Location/Qualifiers
REGION                  1..5
                        note = Synthetic peptide
VARIANT                 4
                        note = X can be S or N
source                  1..5
                        mol_type = protein
                        organism = synthetic construct
SEQUENCE: 644
ESRXI                                                                            5

SEQ ID NO: 645          moltype = AA  length = 6
FEATURE                 Location/Qualifiers
REGION                  1..6
                        note = Synthetic peptide
VARIANT                 4
                        note = X can be any amino acid
VARIANT                 5
                        note = X can be Q or N
source                  1..6
                        mol_type = protein
                        organism = synthetic construct
SEQUENCE: 645
HPDXXL                                                                           6

SEQ ID NO: 646          moltype = AA  length = 6
FEATURE                 Location/Qualifiers
source                  1..6
                        mol_type = protein
                        organism = synthetic construct
VARIANT                 3
                        note = X can be any amino acid
VARIANT                 5
                        note = F can be replaced by Y
VARIANT                 6
                        note = E can be replaced by D
SEQUENCE: 646
RYXHFE                                                                           6

SEQ ID NO: 647          moltype = AA  length = 7
FEATURE                 Location/Qualifiers
REGION                  1..7
                        note = Synthetic peptide
VARIANT                 2
                        note = X can be A or S
VARIANT                 3
                        note = X can be any amino acid
VARIANT                 6
                        note = X can be any amino acid
source                  1..7
                        mol_type = protein
                        organism = synthetic construct
SEQUENCE: 647
FXXRQXP                                                                          7

SEQ ID NO: 648          moltype = AA  length = 5
FEATURE                 Location/Qualifiers
REGION                  1..5
                        note = Synthetic peptide
VARIANT                 3
                        note = X can be A or P
source                  1..5
                        mol_type = protein
                        organism = synthetic construct
SEQUENCE: 648
QDXRN                                                                            5

SEQ ID NO: 649          moltype = AA  length = 7
FEATURE                 Location/Qualifiers
REGION                  1..7
                        note = Synthetic peptide
VARIANT                 2..3
                        note = X can be any amino acid
VARIANT                 4
                        note = X can be I, L or M
```

```
                        -continued source                  1..7
                        mol_type = protein
                        organism = synthetic construct
SEQUENCE: 649
LXXXNQQ                                                                 7

SEQ ID NO: 650          moltype = AA  length = 6
FEATURE                 Location/Qualifiers
source                  1..6
                        mol_type = protein
                        organism = synthetic construct
VARIANT                 1
                        note = V can be replaced by A
VARIANT                 6
                        note = W can be replaced by F
VARIANT                 2
                        note = X can be any amino acid
SEQUENCE: 650
VXDGAW                                                                  6

SEQ ID NO: 651          moltype = AA  length = 6
FEATURE                 Location/Qualifiers
REGION                  1..6
                        note = Synthetic peptide
VARIANT                 2
                        note = X can be any amino acid
VARIANT                 6
                        note = X can be M, T or S
source                  1..6
                        mol_type = protein
                        organism = synthetic construct
SEQUENCE: 651
CXLPEX                                                                  6

SEQ ID NO: 652          moltype = AA  length = 7
FEATURE                 Location/Qualifiers
REGION                  1..7
                        note = Synthetic peptide
VARIANT                 2..3
                        note = X can be any amino acid
VARIANT                 6
                        note = X can be T, H or S
source                  1..7
                        mol_type = protein
                        organism = synthetic construct
SEQUENCE: 652
FXXMQXK                                                                 7

SEQ ID NO: 653          moltype = AA  length = 6
FEATURE                 Location/Qualifiers
REGION                  1..6
                        note = Synthetic peptide
VARIANT                 3
                        note = X can be G, A or S
VARIANT                 4
                        note = X can be any amino acid
source                  1..6
                        mol_type = protein
                        organism = synthetic construct
SEQUENCE: 653
GHXXLR                                                                  6

SEQ ID NO: 654          moltype = AA  length = 9
FEATURE                 Location/Qualifiers
source                  1..9
                        mol_type = protein
                        organism = synthetic construct
VARIANT                 2..3
                        note = X can be any amino acid
VARIANT                 6..7
                        note = X can be any amino acid
VARIANT                 4
                        note = D can be replaced by E
VARIANT                 9
                        note = V can be replaced by E
SEQUENCE: 654
WXXDYXXLV                                                               9

SEQ ID NO: 655          moltype = AA  length = 5
```

```
FEATURE             Location/Qualifiers
source              1..5
                    mol_type = protein
                    organism = synthetic construct
VARIANT             2
                    note = H can be replaced by N or D
VARIANT             3
                    note = Y can be replaced by F
SEQUENCE: 655
FHYPR                                                                     5

SEQ ID NO: 656      moltype = AA  length = 5
FEATURE             Location/Qualifiers
REGION              1..5
                    note = Synthetic peptide
VARIANT             3
                    note = X can be F or Y
source              1..5
                    mol_type = protein
                    organism = synthetic construct
SEQUENCE: 656
PEXTS                                                                     5

SEQ ID NO: 657      moltype = AA  length = 9
FEATURE             Location/Qualifiers
REGION              1..9
                    note = Synthetic peptide
VARIANT             3
                    note = X can be any amino acid
VARIANT             6..8
                    note = X can be any amino acid
source              1..9
                    mol_type = protein
                    organism = synthetic construct
SEQUENCE: 657
CDXPSXXXC                                                                 9

SEQ ID NO: 658      moltype = AA  length = 8
FEATURE             Location/Qualifiers
REGION              1..8
                    note = Synthetic peptide
VARIANT             1
                    note = X can be F or Y
VARIANT             2..3
                    note = X can be any amino acid
VARIANT             7
                    note = X can be any amino acid
source              1..8
                    mol_type = protein
                    organism = synthetic construct
SEQUENCE: 658
XXXNGHXF                                                                  8

SEQ ID NO: 659      moltype = AA  length = 9
FEATURE             Location/Qualifiers
REGION              1..9
                    note = Synthetic peptide
VARIANT             2
                    note = X can be any amino acid
VARIANT             5
                    note = X can be any amino acid
VARIANT             7..8
                    note = X can be any amino acid
source              1..9
                    mol_type = protein
                    organism = synthetic construct
SEQUENCE: 659
YXICXEXXC                                                                 9

SEQ ID NO: 660      moltype = AA  length = 7
FEATURE             Location/Qualifiers
REGION              1..7
                    note = Synthetic peptide
VARIANT             5..6
                    note = X can be any amino acid
source              1..7
                    mol_type = protein
                    organism = synthetic construct
SEQUENCE: 660
```

```
DCMGXXC                                                                    7

SEQ ID NO: 661         moltype = AA  length = 7
FEATURE                Location/Qualifiers
source                 1..7
                       mol_type = protein
                       organism = synthetic construct
VARIANT                1
                       note = M can be replaced by L
VARIANT                7
                       note = D can be replaced by E
VARIANT                2
                       note = X can be any amino acid
VARIANT                6
                       note = X can be any amino acid
SEQUENCE: 661
MXTGLXD                                                                    7

SEQ ID NO: 662         moltype = AA  length = 6
FEATURE                Location/Qualifiers
REGION                 1..6
                       note = Synthetic peptide
VARIANT                2
                       note = X can be any amino acid
source                 1..6
                       mol_type = protein
                       organism = synthetic construct
SEQUENCE: 662
MXLGYY                                                                     6

SEQ ID NO: 663         moltype = AA  length = 6
FEATURE                Location/Qualifiers
source                 1..6
                       mol_type = protein
                       organism = synthetic construct
VARIANT                5
                       note = X can be any amino acid
VARIANT                3
                       note = L can be replaced by T
VARIANT                6
                       note = Y can be replaced by H
SEQUENCE: 663
MPLGXY                                                                     6

SEQ ID NO: 664         moltype = AA  length = 6
FEATURE                Location/Qualifiers
source                 1..6
                       mol_type = protein
                       organism = synthetic construct
VARIANT                1
                       note = F can be replaced by L
VARIANT                5
                       note = X can be any amino acid
SEQUENCE: 664
FQTGXJ                                                                     6

SEQ ID NO: 665         moltype = AA  length = 6
FEATURE                Location/Qualifiers
REGION                 1..6
                       note = Synthetic peptide
VARIANT                2
                       note = X can be any amino acid
VARIANT                3
                       note = X can be T or S
source                 1..6
                       mol_type = protein
                       organism = synthetic construct
SEQUENCE: 665
KXXCPC                                                                     6

SEQ ID NO: 666         moltype = AA  length = 5
FEATURE                Location/Qualifiers
REGION                 1..5
                       note = Synthetic peptide
VARIANT                4
                       note = X can be T, S or D
source                 1..5
                       mol_type = protein
                       organism = synthetic construct
```

```
SEQUENCE: 666
CKDXC                                                                        5

SEQ ID NO: 667         moltype = AA  length = 5
FEATURE                Location/Qualifiers
source                 1..5
                       mol_type = protein
                       organism = synthetic construct
VARIANT                3
                       note = V can be replaced by A
VARIANT                5
                       note = E can be replaced by Q
SEQUENCE: 667
CGVFE                                                                        5

SEQ ID NO: 668         moltype = AA  length = 8
FEATURE                Location/Qualifiers
source                 1..8
                       mol_type = protein
                       organism = synthetic construct
VARIANT                4
                       note = I can be replaced by V, A or E
VARIANT                8
                       note = I can be replaced by M or L
VARIANT                3
                       note = X can be any amino acid
VARIANT                6..7
                       note = X can be any amino acid
SEQUENCE: 668
SNXIAXXI                                                                     8

SEQ ID NO: 669         moltype = AA  length = 8
FEATURE                Location/Qualifiers
REGION                 1..8
                       note = Synthetic peptide
VARIANT                3
                       note = X can be any amino acid
VARIANT                5
                       note = X can be any amino acid
VARIANT                7
                       note = X can be any amino acid
VARIANT                8
                       note = X can be K or R
source                 1..8
                       mol_type = protein
                       organism = synthetic construct
SEQUENCE: 669
PTXLXHXX                                                                     8

SEQ ID NO: 670         moltype = AA  length = 5
FEATURE                Location/Qualifiers
REGION                 1..5
                       note = Synthetic peptide
source                 1..5
                       mol_type = protein
                       organism = synthetic construct
SEQUENCE: 670
WPVNN                                                                        5

SEQ ID NO: 671         moltype = AA  length = 9
FEATURE                Location/Qualifiers
source                 1..9
                       mol_type = protein
                       organism = synthetic construct
VARIANT                5..8
                       note = X can be any amino acid
VARIANT                1
                       note = V can be replaced by I or A
VARIANT                4
                       note = G can be replaced by D
SEQUENCE: 671
VCNGXXXXC                                                                    9

SEQ ID NO: 672         moltype = AA  length = 5
FEATURE                Location/Qualifiers
source                 1..5
                       mol_type = protein
                       organism = synthetic construct
VARIANT                1
```

-continued

```
                              note = K can be replaced by R
VARIANT                       4
                              note = Y can be replaced by S
SEQUENCE: 672
KNPYL                                                                  5

SEQ ID NO: 673                moltype = AA  length = 10
FEATURE                       Location/Qualifiers
REGION                        1..10
                              note = Synthetic peptide
VARIANT                       2..4
                              note = X can be any amino acid
VARIANT                       7
                              note = X can be any amino acid
VARIANT                       9
                              note = X can be any amino acid
source                        1..10
                              mol_type = protein
                              organism = synthetic construct
SEQUENCE: 673
CXXXPMXVXC                                                            10

SEQ ID NO: 674                moltype = AA  length = 7
FEATURE                       Location/Qualifiers
source                        1..7
                              mol_type = protein
                              organism = synthetic construct
VARIANT                       2
                              note = L can be replaced by M
VARIANT                       3
                              note = K can be replaced by Q or T
VARIANT                       5..6
                              note = X can be any amino acid
SEQUENCE: 674
GLKFXXD                                                                7

SEQ ID NO: 675                moltype = AA  length = 6
FEATURE                       Location/Qualifiers
source                        1..6
                              mol_type = protein
                              organism = synthetic construct
VARIANT                       4
                              note = X can be any amino acid
VARIANT                       1
                              note = I can be replaced by A
VARIANT                       5
                              note = P can be replaced by A or K
SEQUENCE: 675
IPMXPN                                                                 6

SEQ ID NO: 676                moltype = AA  length = 10
FEATURE                       Location/Qualifiers
REGION                        1..10
                              note = Synthetic peptide
VARIANT                       2
                              note = X can be any amino acid
VARIANT                       5
                              note = X can be any amino acid
VARIANT                       6
                              note = X can be H or T
VARIANT                       7..9
                              note = X can be any amino acid
source                        1..10
                              mol_type = protein
                              organism = synthetic construct
SEQUENCE: 676
WXWCXXXXXC                                                            10

SEQ ID NO: 677                moltype = AA  length = 7
FEATURE                       Location/Qualifiers
source                        1..7
                              mol_type = protein
                              organism = synthetic construct
VARIANT                       2..3
                              note = X can be any amino acid
VARIANT                       5
                              note = Q can be replaced by M, H or E
VARIANT                       6
                              note = T can be replaced by H
```

```
SEQUENCE: 677
FXXMQTK                                                                   7

SEQ ID NO: 678         moltype = AA  length = 8
FEATURE                Location/Qualifiers
REGION                 1..8
                       note = Synthetic peptide
VARIANT                2
                       note = X can be any amino acid
VARIANT                4
                       note = X can be any amino acid
VARIANT                5
                       note = X can be V or I
VARIANT                6
                       note = X can be any amino acid
source                 1..8
                       mol_type = protein
                       organism = synthetic construct
SEQUENCE: 678
KXEXXXWR                                                                  8

SEQ ID NO: 679         moltype = AA  length = 6
FEATURE                Location/Qualifiers
REGION                 1..6
                       note = Synthetic peptide
VARIANT                3
                       note = X can be N or T
VARIANT                5
                       note = X can be any amino acid
source                 1..6
                       mol_type = protein
                       organism = synthetic construct
SEQUENCE: 679
CHXGXC                                                                    6

SEQ ID NO: 680         moltype = AA  length = 5
FEATURE                Location/Qualifiers
REGION                 1..5
                       note = Synthetic peptide
source                 1..5
                       mol_type = protein
                       organism = synthetic construct
SEQUENCE: 680
HEPGD                                                                     5

SEQ ID NO: 681         moltype = AA  length = 5
FEATURE                Location/Qualifiers
REGION                 1..5
                       note = Synthetic peptide
source                 1..5
                       mol_type = protein
                       organism = synthetic construct
SEQUENCE: 681
REPGD                                                                     5

SEQ ID NO: 682         moltype = AA  length = 5
FEATURE                Location/Qualifiers
REGION                 1..5
                       note = Synthetic peptide
source                 1..5
                       mol_type = protein
                       organism = synthetic construct
SEQUENCE: 682
KEPGD                                                                     5

SEQ ID NO: 683         moltype = AA  length = 5
FEATURE                Location/Qualifiers
REGION                 1..5
                       note = Synthetic peptide
source                 1..5
                       mol_type = protein
                       organism = synthetic construct
SEQUENCE: 683
REPGD                                                                     5

SEQ ID NO: 684         moltype = AA  length = 9
FEATURE                Location/Qualifiers
REGION                 1..9
                       note = Synthetic peptide
```

```
source                       1..9
                             mol_type = protein
                             organism = synthetic construct
SEQUENCE: 684
CKKIVNETC                                                              9

SEQ ID NO: 685               moltype = AA  length = 5
FEATURE                      Location/Qualifiers
REGION                       1..5
                             note = Synthetic peptide
source                       1..5
                             mol_type = protein
                             organism = synthetic construct
SEQUENCE: 685
ESRSI                                                                  5

SEQ ID NO: 686               moltype = AA  length = 5
FEATURE                      Location/Qualifiers
REGION                       1..5
                             note = Synthetic peptide
source                       1..5
                             mol_type = protein
                             organism = synthetic construct
SEQUENCE: 686
ESRNI                                                                  5

SEQ ID NO: 687               moltype = AA  length = 6
FEATURE                      Location/Qualifiers
REGION                       1..6
                             note = Synthetic peptide
source                       1..6
                             mol_type = protein
                             organism = synthetic construct
SEQUENCE: 687
HPDVNL                                                                 6

SEQ ID NO: 688               moltype = AA  length = 6
FEATURE                      Location/Qualifiers
REGION                       1..6
                             note = Synthetic peptide
source                       1..6
                             mol_type = protein
                             organism = synthetic construct
SEQUENCE: 688
HPDGNL                                                                 6

SEQ ID NO: 689               moltype = AA  length = 6
FEATURE                      Location/Qualifiers
REGION                       1..6
                             note = Synthetic peptide
source                       1..6
                             mol_type = protein
                             organism = synthetic construct
SEQUENCE: 689
HPDKNL                                                                 6

SEQ ID NO: 690               moltype = AA  length = 6
FEATURE                      Location/Qualifiers
REGION                       1..6
                             note = Synthetic peptide
source                       1..6
                             mol_type = protein
                             organism = synthetic construct
SEQUENCE: 690
HPDEQL                                                                 6

SEQ ID NO: 691               moltype = AA  length = 6
FEATURE                      Location/Qualifiers
REGION                       1..6
                             note = Synthetic peptide
source                       1..6
                             mol_type = protein
                             organism = synthetic construct
SEQUENCE: 691
HPDTQL                                                                 6

SEQ ID NO: 692               moltype = AA  length = 6
FEATURE                      Location/Qualifiers
REGION                       1..6
```

```
                    note = Synthetic peptide
source              1..6
                    mol_type = protein
                    organism = synthetic construct
SEQUENCE: 692
RYCHFD                                                                          6

SEQ ID NO: 693      moltype = AA  length = 6
FEATURE             Location/Qualifiers
REGION              1..6
                    note = Synthetic peptide
source              1..6
                    mol_type = protein
                    organism = synthetic construct
SEQUENCE: 693
RYYHYD                                                                          6

SEQ ID NO: 694      moltype = AA  length = 6
FEATURE             Location/Qualifiers
REGION              1..6
                    note = Synthetic peptide
source              1..6
                    mol_type = protein
                    organism = synthetic construct
SEQUENCE: 694
RYKHFD                                                                          6

SEQ ID NO: 695      moltype = AA  length = 7
FEATURE             Location/Qualifiers
REGION              1..7
                    note = Synthetic peptide
source              1..7
                    mol_type = protein
                    organism = synthetic construct
SEQUENCE: 695
FSFRQQP                                                                         7

SEQ ID NO: 696      moltype = AA  length = 7
FEATURE             Location/Qualifiers
REGION              1..7
                    note = Synthetic peptide
source              1..7
                    mol_type = protein
                    organism = synthetic construct
SEQUENCE: 696
FAHRQQP                                                                         7

SEQ ID NO: 697      moltype = AA  length = 7
FEATURE             Location/Qualifiers
REGION              1..7
                    note = Synthetic peptide
source              1..7
                    mol_type = protein
                    organism = synthetic construct
SEQUENCE: 697
FAHRQRP                                                                         7

SEQ ID NO: 698      moltype = AA  length = 7
FEATURE             Location/Qualifiers
REGION              1..7
                    note = Synthetic peptide
source              1..7
                    mol_type = protein
                    organism = synthetic construct
SEQUENCE: 698
FATRQGP                                                                         7

SEQ ID NO: 699      moltype = AA  length = 5
FEATURE             Location/Qualifiers
REGION              1..5
                    note = Synthetic peptide
source              1..5
                    mol_type = protein
                    organism = synthetic construct
SEQUENCE: 699
QDPRN                                                                           5

SEQ ID NO: 700      moltype = AA  length = 7
FEATURE             Location/Qualifiers
```

```
REGION                    1..7
                          note = Synthetic peptide
source                    1..7
                          mol_type = protein
                          organism = synthetic construct
SEQUENCE: 700
LLQLNQQ                                                                  7

SEQ ID NO: 701            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 701
LSLMNQQ                                                                  7

SEQ ID NO: 702            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 702
LFWINQQ                                                                  7

SEQ ID NO: 703            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 703
LQKLNQQ                                                                  7

SEQ ID NO: 704            moltype = AA  length = 7
FEATURE                   Location/Qualifiers
REGION                    1..7
                          note = Synthetic peptide
source                    1..7
                          mol_type = protein
                          organism = synthetic construct
SEQUENCE: 704
LILLNQQ                                                                  7

SEQ ID NO: 705            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 705
APDGAF                                                                   6

SEQ ID NO: 706            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 706
VQDGAF                                                                   6

SEQ ID NO: 707            moltype = AA  length = 6
FEATURE                   Location/Qualifiers
REGION                    1..6
                          note = Synthetic peptide
source                    1..6
                          mol_type = protein
                          organism = synthetic construct
SEQUENCE: 707
ACDGAF                                                                   6

SEQ ID NO: 708            moltype = AA  length = 6
```

```
                        -continued

FEATURE                 Location/Qualifiers
REGION                  1..6
                        note = Synthetic peptide
source                  1..6
                        mol_type = protein
                        organism = synthetic construct
SEQUENCE: 708
AIDGAF                                                                   6

SEQ ID NO: 709          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 709
AIDGAF                                                                   6

SEQ ID NO: 710          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 710
CSLPES                                                                   6

SEQ ID NO: 711          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 711
CPLPET                                                                   6

SEQ ID NO: 712          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 712
CVLPES                                                                   6

SEQ ID NO: 713          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 713
CRLPET                                                                   6

SEQ ID NO: 714          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 714
CPLPET                                                                   6

SEQ ID NO: 715          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 715
CDLPET                                                                   6
```

```
SEQ ID NO: 716         moltype = AA   length = 7
FEATURE                Location/Qualifiers
REGION                 1..7
                       note = Synthetic peptide
source                 1..7
                       mol_type = protein
                       organism = synthetic construct
SEQUENCE: 716
FKKMQSK                                                                    7

SEQ ID NO: 717         moltype = AA   length = 7
FEATURE                Location/Qualifiers
REGION                 1..7
                       note = Synthetic peptide
source                 1..7
                       mol_type = protein
                       organism = synthetic construct
SEQUENCE: 717
FLFMQHK                                                                    7

SEQ ID NO: 718         moltype = AA   length = 6
FEATURE                Location/Qualifiers
REGION                 1..6
                       note = Synthetic peptide
source                 1..6
                       mol_type = protein
                       organism = synthetic construct
SEQUENCE: 718
GHSTLR                                                                     6

SEQ ID NO: 719         moltype = AA   length = 6
FEATURE                Location/Qualifiers
REGION                 1..6
                       note = Synthetic peptide
source                 1..6
                       mol_type = protein
                       organism = synthetic construct
SEQUENCE: 719
GHSALR                                                                     6

SEQ ID NO: 720         moltype = AA   length = 6
FEATURE                Location/Qualifiers
REGION                 1..6
                       note = Synthetic peptide
source                 1..6
                       mol_type = protein
                       organism = synthetic construct
SEQUENCE: 720
GHGTLR                                                                     6

SEQ ID NO: 721         moltype = AA   length = 6
FEATURE                Location/Qualifiers
REGION                 1..6
                       note = Synthetic peptide
source                 1..6
                       mol_type = protein
                       organism = synthetic construct
SEQUENCE: 721
GHGRLR                                                                     6

SEQ ID NO: 722         moltype = AA   length = 6
FEATURE                Location/Qualifiers
REGION                 1..6
                       note = Synthetic peptide
source                 1..6
                       mol_type = protein
                       organism = synthetic construct
SEQUENCE: 722
GHGFLR                                                                     6

SEQ ID NO: 723         moltype = AA   length = 9
FEATURE                Location/Qualifiers
REGION                 1..9
                       note = Synthetic peptide
source                 1..9
                       mol_type = protein
                       organism = synthetic construct
SEQUENCE: 723
WQIDYTSLV                                                                  9
```

```
SEQ ID NO: 724         moltype = AA  length = 5
FEATURE                Location/Qualifiers
REGION                 1..5
                       note = Synthetic peptide
source                 1..5
                       mol_type = protein
                       organism = synthetic construct
SEQUENCE: 724
FDFPR                                                                    5

SEQ ID NO: 725         moltype = AA  length = 5
FEATURE                Location/Qualifiers
REGION                 1..5
                       note = Synthetic peptide
source                 1..5
                       mol_type = protein
                       organism = synthetic construct
SEQUENCE: 725
FDYPR                                                                    5

SEQ ID NO: 726         moltype = AA  length = 5
FEATURE                Location/Qualifiers
REGION                 1..5
                       note = Synthetic peptide
source                 1..5
                       mol_type = protein
                       organism = synthetic construct
SEQUENCE: 726
FNYPR                                                                    5

SEQ ID NO: 727         moltype = AA  length = 5
FEATURE                Location/Qualifiers
REGION                 1..5
                       note = Synthetic peptide
source                 1..5
                       mol_type = protein
                       organism = synthetic construct
SEQUENCE: 727
PEFTS                                                                    5

SEQ ID NO: 728         moltype = AA  length = 8
FEATURE                Location/Qualifiers
REGION                 1..8
                       note = Synthetic peptide
source                 1..8
                       mol_type = protein
                       organism = synthetic construct
SEQUENCE: 728
YYQNGHEF                                                                 8

SEQ ID NO: 729         moltype = AA  length = 8
FEATURE                Location/Qualifiers
REGION                 1..8
                       note = Synthetic peptide
source                 1..8
                       mol_type = protein
                       organism = synthetic construct
SEQUENCE: 729
YHVNGHRF                                                                 8

SEQ ID NO: 730         moltype = AA  length = 7
FEATURE                Location/Qualifiers
REGION                 1..7
                       note = Synthetic peptide
source                 1..7
                       mol_type = protein
                       organism = synthetic construct
SEQUENCE: 730
LITGLPD                                                                  7

SEQ ID NO: 731         moltype = AA  length = 7
FEATURE                Location/Qualifiers
REGION                 1..7
                       note = Synthetic peptide
source                 1..7
                       mol_type = protein
                       organism = synthetic construct
SEQUENCE: 731
```

```
MYTGLPE                                                                     7

SEQ ID NO: 732         moltype = AA  length = 7
FEATURE                Location/Qualifiers
REGION                 1..7
                       note = Synthetic peptide
source                 1..7
                       mol_type = protein
                       organism = synthetic construct
SEQUENCE: 732
LWTGLEE                                                                     7

SEQ ID NO: 733         moltype = AA  length = 7
FEATURE                Location/Qualifiers
REGION                 1..7
                       note = Synthetic peptide
source                 1..7
                       mol_type = protein
                       organism = synthetic construct
SEQUENCE: 733
LLTGLAD                                                                     7

SEQ ID NO: 734         moltype = AA  length = 7
FEATURE                Location/Qualifiers
REGION                 1..7
                       note = Synthetic peptide
source                 1..7
                       mol_type = protein
                       organism = synthetic construct
SEQUENCE: 734
LLTGLLD                                                                     7

SEQ ID NO: 735         moltype = AA  length = 7
FEATURE                Location/Qualifiers
REGION                 1..7
                       note = Synthetic peptide
source                 1..7
                       mol_type = protein
                       organism = synthetic construct
SEQUENCE: 735
MDTGLVD                                                                     7

SEQ ID NO: 736         moltype = AA  length = 6
FEATURE                Location/Qualifiers
REGION                 1..6
                       note = Synthetic peptide
source                 1..6
                       mol_type = protein
                       organism = synthetic construct
SEQUENCE: 736
MRLGYY                                                                      6

SEQ ID NO: 737         moltype = AA  length = 6
FEATURE                Location/Qualifiers
REGION                 1..6
                       note = Synthetic peptide
source                 1..6
                       mol_type = protein
                       organism = synthetic construct
SEQUENCE: 737
MPTGGH                                                                      6

SEQ ID NO: 738         moltype = AA  length = 6
FEATURE                Location/Qualifiers
REGION                 1..6
                       note = Synthetic peptide
source                 1..6
                       mol_type = protein
                       organism = synthetic construct
SEQUENCE: 738
LQTGTL                                                                      6

SEQ ID NO: 739         moltype = AA  length = 6
FEATURE                Location/Qualifiers
REGION                 1..6
                       note = Synthetic peptide
source                 1..6
                       mol_type = protein
                       organism = synthetic construct
```

-continued

```
SEQUENCE: 739
LQTGKL                                                                          6

SEQ ID NO: 740          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 740
FQTGDI                                                                          6

SEQ ID NO: 741          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 741
CGAFE                                                                           5

SEQ ID NO: 742          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 742
CGVFQ                                                                           5

SEQ ID NO: 743          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 743
SNRVASFL                                                                        8

SEQ ID NO: 744          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 744
SNKAARQM                                                                        8

SEQ ID NO: 745          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 745
SNSAAVDL                                                                        8

SEQ ID NO: 746          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 746
SNDVAKII                                                                        8

SEQ ID NO: 747          moltype = AA  length = 8
FEATURE                 Location/Qualifiers
REGION                  1..8
                        note = Synthetic peptide
source                  1..8
                        mol_type = protein
```

```
                        organism = synthetic construct
SEQUENCE: 747
SNAVAQVL                                                                            8

SEQ ID NO: 748          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 748
SNNVAFEI                                                                            8

SEQ ID NO: 749          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 749
PTGLDHHR                                                                            8

SEQ ID NO: 750          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 750
PTYLIHER                                                                            8

SEQ ID NO: 751          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 751
ICNDSSRRC                                                                           9

SEQ ID NO: 752          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 752
ACNGHSITC                                                                           9

SEQ ID NO: 753          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 753
VCNGHADTC                                                                           9

SEQ ID NO: 754          moltype = AA  length = 9
FEATURE                 Location/Qualifiers
REGION                  1..9
                        note = Synthetic peptide
source                  1..9
                        mol_type = protein
                        organism = synthetic construct
SEQUENCE: 754
ACNGEHSQC                                                                           9

SEQ ID NO: 755          moltype = AA  length = 5
FEATURE                 Location/Qualifiers
REGION                  1..5
                        note = Synthetic peptide
source                  1..5
```

```
                        mol_type = protein
                        organism = synthetic construct
SEQUENCE: 755
RNPSL                                                                    5

SEQ ID NO: 756          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 756
KNPSL                                                                    5

SEQ ID NO: 757          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 757
GLTFQAD                                                                  7

SEQ ID NO: 758          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 758
GLQFAFD                                                                  7

SEQ ID NO: 759          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 759
GMKFTRD                                                                  7

SEQ ID NO: 760          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 760
GLQFPSD                                                                  7

SEQ ID NO: 761          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 761
GLKFSPD                                                                  7

SEQ ID NO: 762          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 762
GLTFTPD                                                                  7

SEQ ID NO: 763          moltype = AA  length = 6
FEATURE                 Location/Qualifiers
REGION                  1..6
                        note = Synthetic peptide
```

```
source                     1..6
                           mol_type = protein
                           organism = synthetic construct
SEQUENCE: 763
APMDAN                                                                  6

SEQ ID NO: 764             moltype = AA  length = 6
FEATURE                    Location/Qualifiers
REGION                     1..6
                           note = Synthetic peptide
source                     1..6
                           mol_type = protein
                           organism = synthetic construct
SEQUENCE: 764
IPMDPN                                                                  6

SEQ ID NO: 765             moltype = AA  length = 6
FEATURE                    Location/Qualifiers
REGION                     1..6
                           note = Synthetic peptide
source                     1..6
                           mol_type = protein
                           organism = synthetic construct
SEQUENCE: 765
APMPKN                                                                  6

SEQ ID NO: 766             moltype = AA  length = 6
FEATURE                    Location/Qualifiers
REGION                     1..6
                           note = Synthetic peptide
source                     1..6
                           mol_type = protein
                           organism = synthetic construct
SEQUENCE: 766
APMFKN                                                                  6

SEQ ID NO: 767             moltype = AA  length = 7
FEATURE                    Location/Qualifiers
REGION                     1..7
                           note = Synthetic peptide
source                     1..7
                           mol_type = protein
                           organism = synthetic construct
SEQUENCE: 767
FLFMQHK                                                                 7

SEQ ID NO: 768             moltype = AA  length = 7
FEATURE                    Location/Qualifiers
REGION                     1..7
                           note = Synthetic peptide
source                     1..7
                           mol_type = protein
                           organism = synthetic construct
SEQUENCE: 768
FFDMETK                                                                 7

SEQ ID NO: 769             moltype = AA  length = 7
FEATURE                    Location/Qualifiers
REGION                     1..7
                           note = Synthetic peptide
source                     1..7
                           mol_type = protein
                           organism = synthetic construct
SEQUENCE: 769
FEEMQTK                                                                 7

SEQ ID NO: 770             moltype = AA  length = 6
FEATURE                    Location/Qualifiers
REGION                     1..6
                           note = Synthetic peptide
source                     1..6
                           mol_type = protein
                           organism = synthetic construct
SEQUENCE: 770
CHTGPC                                                                  6

SEQ ID NO: 771             moltype = AA  length = 7
FEATURE                    Location/Qualifiers
REGION                     1..7
```

```
                        note = Synthetic peptide
VARIANT                 1
                        note = X can be V or I
VARIANT                 5
                        note = X can be any amino acid
VARIANT                 7
                        note = X can be S or A
source                  1..7
                        mol_type = protein
                        organism = synthetic construct
SEQUENCE: 771
XPEFXGX                                                                       7

SEQ ID NO: 772          moltype = AA  length = 7
FEATURE                 Location/Qualifiers
source                  1..7
                        mol_type = protein
                        organism = synthetic construct
VARIANT                 2
                        note = I can be replaced by V or M
VARIANT                 6
                        note = L can be replaced by M
VARIANT                 4..5
                        note = X can be any amino acid
SEQUENCE: 772
YIDXXLN                                                                       7

SEQ ID NO: 773          moltype = AA  length = 5
FEATURE                 Location/Qualifiers
REGION                  1..5
                        note = Synthetic peptide
source                  1..5
                        mol_type = protein
                        organism = synthetic construct
SEQUENCE: 773
DDKGK                                                                         5

SEQ ID NO: 774          moltype = AA  length = 6
FEATURE                 Location/Qualifiers
REGION                  1..6
                        note = Synthetic peptide
VARIANT                 2
                        note = X can be any amino acid
source                  1..6
                        mol_type = protein
                        organism = synthetic construct
SEQUENCE: 774
KXPEEP                                                                        6

SEQ ID NO: 775          moltype = AA  length = 6
FEATURE                 Location/Qualifiers
REGION                  1..6
                        note = Synthetic peptide
VARIANT                 1
                        note = X can be L or M
VARIANT                 2
                        note = X can be any amino acid
source                  1..6
                        mol_type = protein
                        organism = synthetic construct
SEQUENCE: 775
XXLPDK                                                                        6

SEQ ID NO: 776          moltype = AA  length = 6
FEATURE                 Location/Qualifiers
source                  1..6
                        mol_type = protein
                        organism = synthetic construct
VARIANT                 3..4
                        note = X can be any amino acid
VARIANT                 1
                        note = I can be replaced by V or Y
SEQUENCE: 776
IDXXGN                                                                        6

SEQ ID NO: 777          moltype = AA  length = 6
FEATURE                 Location/Qualifiers
source                  1..6
                        mol_type = protein
```

```
                        organism = synthetic construct
VARIANT                 2..4
                        note = V can be replaced by I
SEQUENCE: 777
EVVVDK                                                              6

SEQ ID NO: 778          moltype = AA   length = 6
FEATURE                 Location/Qualifiers
REGION                  1..6
                        note = Synthetic peptide
VARIANT                 1
                        note = X can be M or L
VARIANT                 2
                        note = X can be W or Y
source                  1..6
                        mol_type = protein
                        organism = synthetic construct
SEQUENCE: 778
XXWMDK                                                              6

SEQ ID NO: 779          moltype = AA   length = 4
FEATURE                 Location/Qualifiers
REGION                  1..4
                        note = Synthetic peptide
source                  1..4
                        mol_type = protein
                        organism = synthetic construct
SEQUENCE: 779
NPVE                                                                4

SEQ ID NO: 780          moltype = AA   length = 6
FEATURE                 Location/Qualifiers
REGION                  1..6
                        note = Synthetic peptide
VARIANT                 4..5
                        note = X can be any amino acid
source                  1..6
                        mol_type = protein
                        organism = synthetic construct
SEQUENCE: 780
CMNXXC                                                              6

SEQ ID NO: 781          moltype = AA   length = 6
FEATURE                 Location/Qualifiers
source                  1..6
                        mol_type = protein
                        organism = synthetic construct
VARIANT                 1
                        note = R can be replaced by K
VARIANT                 4
                        note = M can be replaced by L
VARIANT                 3
                        note = X can be any amino acid
SEQUENCE: 781
RDXMGR                                                              6

SEQ ID NO: 782          moltype = AA   length = 8
FEATURE                 Location/Qualifiers
source                  1..8
                        mol_type = protein
                        organism = synthetic construct
VARIANT                 2..3
                        note = X can be any amino acid
VARIANT                 5
                        note = X can be any amino acid
VARIANT                 1
                        note = I can be replaced by V
VARIANT                 7
                        note = D can be replaced by E
SEQUENCE: 782
IXXPXYDK                                                            8

SEQ ID NO: 783          moltype = AA   length = 7
FEATURE                 Location/Qualifiers
REGION                  1..7
                        note = Synthetic peptide
VARIANT                 2
                        note = X can be any amino acid
VARIANT                 4
```

```
                        note = X can be T or V
VARIANT                 6
                        note = X can be any amino acid
source                  1..7
                        mol_type = protein
                        organism = synthetic construct
SEQUENCE: 783
PXGXLXK                                                                    7

SEQ ID NO: 784          moltype = AA  length = 8
FEATURE                 Location/Qualifiers
REGION                  1..8
                        note = Synthetic peptide
VARIANT                 1
                        note = X can be V or I
VARIANT                 2..3
                        note = X can be any amino acid
VARIANT                 6
                        note = X can be any amino acid
source                  1..8
                        mol_type = protein
                        organism = synthetic construct
SEQUENCE: 784
XXXQPXKP                                                                   8

SEQ ID NO: 785          moltype = AA  length = 5
FEATURE                 Location/Qualifiers
source                  1..5
                        mol_type = protein
                        organism = synthetic construct
VARIANT                 5
                        note = R can be replaced by K
VARIANT                 3
                        note = X can be any amino acid
SEQUENCE: 785
DTXPR                                                                      5

SEQ ID NO: 786          moltype = AA  length = 10
FEATURE                 Location/Qualifiers
REGION                  1..10
                        note = Synthetic peptide
VARIANT                 2..3
                        note = X can be any amino acid
VARIANT                 6..7
                        note = X can be any amino acid
VARIANT                 9
                        note = X can be any amino acid
source                  1..10
                        mol_type = protein
                        organism = synthetic construct
SEQUENCE: 786
CXXPWXXEXC                                                                10

SEQ ID NO: 787          moltype = AA  length = 7
FEATURE                 Location/Qualifiers
REGION                  1..7
                        note = Synthetic peptide
VARIANT                 2
                        note = X can be W or F
VARIANT                 3
                        note = X can be any amino acid
VARIANT                 4
                        note = X can be Q, I or V
source                  1..7
                        mol_type = protein
                        organism = synthetic construct
SEQUENCE: 787
WXXXPDK                                                                    7

SEQ ID NO: 788          moltype = AA  length = 4
FEATURE                 Location/Qualifiers
REGION                  1..4
                        note = Synthetic peptide
source                  1..4
                        mol_type = protein
                        organism = synthetic construct
SEQUENCE: 788
PPWW                                                                       4
```

```
SEQ ID NO: 789        moltype = AA   length = 4
FEATURE               Location/Qualifiers
source                1..4
                      mol_type = protein
                      organism = synthetic construct
VARIANT               3
                      note = K can be replaced by R
SEQUENCE: 789
JNKP                                                                       4

SEQ ID NO: 790        moltype = AA   length = 8
FEATURE               Location/Qualifiers
source                1..8
                      mol_type = protein
                      organism = synthetic construct
VARIANT               6
                      note = H can be replaced by P
VARIANT               3
                      note = X can be any amino acid
VARIANT               5
                      note = X can be any amino acid
VARIANT               7
                      note = X can be any amino acid
SEQUENCE: 790
PJXNXHXW                                                                   8

SEQ ID NO: 791        moltype = AA   length = 7
FEATURE               Location/Qualifiers
source                1..7
                      mol_type = protein
                      organism = synthetic construct
VARIANT               2
                      note = X can be any amino acid
VARIANT               4..5
                      note = X can be any amino acid
VARIANT               1
                      note = F can be replaced by Y
VARIANT               6
                      note = L can be replaced by I or M
SEQUENCE: 791
FXHXXLN                                                                    7

SEQ ID NO: 792        moltype = AA   length = 8
FEATURE               Location/Qualifiers
REGION                1..8
                      note = Synthetic peptide
VARIANT               1
                      note = X can be P or W
VARIANT               3..4
                      note = X can be any amino acid
source                1..8
                      mol_type = protein
                      organism = synthetic construct
SEQUENCE: 792
XFXXMBKP                                                                   8

SEQ ID NO: 793        moltype = AA   length = 5
FEATURE               Location/Qualifiers
REGION                1..5
                      note = Synthetic peptide
VARIANT               2
                      note = X can be F, Y or W
source                1..5
                      mol_type = protein
                      organism = synthetic construct
SEQUENCE: 793
KXTHP                                                                      5

SEQ ID NO: 794        moltype = AA   length = 7
FEATURE               Location/Qualifiers
source                1..7
                      mol_type = protein
                      organism = synthetic construct
VARIANT               7
                      note = W can be replaced by Y
VARIANT               2
                      note = X can be any amino acid
VARIANT               5..6
                      note = X can be any amino acid
```

```
SEQUENCE: 794
YXPTXXW                                                                  7

SEQ ID NO: 795          moltype = AA  length = 8
FEATURE                 Location/Qualifiers
REGION                  1..8
                        note = Synthetic peptide
VARIANT                 2
                        note = X can be any amino acid
VARIANT                 5
                        note = X can be any amino acid
VARIANT                 7
                        note = X can be L, M or I
VARIANT                 8
                        note = X can be L, V or I
source                  1..8
                        mol_type = protein
                        organism = synthetic construct
SEQUENCE: 795
PXAIXDXX                                                                 8

SEQ ID NO: 796          moltype = AA  length = 7
FEATURE                 Location/Qualifiers
source                  1..7
                        mol_type = protein
                        organism = synthetic construct
VARIANT                 2
                        note = X can be any amino acid
VARIANT                 4..5
                        note = X can be any amino acid
VARIANT                 6
                        note = L can be replaced by M
SEQUENCE: 796
YXDXXLM                                                                  7

SEQ ID NO: 797          moltype = AA  length = 6
FEATURE                 Location/Qualifiers
source                  1..6
                        mol_type = protein
                        organism = synthetic construct
VARIANT                 2
                        note = W can be replaced by N
VARIANT                 4
                        note = W can be replaced by R
VARIANT                 3
                        note = X can be any amino acid
VARIANT                 5
                        note = X can be any amino acid
SEQUENCE: 797
CWXWXC                                                                   6

SEQ ID NO: 798          moltype = AA  length = 8
FEATURE                 Location/Qualifiers
REGION                  1..8
                        note = Synthetic peptide
VARIANT                 2
                        note = X can be any amino acid
VARIANT                 6..7
                        note = X can be any amino acid
source                  1..8
                        mol_type = protein
                        organism = synthetic construct
SEQUENCE: 798
KXDPDXXW                                                                 8

SEQ ID NO: 799          moltype = AA  length = 6
FEATURE                 Location/Qualifiers
source                  1..6
                        mol_type = protein
                        organism = synthetic construct
VARIANT                 1
                        note = R can be replaced by K
VARIANT                 3
                        note = Y can be replaced by F
VARIANT                 4
                        note = L can be replaced by I, V or M
VARIANT                 6
                        note = E can be replaced by D
SEQUENCE: 799
```

```
RCYLCE                                                                                6

SEQ ID NO: 800          moltype = AA  length = 5
FEATURE                 Location/Qualifiers
REGION                  1..5
                        note = Synthetic peptide
VARIANT                 5
                        note = X can be D or E
source                  1..5
                        mol_type = protein
                        organism = synthetic construct
SEQUENCE: 800
WCWKX                                                                                 5

SEQ ID NO: 801          moltype = AA  length = 6
FEATURE                 Location/Qualifiers
source                  1..6
                        mol_type = protein
                        organism = synthetic construct
VARIANT                 1
                        note = V can be replaced by I
VARIANT                 3
                        note = L can be replaced by F or M
VARIANT                 2
                        note = X can be any amino acid
SEQUENCE: 801
VXLPHW                                                                                6

SEQ ID NO: 802          moltype = AA  length = 7
FEATURE                 Location/Qualifiers
source                  1..7
                        mol_type = protein
                        organism = synthetic construct
VARIANT                 2
                        note = X can be any amino acid
VARIANT                 5..6
                        note = X can be any amino acid
VARIANT                 4
                        note = S can be replaced by T
SEQUENCE: 802
PXLSXXE                                                                               7

SEQ ID NO: 803          moltype = AA  length = 9
FEATURE                 Location/Qualifiers
source                  1..9
                        mol_type = protein
                        organism = synthetic construct
VARIANT                 3
                        note = I can be replaced by V
VARIANT                 9
                        note = F can be replaced by W
VARIANT                 2
                        note = X can be any amino acid
VARIANT                 4
                        note = X can be any amino acid
VARIANT                 6..7
                        note = X can be any amino acid
SEQUENCE: 803
PXIXEXXMF                                                                             9

SEQ ID NO: 804          moltype = AA  length = 7
FEATURE                 Location/Qualifiers
REGION                  1..7
                        note = Synthetic peptide
VARIANT                 5..6
                        note = X can be any amino acid
VARIANT                 7
                        note = X can be W or F
source                  1..7
                        mol_type = protein
                        organism = synthetic construct
SEQUENCE: 804
DPYQXXX                                                                               7

SEQ ID NO: 805          moltype = AA  length = 8
FEATURE                 Location/Qualifiers
source                  1..8
                        mol_type = protein
                        organism = synthetic construct
```

```
VARIANT                     1
                            note = V can be replaced by I
VARIANT                     3
                            note = X can be any amino acid
VARIANT                     5..7
                            note = X can be any amino acid
SEQUENCE: 805
VPXLXXXE                                                                                     8

SEQ ID NO: 806              moltype = AA   length = 4
FEATURE                     Location/Qualifiers
REGION                      1..4
                            note = Synthetic peptide
source                      1..4
                            mol_type = protein
                            organism = synthetic construct
SEQUENCE: 806
YNPF                                                                                         4

SEQ ID NO: 807              moltype = AA   length = 6
FEATURE                     Location/Qualifiers
REGION                      1..6
                            note = Synthetic peptide
VARIANT                     3
                            note = X can be any amino acid
source                      1..6
                            mol_type = protein
                            organism = synthetic construct
SEQUENCE: 807
PVXFBK                                                                                       6

SEQ ID NO: 808              moltype = AA   length = 6
FEATURE                     Location/Qualifiers
REGION                      1..6
                            note = Synthetic peptide
VARIANT                     2..3
                            note = X can be any amino acid
source                      1..6
                            mol_type = protein
                            organism = synthetic construct
SEQUENCE: 808
PXXFYN                                                                                       6

SEQ ID NO: 809              moltype = AA   length = 6
FEATURE                     Location/Qualifiers
REGION                      1..6
                            note = Synthetic peptide
VARIANT                     3..4
                            note = X can be any amino acid
source                      1..6
                            mol_type = protein
                            organism = synthetic construct
SEQUENCE: 809
PYXXYQ                                                                                       6

SEQ ID NO: 810              moltype = AA   length = 5
FEATURE                     Location/Qualifiers
source                      1..5
                            mol_type = protein
                            organism = synthetic construct
VARIANT                     1
                            note = R can be replaced by H
VARIANT                     2
                            note = R can be replaced by K
VARIANT                     3
                            note = P can be replaced by W
SEQUENCE: 810
RRPFF                                                                                        5

SEQ ID NO: 811              moltype = AA   length = 6
FEATURE                     Location/Qualifiers
REGION                      1..6
                            note = Synthetic peptide
VARIANT                     2
                            note = X can be any amino acid
VARIANT                     5
                            note = X can be any amino acid
source                      1..6
                            mol_type = protein
```

```
                        organism = synthetic construct
SEQUENCE: 811
KXRPXW                                                                          6

SEQ ID NO: 812          moltype = AA  length = 8
FEATURE                 Location/Qualifiers
REGION                  1..8
                        note = Synthetic peptide
VARIANT                 2
                        note = X can be any amino acid
VARIANT                 5..7
                        note = X can be any amino acid
source                  1..8
                        mol_type = protein
                        organism = synthetic construct
SEQUENCE: 812
CXNWXXXC                                                                        8

SEQ ID NO: 813          moltype = AA  length = 7
FEATURE                 Location/Qualifiers
REGION                  1..7
                        note = Synthetic peptide
VARIANT                 2
                        note = X can be I, W, M or L
VARIANT                 4..5
                        note = X can be any amino acid
source                  1..7
                        mol_type = protein
                        organism = synthetic construct
SEQUENCE: 813
CXNXXDC                                                                         7

SEQ ID NO: 814          moltype = AA  length = 7
FEATURE                 Location/Qualifiers
REGION                  1..7
                        note = Synthetic peptide
VARIANT                 2
                        note = X can be any amino acid
VARIANT                 4
                        note = X can be any amino acid
VARIANT                 6
                        note = X can be any amino acid
source                  1..7
                        mol_type = protein
                        organism = synthetic construct
SEQUENCE: 814
KXDXMXN                                                                         7

SEQ ID NO: 815          moltype = AA  length = 8
FEATURE                 Location/Qualifiers
REGION                  1..8
                        note = Synthetic peptide
VARIANT                 2
                        note = X can be any amino acid
VARIANT                 4..5
                        note = X can be any amino acid
VARIANT                 7
                        note = X can be any amino acid
source                  1..8
                        mol_type = protein
                        organism = synthetic construct
SEQUENCE: 815
WXKXXGXW                                                                        8

SEQ ID NO: 816          moltype = AA  length = 7
FEATURE                 Location/Qualifiers
REGION                  1..7
                        note = Synthetic peptide
VARIANT                 2
                        note = X can be any amino acid
VARIANT                 5
                        note = X can be S or A
source                  1..7
                        mol_type = protein
                        organism = synthetic construct
SEQUENCE: 816
PXDTXPR                                                                         7

SEQ ID NO: 817          moltype = AA  length = 6
```

```
FEATURE              Location/Qualifiers
REGION               1..6
                     note = Synthetic peptide
VARIANT              4
                     note = X can be Y, F or W
VARIANT              5
                     note = X can be L or M
source               1..6
                     mol_type = protein
                     organism = synthetic construct
SEQUENCE: 817
PPTXXG                                                                   6

SEQ ID NO: 818       moltype = AA   length = 7
FEATURE              Location/Qualifiers
source               1..7
                     mol_type = protein
                     organism = synthetic construct
VARIANT              1
                     note = Y can be replaced by F
VARIANT              3
                     note = Y can be replaced by F
VARIANT              2
                     note = X can be any amino acid
VARIANT              4..5
                     note = X can be any amino acid
SEQUENCE: 818
YXYXXFN                                                                  7

SEQ ID NO: 819       moltype = AA   length = 9
FEATURE              Location/Qualifiers
REGION               1..9
                     note = Synthetic peptide
VARIANT              1
                     note = X can be L or M
VARIANT              2..3
                     note = X can be any amino acid
VARIANT              7
                     note = X can be any amino acid
source               1..9
                     mol_type = protein
                     organism = synthetic construct
SEQUENCE: 819
XXXGWNXKP                                                                9

SEQ ID NO: 820       moltype = AA   length = 7
FEATURE              Location/Qualifiers
REGION               1..7
                     note = Synthetic peptide
VARIANT              2
                     note = X can be any amino acid
VARIANT              3
                     note = X can be I, V or F
VARIANT              5
                     note = X can be any amino acid
source               1..7
                     mol_type = protein
                     organism = synthetic construct
SEQUENCE: 820
KXXPXYL                                                                  7

SEQ ID NO: 821       moltype = AA   length = 7
FEATURE              Location/Qualifiers
source               1..7
                     mol_type = protein
                     organism = synthetic construct
VARIANT              2..3
                     note = X can be any amino acid
VARIANT              4
                     note = I can be replaced by V
VARIANT              7
                     note = M can be replaced by L
SEQUENCE: 821
YXXIPWM                                                                  7

SEQ ID NO: 822       moltype = AA   length = 5
FEATURE              Location/Qualifiers
REGION               1..5
                     note = Synthetic peptide
```

```
source                     1..5
                           mol_type = protein
                           organism = synthetic construct
SEQUENCE: 822
GAGGG                                                                5

SEQ ID NO: 823             moltype = AA  length = 8
FEATURE                    Location/Qualifiers
source                     1..8
                           mol_type = protein
                           organism = synthetic construct
VARIANT                    2
                           note = X can be any amino acid
VARIANT                    4
                           note = X can be any amino acid
VARIANT                    6..7
                           note = X can be any amino acid
SEQUENCE: 823
CXBXPXXC                                                             8

SEQ ID NO: 824             moltype = AA  length = 6
FEATURE                    Location/Qualifiers
source                     1..6
                           mol_type = protein
                           organism = synthetic construct
VARIANT                    2
                           note = X can be any amino acid
VARIANT                    4
                           note = M can be replaced by L
VARIANT                    5
                           note = F can be replaced by M or Y
SEQUENCE: 824
HXPMFY                                                               6

SEQ ID NO: 825             moltype = AA  length = 6
FEATURE                    Location/Qualifiers
REGION                     1..6
                           note = Synthetic peptide
VARIANT                    5
                           note = X can be S or G
source                     1..6
                           mol_type = protein
                           organism = synthetic construct
SEQUENCE: 825
PDDIXK                                                               6

SEQ ID NO: 826             moltype = AA  length = 7
FEATURE                    Location/Qualifiers
REGION                     1..7
                           note = Synthetic peptide
VARIANT                    3..4
                           note = X can be any amino acid
source                     1..7
                           mol_type = protein
                           organism = synthetic construct
SEQUENCE: 826
FPXXWYP                                                              7

SEQ ID NO: 827             moltype = AA  length = 5
FEATURE                    Location/Qualifiers
REGION                     1..5
                           note = Synthetic peptide
VARIANT                    4
                           note = X can be any amino acid
source                     1..5
                           mol_type = protein
                           organism = synthetic construct
SEQUENCE: 827
DMNXH                                                                5

SEQ ID NO: 828             moltype = AA  length = 7
FEATURE                    Location/Qualifiers
source                     1..7
                           mol_type = protein
                           organism = synthetic construct
VARIANT                    1
                           note = K can be replaced by R
VARIANT                    2
                           note = L can be replaced by M or I
```

```
VARIANT                   7
                          note = S can be replaced by N
VARIANT                   4
                          note = X can be any amino acid
SEQUENCE: 828
KLVXQSS                                                                     7

SEQ ID NO: 829            moltype = AA   length = 6
FEATURE                   Location/Qualifiers
REGION                    1..6
                          note = Synthetic peptide
VARIANT                   3..4
                          note = X can be any amino acid
source                    1..6
                          mol_type = protein
                          organism = synthetic construct
SEQUENCE: 829
WDXXDG                                                                      6

SEQ ID NO: 830            moltype = AA   length = 8
FEATURE                   Location/Qualifiers
source                    1..8
                          mol_type = protein
                          organism = synthetic construct
VARIANT                   2..3
                          note = X can be any amino acid
VARIANT                   5..6
                          note = X can be any amino acid
VARIANT                   8
                          note = T can be replaced by S
SEQUENCE: 830
PXXNXXJT                                                                    8

SEQ ID NO: 831            moltype = AA   length = 6
FEATURE                   Location/Qualifiers
REGION                    1..6
                          note = Synthetic peptide
VARIANT                   1
                          note = X can be V, M or I
VARIANT                   5
                          note = X can be any amino acid
source                    1..6
                          mol_type = protein
                          organism = synthetic construct
SEQUENCE: 831
XVPEXK                                                                      6

SEQ ID NO: 832            moltype = AA   length = 8
FEATURE                   Location/Qualifiers
source                    1..8
                          mol_type = protein
                          organism = synthetic construct
VARIANT                   3
                          note = V can be replaced by I
VARIANT                   4
                          note = F can be replaced by Y or W
VARIANT                   2
                          note = X can be any amino acid
VARIANT                   5
                          note = X can be any amino acid
VARIANT                   7
                          note = X can be any amino acid
SEQUENCE: 832
PXVFXNXP                                                                    8

SEQ ID NO: 833            moltype = AA   length = 5
FEATURE                   Location/Qualifiers
source                    1..5
                          mol_type = protein
                          organism = synthetic construct
VARIANT                   4
                          note = K can be replaced by R
VARIANT                   5
                          note = H can be replaced by Y
SEQUENCE: 833
SGPKH                                                                       5

SEQ ID NO: 834            moltype = AA   length = 6
FEATURE                   Location/Qualifiers
```

```
REGION                 1..6
                       note = Synthetic peptide
VARIANT                2..3
                       note = X can be any amino acid
source                 1..6
                       mol_type = protein
                       organism = synthetic construct
SEQUENCE: 834
KXXFPQ                                                              6

SEQ ID NO: 835         moltype = AA   length = 7
FEATURE                Location/Qualifiers
REGION                 1..7
                       note = Synthetic peptide
VARIANT                3..4
                       note = X can be any amino acid
VARIANT                6
                       note = X can be any amino acid
source                 1..7
                       mol_type = protein
                       organism = synthetic construct
SEQUENCE: 835
PDXXWXK                                                             7

SEQ ID NO: 836         moltype = AA   length = 5
FEATURE                Location/Qualifiers
source                 1..5
                       mol_type = protein
                       organism = synthetic construct
VARIANT                3
                       note = L can be replaced by M
VARIANT                4
                       note = F can be replaced by M
SEQUENCE: 836
QPLFY                                                               5

SEQ ID NO: 837         moltype = AA   length = 7
FEATURE                Location/Qualifiers
REGION                 1..7
                       note = Synthetic peptide
VARIANT                1
                       note = X can be Y or F
VARIANT                2
                       note = X can be any amino acid
VARIANT                5
                       note = X can be F, Y or M
source                 1..7
                       mol_type = protein
                       organism = synthetic construct
SEQUENCE: 837
XXCTXMC                                                             7

SEQ ID NO: 838         moltype = AA   length = 8
FEATURE                Location/Qualifiers
source                 1..8
                       mol_type = protein
                       organism = synthetic construct
VARIANT                1
                       note = F can be replaced by W
VARIANT                6
                       note = L can be replaced by M or I
VARIANT                7
                       note = Q can be replaced by N
VARIANT                8
                       note = R can be replaced by K
VARIANT                2
                       note = X can be any amino acid
VARIANT                4..5
                       note = X can be any amino acid
SEQUENCE: 838
FXPXXLQR                                                            8

SEQ ID NO: 839         moltype = AA   length = 6
FEATURE                Location/Qualifiers
source                 1..6
                       mol_type = protein
                       organism = synthetic construct
VARIANT                5
                       note = X can be any amino acid
```

```
VARIANT                 1
                        note = I can be replaced by V
VARIANT                 6
                        note = P can be replaced by C
SEQUENCE: 839
ICWSXP                                                                          6

SEQ ID NO: 840          moltype = AA   length = 6
FEATURE                 Location/Qualifiers
REGION                  1..6
                        note = Synthetic peptide
VARIANT                 3
                        note = X can be any amino acid
VARIANT                 5
                        note = X can be V or I
source                  1..6
                        mol_type = protein
                        organism = synthetic construct
SEQUENCE: 840
PDXPXS                                                                          6

SEQ ID NO: 841          moltype = AA   length = 7
FEATURE                 Location/Qualifiers
REGION                  1..7
                        note = Synthetic peptide
VARIANT                 3
                        note = X can be any amino acid
VARIANT                 5
                        note = X can be any amino acid
source                  1..7
                        mol_type = protein
                        organism = synthetic construct
SEQUENCE: 841
PJXGXPW                                                                         7

SEQ ID NO: 842          moltype = AA   length = 6
FEATURE                 Location/Qualifiers
REGION                  1..6
                        note = Synthetic peptide
VARIANT                 5
                        note = X can be any amino acid
VARIANT                 6
                        note = X can be Y, M or L
source                  1..6
                        mol_type = protein
                        organism = synthetic construct
SEQUENCE: 842
ELPRXX                                                                          6

SEQ ID NO: 843          moltype = AA   length = 6
FEATURE                 Location/Qualifiers
REGION                  1..6
                        note = Synthetic peptide
VARIANT                 6
                        note = X can be D or W
source                  1..6
                        mol_type = protein
                        organism = synthetic construct
SEQUENCE: 843
PESHNX                                                                          6

SEQ ID NO: 844          moltype = AA   length = 7
FEATURE                 Location/Qualifiers
source                  1..7
                        mol_type = protein
                        organism = synthetic construct
VARIANT                 2..3
                        note = X can be any amino acid
VARIANT                 6
                        note = X can be any amino acid
VARIANT                 7
                        note = Y can be replaced by W
SEQUENCE: 844
YXXTLXY                                                                         7

SEQ ID NO: 845          moltype = AA   length = 6
FEATURE                 Location/Qualifiers
source                  1..6
                        mol_type = protein
```

```
                        organism = synthetic construct
VARIANT                 1
                        note = V can be replaced by I
VARIANT                 2
                        note = X can be any amino acid
VARIANT                 5
                        note = X can be any amino acid
SEQUENCE: 845
VXWNXP                                                                    6

SEQ ID NO: 846          moltype = AA  length = 7
FEATURE                 Location/Qualifiers
source                  1..7
                        mol_type = protein
                        organism = synthetic construct
VARIANT                 2
                        note = W can be replaced by Y or F
VARIANT                 7
                        note = G can be replaced by P
VARIANT                 4..5
                        note = X can be any amino acid
SEQUENCE: 846
GWDXXDG                                                                   7

SEQ ID NO: 847          moltype = AA  length = 7
FEATURE                 Location/Qualifiers
REGION                  1..7
                        note = Synthetic peptide
VARIANT                 2
                        note = X can be any amino acid
VARIANT                 3
                        note = X can be T,S or N
VARIANT                 7
                        note = X can be E or D
source                  1..7
                        mol_type = protein
                        organism = synthetic construct
SEQUENCE: 847
KXXHPGX                                                                   7

SEQ ID NO: 848          moltype = AA  length = 5
FEATURE                 Location/Qualifiers
REGION                  1..5
                        note = Synthetic peptide
VARIANT                 3
                        note = X can be any amino acid
source                  1..5
                        mol_type = protein
                        organism = synthetic construct
SEQUENCE: 848
MMXHI                                                                     5

SEQ ID NO: 849          moltype = AA  length = 7
FEATURE                 Location/Qualifiers
REGION                  1..7
                        note = Synthetic peptide
VARIANT                 3
                        note = X can be any amino acid
VARIANT                 6
                        note = X can be any amino acid
VARIANT                 7
                        note = X can be K or R
source                  1..7
                        mol_type = protein
                        organism = synthetic construct
SEQUENCE: 849
KPXLGXX                                                                   7

SEQ ID NO: 850          moltype = AA  length = 5
FEATURE                 Location/Qualifiers
REGION                  1..5
                        note = Synthetic peptide
VARIANT                 2
                        note = X can be S or D
source                  1..5
                        mol_type = protein
                        organism = synthetic construct
SEQUENCE: 850
NXSMN                                                                     5
```

```
SEQ ID NO: 851         moltype =    length =
SEQUENCE: 851
000

SEQ ID NO: 852         moltype = AA   length = 6
FEATURE                Location/Qualifiers
REGION                 1..6
                       note = Synthetic peptide
VARIANT                4
                       note = X can be any amino acid
source                 1..6
                       mol_type = protein
                       organism = synthetic construct
SEQUENCE: 852
GELXGQ                                                                   6

SEQ ID NO: 853         moltype = AA   length = 6
FEATURE                Location/Qualifiers
REGION                 1..6
                       note = Synthetic peptide
VARIANT                1
                       note = X can be M, L or F
VARIANT                2
                       note = X can be any amino acid
source                 1..6
                       mol_type = protein
                       organism = synthetic construct
SEQUENCE: 853
XXNPQQ                                                                   6

SEQ ID NO: 854         moltype = AA   length = 6
FEATURE                Location/Qualifiers
REGION                 1..6
                       note = Synthetic peptide
VARIANT                5
                       note = X can be any amino acid
source                 1..6
                       mol_type = protein
                       organism = synthetic construct
SEQUENCE: 854
TTESXV                                                                   6

SEQ ID NO: 855         moltype = AA   length = 5
FEATURE                Location/Qualifiers
REGION                 1..5
                       note = Synthetic peptide
VARIANT                4
                       note = X can be G or A
source                 1..5
                       mol_type = protein
                       organism = synthetic construct
SEQUENCE: 855
KDVXE                                                                    5

SEQ ID NO: 856         moltype = AA   length = 8
FEATURE                Location/Qualifiers
REGION                 1..8
                       note = Synthetic peptide
VARIANT                3
                       note = X can be any amino acid
VARIANT                5
                       note = X can be F, W or M
VARIANT                7
                       note = X can be any amino acid
source                 1..8
                       mol_type = protein
                       organism = synthetic construct
SEQUENCE: 856
KPXDXGXK                                                                 8

SEQ ID NO: 857         moltype = AA   length = 6
FEATURE                Location/Qualifiers
REGION                 1..6
                       note = Synthetic peptide
VARIANT                2
                       note = X can be any amino acid
source                 1..6
                       mol_type = protein
```

```
                          -continued organism = synthetic construct
SEQUENCE: 857
VXADGT                                                                  6

SEQ ID NO: 858            moltype = AA  length = 5
FEATURE                   Location/Qualifiers
source                    1..5
                          mol_type = protein
                          organism = synthetic construct
VARIANT                   2
                          note = A can be replaced by P
VARIANT                   3
                          note = A can be replaced by T
SEQUENCE: 858
MAAAD                                                                   5

SEQ ID NO: 859            moltype = AA  length = 6
FEATURE                   Location/Qualifiers
REGION                    1..6
                          note = Synthetic peptide
VARIANT                   3
                          note = X can be any amino acid
VARIANT                   6
                          note = X can be D or G
source                    1..6
                          mol_type = protein
                          organism = synthetic construct
SEQUENCE: 859
VPXPKX                                                                  6

SEQ ID NO: 860            moltype = AA  length = 6
FEATURE                   Location/Qualifiers
REGION                    1..6
                          note = Synthetic peptide
VARIANT                   2
                          note = X can be any amino acid
VARIANT                   5
                          note = X can be T or S
source                    1..6
                          mol_type = protein
                          organism = synthetic construct
SEQUENCE: 860
QXKPXD                                                                  6

SEQ ID NO: 861            moltype = AA  length = 6
FEATURE                   Location/Qualifiers
REGION                    1..6
                          note = Synthetic peptide
VARIANT                   2
                          note = X can be T or S
VARIANT                   3
                          note = X can be any amino acid
source                    1..6
                          mol_type = protein
                          organism = synthetic construct
SEQUENCE: 861
FXXDGF                                                                  6

SEQ ID NO: 862            moltype = AA  length = 6
FEATURE                   Location/Qualifiers
source                    1..6
                          mol_type = protein
                          organism = synthetic construct
VARIANT                   3
                          note = R can be replaced by K
VARIANT                   6
                          note = V can be replaced by A
VARIANT                   2
                          note = X can be any amino acid
SEQUENCE: 862
WXRVYV                                                                  6

SEQ ID NO: 863            moltype = AA  length = 8
FEATURE                   Location/Qualifiers
source                    1..8
                          mol_type = protein
                          organism = synthetic construct
VARIANT                   5..7
                          note = X can be any amino acid
```

```
VARIANT                 1
                        note = C can be replaced by S
VARIANT                 3
                        note = T can be replaced by S
VARIANT                 8
                        note = Y can be replaced by F
SEQUENCE: 863
CTTEXXXY                                                                   8

SEQ ID NO: 864          moltype = AA  length = 6
FEATURE                 Location/Qualifiers
REGION                  1..6
                        note = Synthetic peptide
VARIANT                 2
                        note = X can be any amino acid
VARIANT                 6
                        note = X can be T or I
source                  1..6
                        mol_type = protein
                        organism = synthetic construct
SEQUENCE: 864
YXETCX                                                                     6

SEQ ID NO: 865          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 865
VQHYMHR                                                                    7

SEQ ID NO: 866          moltype = AA  length = 6
FEATURE                 Location/Qualifiers
REGION                  1..6
                        note = Synthetic peptide
source                  1..6
                        mol_type = protein
                        organism = synthetic construct
SEQUENCE: 866
RQPQGR                                                                     6

SEQ ID NO: 867          moltype = AA  length = 7
FEATURE                 Location/Qualifiers
REGION                  1..7
                        note = Synthetic peptide
source                  1..7
                        mol_type = protein
                        organism = synthetic construct
SEQUENCE: 867
DCMGTFC                                                                    7

SEQ ID NO: 868          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 868
KREIVFWR                                                                   8

SEQ ID NO: 869          moltype = AA  length = 7
FEATURE                 Location/Qualifiers
REGION                  1..7
                        note = Synthetic peptide
VARIANT                 3
                        note = X can be any amino acid
VARIANT                 6
                        note = X can be any amino acid
source                  1..7
                        mol_type = protein
                        organism = synthetic construct
SEQUENCE: 869
PDXGVXP                                                                    7

SEQ ID NO: 870          moltype = DNA  length = 53
FEATURE                 Location/Qualifiers
```

```
misc_feature            1..53
                        note = Synthetic
source                  1..53
                        mol_type = other DNA
                        organism = synthetic construct
SEQUENCE: 870
tcgtcggcag cgtcagatgt gtataagaga cagnnnnncc agtctggcca ggg          53

SEQ ID NO: 871          moltype = DNA  length = 54
FEATURE                 Location/Qualifiers
misc_feature            1..54
                        note = Synthetic
source                  1..54
                        mol_type = other DNA
                        organism = synthetic construct
SEQUENCE: 871
ccagtactac ggcatcactg ctgtctctta tacacatctc cgagcccacg agac         54

SEQ ID NO: 872          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 872
SARQPEFRGS LP                                                        12

SEQ ID NO: 873          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 873
VAGLGTVPEF AG                                                        12

SEQ ID NO: 874          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 874
LNAQVPEFNG AF                                                        12

SEQ ID NO: 875          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 875
AQLPALTAAL TA                                                        12

SEQ ID NO: 876          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 876
SGFLKPVEFY GS                                                        12

SEQ ID NO: 877          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 877
SARQPEFRGS LPAKV                                                     15

SEQ ID NO: 878          moltype = AA  length = 15
```

```
FEATURE              Location/Qualifiers
REGION               1..15
                     note = Description of Artificial Sequence: Synthetic peptide
source               1..15
                     mol_type = protein
                     organism = synthetic construct
SEQUENCE: 878
VAGLGTVPEF AGSYV                                                            15

SEQ ID NO: 879       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 879
LNAQVPEFNG AFTGA                                                            15

SEQ ID NO: 880       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 880
VGLSASEQGA LRDKR                                                            15

SEQ ID NO: 881       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 881
DVLTYGARRP FWTGS                                                            15

SEQ ID NO: 882       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 882
CSEVNGRRPF FGGPR                                                            15

SEQ ID NO: 883       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 883
RLAGCDGGSR SACSM                                                            15

SEQ ID NO: 884       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 884
DFVGKPEYAS LLKEW                                                            15

SEQ ID NO: 885       moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 885
NAWSLTGRRP FWDML                                                            15
```

```
SEQ ID NO: 886            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 886
GPARDHGRRP WFSQA                                                          15

SEQ ID NO: 887            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 887
KPPVKPATRG SETKM                                                          15

SEQ ID NO: 888            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 888
SSGRRPFFGY QSTYV                                                          15

SEQ ID NO: 889            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 889
VFRRPFFMEG SQVSM                                                          15

SEQ ID NO: 890            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 890
GRCVGDGERR PFFGS                                                          15

SEQ ID NO: 891            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 891
LPGRRPFWCF NAYGT                                                          15

SEQ ID NO: 892            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 892
KRTSSGGAGP LMNAK                                                          15

SEQ ID NO: 893            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 893
AQLPALTAAL TAFGR                                                          15
```

```
SEQ ID NO: 894            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 894
SGFLKPVEFY GSLAS                                                           15

SEQ ID NO: 895            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
VARIANT                   1
                          note = X can be I, V or M
VARIANT                   2
                          note = X can be any amino acid
VARIANT                   4
                          note = X can be any amino acid
VARIANT                   7
                          note = X can be any amino acid
SEQUENCE: 895
XXLXGMXD                                                                   8

SEQ ID NO: 896            moltype = AA  length = 7
FEATURE                   Location/Qualifiers
source                    1..7
                          mol_type = protein
                          organism = synthetic construct
VARIANT                   4..5
                          note = X can be any amino acid
VARIANT                   6
                          note = T can be replaced by V or S
VARIANT                   7
                          note = E can be replaced by D
SEQUENCE: 896
RGLXXTE                                                                    7

SEQ ID NO: 897            moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
VARIANT                   3
                          note = X can be any amino acid
SEQUENCE: 897
GEXEDK                                                                     6

SEQ ID NO: 898            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
VARIANT                   3
                          note = X can be any amino acid
VARIANT                   5
                          note = X can be any amino acid
VARIANT                   7
                          note = X can be any amino acid
SEQUENCE: 898
ALXLXEXVI                                                                  9

SEQ ID NO: 899            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
VARIANT                   1
```

```
                        note = X can be R or K
VARIANT                 4
                        note = X can be any amino acid
VARIANT                 7
                        note = X can be G or A
SEQUENCE: 899
XNCXICX                                                                      7

SEQ ID NO: 900          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
VARIANT                 4..5
                        note = X can be any amino acid
SEQUENCE: 900
KDRXXDE                                                                      7

SEQ ID NO: 901          moltype = AA   length = 7
FEATURE                 Location/Qualifiers
source                  1..7
                        mol_type = protein
                        organism = synthetic construct
VARIANT                 3
                        note = L can be replaced by V
VARIANT                 4
                        note = M can be replaced by L or F
VARIANT                 5..6
                        note = X can be any amino acid
SEQUENCE: 901
TTLMXXG                                                                      7

SEQ ID NO: 902          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
VARIANT                 4..6
                        note = X can be any amino acid
SEQUENCE: 902
DLDXXXLE                                                                     8

SEQ ID NO: 903          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
VARIANT                 2..4
                        note = X can be any amino acid
SEQUENCE: 903
RXXXRCRGC                                                                    9

SEQ ID NO: 904          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 904
TEEDQ                                                                        5

SEQ ID NO: 905          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
VARIANT                 4..5
                        note = X can be any amino acid
SEQUENCE: 905
MMHXXEHK                                                                     8
```

```
SEQ ID NO: 906           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
VARIANT                  1
                         note = X can be L or E
VARIANT                  5..6
                         note = X can be any amino acid
VARIANT                  8
                         note = X can be any amino acid
SEQUENCE: 906
XRITXXMXE                                                                  9

SEQ ID NO: 907           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
VARIANT                  4..5
                         note = X can be any amino acid
VARIANT                  7..10
                         note = X can be any amino acid
SEQUENCE: 907
LLAXXAXXXX R                                                              11

SEQ ID NO: 908           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 908
DESTK                                                                      5

SEQ ID NO: 909           moltype = AA  length = 7
FEATURE                  Location/Qualifiers
source                   1..7
                         mol_type = protein
                         organism = synthetic construct
VARIANT                  2
                         note = F can be replaced by Y or L
VARIANT                  3..4
                         note = X can be any amino acid
SEQUENCE: 909
FFXXJER                                                                    7

SEQ ID NO: 910           moltype = AA  length = 5
FEATURE                  Location/Qualifiers
source                   1..5
                         mol_type = protein
                         organism = synthetic construct
VARIANT                  2
                         note = E can be replaced by D or Q
VARIANT                  4
                         note = X can be any amino acid
SEQUENCE: 910
DERXT                                                                      5

SEQ ID NO: 911           moltype = AA  length = 7
FEATURE                  Location/Qualifiers
source                   1..7
                         mol_type = protein
                         organism = synthetic construct
VARIANT                  2
                         note = L can be replaced by V
VARIANT                  6
                         note = X can be any amino acid
SEQUENCE: 911
ELLVPXI                                                                    7

SEQ ID NO: 912           moltype = AA  length = 8
FEATURE                  Location/Qualifiers
```

```
REGION                  1..8
                        note = Description of Artificial Sequence: Synthetic peptide
source                  1..8
                        mol_type = protein
                        organism = synthetic construct
VARIANT                 3
                        note = X can be any amino acid
VARIANT                 6
                        note = X can be any amino acid
SEQUENCE: 912
GGXGTXAG                                                                            8

SEQ ID NO: 913          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
VARIANT                 2..4
                        note = X can be any amino acid
VARIANT                 6..8
                        note = X can be any amino acid
VARIANT                 11
                        note = X can be any amino acid
SEQUENCE: 913
RXXXRXXXIT XE                                                                      12

SEQ ID NO: 914          moltype = AA  length = 7
FEATURE                 Location/Qualifiers
source                  1..7
                        mol_type = protein
                        organism = synthetic construct
VARIANT                 1
                        note = F can be replaced by Y
VARIANT                 2
                        note = L can be replaced by I or V
VARIANT                 4..5
                        note = X can be any amino acid
SEQUENCE: 914
FLGXXHG                                                                             7

SEQ ID NO: 915          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 915
VGLSLSGMGD LR                                                                      12

SEQ ID NO: 916          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 916
DVLTYGARRP FW                                                                      12

SEQ ID NO: 917          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 917
CSEVNGRRPF FG                                                                      12

SEQ ID NO: 918          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
```

```
SEQUENCE: 918
RLAGCDGGSR SA                                                                    12

SEQ ID NO: 919         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 919
DFVGKPEYAS LL                                                                    12

SEQ ID NO: 920         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 920
NAWSLTGRRP FW                                                                    12

SEQ ID NO: 921         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 921
GPARDHGRRP WF                                                                    12

SEQ ID NO: 922         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 922
KPPVKPATRG SE                                                                    12

SEQ ID NO: 923         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 923
SSGRRPFFGY QS                                                                    12

SEQ ID NO: 924         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 924
KRTSSGGAGP LM                                                                    12

SEQ ID NO: 925         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 925
GGPAITLAGM AD                                                                    12

SEQ ID NO: 926         moltype = AA  length = 12
FEATURE                Location/Qualifiers
REGION                 1..12
                       note = Description of Artificial Sequence: Synthetic peptide
source                 1..12
                       mol_type = protein
```

```
                        organism = synthetic construct
SEQUENCE: 926
KTLFFAEDYT MN                                                                   12

SEQ ID NO: 927          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 927
IDDNGGAGTE WW                                                                   12

SEQ ID NO: 928          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 928
RREQQASTAG GA                                                                   12

SEQ ID NO: 929          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
VARIANT                 3
                        note = X can be any amino acid
VARIANT                 5
                        note = X can be any amino acid
VARIANT                 7
                        note = X can be any amino acid
SEQUENCE: 929
KPXFXGXK                                                                        8

SEQ ID NO: 930          moltype = AA  length = 5
FEATURE                 Location/Qualifiers
source                  1..5
                        mol_type = protein
                        organism = synthetic construct
VARIANT                 1
                        note = R can be replaced by H
VARIANT                 3
                        note = P can be replaced by W
SEQUENCE: 930
RRPFF                                                                           5

SEQ ID NO: 931          moltype = AA  length = 6
FEATURE                 Location/Qualifiers
source                  1..6
                        mol_type = protein
                        organism = synthetic construct
VARIANT                 1
                        note = R can be replaced by K
VARIANT                 3
                        note = I can be replaced by L or V
VARIANT                 5
                        note = D can be replaced by E
VARIANT                 6
                        note = L can be replaced by M or V
VARIANT                 4
                        note = X can be any amino acid
SEQUENCE: 931
RGIXDL                                                                          6

SEQ ID NO: 932          moltype = AA  length = 4
FEATURE                 Location/Qualifiers
source                  1..4
                        mol_type = protein
                        organism = synthetic construct
VARIANT                 1
                        note = R can be replaced by K
SEQUENCE: 932
RKRD                                                                            4
```

```
SEQ ID NO: 933         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 933
QPEQPFPE                                                                          8

SEQ ID NO: 934         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 934
KIRAEF                                                                            6

SEQ ID NO: 935         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 935
CDAPSTRSC                                                                         9

SEQ ID NO: 936         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 936
KTDKTNDF                                                                          8

SEQ ID NO: 937         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 937
RRPFF                                                                             5
```

What is claimed is:

1. An array comprising a peptide comprising a binding motif sequence LxGM[RQ]K (SEQ ID NO: 365), wherein a length of the peptide comprising the binding motif sequence is 30 amino acids or less, and wherein the peptide is operably linked to an array surface to present the peptide for binding by an antibody, wherein the array surface comprises:

(i) a solid surface, wherein the peptide is attached to the solid surface, or (ii) a biological particle, wherein the biological particle is engineered to express the peptide operably linked to a display scaffold, wherein the display scaffold is configured to display the peptide on the outer surface of the biological particle, and wherein the amino acid sequence of the peptide is heterologous to the biological particle.

2. The array of claim 1, wherein the array further comprises a second peptide comprising a binding motif selected from the group consisting of: [LI]xxA[ILV]xxRG (SEQ ID NO: 362), I[IV]Ixx[MT]xK (SEQ ID NO: 383), Ix[LM]xGFxK (SEQ ID NO: 364), [KR]x[DE]xTNxF (SEQ ID NO: 368), [ET][ML]HKF (SEQ ID NO: 369), VxxYFxx[LV]xK (SEQ ID NO: 374), KxVDxDR (SEQ ID NO: 375), [DN][AS]A[AG]F (SEQ ID NO: 376), and Kx[GRST]AE[YF] (SEQ ID NO: 378), wherein the second peptide is operably linked to an array surface to present the second peptide for binding by a second antibody, wherein the array surface comprises:

(i) the solid surface, wherein the peptide of claim 1 and the second peptide are each attached to the same solid surface, or (ii) a second biological particle, wherein the second biological particle is engineered to express the second peptide operably linked to a display scaffold, wherein the display scaffold is configured to display the second peptide on the outer surface of the second biological particle, and wherein the amino acid sequence of the second peptide is heterologous to the second biological particle.

3. The array of claim 2, wherein the second peptide comprises the binding motif sequence [LI]xxA[ILV]xxRG (SEQ ID NO: 362).

4. An array comprising at least two peptides, comprising:

(i) a first peptide comprising a binding motif sequence LxGM[RQ]K (SEQ ID NO: 365), wherein a length of the peptide comprising the binding motif sequence LxGM[RQ]K (SEQ ID NO: 365) is 30 amino acids or less; and
(ii) a second peptide comprising a binding motif selected from the group consisting of: [LI]xxA[ILV]xxRG (SEQ ID NO: 362), I[IV]Ixx[MT]xK (SEQ ID NO: 383), Ix[LM]xGFxK (SEQ ID NO: 364), [KR]x[DE]xTNxF (SEQ ID NO: 368), [ET][ML]HKF (SEQ ID NO: 369), VxxYFxx[LV]xK (SEQ ID NO: 374), KxVDxDR (SEQ ID NO: 375), [DN][AS]A[AG]F (SEQ ID NO: 376), and Kx[GRST]AE[YF] (SEQ ID NO: 378,
wherein each of the at least two peptides is operably linked to an array surface to present the peptides for binding by one or more antibodies, wherein the array surface comprises:
(i) a solid surface, wherein the first peptide and the second peptide are each attached to the same solid surface, or
(ii) a first biological particle, wherein the first biological particle is engineered to express the first peptide, and a second biological particle, wherein the second biological particle is engineered to express the second peptide, wherein each biological particle expresses each respective peptide operably linked to a display scaffold, wherein the display scaffold is configured to display the respective peptides on the outer surface of the respective biological particle, and wherein the amino acid sequence of the peptide is heterologous to the respective biological particle.

5. The array of claim 4, wherein the second peptide comprises the binding motif sequence [LI]xxA[ILV]xxRG (SEQ ID NO: 362).

6. The array of claim 1, wherein the peptide is capable of binding to an antibody associated with a *Borrelia burgdorferi* infection.

7. The array of claim 1, wherein the array surface comprises the solid surface.

8. The array of claim 7, wherein the solid surface comprises a microparticle.

9. The array of claim 7, wherein the solid surface comprises a plate well.

10. The array of claim 1, wherein the array surface comprises the biological particle.

11. The array of claim 10, wherein the biological particle comprises a cell, a virus, or a bacteriophage.

12. The array of claim 11, wherein the biological particle is an *Escherichia coli* cell.

13. The array of claim 1, wherein the display scaffold comprises at least a portion of an *Escherichia coli* eCPX scaffold.

14. A method of detecting antibodies associated with a *Borrelia burgdorferi* infection in a subject comprising:
contacting the array of claim 1 with a biological sample from the subject, wherein the biological sample comprises a plurality of antibodies, optionally wherein the biological sample comprises a bodily fluid;
incubating the biological sample and the array under conditions sufficient for binding of the peptide to a target antibody;
measuring the binding of the peptide to the target antibody in the biological sample thereby detecting antibodies associated with a *Borrelia burgdorferi* infection; and
wherein detecting antibodies associated with a *Borrelia burgdorferi* infection that bind to the peptide indicates the subject is positive for the *Borrelia burgdorferi* infection.

15. The method of claim 14, wherein the method further comprises contacting the biological sample with at least one reagent configured to remove antibodies that bind to array components other than the peptide before contacting the array of claim 1 with a biological sample from the subject, optionally wherein the at least one reagent is the array surface free of the peptide.

16. The method of claim 14, wherein the measuring comprises a peptide library display system.

17. The method of claim 16, wherein the peptide library display system comprises an *E. coli* display system.

18. A method of detecting antibodies associated with a *Borrelia burgdorferi* infection in a subject comprising:
contacting the array of claim 4 with a biological sample from the subject, wherein the biological sample comprises a plurality of antibodies, optionally wherein the biological sample comprises a bodily fluid;
incubating the biological sample and the array under conditions sufficient for binding of the at least two peptides to one or more target antibodies;
measuring the binding of the at least two peptides to the target antibodies in the biological sample thereby detecting antibodies associated with a *Borrelia burgdorferi* infection; and
wherein detecting antibodies associated with a *Borrelia burgdorferi* infection that bind to each of the at least two peptides indicates the subject is positive for the *Borrelia burgdorferi* infection.

19. The method of claim 18, wherein the measuring comprises detecting binding of each of the at least two peptides to their respective target antibodies.

20. The method of claim 18, wherein the measuring comprises calculating the sum of z-scores for the at least two peptides.

21. The method of claim 18, wherein the method has a sensitivity of at least 80%.

22. The method of claim 18, wherein the method has a specificity of at least 99%.

23. The method of claim 18, wherein the method has a sensitivity of at least 80% and a specificity of at least 99%.

24. The method of claim 18, wherein the measuring comprises a peptide library display system.

25. The method of claim 24, wherein the peptide library display system comprises an *E. coli* display system.

26. A kit for diagnosing a *Borrelia burgdorferi* infection, comprising the array of claim 1 and a system for detecting the binding of the peptide to its target antibody.

27. The array of claim 9, wherein the plate well is an enzyme-linked immunosorbent assay (ELISA) plate well.

* * * * *